(12) United States Patent
Mitcham et al.

(10) Patent No.: US 6,699,664 B1
(45) Date of Patent: Mar. 2, 2004

(54) COMPOSITIONS AND METHODS FOR THE THERAPY AND DIAGNOSIS OF OVARIAN CANCER

(75) Inventors: Jennifer L. Mitcham, Redmond, WA (US); Gordon E. King, Seattle, WA (US); Paul A. Algate, Issaquah, WA (US); Steven P. Fling, Bainbridge Island, WA (US); Marc W. Retter, Carnation, WA (US); Gary R. Fanger, Mill Creek, WA (US); Steven G. Reed, Bellevue, WA (US); Thomas S. Vedvick, Federal Way, WA (US); Darrick Carter, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/667,857

(22) Filed: Sep. 20, 2000

Related U.S. Application Data

(63) Continuation-in-part of application No. 09/636,801, filed on Aug. 10, 2000, now abandoned, which is a continuation-in-part of application No. 09/617,747, filed on Jul. 17, 2000, now abandoned, which is a continuation-in-part of application No. 09/404,879, filed on Sep. 24, 1999, now Pat. No. 6,468,546, which is a continuation-in-part of application No. 09/338,933, filed on Jun. 23, 1999, now Pat. No. 6,488,931, which is a continuation-in-part of application No. 09/216,003, filed on Dec. 17, 1998, which is a continuation-in-part of application No. 09/215,681, filed on Dec. 17, 1998, now Pat. No. 6,528,253.

(51) Int. Cl.[7] .............................. C12Q 1/68; C12N 1/20; C12N 15/00; C12N 15/09; C12N 5/00; C07H 21/02; C07H 21/04
(52) U.S. Cl. ..................... 435/6; 435/252.3; 435/320.1; 435/325; 536/23.1; 536/24.1
(58) Field of Search .................. 435/6, 320.1, 325, 435/252.3; 536/23.1, 24.1

(56) References Cited

FOREIGN PATENT DOCUMENTS

| WO | WO 00/36107 | 6/2000 |
|---|---|---|
| WO | WO 01/16318 | 3/2001 |
| WO | WO 01/57272 | 8/2001 |
| WO | WO 02/02587 | 1/2002 |
| WO | WO 02/02624 | 1/2002 |
| WO | WO 02/10187 | 2/2002 |
| WO | WO 02/16429 | 2/2002 |
| WO | WO 02/16581 | 2/2002 |

OTHER PUBLICATIONS

GIBCO GRL, Random Primers DNA Labeling System, GIBCO BRL Catalogue and Reference Guide, Life Technologies, Inc. Gaithersburg, MD 20877, USA, p. 404. 1990.*
Watson et al., Recombinant DNA, Chapter 5, pp. 63–77, Scientific American Books, 1994.*
Geneseq, Acc. No. AAT23436, Aug. 16, 1996.*
GenBank Acc. No. U97694, Aug. 27, 1997.*
Hovig, E. et al., "CA125: The End of the Beginning," *Tumor Biology* 22: 345–347, 2001.
O'Brien, T.J. et al., "The CA 125 Gene: A Newly Discovered Extension of the Glycosylated N–Terminal Domain Doubles the Size of This Extracellular Superstructure," *Tumor Biology* 23: 154–169, 2002.
O'Brien, T.J. et al., "The CA 125 Gene: An Extracellular Superstructure Dominated by Repeat Sequences," *Tumor Biology* 22: 348–366, 2001.
Schummer, M. et al., "Comparative hybridization of an array of 21 500 ovarian cDNAs for the discovery of genes overexpressed in ovarian carcinomas," *Gene* 238: 375–385, 1999.
Whitehouse, C. et al., "NBR1 interacts with fasciculation and elongation protein zeta–1 (FEZ1) and calcium and integrin binding protein (CIB) and shows developmentally restricted expression in the neural tube," *Eur. J. Biochem.* 269: 538–545, 2002.
Yin and Lloyd, "Molecular Cloning of the CA125 Ovarian Cancer Antigen. Identification as a new mucin, MUC16," *Journal of Biological Chemistry* 276(29): 27371–27375, Jul. 20, 2001.
Yin, B.W.T. et al., "Ovarian cancer antigen CA125 is encoded by the MUC16 mucin gene," *International Journal of Cancer* 98: 737–740, 2002.
Bookman et al., "Biological therapy of ovarian cancer: Current directions," *Seminars in Oncology*, 25(3):381–396.
Gillespie et al., "Mage, Bage and Gage: Tumour antigen expression in benign and malignant ovarian tissue," *British Journal of Cancer*, 78(6):816–821, Sep., 1998.
Heller et al., "Discovery and analysis of inflammatory disease–related genes using cDNA microarrays," *Proc. Natl. Acad. Sci. USA* 94:2150–2155, Mar., 1997.
Ishikawa et al., "Prediction of the coding sequence of unidentified human genes. The complete sequence of 100 new cDNA clones from brain which can code for large proteins i vitro," *DNA Res.*, 5:169–176, 1998.
Jin et al., "Human T cell leukemia virus type 1 oncoprotein tax targets the human mitotic checkpoint protein MAD1," *Cell* 93:81–91, Apr. 3, 1998.

(List continued on next page.)

*Primary Examiner*—John S. Brusca
*Assistant Examiner*—Shubo Zhou
(74) *Attorney, Agent, or Firm*—Seed Intellectual Property Law Group PLLC

(57) ABSTRACT

Compositions and methods for the therapy and diagnosis of cancer, such as ovarian cancer, are disclosed. Compositions may comprise one or more ovarian carcinoma proteins, immunogenic portions thereof, polynucleotides that encode such portions or antibodies or immune system cells specific for such proteins. Such compositions may be used, for example, for the prevention and treatment of diseases such as ovarian cancer. Methods are further provided for identifying tumor antigens that are secreted from ovarian carcinomas and/or other tumors. Polypeptides and polynucleotides as provided herein may further be used for the diagnosis and monitoring of ovarian cancer.

7 Claims, 100 Drawing Sheets

OTHER PUBLICATIONS

Köhler et al., "Immotherapy of Ovarian Carcinoma with the Monoclonal Anti–Idiotype Antibody ACA125—Results of the Phase LB Study," *Gebrutshilfe und Fraenheilkunde, 58*(4):180–186, Apr. 1998 + (English Abstract).

Ma et al., "Use of encapsulated single chain antibodies for induction of anti–idiotypic humoral and cellular immune responses," *Journal of Pharmaceutical Sciences, 87*(11):1375 1378, Nov., 1998.

Parker et al., "Scheme for ranking potential HLA–A2 binding peptides based on independent binding of individual peptide side–chains," *The Journal of Immunology 152*(1):163–175, Jan. 1, 1994.

Peoples et al., "Ovarian cancer–associated lymphocyte recognition of folate binding protein peptides," *Annals of Surgical Oncology, 5*(8):743–750, Dec., 1998.

Schena et al., "Parallel human genome analysis: Microarray–based expression monitoring of 1000 genes," *Proc. Natl. Acad. Sci., 93*:10614–10619, Oct., 1996.

* cited by examiner 11729.1 contg

```
TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC
```

11729-45.21.21.cons1

```
TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA
```

11729-45.21.21.cons2

```
TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC
```

11731.1contig

```
TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTTAATTCTTTCGTTTAATAGCTGCTTCTCAGGGACCAGATAGATA
AGCTTATTTTGATATTCCTTAAGCTCTTGTTGAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT
```

*Fig. 1A*

11731.2contig

```
AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTA
```

11734.1contig

```
AATAGATTTAATGCAGAGTGTCAACTTCAATTGATTGATAGTGGCTGCCTAGAGTGCTGTGTTGAGTAGGTTTCTG
AGGATGCACCCTGGCTTGAAGAGAAAGACTGGCAGGATTAACAATATCTAAAATCTCACTTGTAGGAGAAACCACA
GGCACCAGAGCTGCCACTGGTGCTGGCACCAGCTCCACCAAGGCCAGCGAAGAGCCCAAATGTGAGAGTGGCGGTC
AGGCTGGCACCAGCACTGAAGCCACCACTGGTGCTGGCACTGGCACTGGCACTGTTATTGGTACTGGTACTGGCAC
CAGTGCTGGCACTGCCACTCTCTTGGGCTTTGGCTTTAGCTTCTGCTCCCGCCTGGATCCGGGCTTTGGCCCAGGG
TCCGATATCAGCTTCGTCCCAGTTGCAGGGCCCGGCAGCATTCTCCGAGCCGAGCCCAATGCCCATTCGAGCTCTA
ATCTCGGCCCTAGCCTTGGCTTCAGCTGCAGCCTCAGCTGCAGCCTTCAAATCCGCTTCCATCGCCTCTCGGTAC
```

11734.2contig

```
GCCAAGAAAGCCCGAAAGGTGAAGCATCTGGATGGGGAAGAGGATGGCAGCAGTGATCAGAGTCAGGCTTCTGGAA
CCACAGGTGGCCGAAGGGTCTCAAAGGCCCTAATGGCCTCAATGGCCCGCAGGGCTTCAAGGGGTCCCATAGCCTT
TTGGGCCCGCAGGGCATCAAGGACTCGGTTGGCTGCTTGGGCCCGGAGAGCCTTGCTCTCCCTGAGATCACCTAAA
GCCCGTAGGGGCAAGGCTCGCCGTAGAGCTGCCAAGCTCCAGTCATCCCAAGAGCCTGAAGCACCACCACCTCGGG
ATGTGGCCCTTTTGCAAGGGAGGGCAAATGATTTGGTGAAGTACCTTTTGGCTAAAGACCAGACGAAGATTCCCAT
CAAGCGCTCGGACATGCTGAAGGACATCATCAAAGAATACACTGATGTGTACCCCGAAATCATTGAACGAGCAGGC
TATTCCTTGGAGAAGGTATTTGGGATTCAATTGAAGGAAATTGATAAGAATGACCACTTGTACATTCTTCTCAGC
```

11736.1contg

```
GAGGTCTCACTATGTTGCCCAGGCTGTTCTTGAACTCCTGGGATCAAGCAATCCACCCATGTTGGTCTCCAAAAGT
GCTGGGATCATAGGCGTGAGCCACCTCACCCAGCCACCAATTTTCAATCAGGAAGACTTTTTCCTTCTTCAAGAAG
TGAAGGGTTTCCAGAGTATAGCTACACTATTGCTTGCCTGAGGGTGACTACAAAATTGCTTGCTAAAAGGTTAGGA
TGGGTAAAGAATTAGATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCTTGGAGTAAACTCCA
TTACTCATCCCAAGAAACCATATTATAAGTATCACTGATAATAAGAACAACAGGACCTTGTCATAAATTCTGGATA
AGAGAAATAGTCTCTGGGTGTTTGXTCTTAATTGATAAAATTTACTTGTCCATCTTTTAGTTCAGAATCACAAAA
```

*Fig. 1B*

11736.2contig

AAGCGGAAATGAGAAAGGAGGGAAAATCATGTGGTATTGAGCGGAAAACTGCTGGATGACAGGGCTCAGTCCTGTT
GGAGAACTCTGGGTGGTGCTGTAGAACAGGGCCACTCACAGTGGGGTGCACAGACCAGCACGGCTCTGTGACCTGT
TTGTTACAGGTCCATGATGAGGTAAACAATACACTGAGTATAAGGGTTGGTTTAGAAACTCTTACAGCAATTTGAC
AAAGTAATCTTCTGTGCAGTGAATCTAAGAAAAAAATTGGGGCTGTATTTGTATGTTCCTTTTTTTCATTTCATGT
TCTGAGTTACCTATTTTTATTGCATTTTACAAAAGCATCCTTCCATGAAGGACCGGAAGTTAAAAACAAAGCAGGT
CCTTTATCACAGCACTGTCGTAGAACACAGTTCAGAGTTATCCACCCAAGGAGCCAGGGAGCTGGGCTAAACCAAA
GAATTTTGCTTTTGGTTAATCATCAGGTACTTGAGTTGGAATTGTTTTAATCCCATCATTACCAGGCTGGAXGTG

11739-1&2

CCGCGGCTCCTGTCCAGACCCTGACCCTCCCTCCCAAGGCTCAACCGTCCCCCAACAACCGCCAGCCTTGTACTGA
TGTCGGCTGCGAGAGCCTGTGCTTAAGTAAGAATCAGGCCTTATTGGAGACATTCAAGCAAAGGTTGGACAACTAC
TTTTCCAGAACAGAAAGGAAACTCATGCATCAGAAAAGGTGACTAATAAAGGTACCAGAAGAATATGGCTGCACAA
ATACCAGAATCTGATCAGATAAAACAGTTTAAGGAATTTCTGGGGACCTACAATAAACTTACAGAGACCTGCTTTT
TGGACTGTGTTAGAGACTTCACAACAAGAGAAGTAAAACCTGAAGAGACCACCTGTTCAGAACATTGCTTACAGAA
ATATTTAAAAATGACACAAAGAATATCCATGAGATTTCAGGAATATCATATTCAGCAGAATGAAGCCCTGGCAGCC
AAAGCAGGACTCCTTGGCCAACCACGATAGAGAAGTCCTGATGGATGAACTTTTGATGAAAGATTGCCAACAGCTG
CTTTATTGGAAATGAGGACTCATCTGATAGAATCCCCTGAAAGCAGTAGCCACCATGTTCAACCATCTGTCATGAC
TGTTTGGCAAATGGAAACCGCTGGAGAAACAAAATTGCTATTTACCAGGAATAATCACAATAGAAGGTCTTATTGT
TCAGTGAAATAATAAGATGCAACATTTGTTGAGGCCTTATGATTCAGCAGCTTGGTCACTTGATTAGAAAAATAAA
CCATTGTTTCTTCAATTGTGACTGTTAATTTTAAAGCAACTTATGTGTTCGATCATGTATGAGATAGAAAAATTTT
TATTACTCAAAGTAAAATAAATGGA

11740.1.contig

GAAAAAAAATATAAAACACACTTTTGCGAAAACGGTGGCCCTAAAAGAGGAAAAGAATTTCACCAATATAAATCCA
ATTTTATGAAAACTGACAATTTAATCCAAGAATCACTTTTGTAAATGAAGCTAGCAAGTGATGATATGATAAAATA
AACGTGGAGGAAATAAAAACACAAGACTTGGCATAAGATATATCCACTTTTGATATTAAACTTGTGAAGCATATTC
TTCGACAAATTGTGAAAGCGTTCCTGATCTTGCTTGTTCTCCATTTCAAATAAGGAGGCATATCACATCCCAAGAG
TAACAGAAAAAGAAAAAAGACATTTTTGCATTTTGAGATGAACCAAAGACACAAAACAAAACGAACAAAGTGTCAT
GTCTAATTCTAGCCTCTGAAATAAACCTTGAACATCTCCTACAAGGCACCGTGATTTTTGTAATTCTAACCTGAAG
AAATGTGATGACTTTTGTGGACATGAAAATCAGATGAGAAAACTGTGGTCTTTCCAAAGCCTGAACTCCCCTGAAA
ACCTTTGCA

*Fig. 1C*

11766.1.contig

CTGGGATCATTTCTCTTGATGTCATAAAAGACTCTTCTTCTTCCTCTTCATCCTCTTCTTCATCCTCTTCTGTACA
GTGCTGCCGGGTACAACGGCTATCTTTGTCTTTATCCTGAGATGAAGATGATGCTTCTGTTTCTCCTACCATAACT
GAAGAAATTTCGCTGGAAGTCGTTTGACTGGCTGTTTCTCTGACTTCACCTTCTTTGTCAAACCTGAGTCTTTTTA
CCTCATGCCCCTCAGCTTCCACAGCATCTTCATCTGGATGTTTATTTTTCAAAGGGCTCACTGAGGAAACTTCTGA
TTCAGAGGTCGAAGAGTCACTGTGATTTTTCTCCTCATTTTGCTGCAAATTTGCCTCTTTGCTGTCTGTGCTCTCA
GGCAACCCATTTGTTGTCATGGGGGCTGACAAAGAAACCTTTGGTCGATTAAGTGGCCTGGGTGTCCCAGGCCCAT
TTATATTAGACCTCTCAGTATAGCTTGGTGAATTTCCAGGAAACATAACACCATTCATTCGATTTAAACTATTGGA
ATTGGTTTT 11766.2.contig GAGGGTTGGTGGTAGCGGCTTGGGGAGGTGCTCGCTCTGTCGGTCTTGCTCTCTCGCACGCTTCCCCCGGCTCCCT
TCGTTTCCCCCCCCCGGTCGCCTGCGTGCCGGAGTGTGTGCGAGGGAGGGGGAGGGCGTCGGGGGGGTGGGGGGAG
GCGTTCCGGTCCCCAAGAGACCCGCGGAGGGAGGCGGAGGCTGTGAGGGACTCCGGGAAGCCATGGACGTCGAGAG
GCTCCAGGAGGCGCTGAAAGATTTTGAGAAGAGGGGGAAAAAGGAAGTTTGTCCTGTCCTGGATCAGTTTCTTTGT
CATGTAGCCAAGACTGGAGAAACAATGATTCAGTGGTCCCAATTTAAAGGCTATTTTATTTTCAAACTGGAGAAAG
TGATGGATGATTTCAGAACTTCAGCTCCTGAGCCAAGAGGTCCTCCCAACCCTAATGTCGA 11773.2.contig AAGCAGGCGGCTCCCGCGCTCGCAGGGCCGTGCCACCTGCCCGCCCGCCCGCTCGCTCGCTCGCCCGCCGCGCCGC
GCTGCCGACCGCCAGCATGCTGCCGAGAGTGGGCTGCCCCGCGCTGCCGXTGCCG 11775-1&2

ATCTCTTGTATGCCAAATATTTAATATAAATCTTTGAAACAAGTTCAGATGAAATAAAAATCAAAGTTTGCAAAAA
CGTGAAGATTAACTTAATTGTCAAATATTCCTCATTGCCCCAAATCAGTATTTTTTTTATTTCTATGCAAAAGTAT
GCCTTCAAACTGCTTAAATGATATATGATATGATACACAAACCAGTTTTCAAATAGTAAAGCCAGTCATCTTGCAA
TTGTAAGAAATAGGTAAAAGATTATAAGACACCTTACACACACACACACACACACACGTGTGCACGCCAATGAC
AAAAAACAATTTGGCCTCTCCTAAAATAAGAACATGAAGACCCTTAATTGCTGCCAGGAGGGAACACTGTGTCACC
CCTCCCTACAATCCAGGTAGTTTCCTTTAATCCAATAGCAAATCTGGGCATATTTGAGAGGAGTGATTCTGACAGC
CACGTTGAAATCCTGTGGGGAACCATTCATGTCCACCCACTGGTGCCCTGAAAAAATGCCAATAATTTTTCGCTCC
CACTTCTGCTGCTGtCTCTTCCACATCCTCACATAGACCCCAGACCCGCTGGCCCCTGGCTGGGCATCGCATTGCT
GGTAGAGCAAGTCATAGGTCTCGTCTTTGACGTCACAGAAGCGATACACCAAATTGCCTGGTCGGTCATTGTCATA
ACCAGAGA

*Fig. 1D*

11777.1&2.cons

```
CAGACGGGGTTTCACTATGTTGGCTAGGCTGGTCTTGAACTCCTGACTTCAGGTGATCTGCCTGCCTTGGCCTCCC
AAAGTGCTGGGATTACAGGCATAAGCCACTGCGCCCGGCTGATCTGATGGTTTTCATAAGGCTTTTCCCCCTTTTGC
TCAGCACTTCTCCTTCCTGCCGCCATGTGAAGAAGGACATGTTTGCTTCCCCTTCCACCACGATTGTAAGTTGTTT
CCTGAGGCCTCCCCGGCCATGCTGAACTGTGAGTCAATTAAACCTCTTTCCTTTATAAATTATCCAGTTTTGGGTA
TGTCTTTATTAGTAGAATGAGAACAGACTAATACAACCCTTAAAGGAGACTGACGGAGAGGATTCTTCCTGGATCC
CAGCACTTCCTCTGAATGCTACTGACATTCTTCTTGAGGACTTTAAACTGGGAGATAGAAAACAGATTCCATGGCT
CAGCAGCCTGAGAGCAGGGAGGGAGCCAAGCTATAGATGACATGGGCAGCCTCCCCTGAGGCCAGGTGTGGCCGAA
CCTGGGCAGTGCTGCcACCCACCCCACCAGGGCCAAGTCCTGTCCTTGGAGAGCCAAGCCTCAATCACTGCTAGCC
TCAAGTGTCCCCAAGCCACAGTGGCTAGGGGGACTCAGGGAACAGTTCCCAGTCTGCCCTACTTCTCTTACCTTTA
CCCCTCATACCTCCAAAGTAGACCATGTTCATGAGGTCCAAAGG
```

11779.2.contig

```
AAGCGAGGAAGCCACTGCGGCTCCTGGCTGAAAAGCGGCGCCAGGCTCGGGAACAGAGGGAACGCGAAGAACAGGA
GCGGAAGCTGCAGGCTGAAAGGGACAAGCGAATGCGAGAGGAGCAGCTGGCCCGGGAGGCTGAAGCCCGGGCTGAA
CGTGAGGCCGAGGCGCGGAGACGGGAGGAGCAGGAGGCTCGAGAGAAGGCGCAGGCTGAGCAGGAGGAGCAGGAGC
GACTGCAGAAGCAGAAAGAGGAAGCCGAAGCCCGGTCCCGGGAAGAAGCTGAGCGCCAGCGCCAGGAGCGGGAAAA
GCACTTTCAGAAGGAGGAACAGGAGAGACAAGAGCGAAGAAAGCGGCTGGAGGAGATAATGAAGAGGACTCGGAAA
TCAGAAGCCGCCGAAACCAAGAAGCAGGATGCAAAGGAGACCGCAGCTAACAATTCCGGCCCAGACCCTTGTGAAA
GCTGTAGAGACTCGGCCCTCTGGGCTTCCAGAAAGGATTCTATTGCAGAAAGGAAGGAGCTXGGCCCCCCAXGGA
```

11781 & 37.cons

```
CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACXTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAAT
```

```
CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACCTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAATTA
```

11784-1 & 2

```
GGACGACAAGGCCATGGCGATATCGGATCCGAATTCAAGCCTTTGGAATTAAATAAACCTGGAACAGGGAAGGTGA
AAGTTGGAGTGAGATGTCTTCCATATCTATACCTTTGTGCACAGTTGAATGGGAACTGTTTGGGTTTAGGGCATCT
TAGAGTTGATTGATGGAAAAAGCAGACAGGAACTGGTGGGAGGTCAAGTGGGGAAGTTGGTGAATGTGGAATAACT
TACCTTTGTGCTCCACTTAAACCAGATGTGTTGCAGCTTTCCTGACATGCAAGGATCTACTTTAATTCCACACTCT
CATTAATAAATTGAATAAAAGGGAATGTTTTGGCACCTGATATAATCTGCCAGGCTATGTGACAGTAGGAAGGAAT
GGTTTCCCCTAACAAGCCCAATGCACTGGTCTGACTTTATAAATTATTTAATAAAATGAACTATTATC
```

11785.2.contig

```
GGCAGTGACATTCACCATCATGGGAACCACCTTCCCTTTTCTTCAGGATTCTCTGTAGTGGAAGAGAGCACCCAGT
GTTGGGCTGAAAACATCTGAAAGTAGGGAGAAGAACCTAAAATAATCAGTATCTCAGAGGGCTCTAAGGTGCCAAG
AAGTCTCACTGGACATTTAAGTGCCAACAAAGGCATACTTTCGGAATCGCCAAGTCAAAACTTTCTAACTTCTGTC
TCTCTCAGAGACAAGTGAGACTCAAGAGTCTACTGCTTTAGTGGCAACTACAGAAAACTGGTGTTACCCAGAAAAA
CAGGAGCAATTAGAAATGGTTCCAATATTTCAAAGCTCCGCAAACAGGATGTGCTTTCCTTTGCCCATTTAGGGTT
TCTTCTCTTTCCTTTCTCTTTATTAACCACT
```

*Fig. 1F*

11718-1&2 cons

TGCGCTGAAAACAACGGCCTCCTTTACTGTTAAAATGCAGCCACAGGTGCTTAGCCGTGGGCATCTCAACCACCAG
CCTCTGTGGGGGGCAGGTGGGCGTCCCTGTGGGCCTCTGGGCCCACGTCCAGCCTCTGTCCTCTGCCTTCCGTTCT
TCGACAGTGTTCCCGGCATCCCTGGTCACTTGGTACTTGGCGTGGGCCTCCTGTGCTGCTCCAGCAGCTCCTCCAG
GXGGTCGGCCCGCTTCACCGCAGCCTCATGTTGTGTCCGGAGGCTGCTCACGGCCTCCTCCTTCCTCGCGAGGGCT
GTCTTCACCCTCCGGXGCACCTCCTCCAGCTCCAGCTGCTGGCGGGCCTGCAGCGTGGCCAGCTCGGCCTTGGCCT
GCCGCGTCTCCTCCTCARAGGCTGCCAGCCGGTCCTCGAACTCCTGGCGGATCACCTGGGCCAGGTTGCTGCGCTC
GCTAGAAAGCTGCTCGTTCACCGCCTGCGCATCCTCCAGCGCCCGCTCCTTCTGCCGCACAAGGCCCTGCAGACGC
AGATTCTCGCCCTCGGCcTCCCCAAGCTGGCCCTTCAGCTCCGAGCACCGCTCCTGAAGCTTCCGCTCCGACTGCT
CCAGCTCGGAGAGCTCGGCCTCGTACTTGTCCCGTAAGCGCTTGATGCGGCTCTCGGCAGCCTTCTCACTCTCCTC
CTTGGCCAGCGCCATGTCGGCCTCCAGCCGGTGAATGACCAGCTCAATCTCCTTGTCCCGGCCTTTCCGGATTTCT
TCCCTCAGCTCCTGTTCCCGGTTCAGCAGCCACGCCTCCTCCTTCCTGGTGCGGCCGGCCTCCCACGCCTGCCTCT
CCAGCTCCAGCTGCTGCTTCAGGGTATTCAGCTCCATCTGGCGGGCCTGCAGCGTGGCCA

13690.4

CAACTTATTACTTGAAATTATAATATAGCCTGTCCGTTTGCTGTTTCCAGGCTGTGATATATTTTCCTAGTGGTTT
GACTTTAAAAATAAATAAGGTTTAATTTTCTCCCC

13693.1

TGCAAGTCACGGGAGTTTATTTATTTAATTTTTTTCCCCAGATGGAGACTCTGTCGCCCAGGCTGGAGTGCAATGG
TGTGATCTTGGCTCACTGCAACCTCCACCTCCTGGGTTCAAGCGATTCTCCTGCCACAGCCTCCCGAGTAGCTGGG
ATTACAGGTGCCCGCCACCACACCCAGCTAATTTTTATATTTTTAGTAAAGACAGGGTTTCCCCATGTTGGCCAGG
CTGGTCTTGAACTTCTGACCTCAGGTGATCCACCTGCCTCGGCCTCCCAAAGTGTTGGGATTACAGGCGTGAGCTA
CCCGTGCCTGGCCAGCCACTGGAGTTTAAAGGACAGTCATGTTGGCTCCAGCCTAAGGCGGCATTTTCCCCCATCA
GAAAGCCCGCGGCTCCTGTACCTCAAAATAGGGCACCTGTAAAGTCAGTCAGTGAAGTCTCTGCTCTAACTGGCCA
CCCGGGGCCATTGGCNTCTGACACAGCCTTGCCAGGANGCCTGCATCTGCAAAAGAAAAGTTCACTTCCTTTCCG

13694.1

CAGAGAATCTKAGAAAGATGTCGCGTTTTCTTTTAATGAATGAGAGAAGCCCATTTGTATCCCTGAATCATTGAGA
AAAGGCGGCGGTGGCGACAGCGGCGACCTAGGGATCGATCTGGAGGGACTTGGGGAGCGTGCAGAGACCTCTAGCT
CGAGCGCGAGGGACCTCCCGCCGGGATGCCTGGGGAGCAGATGGACCCTACTGGAAGTCAGTTGGATTCAGATTTC
TCTCAGCAAGATACTCCTTGCCTGATAATTGAAGATTCTCAGCCTGAAAGCCAGGTTCTAGAGGATGATTCTGGTT
CTCACTTCAGTATGCTATCTCGACACCTTCCTAATCTCCAGACGCACAAAGAAAATCCTGTGTTGGATGTTGNGTC
CAATCCTTGAACAAACAGCTGGAGAAGAACGAGGAGACCGGTAATAGTGGGTTCAATGAACATTTGAAAGAAAACC
AGGTTGCAGACCCTG

```
GACTGTCCTGAACAAGGGACCTCTGACCAGAGAGCTGCAGGAGATGCAGAGTGGTGGCAGGAGTGGAAGCCAAAGA
ACACCCACCTTCCTCCCTTGAAGGAGTAGAGCAACCATCAGAAGATACTGTTTTATTGCTCTGGTCAAACAAGTCT
TCCTGAGTTGACAAAACCTCAGGCTCTGGTGACTTCTGAATCTGCAGTCCACTTTCCATAAGTTCTTGTGCAGACA
ACTGTTCTTTTGCTTCCATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGCTGGACTGTTCTGCT
ATGGGGATATCTTCGTTGGACTGTTCTTCATGCTTAATTGCAGTATTAGCATCCACATCAGACAGCCTGGTATAAC
CAGAGTTGGTGGTTACTGATTGTAGCTGCTCTTTGTCCACTTCATATGGCACAAGTATTTTCCTCAACATCCTGGC
TCTGGGAAG
```

13695.1

```
GAAATGTATATTTAATCATTCTCTTGAACGATCAGAACTCTRAAATCAGTTTTCTATAACARCATGTAATACAGTC
ACCGTGGCTCCAAGGTCCAGGAAGGCAGTGGTTAACACATGAAGAGTGTGGGAAGGGGGCTGGAAACAAAGTATTC
TTTTCCTTCAAAGCTTCATTCCTCAAGGCCTCAATTCAAGCAGTCATTGTCCTTGCTTTCAAAAGTCTGTGTGTGC
TTCATGGAAGGTATATGTTTGTTGCCTTAATTTGAATTGTGGCCAGGAAGGGTCTGGAGATCTAAATTCAGAGTAA
GAAAACCTGAGCTAGAACTCAGGCATTTCTCTTACAGAACTTGGCTTGCAGGGTAGAATGAAGGGAAAGAAACTTA
GAAGCTCAACAAGCTGAAGATAATCCCATCAGGCATTTCCCATAGGCCTTGCAACTCTGTTCACTGAGAGATGTTA
TCCTG
```

13695.2

```
AGTCTGGAGTGAGCAAACAAGAGCAAGAAACAARRAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGAGTGATAAGTAA
AATGCACGTGGAGACAAGTGCATCCCCAGATCTCAGGGACCTCCCCCTGCCTGTCACCTGGGGAGTGAGAGGACAG
GATAGTGCATGTTCTTTGTCTCTGAATTTTTAGTTATATGTGCTGTAATGTTGCTCTGAGGAAGCCCCTGGAAAGT
CTATCCCAACATATCCACATCTTATATTCCACAAATTAAGCTGTAGTATGTACCCTAAGACGCTGCTAATTGACTG
CCACTTCGCAACTCAGGGGCGGCTGCATTTTAGTAATGGGTCAAATGATTCACTTTTTATGATGCTTCCCAAGGTG
CCTTGGCTTCTCTTCCCAACTGACAAATGCCCAAGTTGAGAAAAATGATCATAATTTTAGCATAAACCGAGCAATC
GGCGACCCC
```

13697.1

```
TAGCTGTCTTCCTCACTCTTATGGCAATGACCCCATATCTTAATGGATTAAGATAATGAAAGTGTATTTCTTACAC
TCTGTATCTATCACCAGAAGCTGAGGTGATAGCCCGCTTGTCATTGTCATCCATATTCTGGGACTCAGGCGGGAAC
TTTCTGGAATATTGCCAGGGAGCATGGCAGAGGGGCACAGTGCATTCTGGGGGAATGCACATTGGCTCAGCCTGGG
TAATGAGTGATATACATTACCTCTGTTCACAACTCATTGCCCAGCACCAGTCACAAGGCCCCACCAAATACCAGAG
CCCAAGAAATGTAGTCCTGTTGATATGGTTTTGCTGTGTCCCAACCCAAATCTCATCTTGAATTGTAAGCTCCCAT
AATTCCCATGTGTTGTGGGAGGGACCTGGTG
```

ATCATGAGGATGTTACCAAAGGGATGGTACTAAACCATTTGTATTCGTCTGTTTTCACACTGCTTTGAAGATACTA
CCTGAGACTGGGTAATTTATAAACAAAAGAGATTTAATTGACTCACAGTTCTGCATGGCTGAAGAGGCCTCAGGAA
ACTTACAGTCATGGTGGAAGGCAAAGGAGGAGCAAGGCATGTCTTACATGTCAGTAGGAGAGAGAGCGAGAGCAGG
AGAACCTGCCACTTATAAACCATTCAGATCTCATAACTCCCTATCATGAGAAAAACATGGAGGAAACCACCCTCAT
GATCCAATCACCTCCCGCCAGGTCCCTCCCTCGACACGTGGGGATTATAATTCAGGATTAGAGGGACACAGAGACA
AACCATATCATCATTCATGAGAAATCCACCCTCATAGTCCAATCAGCTCCTACCAGGCCCCACCTCCAACACTGGG
GATTGCAATTCAACATGAGATTTGGATGGGGACACAGATTCAAACCATATCATAC 13699.1&2

CATGGCCTTTCTCCTTAGAGGCCAGAGGTGCTGCCCTGGCTGGGAGTGAAGCTCCAGGCACTACCAGCTTTCCTGA
TTTTCCCGTTTGGTCCATGTGAAGAGCTACCACGAGCCCCAGCCTCACAGTGTCCACTCAAGGGCAGCTTGGTCCT
CTTGTCCTGCAGAGGCAGGCTGGTGTGACCCTGGGAACTTGACCCGGGAACAACAGGTGGCCCAGAGTGAGTGTGG
CCTGGCCCCTCAACCTAGTGTCCGTCCTCCTCTCTCCTGGAGCCAGTCTTGAGTTTAAAGGCATTAAGTGTTAGAT
ACAAGCTCCTTGTGGCTGGAAAAACACCCCTCTGCTGATAAAGCTCAGGGGGCACTGAGGAAGCAGAGGCCCCTTG
GGGGTGCCCTCCTGAAGAGAGCGTCAGGCCATCAGCTCTGTCCCTCTGGTGCTCCCACGTCTGTTCCTCACCCTCC
ATCTCTGGGAGCAGCTGCACCTGACTGGCCACGCGGGGGCAGTGGAGGCACAGGCTCAGGGTGGCCGGGCTACCTG
GCACCCTATGGCTTACAAAGTAGAGTTGGCCCAGTTTCCTTCCACCTGAGGGGAGCACTCTGACTCCTAACAGTCT
TCCTTGCCCTGCCATCATCTGGGGTGGCTGGCTGTCAAGAAAGGCCGGGCATGCTTTCTAAACACAGCCACAGGAG
GCTTGTAGGGCATCTTCCAGGTGGGGAAACAGTCTTAGATAAGTAAGGTGACTTGCCTAAGGCCTCCCAGCACCCT
TGATCTTGGAGTCTCACAGCAGACTGCATGTAACAACTGGAACCGAAAACATGCCTCAGTATAAAA 13703.3

CCAGAACCTCCTTCTCTTTGGAGAATGGGGAGGCCTCTTGGAGACACAGAGGGTTTCACCTTGGATGACCTCTAGA
GAAATTGCCCAAGAAGCCCACCTTCTGGTCCCAACCTGCAGACCCCACAGCAGTCAGTTGGTCAGGCCCTGCTGTA
GAAGGTCACTTGGCTCCATTGCCTGCTTCCAACCAATGGGCAGGAGAGAAGGCCTTTATTTCTCGCCCACCCATTC
TCCTGTACCAGCACCTCCGTTTTCAGTCAGYGTTGTCCAGCAACGGTACCGTTTACACAGTCA 13705.1

TGCATGTAGTTTTATTTATGTGTTTTSGTCTGGAAAACCAAGTGTCCCAGCAGCATGACTGAACATCACTCACTTC
CCCTACTTGATCTACAAGGCCAACGCCGAGAGCCCAGACCAGGATTCCAAACACACTGCACGAGAATATTGTGGAT
CCGCTGTCAGGTAAGTGTCCGTCACTGACCCARACGCTGTTACGTGGCACATGACTGTACAGTGCCACGTAACAGC
ACTGTACTTTTCTCCCATGAACAGTTACCTGCCATGTATCTACATGATTCAGAACATTTTGAACAGTTAATTCTGA
CACTTGAATAATCCCATCAAAAACCGTAAAATCACTTTGATGTTTGTAACGACAACATAGCATCACTTTACGACAG
AATCATCTGGAAAAACAGAACAACGAATACATACATCTTAAAAAATGCTGGGGTGGGCCAGGCACAGCTTCACGCC
TGTAATCCCAGCACTTTGGGAGGCTTAAGCGGGTG

```
TGGGGCGGAAAGAAGCCAAGGCCAAGGAGCTGGTGCGGCAGCTGCAGCTGGAGGCCGAGGAGCAGAGGAAGCAGAA
GAAGCGGCAGAGTGTGTCGGGCCTGCACAGATACCTTCACTTGCTGGATGGAAATGAAAATTACCCGTGTCTTGTG
GATGCAGACGGTGATGTGATTTCCTTCCCACCAATAACCAACAGTGAGAAGACAAAGGTTAAGAAAACGACTTCTG
ATTTGTTTTTGGAAGTAACAAGTGCCACCAGTCTGCAGATTTGCAAGGATGTCATGGATGCCCTCATTCTGAAAAT
GGCAAGAAATGAAAAAGTACACTTTAGAAAATAAAGAGGAAGGATCACTCTCAGATACTGAAGCCGATGCAGTCTC
TGGACAACTTCCAGATCCCACAACGAATCCCAGTGCTGGAAAGGACGGGCCCTTCCTTCTGGTGGTGGAACANGTC
CCGGTGGTGGATCTTGGAANGGAACCTGAANGTGGTGTACCCCGTCCAAGGCCGACCTTGGCCAC
```

13707.4

```
TCCCGCGCTCGCAGGGCNCGTGCCACCTGCCCYGTCCGCCCGCTCGCTCGCTCGCCCGCCGCGCCGCGCTGCCGACC
GYCAGCATGCTGCCGAGAGTGGGCTGCCCCGCGCTGCCGCTGCCGCCGCCGCCGCTGCTGCCGCTGCTGCCGCTGC
TGCTGCTGC
```

13708.1&2

```
GGCGGGTAGGCATGGAACTGAGAAGAACGAAGAAGCTTTCAGACTACGTGGGGAAGAATGAAAAAACCAAAATTAT
CGCCAAGATTCAGCAAAGGGGACAGGGAGCTCCAGCCCGAGAGCCTATTATTAGCAGTGAGGAGCAGAAGCAGCTG
ATGCTGTACTATCACAGAAGACAAGAGGAGCTCAAGAGATTGGAAGAAAATGATGATGATGCCTATTTAAACTCAC
CATGGGCGGATAACACTGCTTTGAAAAGACATTTTCATGGAGTGAAAGACATAAAGTGGAGACCAAGATGAAGTTC
ACCAGCTGATGACACTTCCAAAGAGATTAGCTCACCT
```

13709.1

```
TCTGAAGGTTAAATGTTTCATCTAAATAGGGATAATGRTAAACACCTATAGCATAGAGTTGTTTGAGATTAAATGA
GATAATACATGTAAAATTATGTGCCTGGCATACAGCAAGATTGTTGTTGTTGTTGATGATGATGATGATGATGATA
ATATTTTTCTATCCCCAGTGCACAACTGCTTGAACCTATTAGATAATCAATACATGTTTCTTGAACTGAGATCAAT
TTCCCCATGTTGTCTGACTGATGAAGCCCTACATTTTCTTCTAGAGGAGATGACATTTGAGCAAGATCTTAAAGAA
AATCAGATGCCTTCACCTGACCACTGCTTGGTGATCCCATGGCACTTTGTACATCTCTCCATTAGCTCTCATCTCA
CCAGCCCATCATTATTGTATGTGCTGCCTTCTGAAGCTTGCAGCTGGCTACCATCMGGTAGAATAAAAATCATCCT
TTCATAAAATAGTGACCCTCCTTTTTTATTTGCATTTCCCAAAGCCAAGCACCGTGGGANGGTAG
```

TATGAAGAAGGGAAAAGAAGATAATTTGTGAAAGAAATGGGTCCAGTTACTAGTCTTTGAAAAGGGTCAGTCTGTA
GCTCTTCTTAATGAGAATAGGCAGCTTTCAGTTGCTCAGGGTCAGATTTCCTTAGTGGTGTATCTAATCACAGGAA
ACATCTGTGGTTCCCTCCAGTCTCTTTCTGGGGGACTTGGGCCCACTTCTCATTTCATTTAATTAGAGGAAATAGA
ACTCAAAGTACAATTTACTGTTGTTTAACAATGCCACAAAGACATGGTTGGGAGCTATTTCTTGATTTGTGTAAAA
TGCTGTTTTTGTGTGCTCATAATGGTTCCAAAAATTGGGTGCTGGCCAAAGAGAGATACTGTTACAGAAGCCAGCA
AGAAGACCTCTGTTCATTCACACCCCCGGGGATATCAGGAATTGACTCCAGTGTGTGCAAATCCAGTTTGGCCTAT
CTTCT 13712.1&2

TGAGGGACTGATTGGTTTGCTCTCTGCTATTCAATTCCCCAAGCCCACTTGTTCCTGCAGCGTCCTCCTTCTCATT
CCCTTTAGTTGTACCCTCTCTTTCATCTGAGACCTTTCCTTCTTGATGTCGCCTTTTCTTCTTCTTGCTTTTTCTG
ATGTTCTGCTCAGCATGTTCTGGGTGCTTCTCATCTGCATCATTCCTTTCAGATGCTGTAGCTTCTTCCTCCTCTT
TCTGCCTCCTTTTCTTTTTCTTTTTTTTGGGGGGCTTGCTCTCTGACTGCAGTTGAGGGGCCCCAGGGTCCTGGCC
TTTGAGACGAGCCAGGAAGGCCTGCTCCTGGGCCTCTAGGCGAGCAAGCTTGGCCTTCATTGTGATCCCAAGACGG
GCAGCCTTGTGTGCTGTTCGCCCCTCACAGGCTTGGAGCAGCATCTCATCAGTCAGAATCTTTGGGGACTTGGACC
CCTGGTTGTCGTCATCACTGCAGCTCTCCAAGTCTTTGTTTGGCTTCTCTCCACCTGAAGTCAATGTAGCCATCTT
CACAAACTTCTGATACAGCAAGTTGGGCTTGGGATGATTATAACGGGTGGTCTCCTTAGAAAGGCTCCTTATCTGT
ACTCCATCCTGCCCAGTTTCCACTACCAAGTTGGCCGCAGTCTTGTTGAAGAGCTCATTCCACCAGTGGTTTGTGA
ACTCCTTGGCAGGGTCATGTCCTACCCCATGAGTGTCTTGCTTCAGYGTCACCCTGAGAGCCTGAGTGATACCATT
CTCCTTCCG 13714.1&2

GACAACATGAAATAAATCCTAGAGGACAAAATTAAACTCAATAGAGTGTAGTCTAGTTAAAAACTCGAAAAATGAG
CAAGTCTGGTGGGAGTGGAGGAAGGGCTATACTATAAATCCAAGTGGGCCTCCTGATCTTAACAAGCCATGCTCAT
TATACACATCTCTGAACTGGACATACCACCTTTACGCAGGAAACAGGGCTTGGAACTTCTAAGGGAAATTAACATG
CACCACCCACATCTAACCTACCTGCCGGGTAGGTACCATCCCTGCTTCGCTGAAATCAGTGCTC 13716.1&2

TTGGAATTAAATAAACCTGGAACAGGGAAGGTGAAAGTTGGAGTGAGATGTCTTCCATATCTATACCTTTGTGCAC
AGTTGAATGGGAACTGTTTGGGTTTAGGGCATCTTAGAGTTGATTGATGGAAAAAGCAGACAGGAACTGGTGGGAG
GTCAAGTGGGGAAGTTGGTGAATGTGGAATAACTTACCTTTGTGCTCCACTTAAACCAGATGTGTTGCAGCTTTCC
TGACATGCAAGGATCTACTTTAATTCCACACTCTCATTAATAAATTGAATAAAAGGGAATGTTTTGGCACCTGATA
TAATCTGCCAGGCTATGTGACAGTAGGAAGGAATGGTTTCCCCTAACAAGCCCAATGCACTGGTCTGACTTTATAA
ATTATTTAATAAAATGAACTATTATC

```
AAACTGGACCTGCAACAGGGACATGAATTTACTGCARGGTCTGAGCAAGCTCAGCCCCTCTACCTCAGGGCCCCAC
AGCCATGACTACCTCCCCCAGGAGCGGGAGGGTGAAGGGGGCCTGTCTCTGCAAGTGGAGCCAGAGTGGAGGAATG
AGCTCTGAAGACACAGCACCCAGCCTTCTCGCACCAGCCAAGCCTTAACTGCCTGCCTGACCCTGAACCAGAACCC
AGCTGAACTGCCCCTCCAAGGGACAGGAAGGCTGGGGGAGGGAGTTTACAACCCAAGCCATTCCACCCCCTCCCCT
GCTGGGGAGAATGACACATCAAGCTGCTAACAATTGGGGGAAGGGGAAGGAAGAAAACTCTGAAAACAAATCTTG
T
```

13722.3

```
CATGCGTTTCACCACTGTTGGCCAGGCTGGTCTCGAACTCCTGGCCTCAAGCAATCCACCCGCCTCAGCCTCCAAA
AGTGCTGGGATTACAGATGTGAGCCATGGCACCATGCCAAAAGGCTATATTCCTGGCTCTGTGTTTCCGAGACTGC
TTTTAATCCCAACTTCTCTACATTTAGATTAAAAAATATTTTATTCATGGTCAATCTGGAACATAATTACTGCATC
TTAAGTTTCCACTGATGTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCTGATAGGTTCTTTAT
TTTTTCAAAATATATTTGCCATGGGATGCTAATTTGCAATAAGGCGCATAATGAGAATACCCCAAACTGGA
```

13722.4

```
GTTGGACCCCCAGGGACTGGAAAGACACTTCTTGCCCGAGCTGTGGCGGGAGAAGCTGATGTTCCTTTTTATTATG
CTTCTGGATCCGAATTTGATGAGATGTTTGTGGGTGTGGGAGCCAGCCGTATCAGAAATCTTTTTAGGGAAGCAAA
GGCGAATGCTCCTTGTGTTATATTTATTGATGAATTAGATTCTGTTGGTGGGAAGAGAATTGAATCTCCAATGCAT
CCATATTCAAGGCAGACCATAAATCAACTTCTTGCTGAAATGGATGGTTTTAAACCCAATGAAGGAGTTATCATAA
TAGGAGCCACAAACTTCCCAGAGGCATTAGATAATGCCTTAATACCGTCCTGGTCGTTTTGACATGCAAGTTACAG
TTCCAAGGCCAGATGTAAAAGGTCGAACAGAAATTTTGAAATGGTATCTCAATAAAATAAAGTTTGATCAATCCCG
TTGATCCAGAAATTATAGCCTCGAGGTACTGGTGGCTTTTCCGGAAGCAGAGTTGGGAGAATCTT
```

13724-13698-13748

```
GCCTACAACATCCAGAAAGAGTCTACCCTGCACCTGGTGCTSCGTCTCAGAGGTGGGATGCAGATCTTCGTGAAGA
CCCTGACTGGTAAGACCATCACTCTCGAAGTGGAGCCGAGTGACACCATYGAGAACGTCAAAGCAAAGATCCARGA
CAAGGAAGGCRTYCCTCCTGACCAGCAGAGGTTGATCTTTGCCGGAAAGCAGCTGGAAGATGGDCGCACCCTGTCT
GACTACAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGATCCAAGA
TAAGGAAGGCATCCCTCCTGATCAGCAGAGGTTGATCTTTGCTGGGAAACAGCTGGAAGATGGACGCACCCTGTCT
GACTACAACATCCAGAAAGAGTCCACTCTGCACTTGGTCCTGCGCTTGAGGGGGGGTGTCTAAGTTTCCCCTTTTA
AGGTTTCMACAAATTTCATTGCACTTTCCTTTCAATAAAGTTGTTGCATTCCC
```

GAACTGGGCCCTGAGCCCAAGTCATGCCTTGTGTCCGCATCTGCCGTGTCACCTCTGTKCCTGCCCCTCACCCCTC
CCTCCTGGTCTTCTGAGCCAGCACCATCTCCAAATAGCCTATTCCTTCCTGCAAATCACACACACATGCGGGCCAC
ACATACCTGCTGCCCTGGAGATGGGGAAGTAGGAGAGATGAATAGAGGCCCATACATTGTACAGAAGGAGGGGCAG
GTGCAGATAAAAGCAGCAGACCCAGCGGCAGCTGAGGTGCATGGAGCACGGTTGGGGCCGGCATTGGGCTGAGCAC
CTGATGGGCCTCATCTCGTGAATCCTCGAGGCAGCGCCACAGCAGAGGAGTTAAGTGGCACCTGGGCCGAGCAGAG
CAGGAGACTGAGGGTCAGAGTGGAGGCTAAGCTGCCCTGGAACTCCTCAATCTTGCCTGCCCCCTAGTATGAAGCC
CCCTTCCTGCCCCTACAATTCCTGA 13732.1

ATGGATCTTACTTTGCCACCCAGGTTGGAGTGCAGTGCTGCAATCTTGGCTCACTGCAGCCTTAACCTCCCAGGCT
CAAGCTATCCTCCTGCCAAAGCCTTCCACATAGCTGGGACTACAGGTACACNGCCACCACACCCAGCTAAAATTTT
TGTATTTTTTGTAGAGACGGGATCTCGCCACGTTGCCCAGGCTGGTCCCATCCTGACCTCAAGCAGATCTGCCCAC
CTCAGCCCCCCAACGTGCTAGGATTACAGGCGTGAGCCACCGCACCCAGCCTTTGTTTTGCTTTTAATGGAATCAC
CAGTTCCCCTCCGTGTCTCAGCAGCAGCTGTGAGAAATGCTTTGCATCTGTGACCTTTATGAAGGGGAACTTCCAT
GCTGAATGAGGGTAGGATTACATGCTCCTGTTTCCCGGGGGTCAAGAAAGCCTCAGACTCCAGCATGATAAGCAGG
GTGAG 13732.2

ATAGGGGCTTTAAGGAGGGAATTCAGGTTCAATGAGGTCGTAAGGCCAGGGCTCTTATCCAGTAAGACTGGGGTCC
TTAGATGAGAAAGAGACACCCGAGGTCCTTCTCTCTGCCGTGTGAGGATGCATCAAGAAGGCGGCCGTCTGCAAGC
GAAGGAGAGGCCGCACCAGAAACCGACACCTTCATCTTGGACTTGCAGCCTCTAGAACTGAGAAAATAACTGTCTG
TTGGTTAAGCCACCCAGTTTGTAGTATTCTCTTATGGCTTCCTAAGCAGACTAACAAACAAACACCCAAAATTAAC
TGATGGCTTCGCTGTCTTCTGTAAAAATTGCTATGAGAGAACTTTTCACTCACTGTTTTGCAGTTTCTCCCTCAGT
CCCTGGTTCTTTCTTCTCACATAATCCCAATTTCAATTTATAGTTCATGGCCCAGGCAGAGTCATTCATCACGGCA
TCTCCTGAGCTAAACCAGCACCTGCTCTGCTCACTTCTTGACTGGCTGCTCATCATCAGCCCTCTTGCAGAGATTT
CATTTCCTCCCGTGCCAGGTACTTCACGCACCAAGCTCA

```
GGATAATGAAGTTGTTTTATTTAGCTTGGACAAAAAGGCATATTCCTCTATTTTCTTATACAACAAATATCCCCAA
AATAAAGCAAGCATATATATCTTGAATGTGTAATAATCCAGTGATAAACAAGAGCAGTACTTTAAAAGAAAAAAAA
ATATGTATTTCTGTCAGGTTAAAATGAGAATCAAAACCATTTACTCTGCTAACTCATTATTTTTTGCTTTCTTTTT
GGTTAAGAGAGGCAATGCAATACACTGAAAAAGGTTTTTATCTTATCTGGCATTGGAATTAGACATATTCAAACCC
CAGCCCCCATTTCCAAACTTTAAGACCACAAACAAGTAATTTACTTTTCTGAACATTGGTTTTTTCTGGAAAATGG
GAATTATAAAATAGACTTTGCAGACTCTTATGAGATTAAATAAGATAATGTATGAAATTCTTTCTTCTTTTTTACT
TCTTTTTCCTTTTTGAGATGGAGTCTCACCCCGTCACCCAGGCTGGAGTACAGTG
```

13735.2

```
CCACTGCACTCCAGCCTGGGTGACGGAGTGAGACTCTGTCTCAAAAAAACAAACAAACAAACAAACAAAAAACTGA
AAAGGAAATAGAGTTCCTCTTTCCTCATATATGAATATATTATTTCAACAGATTGTTGATCACCTACCATATGCTT
GGTATTGTTCTAATTGCTGGGGATACAGCAAGAGGTTCTGCAGAACTTCATGGAGCATGAAAGTAAATAAACAAAG
TTAATTTCAAGGCCAGGCATGGTTGCTCACACCTTTAGTCCCAGCACTTTGGGAGGCTGAGGCAGGTGGATCACTT
GGGCCCAGGAGTTCAAGGCTGCAGTGAGCCAAGATTGTGCCACTACTCTCCAGGCTGGGCAACAGAGCAAGACCCT
GTCTCAGGGGGAACAAAAAGTTAATTTCAGATTTTGTTAAGTGCTGTAAAGGAAGTAAATAGGTTGATATTCAAGA
GAGCACCTGAAGGCCAGGCGTGGTGGCTCACGCCTGTGGTCTAACGCTTTGGGAAGCCCGAGCGGGCGGATCACAA
GGTCAGGAGAATTTTGGCCAGGCATGGTG
```

13736.1

```
AGAATCCATTTATTGGGTTTTAAACTAGTTACACAACTGAAATCAGTTTGGCACTACTTTATACAGGGATTACGCC
TGTGTATGCCGACACTTAAATACTGTACCAGGACCACTGCTGTGCTTAGGTCTGTATTCAGTCATTCAGCATGTAG
ATACTAAAAATATACTGTAGTGTTCCTTTAAGGAAGACTGTACAGGGTGTGTTGCAAGATGACATTCACCAATTTG
TGAATTATTTCAACCCAGAAGATACCTTTCACTCTATAAACTTGTCATAGGCAAACATGTGGTGTTAGCATTGAGA
GATGCACACAAAAATGTTACATAAAAGTTCAGACATTCTAATGATAAGTGAACTGAAAAAAAAAAAAAACCCCACAT
CTCAATTTTTGTAACAAGATAAAGAAAATAATTTAAAAACACAAAAAATGGCATTCAGTGGGTACAAAGCC
```

13737.1&2

```
CAAATATTTAATATAAATCTTTGAAACAAGTTCAGAKGAAATAAAAATCAAAGTTTGCAAAAACGTGAAGATTAAC
TTAATTGTCAAATATTCCTCATTGCCCCAAATCAGTATTTTTTTTATTTCTATGCAAAAGTATGCCTTCAAACTGC
TTAAATGATATATGATATGATACACAAACCAGTTTTCAAATAGTAAAGCCAGTCATCTTGCAATTGTAAGAAATAG
GTAAAAGATTATAAGACACCTTACACACACACACACACACACACACACGTGTGCACcGCCAATGACAAAAAACA
ATTTGGCCTCTCCTAAAATAAGAACATGAAGACCCTTAATTGCTGCCAGGAGGGAACACTGTGTCACCCCTCCCTA
CAATCCAGGTAGTTTCCTTTAATCCAATAGCAAATCTGGGCATATTTGAGAGGAGTGATTCTGACAGCCACSGTTG
AAATCCTGTGGGGAACCATTCATGTCCACCCACTGGTGCCCTGAAAAAATGCCAATAATTTTTCGCTCCCACTTCT
GCTGCTGTCTCTTCCACATCCTCACATAGACCCCAGACCCGCTGGCCCCTGGCTGGGCATCGCATTGCTGGTAGAG
CAAGTCATAGGTCTCGTCTTTGACGTCACAGAAGCGATACACCAAATTGCCTGGTCGGTCATTGTCATAACCAG
```

TTTGACTTTAGTAGGGGTCTGAACTATTTATTTTACTTTGCCMGTAATATTTARACCYTATATATCTTTCATTATG
CCATCTTATCTTCTAATGBCAAGGGAACAGWTGCTAAMCTGGCTTCTGCATTWATCACATTAAAAATGGCTTTCTT
GGAAAATCTTCTTGATATGAATAAAGGATCTTTTAVAGCCATCATTTAAAGCMGGNTTCTCTCCAACACGAGTCTG
CTSASGGGGGGKGAGCTGTGAACTCTGGCTGAAGGCTTTCCCATACACACTGCAATGACMTGGTTTCTGACCAGBG
TGAGTTA

13738.2

AGAGAAGCCCCATAAATGCAATCAGTGTGGGAAGGCCTTCAGTCAGAGCTCAAGCCTTTTCCTCCATCATCGGGTT
CATACTGGAGAGAAACCCTATGTATGTAATGAATGCGGCAGAGCCTTTGGTTTTAACTCTCATCTTACTGAACACG
TAAGGATTCACACAGGAGAAAAACCCTATGTTTGTAATGAGTGCGGCAAAGCCTTTCGTCGGAGTTCCACTCTTGT
TCAGCATCGAAGAGTTCACACTGGGGAGAAGCCCTACCAGTGCGTTGAATGTGGGAAAGCTTTCAGCCAGAGCTCC
CAGCTCACCCTACATCAGCCGAGTTCACACTGGAGAGAAGCCCTATGACTGTGGTGACTGTGGGAAGGCCTTCAGC
CGGAGGTCAACCCTCATTCAGCATCAGAAAGTTCACAGCGGAGAGACTCGTAAGTGCAGAAAACATGGTCCAGCCT
TTGTTCATGGCTCCAGCCTCACAGCAGATGGACAGATTCCCACTGGAGAGAAGCACGGCAGAACCTTTAACCATGG
TGCAAATCTCATTCTGCGCTGGACAGTTC

13739.1&2

GAGACAGGGTCTCACTTTGTCACCCAGGCTGGAATGCAGTGGTGCGATCTTACGTAGCTCACTGCAGCCCTGACCT
CCTGGACTCAAACAATTCTCCTGCCTCAGCCCTGCAAGTAGCTGGGACTGTGGGTGCATGCCACCATGCCTGGCTA
ACTTTTGTAGTTTTTGTAAAGATGGGGTTTTGCCATGTTGCACATGCTGGTCTTGAACTCCTGAGCTCAAACGATC
TGCCCACCTCGGCCTCCCAGAATGTTGGGATTACAGGGGTAAACCACCACGCCTGGCCCCATTAGGGTATTCTTAG
CATCCACTTGCTCACTGAGATTAATCATAAGAGATGATAAGCACTGGAAGAAAAAAATTTTTACTAGGCTTTGGAT
ATTTTTTTCCTTTTTCAGCTTTATACAGAGGATTGGATCTTTAGTTTTCCTTTAACTGATAATAAAACATTGAAAG
GAAATAAGTTTACCTGAGATTCACAGAGATAACCGGCATCACTCCCTTGCTCAATTCCAGTCTTTACCACATCAAT
TATTTTCAGAGGTGCAGGATAAAGGCCTTTAGTCTGCTTTCGCACTTTTTCTTCCACTTTTTTGTAAACCTGTTGC
CTGACAAATGGAATTGACAGCGTATGCCATGACTATTCCATTTGTCAGGCATACGCTGTCAATTTTTCCACCAATC
CCTTGTCTCTCTTTGGAGAGATCTTCTTATCAGCTAGTCCTTTGGCAAAAGTAATTGCAACTTCTTCTAGGTATTC
TATTGTCCGTTCCACTGGTGGAACCCCTGGGACCAGGACTAAAACCTCCAG

13741.1

ATCTCATATATATATTTCTTCCTGACTTTATTTGCTTGCTTCTGNCACGCATTTAAAATATCACAGAGACCAAAAT
AGAGCGGCTTTCTGGTGGAACGCATGGCAGTCACAGGACAAAATACAAAACTAGGGGGCTCTGTCTTCTCATACAT
CATACAATTTTCAAGTATTTTTTTTATGTACAAAGAGCTACTCTATCTGAAAAAAAATTAAAAAATAAATGAGACA
AGATAGTTTATGCATCCTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACAGGGCAAGTGCCAGGG
TAGGTGGGGACCAGTGGAGACAGGAACCAGCAACATACTTTGGCCTGGAAGATAAGGAGAAAGTCTCAGAAACACA
CTGGTGGGAAGCAATCCCACNGGCCGTGCCCCANGAGCTTCCCACCTGCTGCTGGCTCCCTGGGTGGCTTTGGGAA
CAGCTTGGGCAGGCCCTTTTGGGTGGGGNCCAACTGGGCCTTTGGGCCCGTGTGGAAAG

AAACATTGAGATGGAATGATAGGGTTTCCCAGAATCAGGTCCATATTTTAACTAAATGAAAATTATGATTTATAGC
CTTCTCAAATACCTGCCATACTTGATATCTCAACCAGAGCTAATTTTACCTCTTTACAAATTAAATAAGCAAGTAA
CTGGATCCACAATTTATAATACCTGTCAATTTTTTCTGTATTAAACCTCTATCATAGTTTAAGCCTATTAGGGTAC
TTAATCCTTACAAATAAACAGGTTTAAAATCACCTCAATAGGCAACTGCCCTTCTGGTTTTCTTCTTTGACTAAAC
AATCTGAATGCTTAAGATTTTCCACTTTGGGTGCTAGCAGTACACAGTGTTACACTCTGTATTCCAGACTTCTTAA
ATTATAGAAAAAGGAATGTACACTTTTTGTATTCTTTCTGAGCAGGGCCGGGAGGCAACATCATCTACCATGGTAG
GGACTTGTATGCATGGACTACTTTA

14351.1

ACTCTGTCGCCCAGGCTGGAGCCCABTGGMGCGATCTCGACTCCCTGCAAGCTMCGCCTCACAGGWTCATGCCATT
CTCCTGCCTCAGCATCTGGAGTAGCTGGGACTACAGGCGCCAGCCACCATGCCCAGCTAATTTTT

14351.2

ACCTTAAAGACATAGGAGAATTTATACTGGGAGAGAAAGCTTACAAATGTAAGGTTTCTGACAAGACTTGGGAGTG
ATTCACACCTGGAACAACATACTGGACTTCACACTGGABAGAAACCTTACAAGTGTAATGAGTGTGGCAAAGCCTT
TGGCAAGCAGTCAACACTTATTCACCATCAGGCAATTCA

14354.2

AGTCAGGATCATGATGGCTCAGTTTCCCACAGCGATGAATGGAGGGCCAAATATGTGGGCTATTACATCTGAAGAA
CGTACTAAGCATGATAAACAGTTTGATAACCTCAAACCTTCAGGAGGTTACATAACAGGTGATCAAGCCCGTACTT
TTTTCCTACAGTCAGGTCTGCCGGCCCCGGTTTTAGCTGAAATATGGGCCTTATCAGATCTGAACAAGGATGGGAA
GATGGACCAGCAAGAGTTCTCTATAGCTATGAAACTCATCAAGTTAAAGTTGCAGGGCCAACAGCTGCCTGTAGTC
CTCCCTCCTATCATGAAACAACCCCCTATGTTCTCTCCACTAATCTCTGCTCGTTTTGGGATGGGAAGCATGCCCA
ATCTGTCCATTCATCAGCCATTGCCTCCAGTTGCACCTATAGCAACACCCTTGTCTTCTGCTACTTCAGGGACCAG
TATTCCTCCCTAATGATGCCTGCT

14354.1

CTTTCGATTTCCTTCAATTTGTCACGTTTGATTTTATGAAGTTGTTCAAGGGCTAACTGCTGTGTATTATAGCTTT
CTCTGAGTTCCTTCAGCTGATTGTTAAATGAATCCATTTCTGAGAGCTTAGATGCAGTTTCTTTTTCAAGAGCATC
TAATTGTTCTTTAAGTCTTTGGCATAATTCTTCCTTTTCTGATGACTTTCTATGAAGTAAACTGATCCCTGAATCA
GGTGTGTTACTGAGCTGCATGTTTTTAATTCTTTCGTTTAATAGCTGCTTCTCAGGGACCAGATAGATAAGCTTAT
TTTGATATTCCTTAAGCTCTTGGTGAAGTTGTTCGATTTCCATAATTTCCAGGTCACACTGGTTATCCCAAACTTC
T

```
TGGAGGTGAAACGGAGGCAAGAAAGGGGGCTACCTCAGGAGCGAGGGACAAAGGGGGCGTGAGGCACCTAGGCCGC
GGCACCCCGGCGACAGGAAGCCGTCCTGAACCGGGCTACCGGGTAGGGGAAGGGCCCGCGTAGTCCTCGCAGGGCC
CCAGAGCTGGAGTCGGCTCCACAGCCCCGGGCCGTCGGCTTCTCACTTCCTGGACCTCCCCGGCGCCCGGGCCTGA
GGACTGGCTCGGCGGAGGGAGAAGAGGAAACAGACTTGAGCAGCTCCCCGTTGTCTCGCAACTCCACTGCCGAGGA
ACTCTCATTTCTTCCCTCGCTCCTTCACCCCCCACCTCATGTAGAAAGGTGCTGAAGCGTCCGGAGGGAAGAAGAA
CCTGGGCTACCGTCCTGGCCTTCCCMCCCCCTTCCCGGGGCGCTTTGGTGGGCGTGGAGTTGGGGTTGGGGGGGTG
GGTGGGGGTTCTTTTTTGGAGTGCTGGGGAACTTTTTTTCCCTTCTTCAGGTCAGGGGAAAGGGAATGCCCAATTCA
GAGAGACATGGGGGCAAGAAGGACGGGAGTGGAGGAGCTTCTGGAACTTTGCAGCCGTCATCGGGAGGCGGCAGCT
CTAACAGCAGAGAGCGTCACCGCTTGGTATCGAAGCACAAGCGGCATAAGTCCAAACACTCCAAAGACATGGGGTT
GGTGACCCCCGAAGCAGCATCCCTGGGCACAGTTATCAAACCTTTGGTGGAGTATGATGATATCAGCTCTGATTCC
GACACCTTCTCCGATGACATGGCCTTCAAACTAGACCGAAGGGAGAACGACGAACGTCGTGGATCAGATCGGAGCG
ACCGCCTGCACAAACATCGTCACCACCAGCACAGGCGTTCCCGGGACTTACTAAAAGCTAAACAGACCG
```

16432-1

```
GACATGTTTGCCTGCAGGGGACCAGAGACAATGGGATTAGCCAGTGCTCACTGTTCTTTATGCTTCCAGAGAGGAT
GGGGACAGCTCTCAGGTCAGAATCCAGGCTGAGAAGGCCATGCTGGTTGGGGGCCCCCGGAAGCACGGTCCGGATC
CTCCCTGGCATCAGCGTAGACCCGCTGCTCAGGCTTGGGGTACCAAACTCATGCTCTGTACTGTTTTGGCCCCATG
CGGTGAGAGGAAAACCTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGGCCTCTGGAGGCTCGT
GGCCTAAGGCAGGGCTCCGTAAGGCTGATCGGCTGAACTGGGTGGGGTGAGGGTTTCTGACCCTTCGCTTCCCATC
CCATAACCGCTGTCAATGAGCTCACACTGTGGTCA
```

16432-2

```
GATGGCATGGTCGTTGCTAATGTGCCTGCTGGGATGGAGCACTTCCTCCTGTGAGCCCAGGGGACCCGCCTGTCCC
TGGAGCTTGGGGCAAGGAGGGAAGAGTGATACCAGGAAGGTGGGGCTGCAGCCAGGGGCCAGAGTCAGTTCAGGGA
GTGGTCCTCGGCCCTCAAAGCTCCTCCGGGGACTGCTCAGGAGTGATGGTGCCCTGGAGTTTGCCCCAACTTCCCT
GGCCACCCTGGAAGGTGCCTGGCTGCTCCAGGCCTCTAGGCTGGGCTGATGGGTTTCTCCAGGACACAAGTATCAT
TAAAGCCACCCTCTCCTCAGCTTGTCAGGCCGCACATGTGGGACAGGCTGTGCTCACAACCCCCTCGCCTGCCCTG
CCCTCCATCAGGAGGAGCCAGTGGAACCTTCGGAAAGCTCCCAGCATCTCAGCAGCCCTCAAAAGTCGTCCTGGGG
CAAGCTCTGGTTCTCCTGACTGGAGGTCATCTGGGCTTGGCCTGCTCTCTCTCGC
```

17184.3

```
TAAAAAAGTGTAACAAAGGTTTATTTAGACTTTCTTCATGCCCCCAGATCCAGGATGTCTATGTAAACCGTTATCT
TACAAAGAAAGCACAATATTTGGTATAAACTAAGTCAGTGACTTGCTTAACTGAAATAGCGTCCATCCAAAAGTGG
GTTTAAGGTAAAACTACCTGACGATATTGGCGGGGATCCTGCAGTTTGGACTGCTTGCCGGGTTTGTCCAGGGTTC
CGGGTCTGTTCTTGGCACTCATGGGGACAGGCATCCTGCTCGTCTGTGGGGCCCCGCTGGAGCCCTTACGTGAAGC
TGAAGGTATCGACCSTAGGGGGCTCTAGGGCAGTGGGACCTTCATCCGGAACTAACAAGGGTCGGGGAGAGGCCTC
TTGGGCTATGTGGG
```

CAAGCGTTCCTTTATGGATGTAAATTCAAACAGTCATGCTGAGCCATCCCGGGCTGACAGTCACGTTWAAGACACT
AGGTCGGGCGCCACAGTGCCACCCAAGGAGAAGAAGAATTTGGAATTTTTTCCATGAAGATGTACGGAAATCTGATG
TTGAATATGAAAATGGCCCCCAAATGGAATTCCAAAAGGTTACCACAGGGGCTGTAAGACCTAGTGACCCTCCTAA
GTGGGAAAGAGGAATGGAGAATAGTATTTCTGATGCATCAAGAACATCAGAATATAAAACTGAGATCATAATGAAG
GAAAATTCCATATCCAATATGAGTTTACTCAGAGACAGTAGAAACTATTCCCAGG

17185.1

TAGGAATAACAAATGTTTATTCAGAAATGGATAAGTAATACATAATCACCCTTCATCTCTTAATGCCCCTTCCTCT
CCTTCTGCACAGGAGACACAGATGGGTAACATAGAGGCATGGGAAGTGGAGGAGGACACAGGACTAGCCCACCACC
TTCTCTTCCCGGTCTCCCAAGATGACTGCTTATAGAGTGGAGGAGGCAAACAGGTCCCCTCAATGTACCAGATGGT
CACCTATAGCACCAGCTCCAGATGGCCACGTGGTTGCAGCTGGACTCAATGAAACTCTGTGACAACCAGAAGATAC
CTGCTTTGGGATGAGAGGGAGGATAAAGCCATGCAGGGAGGATATTTACCATCCCTACCCTAAGCACAGTGCAAGC
AGTGAGCCCCGGCTCCCAGTACCTGAAAAACCAAGGCCTACTGNCTTTTGGATGCTCTCTTGGGCCACG

17188.2

AAGCCTCCTGCCCTGGAAATCTGGAGCCCCTTGGAGCTGAGCTGGACGGGGCAGGGAGGGGCTGAGAGGCAAGACC
GTCTCCCTCCTGCTGCAGCTGCTTCCCCAGCAGCCACTGCTGGGCACAGCAGAAACGCCAGCAGAGAAAATGGGAG
CCGAGAGTCCTTAGCCCTGGAGCTGAGGCTGCCTCTGGGCTGACCCGCTGGCTGTACGTGGCCAGAACTGGGGTTG
GCATCTGGCATCCATTTGAGGCCAGGGTGGAGGAAAGGGAGGCCAACAGAGGAAAACCTATTCCTGCTGTGACAAC
ACAGCCCTTGTCCCACGCAGCCTAAGTGCAGGGAGCGTGATGAAGTCAGGCAGCCAGTCGGGGAGGACGAGGTAAC
TCAGCAGCAATGTCACCTTGTAGCCTATGCGCTCAATGGCCCGGAGGGGCAGCAACCCCCCGCACACGTCAGCCAA
CAGCAGTGCCTCTGCAGGCACCAAGAGAGCGATGATGGACTTGAGCGCCGTGTTC

17190.1

GTTTGGCAGAAGACATGTTTAATAACATTTTCATATTTAAAAAATACAGCAACAATTCTCTATCTGTCCACCATCT
TGCCTTGCCCTTCCTGGGGCTGAGGCAGACAAAGGAAAGGTAATGAGGTTAGGGCCCCAGGCGGGCTAAGTGCTA
TTGGCCTGCTCCTGCTCAAAGAGAGCCATAGCCAGCTGGGCACGGCCCCCTAGCCCCTCCAGGTTGCTGAGGCGGC
AGCGGTGGTAGAGTTCTTCACTGAGCCGTGGGCTGCAGTCTCGCAGGGAGAACTTCTGCACCAGCCCTGGCTCTAC
GGCCCGAAAGAGGTGGAGCCCTGAGAACCGGAGGAAAACATCCATCACCTCCAGCCCCTCCAGGGCTTCCTCCTCT
TCCTGGCCTGCCAGTTCACCTGCCAGCCGGGCTCGGGCCGCCAGGTAGTCAGCGTTGTAGAAGCAGCCCTCCGCAG
AAGCCTGCCGGTCAAATCTCCCCGCTATAGGAGCCCCCGGGAGGGGTCAGCACC

```
CAAGTTGAACGTCAGGCTTGGCAGAGGTGGAGTGTAGATGAAAACAAAGGTGTGATTATGAAGAGGATGTGAGTCC
TTTGGGTGTAGGAGAGAAAGGCTGTTGAGCTTCTATTTCAAGATACTTTTACCTGTGCAAAAAGCACATTTTCCAC
CTCCTTCTCATGGCATTTGTGTAAGGTGAGTATGATTCCTATTCCATCTGCATTTTAGAGGTGAAGAATAACGTAC
AAGGGATTCAGTGATTAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCATTCCCTCCAACCCAGGC
TCAGATCCGGAACCTGACCGTGCTGACCCCCGAAGGGGAGGCAGGGCTGAGCTGGCCCGTTGGGCTCCCTGCTCCT
TTCACACCACACTCTCGCTTTGAGGTGCTGGGCTGGGACTACTTCACAGAGCAGC
```

17191.2&89.2

```
TGGCCTGGGCAGGATTGGGAGAGAGGTAGCTACCCGGATGCAGTCCTTTGGGATGAAGACTATAGGGTATGACCCC
ATCATTTCCCCAGAGGTCTCGGCCTCCTTTGGTGTTCAGCAGCTGCCCCTGGAGGAGATCTGGCCTCTCTGTGATT
TCATCACTGTGCACACTCCTCTCCTGCCCTCCACGACAGGCTTGCTGAATGACAACACCTTTGCCCAGTGCAAGAA
GGGGGTGCGTGTGGTGAACTGTGCCCGTGGAGGGATCGTGGACGAAGGCGCCCTGCTCCGGGCCCTGCAGTCTGGC
CAGTGTGCCGGGGCTGCACTGGACGTGTTTACGGAAGAGCCGCCACGGGACCGGGCCTTGGTGGACCATGAGAATG
TCATCAGCTGTCCCCACCTGGGTGCCAGCACCAAGGAGGCTCAGAGCCGCTGTGGGGAGGAAATTGCTGTTCAGTT
CGTGGACATGGTGAAGGGGAAATCTCTCACGGGGGTTGTGAATGCCCAGGCCCTT
```

*Fig. 1S*

```
AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTAC
ATCCTCATTACCAAATGGAACTGCCAGTCTCATTCAGCCTTTATCCATTCCTTATTCTTCTTCAACATTGCCTCAT
GCATCATCTTACAGCCTGATGATGGGAGGATTTGGTGGTGCTAGTATCCAGAAGGCCCAGTCTCTGATTGATTTAG
GATCTAGTAGCTCAACTTCCTCAACTGCTTCCCTCTCAGGGAACTCACCTAAGACAGGGACCTCAGAGTGGGCAGT
TCCTCAGCCTTCAAGATTAAAGTATCGGCAAAAATTTAATAGTCTAGACAAAGGCATGAGCGGATACCTCTCAGGT
TTTCAAGCTAGAAATGCCCTTCTTCAGTCAAATCTCTCTCAAACTCAGCTAGCTACTATTTGGACTCTGGCTGACA
TCGATGGTGACGGACAGTTGAAAGCTGAAGAATTTATTCTGGCGATGCACCTCACTGACATGGCCAAAGCTGGACA
GCCACTACCACTGACGTTGCCTCCCGAGCTTGTCCCTCCATCTTTCAGAGGGGGAAAGCAAGTTGATTCTGTTAAT
GGAACTCTGCCTTCATATCAGAAAACACAAGAAGAAGAGCCTCAGAAGAAACTGCCAGTTACTTTTGAGGACAAAC
GGAAAGCCAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGAATGGAAG
AAGCAGCTGGAGTTGGAGAAACGCTTGGAGAAACAGAGAGAGCTGGAGAGACAGCGGGAGGAAGAGAGGAGAAAGG
AGATAGAAAGACGAGAGGCAGCAAAACAGGAGCTTGAGAGACAACGCCGTTTAGAATGGGAAAGACTCCGTCGGCA
GGAGCTGCTCAGTCAGAAGACCAGGGAACAAGAAGACATTGTCAGGCTGAGCTCCAGAAAGAAAAGTCTCCACCTG
GAACTGGAAGCAGTGAATGGAAAACATCAGCAGATCTCAGGCAGACTACAAGATGTCCAAATCAGAAAGCAAACAC
AAAAGACTGAGCTAGAAGTTTTGGATAAACAGTGTGACCTGGAAATTATGGAAATCAAACAACTTCAACAAGAGCT
TAAGGAATATCAAAATAAGCTTATCTATCTGGTCCCTGAGAAGCAGCTATTAAACGAAAGAATTAAAAACATGCAG
CTCAGTAACACACCTGATTCAGGGATCAGTTTACTTCATAAAAAGTCATCAGAAAAGGAAGAATTATGCCAAAGAC
TTAAAGAACAATTAGATGCTCTTGAAAAAGAAACTGCATCTAAGCTCTCAGAAATGGATTCATTTAACAATCAGCT
GAAGGAACTCAGAGAAAGCTATAATACACAGCAGTTAGCCCTTGAACAACTTCATAAAATCAAACGTGACAAATTG
AAGGAAATCGAAAGAAAAAGATTAGAGCAAAAAAAAAAAAA
```

*Fig. 2A*

```
ATGGCAGTGACATTCACCATCATGGGAACCACCTTCCCTTTTCTTCAGGATTCTCTGTAGTGGAAGAGAGCACCCA
GTGTTGGGCTGAAAACATCTGAAAGTAGGGAGAAGAACCTAAAATAATCAGTATCTCAGAGGGCTCTAAGGTGCCA
AGAAGTCTCACTGGACATTTAAGTGCCAACAAAGGCATACTTTCGGAATCGCCAAGTCAAAACTTTCTAACTTCTG
TCTCTCTCAGAGACAAGTGAGACTCAAGAGTCTACTGCTTTAGTGGCAACTACAGAAAACTGGTGTTACCCAGAAA
AACAGGAGCAATTAGAAATGGTTCCAATATTTCAAAGCTCCGCAAACAGGATGTGCTTTCCTTTGCCCATTTAGGG
TTTCTTCTCTTTCCTTTCTCTTTATTAACCACTA
```

*Fig. 2B*

```
ATATCTAGAAGTCTGGAGTGAGCAAACAAGAGCAAGAAACAAAAAGAAGCCAAAAGCAGAAGGCTCCAATATGAAC
AAGATAAATCTATCTTCAAAGACATATTAGAAGTTGGGAAAATAATTCATGTGAACTAGACAAGTGTGTTAAGAGT
GATAAGTAAAATGCACGTGGAGACAAGTGCATCCCCAGATCTCAGGGACCTCCCCCTGCCTGTCACCTGGGGAGTG
AGAGGACAGGATAGTGCATGTTCTTTGTCTCTGAATTTTTAGTTATATGTGCTGTAATGTTGCTCTGAGGAAGCCC
CTGGAAAGTCTATCCCAACATATCCACATCTTATATTCCACAAATTAAGCTGTAGTATGTACCCTAAGACGCTGCT
AATTGACTGCCACTTCGCAACTCAGGGGCGGCTGCATTTTAGTAATGGGTCAAATGATTCACTTTTTATGATGCTT
CCAAAGGTGCCTTGGCTTCTCTTCCCAACTGACAAATGCCAAAGTTGAGAAAAATGATCATAATTTTAGCATAAAC
AGAGCAGTCGGCGACACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATTATGTCATCACAAGCT
CTGAGGCTTCTCCTTTCCATCCTGCGTGGACAGCTAAGACCTCAGTTTTCAATAGCATCTAGAGCAGTGGGACTCA
GCTGGGGTGATTTCGCCCCCCATCTCCGGGGGAATGTCTGAAGACAATTTTGTTACCTCAATGAGGGAGTGGAGGA
GGATACAGTGCTACTACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTGAGTAGAAAAGGGCCT
GGAAAGAGGGGAGCCAACAAATCTGTCTGCTTCCTCACATTAGTCATTGGCAAATAAGCATTCTGTCTCTTTGGCT
GCTGCCTCAGCACAGAGAGCCAGAACTCTATCGGGCACCAGGATAACATCTCTCAGTGAACAGAGTTGACAAGGCC
TATGGGAAATGCCTGATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGACAATG
ACTGCTTGAATTGAGGCCTTGAGGAATGAAGCTTTGAAGGAAAAGAATACTTTGTTTCCAGCCCCCTTCCCACACT
CTTCATGTGTTAACCACTGCCTTCCTGGACCTTGGAGCCACGGTGACTGTATTACATGTTGTTATAGAAAACTGAT
TTTAGAGTTCTGATCGTTCAAGAGAATGATTAAATATACATTTCCTA
```

*Fig. 2C*

| Diff Exp | Probe 1 | Exp | Probe 2 | GEM/Element | Plate/Well | Probe 1 | S/B | AX | Probe 2 | S/B | AX |
|---|---|---|---|---|---|---|---|---|---|---|---|
| +1.7 | 384A Ovary T (mets) | | 272A Dendritic cells | 4224O608 (420) | 421G0196 (C:11) | 2399 | 13.7 | 50 | 1430 | 2.0 | 50 |
| -1.1 | 335A Ovary T | | S7 Ovary N | 4222O626 (420) | 421G0196 (C:11) | 355 | 2.7 | 54 | 382 | 1.8 | 54 |
| +1.8 | 261A Ovary T | | S10 Skeletal muscle N | 4223O621 (420) | 421G0196 (C:11) | 1298 | 6.9 | 51 | 707 | 1.9 | 51 |
| +8.1 | 264A Ovary T | | S2 Pancreas N | 422N0629 (420) | 421G0196 (C:11) | 9590 | 44.0 | 62 | 1190 | 2.3 | 62 |
| -1.2 | 386A Ovary T | | S40 PBMC (activated) | 422J0605 (420) | 421G0196 (C:11) | 516 | 3.8 | 50 | 619 | 2.0 | 50 |
| +4.7 | 265A Ovary T | | CT5 Heart N | 4220O624 (420) | 421G0196 (C:11) | 2305 | 14.6 | 53 | 489 | 2.2 | 53 |
| -1.4 | S25 Ovary T | | CT4 Bone Marrow N | 422H0619 (420) | 421G0196 (C:11) | 531 | 3.5 | 53 | 743 | 2.0 | 53 |
| | 383A Ovary T (mets) | | H Colon N | 422B0609 (420) | 421G0196 (C:11) | 1842 | 10.6 | 39 | 671 | 2.0 | 39 |
| -1.9 | S22 Ovary T | | CT9 Kidney N | 4229O627 (420) | 421G0196 (C:11) | 453 | 3.3 | 66 | 857 | 3.2 | 66 |
| +3.2 | 9485 OT 1-P (SCID) | | 9485 OT 5-P (SCID) | 422Y0602 (420) | 421G0196 (C:11) | 1882 | 12.4 | 57 | 594 | 2.3 | 57 |
| +1.5 | 262A Ovary T | | 334A Large Intestine N | 422A0622 (420) | 421G0196 (C:11) | 1496 | 7.5 | 55 | 965 | 2.2 | 55 |
| -1.1 | S115 Ovary T (mets) | | CT10 Small Intestine N | 422C0604 (420) | 421G0196 (C:11) | 509 | 3.4 | 51 | 573 | 2.0 | 51 |
| +1.1 | 288A Ovary T | | CT12 Lung N | 422V0625 (420) | 421G0196 (C:11) | 700 | 4.5 | 54 | 651 | 2.1 | 54 |
| -2.1 | 201A Ovary T | | S6 Stomach N | 422W0620 (420) | 421G0196 (C:11) | 625 | 4.6 | 46 | 1335 | 3.6 | 46 |
| +7.8 | S23 Ovary T | | S56 Spinal Cord N | 422G0628 (420) | 421G0196 (C:11) | 3896 | 22.4 | 50 | 502 | 2.2 | 50 |
| +1.8 | 205A Ovary T | | 270A Liver N | 422Q0606 (420) | 421G0196 (C:11) | 2251 | 14.7 | 46 | 1256 | 2.0 | 46 |
| -1.9 | 9334 Ovary T (SCID) | | I2 Skin N | 422R0601 (420) | 421G0196 (C:11) | 552 | 3.4 | 72 | 1029 | 2.3 | 72 |
| +5.6 | 365A Ovary T | | S91 Fetal tissue | 422X0607 (420) | 421G0196 (C:11) | 8126 | 35.6 | 50 | 1449 | 2.0 | 50 |
| -3.5 | 263A Ovary T | | S73 Breast N | 422H0623 (420) | 421G0196 (C:11) | 439 | 3.2 | 61 | 1531 | 3.4 | 61 |
| -3.3 | 382A Ovary T | | CT19 Brain N | 422Q0610 (420) | 421G0196 (C:11) | 387 | 3.2 | 50 | 1278 | 2.1 | 50 |
| +4.8 | 266A Ovary T | | S27 Ovary N | 4225O603 (420) | 421G0196 (C:11) | 4242 | 22.4 | 58 | 883 | 2.0 | 58 |

Fig. 3

```
TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT
```

*Fig. 4*

```
TAGCGYGGTCGCGGCCGAGGYCTGCTTYTCTGTCCAGCCCAGGGCCTGTGGGGTCAGGGCGGTGGGTGCAGATGGC
ATCCACTCCGGTGGCTTCCCCATCTTTCTCTGGCCTGAGCAAGGTCAGCCTGCAGCCAGAGTACAGAGGGCCAACA
CTGGTGTTCTTGAACAAGGGCCTTAGCAGGCCCTGAAGGRCCCTCTCTGTAGTGTTGAACTTCCTGGAGCCAGGCC
ACATGTTCTCCTCATACCGCAGGYTAGYGATGGTGAAGTTGAGGGTGAAATAGTATTMANGRAGATGGCTGGCARA
CCTGCCCGGGCGGCCGCTCSAAATCC
```

*Fig. 5*

```
AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA
```

TTGGGGNTTTMGAGCGGCCGCCCGGGCAGGTACCGGGGTGGTCAGCGAGGAGCCATTCACACTGAACTTCACCATC
AACAACCTGCGGTATGAGGAGAACATGCAGCACCCTGGCTCCAGGAAGTTCAACACCACGGAGAGGGTCCTTCAGG
GCCTGCTCAGGTCCCTGTTCAAGAGCACCAGTGTTGGCCCTCTGTACTCTGGCTGCAGACTGACTTTGCTCAGACT
TGAGAAACATGGGGCAGCCACTGGAGTGGACGCCATCTGCACCCTCCGCCTTGATCCCACTGGTCCTGGACTGGAC
AGAGAGCGGCTATACTGGGAGCTGAGCCAGTCCTCTGGCGGNGACNCCNCTT

Fig. 7B

AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 7A and 7B*

```
TGTGGTGTTGAACTTCCTGGAGNCAGGGTGACCCATGTCCTCCCCATACTGCAGGTTGGTGATGGTGAAGTTGAGG
GTGAATGGTACCAGGAGAGGGCCAGCAGCCATAATTGTSGRGCKGSMGMSSGAGGMWGGWGTYYCWGAGGTTCYRA
RRTCCACTGTGGAGGTCCCAGGAGTGCTGGTGGTGGGCACAGAGSTCYGATGGGTGAAACCATTGACATAGAGACT
GTTCCTGTCCAGGGTGTAGGGGCCCAGCTCTTYRATGYCATTGGYCAGTTKGCTYAGCTCCCAGTACAGCCRCTCT
CKGYYGMGWCCAGSGCTTTTGGGGTCAAGATGATGGATGCAGATGGCATCCACTCCAGTGGCTGCTCCATCCTTCT
CGGACCTGAGAGAGGTCAGTCTGCAGCCAGAGTACAGAGGGCCAACACTGGTGTTCTTTGAATA
```

*Fig. 8*

```
TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG
```

*Fig. 9*

| Gene Name | Bal Probe 1 Exp Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|
| 421O0188 [D3] | +7.0 205A Ovary T | | | 270A Liver N | 422Q0606 | 8620 | 1240 | 57.7 | 65 | 2.2 | 65 |
| 421O0188 [D3] | +5.9 S23 Ovary T | | | S56 Spinal Cord N | 422G0628 | 5894 | 1002 | 35.3 | 89 | 3.9 | 89 |
| 421O0188 [D3] | +5.7 385A Ovary T | | | S91 Fetal tissue | 422X0607 | 12151 | 2121 | 54.3 | 73 | 2.8 | 73 |
| 421O0188 [D3] | +5.1 426A Ovary T (met) | | | 415A Aorta N | 422X0611 | 7487 | 1480 | 53.0 | 73 | 9.7 | 73 |
| 421O0188 [D3] | +3.5 263A Ovary T | | | S73 Breast N | 422H0623 | 7302 | 2116 | 39.2 | 84 | 4.5 | 84 |
| 421O0188 [D3] | +3.3 383A Ovary T (met) | | | I1 Colon N | 422B0609 | 3714 | 1113 | 20.4 | 83 | 2.6 | 83 |
| 421O0188 [D3] | +3.0 9334 Ovary T (SCID) | | | I2 Skin N | 422R0601 | 2435 | 814 | 12.1 | 75 | 2.1 | 75 |
| 421O0188 [D3] | +2.6 384A Ovary T (met) | | | 272A Dendritic cell | 422406608 | 4578 | 1754 | 25.0 | 69 | 2.3 | 69 |
| 421O0188 [D3] | +2.2 264A Ovary T | | | S2 Pancreas N | 422N0629 | 7904 | 3596 | 38.5 | 81 | 5.6 | 81 |
| 421O0188 [D3] | +2.0 386A Ovary T | | | S40 PBMC (activat) | 422J0605 | 2191 | 1081 | 14.0 | 90 | 2.9 | 90 |
| 421O0188 [D3] | +2.0 S115 Ovary T (met) | | | CT10 Small intestin | 422C0604 | 1979 | 971 | 10.4 | 80 | 2.7 | 80 |
| 421O0188 [D3] | +2.0 265A Ovary T | | | CT5 Heart N | 422Q0624 | 1911 | 964 | 13.9 | 93 | 3.4 | 93 |
| 421O0188 [D3] | -1.9 335A Ovary T | | | S7 Ovary N | 422Z0626 | 1666 | 817 | 9.8 | 100 | 3.0 | 100 |
| 421O0188 [D3] | +1.6 428A Ovary T | | | 243A Esophagus N | 422A0612 | 1827 | 3480 | 13.4 | 97 | 9.5 | 97 |
| 421O0188 [D3] | +1.6 261A Ovary T | | | S10 Skeletal muscle | 422З0621 | 5914 | 3653 | 30.4 | 86 | 6.0 | 86 |
| 421O0188 [D3] | +1.6 266A Ovary T | | | S27 Ovary N | 422S0603 | 2039 | 1274 | 11.9 | 50 | 2.6 | 50 |
| 421O0188 [D3] | +1.6 S22 Ovary T | | | CT9 Kidney N | 422900627 | 1736 | 1072 | 11.0 | 92 | 4.0 | 92 |
| 421O0188 [D3] | +1.4 9485 OT 1-P (SCID) | | | 9485 OT 5-P (SCID) | 422Y0602 | 4204 | 3074 | 23.0 | 93 | 7.7 | 93 |
| 421O0188 [D3] | +1.4 262A Ovary T | | | 334A Large Intestin | 422A0622 | 3002 | 2101 | 16.6 | 89 | 4.0 | 89 |
| 421O0188 [D3] | +1.3 S25 Ovary T | | | CT4 Bone Marrow | 422H0619 | 1643 | 1297 | 9.6 | 90 | 3.1 | 90 |
| 421O0188 [D3] | +1.2 429A Ovary T (met) | | | 364A Ovary N | 422I0614 | 2521 | 2084 | 22.0 | 65 | 23.9 | 65 |
| 421O0188 [D3] | +1.2 382A Ovary T | | | CT19 Brain N | 422Q0610 | 2072 | 1663 | 10.9 | 88 | 2.3 | 88 |
| 421O0188 [D3] | +1.2 288A Ovary T | | | CT12 Lung N | 422V0625 | 1840 | 1473 | 10.7 | 87 | 3.8 | 87 |
| 421O0188 [D3] | +1.1 201A Ovary T | | | S6 Stomach N | 422W0620 | 1329 | 1204 | 9.1 | 90 | 3.5 | 90 |

Fig. 10

| Gene Name | Bal Exp | Probe 1 Name | P1 | P2 | Probe 2 Name | GEN ID | Probe1 Value | Probe2 Value | Probe1 S/B | Probe1 A% | Probe2 S/B | Probe2 A% |
|---|---|---|---|---|---|---|---|---|---|---|---|---|
| 421B0181 (C3) | +18.8 | 385A Ovary T | | | S91 Fetal tissue | 422X0607 | 26711 | 1424 | 103.3 | 54 | 2.0 | 54 |
| 421B0181 (C3) | +11.5 | S23 Ovary T | | | S56 Spinal Cord N | 422G0628 | 13559 | 1179 | 65.3 | 68 | 3.9 | 68 |
| 421B0181 (C3) | +11.1 | 426A Ovary T (mets) | | | 415A Aorta N | 422X0611 | 14125 | 1273 | 67.3 | 61 | 5.6 | 61 |
| 421B0181 (C3) | +10.8 | 205A Ovary T | | | 270A Liver N | 422Q0606 | 16121 | 1488 | 93.1 | 43 | 2.3 | 43 |
| 421B0181 (C3) | +5.1 | 263A Ovary T | | | S73 Breast N | 422H0623 | 11326 | 2235 | 58.2 | 68 | 4.4 | 68 |
| 421B0181 (C3) | +4.6 | 384A Ovary T (mets) | | | 272A Dendritic cells | 42240608 | 6583 | 1424 | 24.5 | 40 | 2.1 | 40 |
| 421B0181 (C3) | +4.4 | 264A Ovary T | | | S2 Pancreas N | 422N0629 | 9865 | 2245 | 40.9 | 64 | 3.6 | 64 |
| 421B0181 (C3) | +4.4 | 429A Ovary T (mets) | | | 364A Ovary N | 42210614 | 2803 | 638 | 22.6 | 60 | 7.4 | 60 |
| 421B0181 (C3) | +4.2 | 261A Ovary T | | | S10 Skeletal muscle | M22230621 | 8271 | 1949 | 39.5 | 68 | 3.6 | 68 |
| 421B0181 (C3) | +3.8 | S115 Ovary T (mets) | | | CT10 Small intestine | M22C0604 | 2281 | 607 | 11.6 | 60 | 2.1 | 60 |
| 421B0181 (C3) | +2.5 | 265A Ovary T | | | CT5 Heart N | 4229K627 | 3192 | 1293 | 19.2 | 68 | 4.0 | 68 |
| 421B0181 (C3) | -2.3 | S22 Ovary T | | | CT9 Kidney N | 42250603 | 565 | 1276 | 3.6 | 70 | 3.9 | 70 |
| 421B0181 (C3) | +2.2 | 266A Ovary T | | | I2 Skin N | 422R0601 | 2774 | 1260 | 14.3 | 46 | 2.7 | 46 |
| 421B0181 (C3) | +2.1 | 9334 Ovary T (SCID) | | | 9485 OT 5-P (SCID) | 422Y0602 | 1774 | 837 | 8.4 | 56 | 2.1 | 56 |
| 421B0181 (C3) | +1.9 | 9485 OT 1-P (SCID) | | | CT19 Brain N | 422Q0610 | 6967 | 3726 | 41.5 | 70 | 9.2 | 70 |
| 421B0181 (C3) | +1.6 | 382A Ovary T | | | CT12 Lung N | 422V0625 | 2313 | 1471 | 6.2 | 50 | 1.9 | 50 |
| 421B0181 (C3) | +1.6 | 288A Ovary T | | | CT4 Bone Marrow N | 422H0619 | 1657 | 1054 | 9.7 | 69 | 2.9 | 69 |
| 421B0181 (C3) | -1.5 | S25 Ovary T | | | 334A Large Intestine | 422A0622 | 848 | 1243 | 4.5 | 65 | 2.7 | 65 |
| 421B0181 (C3) | +1.4 | 262A Ovary T | | | S40 PBMC (activated) | 42210605 | 3171 | 2214 | 16.8 | 69 | 3.8 | 69 |
| 421B0181 (C3) | +1.2 | 386A Ovary T | | | S7 Ovary N | 42220626 | 630 | 544 | 4.2 | 53 | 1.9 | 53 |
| 421B0181 (C3) | -1.2 | 335A Ovary T | | | S6 Stomach N | 42220626 | 592 | 730 | 3.7 | 75 | 2.6 | 75 |
| 421B0181 (C3) | -1.0 | 201A Ovary T | | | 243A Esophagus N | 422W0620 | 1197 | 1237 | 7.8 | 65 | 3.5 | 65 |
| 421B0181 (C3) | -1.0 | 428A Ovary T (mets) | | | I1 Colon N | 42240612 | 783 | 797 | 4.5 | 95 | 2.4 | 95 |
| 421B0181 (C3) | | 383A Ovary T (mets) | | | | 422B0609 | 3470 | 862 | 8.9 | 24 | 1.7 | 24 |

*Fig. 11*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42110182 [H7] | +16.7 | 426A Ovary T (met) | | | 415A Aorta N | 422X0611 | 7706 | 462 | 46.3 | 75 | 3.5 | 75 |
| 42110182 [H7] | +10.7 | 205A Ovary T | | | 270A Liver N | 422Q0606 | 10171 | 950 | 61.2 | 41 | 1.8 | 41 |
| 42110182 [H7] | +9.9 | 385A Ovary T | | | S91 Fetal tissue | 422X0607 | 14415 | 1459 | 62.1 | 48 | 2.2 | 48 |
| 42110182 [H7] | +8.8 | S23 Ovary T | | | S56 Spinal Cord N | 422G0628 | 7781 | 880 | 47.3 | 73 | 3.4 | 73 |
| 42110182 [H7] | +6.4 | 383A Ovary T (met) | | | I1 Colon N | 422B0609 | 4807 | 748 | 27.6 | 47 | 2.2 | 47 |
| 42110182 [H7] | +5.1 | 263A Ovary T | | | S73 Breast N | 422H0623 | 9815 | 1909 | 57.1 | 74 | 4.2 | 74 |
| 42110182 [H7] | +4.9 | 429A Ovary T (met) | | | 364A Ovary N | 422J0614 | 2661 | 543 | 20.3 | 61 | 6.7 | 61 |
| 42110182 [H7] | +3.5 | 264A Ovary T | | | S2 Pancreas N | 422N0629 | 7934 | 2274 | 38.8 | 71 | 3.9 | 71 |
| 42110182 [H7] | -2.9 | S25 Ovary T | | | CT4 Bone Marrow | 422H0619 | 480 | 1375 | 3.5 | 80 | 3.0 | 80 |
| 42110182 [H7] | +2.8 | 261A Ovary T | | | S10 Skeletal muscle | 42230621 | 8993 | 3245 | 34.6 | 69 | 5.1 | 69 |
| 42110182 [H7] | +2.5 | S115 Ovary T (met) | | | CT10 Small intestin | 422C0604 | 1864 | 738 | 8.1 | 67 | 2.2 | 67 |
| 42110182 [H7] | +2.3 | 9334 Ovary T (SCID) | | | I2 Skin N | 422R0601 | 2552 | 1113 | 12.7 | 41 | 2.6 | 41 |
| 42110182 [H7] | -2.3 | S22 Ovary T | | | CT9 Kidney N | 422Q0627 | 386 | 889 | 3.2 | 69 | 3.4 | 69 |
| 42110182 [H7] | +2.2 | 384A Ovary T (met) | | | 272A Dendritic cells | 42240608 | 3516 | 1567 | 18.7 | 55 | 2.2 | 55 |
| 42110182 [H7] | -2.2 | 382A Ovary T | | | CT19 Brain N | 422Q0610 | 608 | 1320 | 4.2 | 60 | 2.3 | 60 |
| 42110182 [H7] | +1.9 | 265A Ovary T | | | CT5 Heart N | 422O0624 | 2063 | 1080 | 13.6 | 87 | 3.5 | 87 |
| 42110182 [H7] | +1.8 | 266A Ovary T | | | S27 Ovary N | 42250603 | 1550 | 847 | 7.0 | 58 | 2.1 | 58 |
| 42110182 [H7] | +1.5 | 262A Ovary T | | | 334A Large Intestin | 422A0622 | 2559 | 1651 | 13.2 | 73 | 3.2 | 73 |
| 42110182 [H7] | -1.4 | 386A Ovary T | | | S40 PBMC (activat) | 422J0605 | 534 | 738 | 3.9 | 62 | 2.2 | 62 |
| 42110182 [H7] | -1.3 | 288A Ovary T | | | CT12 Lung N | 422V0625 | 893 | 1120 | 5.3 | 66 | 3.1 | 66 |
| 42110182 [H7] | -1.3 | 335A Ovary T | | | S7 Ovary N | 42220626 | 440 | 567 | 3.3 | 60 | 2.2 | 60 |
| 42110182 [H7] | +1.2 | 9485 OT 1-P (SCID) | | | 9485 OT 5-P (SCID) | 422Y0602 | 4188 | 3529 | 21.6 | 66 | 9.5 | 66 |
| 42110182 [H7] | +1.1 | 428A Ovary T (met) | | | 243A Exophagus N | 42240612 | 725 | 689 | 6.2 | 65 | 2.8 | 65 |
| 42110182 [H7] | -1.0 | 201A Ovary T | | | S6 Stomach N | 422W0620 | 1008 | 1018 | 7.4 | 62 | 3.2 | 62 |

*Fig. 12*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189 [D1] | +33.2 | 426A Ovary T (mets) | | | 415A Aorta N | 422X0611 | 8072 | 243 | 55.2 | 67 | 2.4 | 67 |
| 421V0189 [D1] | +13.7 | S23 Ovary T | | | S56 Spinal Cord N | 422G0628 | 7367 | 537 | 42.6 | 69 | 2.5 | 69 |
| 421V0189 [D1] | +12.6 | 429A Ovary T (mets) | | | 364A Ovary N | 422I0614 | 2850 | 227 | 21.7 | 64 | 3.5 | 64 |
| 421V0189 [D1] | +8.0 | 385A Ovary T | | | S91 Fetal tissue | 422X0607 | 11711 | 1469 | 54.0 | 58 | 2.2 | 58 |
| 421V0189 [D1] | +7.3 | 263A Ovary T | | | S73 Breast N | 422H0623 | 6949 | 952 | 37.8 | 69 | 2.6 | 69 |
| 421V0189 [D1] | -5.8 | S25 Ovary T | | | CT4 Bone Marrow | 422H0619 | 208 | 1210 | 2.1 | 44 | 2.9 | 44 |
| 421V0189 [D1] | +5.0 | 205A Ovary T | | | 270A Liver N | 422Q0606 | 8676 | 1737 | 52.3 | 57 | 2.6 | 57 |
| 421V0189 [D1] | +4.5 | 383A Ovary T (mets) | | | I1 Colon N | 422B0609 | 3149 | 707 | 17.4 | 57 | 2.0 | 57 |
| 421V0189 [D1] | +4.4 | 261A Ovary T | | | S10 Skeletal muscle | 42230621 | 6332 | 1443 | 29.1 | 77 | 2.9 | 77 |
| 421V0189 [D1] | +4.2 | 264A Ovary T | | | S2 Pancreas N | 422N0629 | 7612 | 1809 | 38.1 | 79 | 3.3 | 79 |
| 421V0189 [D1] | -3.2 | 382A Ovary T | | | CT19 Brain N | 422Q0610 | 468 | 1508 | 3.4 | 60 | 2.3 | 60 |
| 421V0189 [D1] | +2.9 | 9334 Ovary T (SCID) | | | I2 Skin N | 422R0601 | 2500 | 860 | 12.3 | 51 | 2.1 | 51 |
| 421V0189 [D1] | +2.5 | S115 Ovary T (mets) | | | CT10 Small intestin | 422C0604 | 1424 | 569 | 6.7 | 61 | 2.1 | 61 |
| 421V0189 [D1] | +2.4 | 265A Ovary T | | | CT5 Heart N | 422O0624 | 1742 | 723 | 11.8 | 70 | 2.8 | 70 |
| 421V0189 [D1] | +2.3 | 384A Ovary T (mets) | | | 272A Dendritic cell | 42240608 | 3083 | 1342 | 17.0 | 62 | 2.0 | 62 |
| 421V0189 [D1] | +1.9 | 266A Ovary T | | | S27 Ovary N | 42250603 | 1370 | 732 | 8.0 | 47 | 2.0 | 47 |
| 421V0189 [D1] | -1.9 | 386A Ovary T | | | S40 PBMC (activat | 422J0605 | 307 | 580 | 2.6 | 41 | 2.0 | 41 |
| 421V0189 [D1] | +1.7 | 262A Ovary T | | | 334A Large Intestin | 422A0622 | 2097 | 1202 | 11.2 | 86 | 2.7 | 86 |
| 421V0189 [D1] | -1.3 | 335A Ovary T | | | S7 Ovary N | 42220526 | 373 | 470 | 2.9 | 47 | 2.0 | 47 |
| 421V0189 [D1] | -1.1 | 288A Ovary T | | | CT12 Lung N | 422V0625 | 969 | 1094 | 5.6 | 72 | 2.9 | 72 |
| 421V0189 [D1] | +1.1 | 201A Ovary T | | | S6 Stomach N | 422W0620 | 750 | 672 | 5.6 | 62 | 2.4 | 62 |
| 421V0189 [D1] | +1.1 | 428A Ovary T (mets) | | | 243A Esophagus N | 42240612 | 498 | 446 | 4.2 | 73 | 2.1 | 73 |
| 421V0189 [D1] | -1.0 | 9485 OT 1-P (SCID) | | | 9485 OT 5-P (SCID) | 422Y0602 | 3117 | 3174 | 16.7 | 91 | 8.2 | 91 |
| 421V0189 [D1] | | S22 Ovary T | | | CT9 Kidney N | 42290627 | 224 | 409 | 2.3 | 48 | 2.3 | 48 |

*Fig. 13*

| Gene Name | Bal Probe 1 Exp Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|
| 421H0187 [E11] | +20.2 426A Ovary T (mets) | | | 415A Aorta N | 422X0611 | 5441 | 270 | 36.3 | 50 | 2.3 | 50 |
| 421H0187 [E11] | +10.0 S23 Ovary T | | | S56 Spinal Cord N | 422G0628 | 5318 | 533 | 27.1 | 56 | 2.3 | 56 |
| 421H0187 [E11] | +8.3 429A Ovary T (mets) | | | 364A Ovary N | 422I0614 | 1252 | 150 | 10.1 | 58 | 2.5 | 58 |
| 421H0187 [E11] | +5.7 385A Ovary T | | | S91 Fetal tissue | 422X0607 | 9507 | 1668 | 35.8 | 45 | 2.1 | 45 |
| 421H0187 [E11] | +4.4 205A Ovary T | | | 270A Liver N | 422Q0606 | 5456 | 1235 | 31.1 | 50 | 2.0 | 50 |
| 421H0187 [E11] | +4.2 265A Ovary T | | | CT5 Heart N | 422O0624 | 1834 | 438 | 11.9 | 48 | 2.0 | 48 |
| 421H0187 [E11] | -4.1 382A Ovary T | | | CT19 Brain N | 422Q0610 | 309 | 1259 | 2.6 | 48 | 2.0 | 48 |
| 421H0187 [E11] | +3.6 261A Ovary T | | | S10 Skeletal muscle | 42230621 | 3733 | 1036 | 17.7 | 55 | 2.3 | 55 |
| 421H0187 [E11] | +3.4 263A Ovary T | | | S73 Breast N | 421H0623 | 4163 | 1239 | 23.0 | 62 | 3.0 | 62 |
| 421H0187 [E11] | +2.5 S115 Ovary T (mets) | | | CT10 Small intestin | 422C0604 | 1565 | 627 | 8.8 | 47 | 2.1 | 47 |
| 421H0187 [E11] | +2.1 264A Ovary T | | | S2 Pancreas N | 422N0629 | 3455 | 1630 | 14.9 | 60 | 3.0 | 60 |
| 421H0187 [E11] | +2.1 384A Ovary T (mets) | | | 272A Dendritic cell | 42240608 | 2667 | 1270 | 13.4 | 44 | 1.9 | 44 |
| 421H0187 [E11] | -2.1 S22 Ovary T | | | CT9 Kidney N | 42290627 | 291 | 605 | 2.4 | 51 | 2.5 | 51 |
| 421H0187 [E11] | -1.7 386A Ovary T | | | S40 PBMC (activat) | 42210605 | 410 | 687 | 3.2 | 47 | 2.0 | 47 |
| 421H0187 [E11] | +1.6 9334 Ovary T (SCID | | | I2 Skin N | 422R0601 | 1622 | 984 | 7.9 | 44 | 2.2 | 44 |
| 421H0187 [E11] | +1.5 262A Ovary T | | | 334A Large Intestin | 422A0622 | 1892 | 1245 | 10.1 | 50 | 2.6 | 50 |
| 421H0187 [E11] | -1.5 288A Ovary T | | | CT12 Lung N | 422V0625 | 604 | 908 | 4.1 | 62 | 2.6 | 62 |
| 421H0187 [E11] | -1.4 428A Ovary T (mets) | | | 243A Esophagus N | 42240612 | 236 | 325 | 2.7 | 78 | 1.9 | 78 |
| 421H0187 [E11] | -1.3 335A Ovary T | | | S7 Ovary N | 42220626 | 382 | 501 | 2.9 | 58 | 2.0 | 58 |
| 421H0187 [E11] | -1.2 201A Ovary T | | | S6 Stomach N | 422W0620 | 558 | 677 | 4.2 | 58 | 2.3 | 58 |
| 421H0187 [E11] | +1.0 9485 OT 5-P (SCID) | | | 9485 OT 1-P (SCID | 422Y0602 | 2582 | 2493 | 15.1 | 57 | 6.3 | 57 |
| 421H0187 [E11] | 383A Ovary T (mets) | | | I1 Colon N | 422B0609 | 2261 | 562 | 12.5 | 38 | 1.7 | 38 |
| 421H0187 [E11] | 266A Ovary T | | | S27 Ovary N | 42250603 | 1739 | 965 | 9.7 | 36 | 2.2 | 36 |
| 421H0187 [E11] | S25 Ovary T | | | CT4 Bone Marrow | 422H0619 | 283 | 845 | 2.2 | 44 | 2.2 | 44 |

```
ACGGTTTCAATGGACACTTTTATTGTTTACTTAATGGATCATCAATTTTGTCTCACTACCTACAAATGGAATTTCA
TCTTGTTTCCATGCTGAGTAGTGAAACAGTGACAAAGCTAATCATAATAACCTACATCAAAAGAGAACTAAGCTAA
CACTGCTCACTTTCTTTTTAACAGGCAAAATATAAATATATGCACTCTAXAATGCACAATGGTTTAGTCACTAAAA
AATTCAAATGGGATCTTGAAGAATGTATGCAAATCCAGGGTGCAGTGAAGATGAGCTGAGATGCTGTGCAACTGTT
TAAGGGTTCCTGGCACTGCATCTCTTGGCCACTAGCTGAATCTTGACATGGAAGGTTTTAGCTAATGCCAAGTGGA
GATGCAGAAAATGCTAAGTTGACTTAGGGGCTGTGCACAGGAACTAAAAGGCAGGAAAGTACTAAATATTGCTGAG
AGCATCCACCCCAGGAAGGACTTTACCTTCCAGGAGCTCCAAACTGGCACCACCCCCAGTGCTCACATGGCTGACT
TTATCCTCCGTGTTCCATTTGGCACAGCAAGTGGCAGTG
```

11721-2

```
AAGGCTGGTGGGTTTTTGATCCTGCTGGAGAACCTCCGCTTTCATGTGGAGGAAGAAGGGAAGGGAAAAGATGCTT
CTGGGAACAAGGTTAAAGCCGAGCCAGCCAAAATAGAAGCTTTCCGAGCTTCACTTTCCAAGCTAGGGGATGTCTA
TGTCAATGATGCTTTTGGCACTGCTCACAGAGCCCACAGCTCCATGGTAGGAGTCAATCTGCCACAGAAGGCTGGT
GGGTTTTTGATGAAGAAGGAGCTGAACTACTTTGCAAAGGCCTTGGAGAGCCCAGAGCGACCCTTCCTGGCCATCC
TGGGCGGAGCTAAAGTTGCAGACAAGATCCAGCTCATCAATAATATGCTGGACAAAGTCAATGAGATGATTATTGG
TGGTGGAATGGCTTTTACCTTCCTTAAGGTGCTCAACAACATGGAGATTGGCACTTCTCTGTTTGATGAAGAGGGA
GCCAAGATTGTCAAAGACCTAATGTCCAAAGCTGAGAAGAATGGTGTGAAGATTACCTTGCCTGTTGACTTTGTCA
CTGCTGACAAGTTTGATGA
```

11724-1

```
TTTGTTCCTTACATTTTTCTAAAGAGTTACTTAAATCAGTCAACTGGTCTTTGAGACTCTTAAGTTCTGATTCCAA
CTTAGCTAATTCATTCTGAGAACTGTGGTATAGGTGGCGTGTCTCTTCTAGCTGGGACAAAAGTTCTTTGTTTTCC
CCCTGTAGAGTATCACAGACCTTCTGCTGAAGCTGGACCTCTGTCTGGGCCTTGGACTCCCAAATCTGCTTGTCAT
GTTCAAGCCTGGAAATGTTAATCTTTAATTCTTCCATATGGATGGACATCTGTCTAAGTTGATCCTTTAGAACACT
GCAATTATCTTCTTTGAGTCTAATTTCTTCTTCTTTGCTTTGAATCGCATCACTAAACTTCCTCTCCCATTTCTTA
GCTTCATCTATCACCCTGTCACGATCATCCTGGAGGGAAGACATGCTCTTAGTAAAGGCTGCAAGCTGGGTCACAG
TACTGTCCAAGTTTTCCTGAAGTTGCTGAACTTCCTTGTCTTTCTTGTTCAAAGTAACCTGAATCTCTCCAATTGT
CTCTTCCAAGTGGACTTTTTCTCTGCGCAAAGCATCCAG
```

11724-2

```
TCATTGCCTGTGATGGCATCTGGAATGTGATGAGCAGCCAGGAAGTTGTAGATTTCATTCAATCAAAGGATTCAGC
ATGTGGTGGAAGCTGTGAGGCAAGAGAAACAAGAACTGTATGGCAAGTTAAGAAGCACAGAGGCAAACAAGAAGGA
GACAGAAAAGCAGTTGCAGGAAGCTGAGCAAGAAATGGAGGAAATGAAAGAAAAGATGAGAAAGTTTGCTAAATCT
AAACAGCAGAAAATCCTAGAGCTGGAAGAAGAGAATGACCGGCTTAGGGCAGAGGTGCACCCTGCAGGAGATACAG
CTAAAGAGTGTATGGAAACACTTCTTTCTTCCAATGCCAGCATGAAGGAAGAACTTGAAAGGGTCAAAATGGAGTA
TGAAACCCTTTCTAAGAAGTTTCAGTCTTTAATGTCTGAGAAAGACTCTCTAAGTGAAGAGGTTCAAGATTTAAAG
CATCAGATAGAAGGTAATGTATCTAAACAAGCTAACCTAGAGGCCACCGAGAAACATGATAACCAAACGAATGTCA
CTGAAGAGGGAACACAGTCTATACCAGGT
```

```
AAGCCAATAATCACCATTTATTACTTAATATATGCCAACCACTGTACTTGGCAGTTCACAAATTCTCACCGTTACA
ACAACCCCATGAGGTATTTATTCCCATTCTATAGATAGGGAAACCACAGCTCAAGTAAGTTAGGAAACTGAGCCAA
GTATACACAGAATACGAAGTGGCAAAACTAGAAGGAAAGACTGACACTGCTATCTGCTGGCCTCCAGTGTCCTGGC
TCTTTTCACACGGGtTCAATGTCTCCAGCGCTGCTGCTGCTGCTGCATTACCATGCCCTCATTGTTTTTCTTCCTC
TGGTGTTCAACTGCATCCTTCAAAGAATCTAACTCATTCCAGAGACCACTTATTTCTTTCTCTCTTTCTGAAATTA
CTTTTAATAATTCTTCATGAGGGGGAAAAGAAGATGCCTGTTGGTAGTTTTGTTGTTTAAGCTGCTCAATTTGGGA
CTTAAACAATTTGTTTTCATCTTGTACATCCTGTAACAGCTGTGTTTTGCTAGAAAGATCACTCTCCCTCTCTTTT
AGCATGGCTTCTAACCTCTTCAATTCATTTTCCTTTTCTTTCAACACAATCTCAAGTTCTTCAAACTGTGATGCAG
AAGAGGCCTCTTTCAAGTTATGTTGTGCTACTTCCTGAACATGTGCTTTTAAAGATTCATTTTCTTCTTGAAGATC
CTGTAACCACTTCCCTGTATTGGCTAGGTCTTTCTCTTTCTCTTCCAAAACAGCCTTCATGGTATTCATCTGTTCC
TCTTTTCCTTTTAATAAGTTCAGGAGCTTCAGAAC
```

11726-1&2

```
CAAGCTTTTTTTTTTTTTTTTAAAAAGTGTTAGCATTAATGTTTTATTGTCACGCAGATGGCAACTGGGTTTATGTC
TTCATATTTTATATTTTTGTAAATTAAAAAAAATTACAAGTTTTAAATAGCCAATGGCTGGTTATATTTTCAGAAAA
CATGATTAGACTAATTCATTAATGGTGGCTTCAAGCTTTTCCTTATTGGCTCCAGAAAATTCACCCACCTTTTGTC
CCTTCTTAAAAAACTGGAATGTTGGCATGCATTTGACTTCACACTCTGAAGCAACATCCTGACAGTCATCCACATC
TACTTCAAGGAATATCACGTTGGAATACTTTTCAGAGAGGGAATGAAAGAAAGGCTTGATCATTTTGCAAGGCCCA
CACCACGTGGCTGAGAAGTCAACTACTACAAGTTTATCACCTGCAGCGTCCAAGGCTTCCTGAAAAGCAGTCTTGC
TCTCGATCTGCTTCACCATCTTGGCTGCTGGAGTCTGACGAGCGGCTGTAAGGACCGATGGAAATGGATCCAAAGC
ACCAAACAGAGCTTCAAGACTCGCTGCTTGGCTTGAATTCGGATCCGATATCGCCATGGCCT
```

11727-1&2

```
AAGTGTTAGCATTAATGTTTTATTGTCACGCAGATGGCAACTGGGTTTATGTCTTCATATTTTATATTTTTGTAAA
TTAAAAAAAATTMCAAGTTTTAAATAGCCAATGGCTGGTTATATTTTCAGAAAACATGATTAGACTAATTCATTAAT
GGTGGCTTCAAGCTTTTCCTTATTGGCTCCAGAAAATTCACCCACCTTTTGTCCCTTCTTAAAAAACTGGAATGTT
GGCATGCATTTGACTTCACACTCTGAAGCAACATCCTGACAGTCATCCACATCTACTTCAAGGAATATCACGTTGG
AATACTTTTCAGAGAGGGAATGAAAGAAAGGCTTGATCATTTTGCAAGGCCCACACCACGTGGCTGAGAAGTCAAC
TACTACAAGTTTATCACCTGCAGCGTCCAAGGCTTCCTGAAAAGCAGTCTTGCTCTCGATCTGCTTCACCATCTTG
GCTGCTGGAGTCTGACGAGCGGCTGTAAGGACCGATGGAAATGGATCCAAAGCACCAAACAGAGCTTCAAGACTCG
CTGCTTGGCATGAATTCGGATCCGA
```

```
TACAAACTTTATTGAAACGCACACGCGCACACACACAAACACCCCTGTGGATAGGGAAAAGCACCTGGCCACAGGG
TCCACTGAAACGGGGAGGGGATGGCAGCTTGTAATGTGGCTTTTGCCACAACCCCCTTCTGACAGGGAAGGCCTTA
GATTGAGGCCCCACCTCCCATGGTGATGGGGAGCTCAGAATGGGGTCCAGGGAGAATTTGGTTAGGGGGAGGTGCT
AGGGAGGCATGAGCAGAGGGCACCCTCCGAGTGGGGTCCCGAGGGCTGCAGAGTCTTCAGTACTGTCCCTCACAGC
AGCTGTCTCAAGGCTGGGTCCCTCAAAGGGGCGTCCCAGCGCGGGGCCTCCCTGCGCAAACACTTGGTACCCCTGG
CTGCGCAGCGGAAGCCAGCAGGACAGCAGTGGCGCCGATCAGCACAACAGACGCCCTGGCGGTAGGGACAGCAGGC
CCAGCCCTGTCGGTTGTCTCGGCAGCAGGTCTGGTTATCATGGCAGAAGTGTCCTTCCCACACTTCACGTCCTTCA
CACCCACGTGAXGGCTACXGGCCAGGAAG
```

11728.2.40.19.19

```
CCCGTGGGTGCCATCCACGGAGTTGTTACCTGATCTTTGGAAGCAGGATCGCCCGTCTGCACTGCAGTGGAAGCCC
CGTGGGCAGCAGTGATGGCCATCCCCGCATGCCACGGCCTCTGGGAAGGGGCAGCAACTGGAAGTCCCTGAGACGG
TAAAGATGCAGGAGTGGCCGGCAGAGCAGTGGGCATCAACCTGGCAGGGGCCACCCAGATGCCTGCTCAGTGTTGT
GGGCCATTTGTCCAGAAGGGGACGGCAGCAGCTGTAGCTGGCTCCTCCGGGGTCCAGGCAGCAGGCCACAGGGCAG
AACTGACCATCTGGGCACCGCGTTCCAGCCACCAGCCCTGCTGTTAAGGCCACCCAGCTCACCAGGGTCCACATGG
TCTGCCTGCGTCCGACTCCGCGGTCCTTGGGCCCTGATGGTTCTACCTGCTGTGAGCTGCCCAGTGGGAAGTATGG
CTGCTGCCAATGCCCAACGCCACCTGCTGCTCCGATCACCTGCACTGCTGCCCCAAGACACTGTGTGTGACCTGAT
CCAGAGTAAGTGCCTCTCCAAGGAGAACG
```

11730-1

```
GAATCACCTTTCTGGTTTAGCTAGTACTTTGTACAGAACAATGAGGTTTCCCACAGCGGAGTCTCCCTGGGCTCTG
TTTGGCTCTCGGTAAGGCAGGCCTACACCTTTTCCTCTCCTCTATGGAGAGGGGAATATGCATTAAGGTGAAAAGT
CACCTTCCAAAAGTGAGAAAGGGGATTCGATTGCTGCTTCAGGACTGTGGAATTATTTGGAATGTTTTACAAATGGT
TGCTACAAAACAACAAAAAAGGTAATTACAAAATGTGTACATCACAACATGCTTTTTAAAGACATTATGCATTGTG
CTCACATTCCCTTAAATGTTGTTTCCAAAGGTGCTCAGCCTCTAGCCCAGCTGGATTCTCCGGGAAGAGGCAGAGA
CAGTTTGGCGAAAAAGACACAGGGAAGGAGGGGGTGGTGAAAGGAGAAAGCAGCCTTCCAGTTAAAGATCAGCCCT
CAGTTAAAGGTCAGCTTCCCGCAXGCTGGCCTCAXGCGGAGTCTGGGTCAGAGGGAGGAGCAGCAGCAGGGTGGGA
CTGGGGCGT
```

11730-2

```
AACCGGAGCGCGAGCAGTAGCTGGGTGGGCACCATGGCTGGGATCACCACCATCGAGGCGGTGAAGCGCAAGATCC
AGGTTCTGCAGCAGCAGGCAGATGATGCAGAGGAGCGAGCTGAGCGCCTCCAGCGAGAAGTTGAGGGAGAAAGGCG
GGCCCGGGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGAGAGGTA
TGAAGGTTATTGAAAACCGGGCCTTAAAAGATGAAGAAAAGATGGAACTCCAGGAAATCCAACTCAAAGAAGCTAA
GCACATTGCAGAAGAGGCAGATAGGAAGTATGAAGAGGTGGCTCGTAAGTTGGTGATCATTGAAGGAGACTTGGAA
CGCACAGAGGAACGAGCTGAGCTGGCAGAGTCCCGTTGCCGAGAGATGGATGAGCAGATTAGACTGATGGACCAGA
ACCTGAAGTGTCTGAGTGC
```

*Fig. 15C*

11732.1contig

```
GAGAACTTGGCCTTTATTGTGGGCCCAGGAGGGCACAAAGGTCAGGAGGCCCAAGGGAGGGATCTGGTTTTCTGGA
TAGCCAGGTCATAGCATGGGTATCAGTAGGAATCCGCTGTAGCTGCACAGGCCTCACTTGCTGCAGTTCCGGGGAG
AACACCTGCACTGCATGGCGTTGATGACCTCGTGGTACACGACAGAGCCATTGGTGCAGTGCAAGGGCACGCGCAT
GGGCTCCGTCCTCGAGGGCAGGCAGCAGGAGCATTGCTCCTGCACATCCTCGATGTCAATGGAGTACACAGCTTTG
CTGGCACACTTTCCCTGGCAGTAATGAATGTCCACTTCCTCTTGGGACTTACAATCTCCCACTTTGATGTACTGCA
CCTTGGCTGTGATGTCTTTGCAATCAGGCTCCTCACATGTGTCACAGCAGGTGCCTGGAATTTTCACGATTTTGCC
TCCTTCAGCCAGACACTTGTGTTCATCAAATGGTGGGCAGCCCGTGACCCTCTTCTCCCAGATGTACTCTCCTCT
```

11732.2contig

```
GCCTGGACCTTGCCGGATCAGTGCCACACAGTGACTTGCTTGGCAAATGGCCAGACCTTGCTGCAGAGTCATCGTG
TCAATTGTGACCATGGACCCCGGCCTTCATGTGCCAACAGCCAGTCTCCTGTTCGGGTGGAGGAGACGTGTGGCTG
CCGCTGGACCTGCCCTTGTGTGTGCACGGGCAGTTCCACTCGGCACATCGTCACCTTCGATGGGCAGAATTTCAAG
CTTACTGGTAGCTGCTCCTATGTCATCTTTCAAAACAAGGAGCAGGACCTGGAAGTGCTCCTCCACAATGGGGCCT
GCAGCCCCGGGGCAAAACAAGCCTGCATGAAGTCCATTGAGATTAAGCATGCTGGCGTCTCTGCTGAGCTGCACAG
TAACATGGAGATGGCAGTGGATGGGAGACTGGTCCTTGCCCCGTACGTTGGTGAAAACATGGAAGTCAGCATCTAC
GGCGCTATCATGTATGAAGTCAGGTTTACCCATCTTGGCCACATCCTCACATACACCGCCXCAAAACAACGAGTT
```

11735-1-2

```
AGATCAACCTCTGCTGGTCAGGAGGAATGCCTTCCTTGTCTTGGATCTTTGCTTTGACGTTCTCGATAGTRWCAaC
TKKRYTSRAMSKMAAGKGYRATGRWMTTKSYWGWRASYKTMWWMRSGRARAYTTaGaCAYCCCMCCTCWgAGaCGS
AGKACCARGTGCAgAgGTGGACTCTTTCTGGATGTTGTAGTCAGACAGGGTGCGTCCATCTTCCAGCTGTTTCCCA
GCAAAGATCAACCTCTGCTGATCAGGAGGGATGCCTTCCTTATCTTGGATCTTTGCCTTGACATTCTCGATGGTGT
CACTGGGCTCCACCTCGAGGGTGATGGTCTTACCAGTCAGGGTCTTCACGAAGATYTGCATCCCACCTCTGAGACG
GAGCACCAGGTGCAGGGTRGACTCTTTCTGGATGTTGTAGTCAGACAGGGTGCGYCCATCTTCCAGCTGcTTTCCS
aGCAAAGATCAACCTCTGCTGGTCAGGAGGRATGCCTTCCTTGTCYTGGATCTTTGCYTTGACRTTCTCRATGGTG
TCACTCGGCTCCACTTCGAGAGTGATGGTCTTACCAGTCAGGGTCTTCACGAAGATCTGCATCCCACCTCTAA
```

11740.2.contig

```
AAGTCACAAACAGACAAAGATTATTACCAGCTGCAAGCTATATTAGAAGCTGAACGAAGAGACAGAGGTCATGATT
CTGAGATGATTGGAGACCTTCAAGCTCGAATTACATCTTTACAAGAGGAGGTGAAGCATCTCAAACATAATCTCGA
AAAAGTGGAAGGAGAAAGAAAAGAGGCTCAAGACATGCTTAATCACTCAGAAAAGGAAAAGAATAATTTAGAGATA
GATTTAAACTACAAACTTAAATCATTACAACAACGGTTAGAACAAGAGGTAAATGAACACAAAGTAACCAAAGCTC
GTTTAACTGACAAACATCAATCTATTGAAGAGGCAAAGTCTGTGGCAATGTGTGAGATGGAAAAAAAGCTGAAAGA
AGAAAGAGAAGCTCGAGAGAAGGCTGAAAATCGGGTTGTTCAGATTGAGAAACAGTGTTCCATGCTAGACGTTGAT
CTGAAGCAATCTCAGCAGAAACTAGAACATTTGACTGGAAATAAAGAAAGGATGGAGGATGAAGTTAAGAATCTA
```

*Fig. 15D*

11765.2&64.2.contig

```
CGCCTCCACCATGTCCATCAGGGTGACCCAGAAGTCCTACAAGGTGTCCACCTCTGGCCCCCGGGCCTTCAGCAGC
CGCTCCTACACGAGTGGGCCCGGTTCCCGCATCAGCTCCTCGAGCTTCTCCCGAGTGGGCAGCAGCAACTTTCGCG
GTGGCCTGGGCGGCGGCTATGGTGGGGCCAGCGGCATGGGAGGCATCACCGCAGTTACGGTCAACCAGAGCCTGCT
GAGCCCCCTTGTCCTGGAGGTGGACCCCAACATCCAGGCCGTGCGCACCCAGGAGAAGGAGCAGATCAAGACCCTC
AACAACAAGTTTGCCTCCTTCATAGACAAGGTACGGTTCCTGGAGCAGCAGAACAAGATGCTGGAGACCAAGTGGA
GCCTCCTGCAGCAGCAGAAGACGGCTCGAAGCAACATGGACAACATGTTCGAGAGCTACATCAACARCCTTAGGCG
GCAGCTGGAGACTCTGGGCCAGGAGAAGCTGAAGCTGGAGGCGGAGCTTGGCAACATGCAGGGGCTGGTGGAGGAC
TTCAAGAACAAGTATGAGGATGAGATCAATAAGCGTACAGAGATGGAGAACGAATTTGTCCTCATCAAGAAGGATG
TGGATGAAGCTTACATGAACAAGGTAGAGCTGGAGTCTCGCCTGGAAGGGCTGACCGACGAGATCAACTTCCTCAG
GCAGCTGTATGAAGAGGAGATCCGGGAGCTGCAGTCCCAGATCTCGGACACATCTGTGGTGCTGTCCATGGACAAC
AGCCGCTCCCTGGACATGGACAGCATCATTGCTGAGGTCAAGGCACAGTACGAGGATATTGCCAACCGCAGCCGGG
CTGAGGCTGAGAGCATGTACCAGGTCAAGTATGAGGAGCTGCAGAGCCTGGCTGGGAAGCACGGGGATGACCTGCG
GCGCACAAAGACTGAGATCTCTGAGATGAACCCGGAACATCAGCCCGGCTXCAGGCTGAGATTGAGGGCCTCAAAG
GCCAGAXGGCTTXCCTGGAXGXCCGCCAT
```

11767.2.contig

```
CCCGGAGCCAGCCAACGAGCGGAAAATGGCAGACAATTTTTTCGCTCCATGATGCGTTATCTGGGTCTGGAAACCCA
AACCCTCAAGGATGGCCTGGCGCATGGGGGAACCAGCCTGCTGGGGCAGGGGGCTACCCAGGGGCTTCCTATCCTG
GGGCCTACCCCGGGCAGGCACCCCCAGGGGCTTATCCTGGACAGGCACCTCCAGGCGCCTACCCTGGAGCACCTGG
AGCTTATCCCGGAGCACCTGCACCTGGAGTCTACCCAGGGCCACCCAGCGGCCCTGGGGCCTACCCATCTTCTGGA
CAGCCAAGTGCCACCGGAGCCTACCCTGCCACTGGCCCCTATGGCGCCCCTGCTGGGCCACTGATTGTGCCTTATA
ACCTGCCTTTGCCTGGGGGAGTGGTGCCTCGCATGCTGATAACAATTCTGGGCACGGTGAAGCCCAATGCAAACAG
AATTGCTTTAGATTTCCAAAGAGGGAATGATGTTGCCTTCCACTTTAACCCACGCTTCAATGAGAACAACAGGAGA
GTCATTGGTTGCAATACAAAGCTGGATAA
```

11768-1&2

```
GGGAATGCAACAACTTTATTGAAAGGAAAGTGCAATGAAATTTGTTGAAACCTTAAAAGGGGAAACTTAGACACCC
CCCCTCRAgCGMAGKACCARgTGCARAgGTGGACTCTTTCTGGATGTTGTAGTCAGACAGGGTRCGWCCATCTTCC
AGCTGTTTYCCRGCAAAGATCAACCTCTGCTGATCAGGAGGRATGCCTTCCTTATCTTGGATCTTTGCCTTGACAT
TCTCGATGGTGTCACTGGGCTCCACCTCGAGGGTGATGGTCTTACCAGTCAGGGTCTTCACGAAGATYTGCATCCC
ACCTCTGAGACGGAGCACCAGGTGCAGGGTRGACTCTTTCTGGATGTTGTAGTCAGACAGGGTGCGYCCATCTTCC
AGCTGcTTTCCSaGCAAAGATCAACCTCTGCTGGTCAGGAGGRATGCCTTCCTTGTCYTGGATCTTTGCYTTGACR
TTCTCAATGGTGTCACTCGGCTCCACTTCGAGAGTGATGGTCTTACCAGTCAGGGTCTTCACGAAGATCTGCATCC
CACCTCTAAGACGGAGCACCAGGTGCAGGGTGGACTCTTTCTGGATGgTTGTAGTCAGACAGGGTGCGTCCATCTT
CCAGCTGTTTCCCAGCAAAGATCAACCT
```

```
AGGTTGATCTTTGCTGGGAAACAGCTGGAAGATGGACGCACCCTGTCTGACTACAACCATCCAGAAAGAGTCCACC
CTGCACCTGGTGCTCCGTCTTAGAGGTGGGATGCAGATCTTCGTGAAGACCCTGACTGGTAAGACCATCACTCTCG
AAGTGGAGCCGAGTGACACCATTGAGAAYGTCAARGCAAAGATCCARGACAAGGAAGGCATYCCTCCTGACCAGCA
GAGGTTGATCTTTGCtSGGAAAgCAGCTGGAAGATGGRCGCACCCTGTCTGACTACAACATCCAGAAAGAGTCYAC
CCTGCACCTGGTGCTCCGTCTCAGAGGTGGGATGCARATCTTCGTGAAGACCCTGACTGGTAAGACCATCACCCTC
GAGGTGGAGCCCAGTGACACCATCGAGAATGTCAAGGCAAAGATCCAAGATAAGGAAGGCATCCCTCCTGATCAGC
AGAGGTTGATCTTTGCTGGGAAACAGCTGGAAGATGGACGCACCCTGTCTGACTACAACATCCAGAAAGAGTCCAC
cTYTGCACYTGGTMCTBCGtCTYaGAGGKGGGRTGcaaaTCTWMGTKWagaCaCtCaCTKKYAAGRYYaTCAMCMW
tgAKKTCgAKYSCASTKWCaCTWTCRAKAAMGTYRWWGCAWagaTCCMAGACAAGGAAGGCATTCCTCCTGACCAG
CAGAGGTTGATCT
```

11769.1.contig

```
ATGGAGTCTCACTCTGTCGACCAGGCTGGAGCGCTGTGGTGCGATATCGGCTCACTGCAGTCTCCACTTCCTGGGT
TCAAGCGATCCTCCTGCCTCAGCCTCCCGAGTAGCTGGGACTACAGGCAGGCGTCACCATAATTTTTGTATTTTTA
GTAGAGACATGGTTTCGCCATGTTGGCTGGGCTGGTCTCGAACTCCTGACCTCAAGTGATCTGTCCTGGCCTCCCA
AAGTGTTGGGATTACAGGCGAAAGCCAACGCTCCCGGCCAGGGAACAACTTTAGAATGAAGGAAATATGCAAAAGA
ACATCACATCAAGGATCAATTAATTACCATCTATTAATTACTATATGTGGGTAATTATGACTATTTCCCAAGCATT
CTACGTTGACTGCTTGAGAAGATGTTTGTCCTGCATGGTGGAGAGTGGAGAAGGGCCAGGATTCTTAGGTT
```

11769.2.contig

```
AGCGCGGTCTTCCGGCGCGAGAAAGCTGAAGGTGATGTGGCCGCCCTCAACCGACGCATCCAGCTCGTTGAGGAGG
AGTTGGACAGGGCTCAGGAACGACTGGCCACGGCCCTGCAGAAGCTGGAGGAGGCAGAAAAAGCTGCAGATGAGAG
TGAGAGAGGAATGAAGGTGATAGAAAACCGGGCCATGAAGGATGAGGAGAAGATGGAGATTCAGGAGATGCAGCTC
AAAGAGGCCAAGCACATTGCGGAAGAGGCTGACCGCAAATACGAGGAGGTAGCTCGTAAGCTGGTCATCCTGGAGG
GTGAGCTGGAGAGGGCAGAGGAGCGTGCGGAGGTGTCTGAACTAAAATGTGGTGACCTGGAAGAAGAACTCAAGAA
TGTTACTAACAATCTGAAATCTCTGGAGGCTGCATCTGAAAAGTATTCTGAAAAGGAGGACAAATATGAAGAAGAA
ATTAAACTTCTGTCTGACAAACTGAAAGAGGCTGAGACCCGTGCTGAATTTGCAGAGAGAACGGTTGCAAAACTGG
AAAAAGACAATTGATGACCTGGAAGAGAAACTTGCCCAGC
```

11770.1.contig

```
GTGCACAGGTCCCATTTATTGTAGAAAATAATAATAATTACAGTGATGAATAGCTCTTCTTAAATTACAAAACAGA
AACCACAAAGAAGGAAGAGGAAAAACCCCAGGACTTCCAAGGGTGAAGCTGTCCCCTCCTCCCTGCCACCCTCCCA
GGCTCATTAGTGTCCTTGGAAGGGGCAGAGGACTCAGAGGGGATCAGTCTCCAGGGGCCCTGGGCTGAAGCGGGTG
AGGCAGAGAGTCCTGAGGCCACAGAGCTGGGCAACCTGAGCCGCCTCTCTGGCCCCCTCCCCCACCACTGCCCAAA
CCTGTTTACAGCACCTTCGCCCCTCCCCTCTAAACCCGTCCATCCACTCTGCACTTCCAGGCAGGTGGGTGGGCC
AGGCCTCAGCCATACTCCTGGGCGCGGGTTTCGGTGAGCAAGGCACAGTCCCAGAGGTGATATCAAGGCCT
```

*Fig. 15F*

11770.2.contig

```
GCAAGGAACTGGTCTGCTCACACTTGCTGGCTTGCGCATCAGGACTGGCTTTATCTCCTGACTCACGGTGCAAAGG
TGCACTCTGCGAACGTTAAGTCCGTCCCCAGCGCTTGGAATCCTACGGCCCCCACAGCCGGATCCCCTCAGCCTTC
CAGGTCCTCAACTCCCGTGGACGCTGAACAATGGCCTCCATGGGGCTACAGGTAATGGGCATCGCGCTGGCCGTCC
TGGGCTGGCTGGCCGTCATGCTGTGCTGCGCGCTGCCCATGTGGCGCGTGACGGCCTTCATCGGCAGCAACATTGT
CACCTCGCAGACCATCTGGGAGGGCCTATGGATGAACTGCGTGGTGCAGAGCACCGGCCAGATGCAGTGCAAGGTG
TACGACTCGCTGCTGGCACTGCCGCAGGACCTGCAGGCGGCCCGCGCCCTCGTCATCATCA
```

11773.1.contig

```
TGCAAAAGGGACACAGGGGTTCAAAAATAAAAATTTCTCTTCCCCCTCCCCAAACCTGTACCCCAGCTCCCCGACC
ACAACCCCCTTCCTCCCCCGGGGAAAGCAAGAAGGAGCAGGTGTGGCATCTGCAGCTGGGAAGAGAGAGGCCGGGG
AGGTGCCGAGCTCGGTGCTGGTCTCTTTCCAAATATAAATACXTGTGTCAGAACTGGAAAATCCTCCAGCACCCAC
CACCCAAGCACTCTCCGTTTTCTGCCGGTGTTTGGAGAGGGGCGGGGGGCAGGGGCGCCAGGCACCGGCTGGCTGC
GGTCTACTGCATCCGCTGGGTGTGCACCCCGCGAGCCTCCTGCTGCTCATTGTAGAAGAGATGACACTCGGGGTCC
CCCCGGATGGTGGGGGCTCCCTGGATCAGCTTCCCGGTGTTGGGGTTCACACACCAGCACTCCCCACGCTGCCCGT
TCAGAGACATCTTGCACTGTTTGAGGTTGTACAGGCCATGCTTGTCACAGTTG
```

11778.1.contig

```
GGGTTGGAGGGACTGGTTCTTTATTTCAAAAAGACACTTGTCAATATTCAGTATCAAAACAGTTGCACTATTGATT
TCTCTTTCTCCCAATCGGCCCCAAAGAGACCACATAAAAGGAGAGTACATTTTAAGCCAATAAGCTGCAGGATGTA
CACCTAACAGACCTCCTAGAAACCTTACCAGAAAATGGGGACTGGGTAGGGAAGGAAACTTAAAAGATCAACAAAC
TGCCAGCCCACGGACTGCAGAGGCTGTCACAGCCAGATGGGGTGGCCAGGGTGCCACAAACCCAAAGCAAAGTTTC
AAAATAATATAAAATTTAAAAAGTTTTGTACATAAGCTATTCAAGATTTCTCCAGCACTGACTGATACAAAGCACA
ATTGAGATGGCACTTCTAGAGACAGCAGCTTCAAACCCAGAAAAGGGTGATGAGATGAGTTTCACATGGCTAAATC
AGTGGCAAAAACACAGTCTTCTTTCTTTCTTTCTTTCAAGGAGGCAGGAAAGCAATTAAGTGGTCACCTCAACATA
AGGGGGACATGATCCATTCTGTAAGCAGTTGTGAAGGGG
```

11778-2&30-2

```
CAGGAACCGGAGCGCGAGCAGTAGCTGGGTGGGCACCATGGCTGGGATCACCACCATCGAGGCGGTGAAGCGCAAG
ATCCAGGTTCTGCAGCAGCAGGCAGATGATGCAGAGGAGCGAGCTGAGCGCCTCCAGCGAGAAGTTGAGGGAGAAA
GGCGGGCCCGGGAACAGGCTGAGGCTGAGGTGGCCTCCTTGAACCGTAGGATCCAGCTGGTTGAAGAAGAGCTGGA
CCGTGCTCAGGAGCGCCTGGCCACTGCCCTGCAAAAGCTGGAAGAAGCTGAAAAAGCTGCTGATGAGAGTGAGAGA
GGTATGAAGGTTATTGAAAACCGGGCCTTAAAAGATGAAGAAAAGATGGAACTCCAGGAAATCCAACTCAAAGAAG
CTAAGCACATTGCAGAAGAGGCAGATAGGAAGTATGAAGAGGTGGCTCGTAAGTTGGTGATCATTGAAGGAGACTT
GGAACGCACAGAGGAACGAGCTGAGCTGGCAGAGTCCCGTTGCCGAGAGATGGATGAGCAGATTAGACTGATGGAC
CAGAACCTGAAGTGTCTGAGTGC
```

*Fig. 15G*

11782.1.contig

```
ATCTACGTCATCAATCAGGCTGGAGACACCATGTTCAATCGAGCTAAGCTGCTCAATATTGGCTTTCAAGAGGCCT
TGAAGGACTATGATTACAACTGCTTTGTGTTCAGTGATGTGGACCTCATTCCGATGGACGACCGTAATGCCTACAG
GTGTTTTTCGCAGCCACGGCACATTTCTGTTGCAATGGACAAGTTCGGGTTTAGCCTGCCATATGTTCAGTATTTT
GGAGGTGTCTCTGCTCTCAGTAAACAACAGTTTCTTGCCATCAATGGATTCCCTAATAATTATTGGGGTTGGGGAG
GAGAAGATGACGACATTTTTAACAGATTAGTTCATAAAGGCATGTCTATATCACGTCCAAATGCTGTAGTAGGGAG
GTGTCGAATGATCCGGCATTCAAGAGACAAGAAAAATGAGCCCAATCCTCAGAGGTTTGACCGGATCGCACATACA
AAGGAAACGATGCGCTTCGATGGTTTGAACTCACTTACCTACAAGGTGTTGGATGTCAGAGATACCCGTTATATAC
CCAAATCAC
```

11782.2.contig

```
CTAGACCTCTAATTAAAAGGCACAATCATGCTGGAGAATGAACAGTCTGACCCCGAGGGCCACAGCGAATTTTAGG
GAAGGAGGCAAAGAGGTGAGAAGGGAAAGGAAAGAAGGAAGGAAGGAGAACAATAAGAACTGGAGACGTTGGGTGG
GTCAGGGAGTGTGGTGGAGGCTCGGAGAGATGGTAAACAAACCTGACTGCTATGAGTTTTCAACCCCATAGTCTAG
GGCCATGAGGGCGTCAGTTCTTGGTGGCTGAGGGTCCTTCCACCCAGCCCACCTGGGGGAGTGGAGTGGGGAGTTC
TGCCAGGTAAGCAGATGTTGTCTCCCAAGTTCCTGACCCAGATGTCTGGCAGGATAACGCTGACCTGTTCCCTCAA
CAAGGGACCTGAAAGTAATTTTGCTCTTTAC
```

11783-1 & 2

```
CCGAATTCAAGCGTCAACGATCCYTCCCTTACCATCAAATCAATTGGCCACCAATGGTACTGAACCTACGAGTACA
CCGACTACgGGCGGACTAATCTTCAACTCCTACATACTTCCCCCATTATTCCTAGAACCAGGCGACCTGCGACTCC
TTGACGTTGACAATCGAGTAGTACTCCCGATTGAAGCCCCCATTCGTATAATAATTACATCACAAGACGTCTTGCA
CTCATGAGCTGTCCCCACATTAGGCTTAAAAACAGATGCAATTCCCGGACGTCTAAGCCAAACCACTTTCACCGCT
ACACGACCGGGGGTATACTACGGTCAATGCTCTGAAATCTGTGGAGCAAACCACAGTTTCATGCCCATCGTCCTAG
AATTAATTCCCCTAAAAATCTTTGAAATAGGGCCCGTATTTACCCTATAGCACCCCCTCTACCCCCTCTAG
```

11786.1.contig

```
GCTCTTCACACTTTTATTGTTAATTCTCTTCACATGGCAGATACAGAGCTGTCGTCTTGAAGACCACCACTGACCA
GGAAATGCCACTTTTACAAAATCATCCCCCCTTTTCATGATTGGAACAGTTTTCCTGACCGTCTGGGAGCGTTGAA
GGGTGACCAGCACATTTGCACATGCAAAAAAGGAGTGACCCCAAGGCCTCAACCACACTTCCCAGAGCTCACCATG
GGCTGCAGGTGACTTGCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGATAAGGAACAGCCACAGC
ACTTCATGCTTGTGAGGGTTAGCTGTAGGAGCGGGTGAAAGGATTCCAGTTTATGAAAATTTAAAGCAAACAACGG
TTTTTAGCTGGGTGGGAAACAGGAAAACTGTGATGTCGGCCAATGACCACCATTTTTCTGCCCATGTGAAGGTCCC
CATGAAACC
```

*Fig. 15H*

11786.2.contig

```
CAAGCGCTTGGCGTTTGGACCCAGTTCAGTGAGGTTCTTGGGTTTTGTGCCTTTGGGGATTTTGGTTTGACCCAGG
GGTCAGCCTTAGGAAGGTCTTCAGGAGGAGGCCGAGTTCCCCTTCAGTACCACCCCTCTCTCCCCACTTTCCCTCT
CCCGGCAACATCTCTGGGAATCAACAGCATATTGACACGTTGGAGCCGAGCCTGAACATGCCCCTCGGCCCCAGCA
CATGGAAAACCCCCTTCCTTGCCTAAGGTGTCTGAGTTTCTGGCTCTTGAGGCATTTCCAGACTTGAAATTCTCAT
CAGTCCATTGCTCTTGAGTCTTTGCAGAGAACCTCAGATCAGGTGCACCTGGGAGAAAGACTTTGTCCCCACTTAC
AGATCTATCTCCTCCCTTGGGAAGGGCAGGGAATGGGGACGGTGTATGGAGGGGAAGGGATCTCCTGCGCCCTTCA
TTGCCACACTTGGTGGGACCATGAACATCTTTAGTGTCTGAGCTTCTCAAATTACTGCAATAGGA
```

13691.1&2

```
AGCGTCAAATCAGAATGGAAAAGACTCAAAACCATCATCAACACCAAGATCAAAAGGACAAGRATCCTTCAAGAAA
CAGGAAAAAACTCCTAAAACACCAAAAGGACCTAGTTCTGTAGAAGACATTAAAGCAAAAATGCAAGCAAGTATAG
AAAAAGGTGGTTCTCTTCCCAAAGTGGAAGCCAAATTCATCAATTATGTGAAGAATTGCTTCCGGATGACTGACCA
AGAGGCTATTCAAGATCTCTGGCAGTGGAGGAAGTCTCTTTAAGAAAATAGTTTAAACAATTTGTTAAAAAATTTT
CCGTCTTATTTCATTTCTGTAACAGTTGATATCTGGCTGTCCTTTTTATAATGCAGAGTGAGAACTTTCCCTACCG
TGTTTGATAAATGTTGTCCAGGTTCTATTGCCAAGAATGTGTTGTCCAAAATGCCTGTTTAGTTTTTAAAGATGGA
ACTCCACCCTTTGCTTGGTTTTAAGTATGTATGGAATGTTATGATAGGACATAGTAGTAGCGGTGGTCAGACATGG
AAATGGTGGGSMGACAAAAATATACATGTGAAATAA
```

13692.1&2

```
TCCGAATTCCAAGCGAATTATGGACAAACGATTCCTTTTAGAGGATTACTTTTTTCAATTTCGGTTTTAGTAATCT
AGGCTTTGCCTGTAAAGAATACAACGATGGATTTTAAATACTGTTTGTGGAATGTGTTTAAAGGATTGATTCTAGA
ACCTTTGTATATTTGATAGTATTTCTAACTTTCATTTCTTTACTGTTTGCAGTTAATGTTCATGTTCTGCTATGCA
ATCGTTTATATGCACGTTTCTTTAATTTTTTTAGATTTTCCTGGATGTATAGTTTAAACAACAAAAAGTCTATTTA
AAACTGTAGCAGTAGTTTACAGTTCTAGCAAAGAGGAAAGTTGTGGGGTTAAACTTTGTATTTTCTTTCTTATAGA
GGCTTCTAAAAAGGTATTTTTATATGTTCTTTTTAACAAATATTGTGTACAACCTTTAAAACATCAATGTTTGGAT
CAAAACAAGACCCAGCTTATTTTCTGC
```

13693.2

```
TGTGGTGGCGCGGGCTGAGGTGGAGGCCCAGGACTCTGACCCTGCCCCTGCCTTCAGCAAGGCCCCCGGCAGCGCC
GGCCACTACGAACTGCCGTGGGTTGAAAAATATAGGCCAGTAAAGCTGAATGAAATTGTCGGGAATGAAGACACCG
TGAGCAGGCTAGAGGTCTTTGCAAGGGAAGGAAATGTGCCCAACATCATCATTGCGGGCCCTCCAGGAACCGGCAA
GACCACAAGCATTCTGTGCTTGGCCCGGGCCCTGCTGGGCCCAGCACTCAAAGATGCCATGTTGGAACTCAATGCT
TCAAATGACAGGGGCATTGACGTTGTGAGGAATAAAATTAAAATGTTTGCTCAACAAAAAGTCACTCTTCCCAAAG
GCCGACATAAGATCATCATTCTGGATGAAGCAGACAGCATGACCGACGGAGCCCAGCAAGCCTTGAGGAGAACCAT
GGAAATCTACTCTAAAACCACTCGTTCGCCCTTGCTTGTAATGCTTCGGATAAGATCATCGAGCC
```

```
CTTTGCAAAGCTTTTATTTCATGTCTGCGGCATGGAATCCACCTGCACATGGCATCTTAGCTGTGAAGGAGAAAGC
AGTGCACGAGAAGGAATGAGTGGGCGGAACCAACGGCCTCCACAAGCTGCCTTCCAGCAGCCTGCCAAGGCCATGG
CAGAGAGAGACTGCAAACAAACACAAGCAAACAGAGTCTCTTCACAGCTGGAGTCTGAAAGCTCATAGTGGCATGT
GTGAATCTGACAAAATTAAAAGTGTGCATAGTCCATTACATGCATAAAACACTAATAATAATCCTGTTTACACGTG
ACTGCAGCAGGCAGGTCCAGCTCCACCACTGCCCTCCTGCCACATCACATCAAGTGCCATGGTTTAGAGGGTTTTT
CATATGTAATTCTTTTATTCTGTAAAAGGTAACAAAATATACAGAACAAAACTTTCCCTTTTTAAAACTAATGTTA
CAAATCTGTATTATCACTTGGATATAAATAGTATATAAGCTGATC
```

13700.1

```
CAAGGGATATATGTTGAGGGTACRGRGTGACACTGAACAGATCACAAAGCACGAGAAACATTAGTTCTCTCCCTCC
CCAGCGTCTCCTTCGTCTCCCTGGTTTTCCGATGTCCACAGAGTGAGATTGTCCCTAAGTAACTGCATGATCAGAG
TGCTGKCTTTATAAGACTCTTCATTCAGCGTATCCAATTCAGCAATTGCTTCATCAAATGCCGTTTTTGCCAGGCT
ACAGGCCTTTTCAGGAGAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTTCGACACAAGTGGTT
TGTTTGTTGCTCCAGATGCCACTTCAGAAAGATACCTAAAATAATCTCCTTTCATTTTCAAAGTAGAACAC
```

13700.2

```
TCCGGAGCCGGGGTAGTCGCCGCCGCCGCCGGTGCAGCCACTGCAGGCACCGCTGCCGCCGCCTGAGTAGTGG
GCTTAGGAAGGAAGAGGTCATCTCGCTCGGAGCTTCGCTCGGAAGGGTCTTTGTTCCCTGCAGCCCTCCCACGGGA
ATGACAATGGATAAAAGTGAGCTGGTACAGAAAGCCAAACTCGCTGAGCAGGCTGAGCGATATGATGATATGGCTG
CAGCCATGAAGGCAGTCACAGAACAGGGGCATGAACTCTCCAACGAAGAGAGAAATCTGCTCTCTGTTGCCTACAA
GAATGTGGTAAGGCCGCCCGCCGCTCTTCCTGGCGTGTCATCTCCAGCATTGAGCAGAAAACAGAGAGGAATGAGA
AGAAGCAGCAGATGGGCAAAGAGTACCGTGAGAAGATAGAGGCAGAACTGCAGGACATCTGCAATGATGTTCTGGA
GCTTGTTGGACAAATATCTTATTCCAATGCTACACAACCCAGAAA
```

13701.1

```
AAAAAGCAGCARGTTCAACACAAAATAGAAATCTCAAATGTAGGATAGAACAAAACCAAGTGTGTGAGGGGGGAAG
CAACAGCAAAAGGAAGAAATGAGATGTTGCAAAAAAGATGGAGGAGGGTTCCCCTCTCCTCTGGGGACTGACTCAA
ACACTGATGTGGCAGTATACACCATTCCAGAGTCAGGGGTGTTCATTCTTTTTTGGGAGTAAGAAAAGGTGGGGAT
TAAGAAGACGTTTCTGGAGGCTTAGGGACCAAGGCTGGTCTCTTTCCCCCCTCCCAACCCCCTTGATCCCTTTCTC
TGATCAGGGGAAAGGAGCTCGAATGAGGGAGGTAGAGTTGGAAAGGGAAAGGATTCCACTTGACAGAATGGGACAG
ACTCCTTCCCA
```

TGGCAATAGCACAGCCATCCAGGAGCTCTTCARGCGCATCTCGGAGCAGTTCACTGCCATGTTCCGCCGGAAGGCC
TTCCTCCACTGGTACACAGGCGAGGGCATGGACGAGATGGAGTTCACCGAGGCTGAGAGCAACATGAACGACCTCG
TCTCTGAGTATCAAGCAGTACCAGGATGCCACCGCAGAAGAGGAGGAGGATTTCGGTGAGGAGGCCGAAGAGGAGG
CCTAAGGCAGAGCCCCCATCACCTCAGGCTTCTCAGTTCCCTTAGCCGTCTTACTCAACTGCCCCTTTCCTCTCCC
TCAGAATTTGTGTTTGCTGCCTCTATCTTGTTTTTTGTTTTTTCTTCTGGGGGGGTCTAGAACAGTGCCTGGCACA
TAGTAGGCGCTCAATAAATACTTGGTTGNTGAATGTCTCCT

13702.2

AGCTGGCGCTAGGGCTCGGTTGTGAAATACAGCGTRGTCAGCCCTTGCGCTCAGTGTAGAAACCCACGCCTGTAAG
GTCGGTCTTCGTCCATCTGCTTTTTTCTGAAATACACTAAGAGCAGCCACAAAACTGTAACCTCAAGGAAACCATA
AAGCTTGGAGTGCCTTAATTTTTAACCAGTTTCCAATAAAACGGTTTACTACCT

13704.2-13740.2

GGAGATGAAGATGAGGAAGCTGAGTCAGCTACGGGCARGCGGGCAGCTGAAGATGATGAGGATGACGATGTCGATA
CCAAGAAGCAGAAGACCGACGAGGATGACTAGACAGCAAAAAAGGAAAAGTTAAA

13706.1

GATGAAAATTAAATACTTAAATTAATCAAAAGGCACTACGATACCACCTAAAACCTACTGCCTCAGTGGCAGTAKG
CTAAKGAAGATCAAGCTACAGSACATYATCTAATATGAATGTTAGCAATTACATAKCARGAAGCATGTTTGCTTTC
CAGAAGACTATGGNACAATGGTCATTWGGGCCCAAGAGGATATTTGGCCNGGAAAGGATCAAGATAGATNAANGTA
AAG

13706.2

GAGTAGCAACGCAAAGCGCTTGGTATTGAGTCTGTGGGSGACTTCGGTTCCGGTCTCTGCAGCAGCCGTGATCGCT
TAGTGGAGTGCTTAGGGTAGTTGGCCAGGATGCCGAATATCAAAATCTTCAGCAGGCAGCTCCCACCAGGACTTAT
CTCASAAAATTGCTGACCGCCTGGGCCTGGAGCTAGGCAAGGTGGTGACTAAGAAATTCAGCAACCAGGAGACCTG
TGTGGAAATTGGTGAAAGTGTACCGTGGAGAGGATGTCTACATTGTTCAGAGTGGNTGTGGCGAAATCAATGACAA
TTTAATGGAGCTTTTGATCATGATTAATGCCTGCAAGATTGCTTCAGCCAGCCGGGTTACTGCAGTCATCCCATGC
TTCCCTTATGCCCCGGCAGGATAAGAAAGATNAGAGCCGGGCCGCCAATCTCAGCCAAGCTTGGTGCAAATATGCT
ATCTGTAGCAGTGCAGATCATATTATCACCATGGACCTACATGCTTCTCAAATTCANGGCTTTTT

```
ATGCAAAAGGGGACACAGGGGGTTCAAAAATAAAAATTTCTCTTCCCCCTCCCCAAACCTGTACCCCAGCTCCCCG
ACCACAACCCCCTTCCTCCCCCGGGGAAAGCAAGAAGGAGCAGGTGTGGCATCTGCAGCTGGGAAGAGAGAGGCCG
GGGAGGTGCCGAGCTCGGTGCTGGTCTCTTTCCAAATATAAATACGTGTGTCAGAACTGGAAAATCCTCCAGCACC
CACCACCCAAGCACTCTCCGTTTTCTGCCGGTGTTTGGAGAGGGGCGGNGGGCAGGGGCGCCAGGCACCGGCTGGC
TGCGGTCTACTGCATCCGCTGGGTGTGCACCCCGCGA
```

13710.2

```
AGGTTGGAGAAGGTCATGCAGGTGCAGATTGTCCAGGSKCAGCCACAGGGTCAAGCCCAACAGGCCCAGAGTGGCA
CTGGACAGACCATGCAGGTGATGCAGCAGATCATCACTAACACAGGAGAGATCCAGCAGATCCCGGTGCAGCTGAA
TGCCGGCCAGCTGCAGTATATCCGCTTAGCCCAGCCTGTATCAGGCACTCAAGTTGTGCAGGGACAGATCCAGACA
CTTGCCACCAATGCTCAACAGATTACACAGACAGAGGTCCAGCAAGGACAGCAGCAGTTCAAGCCAGTTCACAAGA
TGGACAGCAGCTCTACCAGATCCAGCAAGTCACCATGCCTGCGGGCCANGACCTCGCCAGCCCATGTTCATCCAGT
CAAGCCAACCAGCCCTTCNACGGGCAGGCCCCCAGGTGACCGGCGACTGAAGGGCCTGAGCTGGCAAGGCCAANG
ACACCCAACACAATTTTTGCCATACAGCCCCCAGGCAATGGGCACAGCCTTTCTTCCCAGAGGAC
```

13710-1

```
TGAGATTTATTGCATTTCATGCAGCTTGAAGTCCATGCAAAGGRGACTAGCACAGTTTTTAATGCATTTAAAAAAT
AAAAGGGAGGTGGGCAGCAAACACACAAAGTCCTAGTTTCCTGGGTCCCTGGGAGAAAAGAGTGTGGCAATGAATC
CACCCACTCTCCACAGGGAATAAATCTGTCTCTTAAATGCAAAGAATGTTTCCATGGCCTCTGGATGCAAATACAC
AGAGCTCTGGGGTCAGAGCAAGGGATGGGGAGAGGACCACGAGTGAAAAAGCAGCTACACACATTCACCTAATTCC
ATCTGAGGGCAAGAACAACGTGGCAAGTCTTGGGGGTAGCAGCTGTT
```

13711.1

```
TCCAGACATGCTCCTGTCCTAGGCGGGGAGCAGGAACCAGACCTGCTATGGGAAGCAGAAAGAGTTAAGGGAAGGT
TTCCTTTCATTCCTGTTCCTTCTCTTTTGCTTTTGAACAGTTTTTAAATATACTAATAGCTAAGTCATTTGCCAGC
CAGGTCCCGGTGAACAGTAGAGAACAAGGAGCTTGCTAAGAATTAATTTTGCTGTTTTTCACCCCATTCAAACAGA
GCTGCCCTGTTCCCTGATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCTACTTAATAAATATAT
TTATACTTTGAAATTATGATAACCGATTTTTCCCATGCGGCATCCTAAGGGCACTTGCCAGCTCTTATCCGGACAG
TCAAGCACTGTTGTTGGACAACAGATAAAGGAAAAGAAAAAGAAGAAAACAACCGCAACTTCTGT
```

TGAGACGGACCACTGGCCTGGTCCCCCCTCATKTGCTGTCGTAGGACCTGACATGAAACGCAGATCTAGTGGCAGA
GAGGAAGATGATGAGGAACTTCTGAGACGTCGGCAGCTTCAAGAAGAGCAATTAATGAAGCTTAACTCAGGCCTGG
GACAGTTGATCTTGAAAGAAGAGATGGAGAAAGAGAGCCGGGAAAGGTCATCTCTGTTAGCCAGTCGCTACGATTC
TCCCATCAACTCAGCTTCACATATTCCATCATCTAAAACTGCATCTCTCCCTGGCTATGGAAGAAATGGGCTTCAC
CGGCCTGTTTCTACCGACTTCGCTCAGTATAACAGCTATGGGGATGTCAGCGGGGGAGTGCGAGATTACCAGACAC
TTCCAGATGGCCACATGCCTGCAATGAGAATGGACCGAGGAGTGTCTATGCCCAACATGTTGGAACCAAAGATATT
TCCATATGAAATGCTCATGGTGACCAACAGAGGGCCGAAACCAAATCTCAGAGAGGTGGACAGAA

13713.1&2

TCACTTTATTTTTCTTGTATAAAAACCCTATGTTGTAGCCACAGCTGGAGCCTGAGTCCGCTGCACGGAGACTCTG
GTGTGGGTCTTGACGAGGTGGTCAGTGAACTCCTGATAGGGAGACTTGGTGAATACAGTCTCCTTCCAGAGGTCGG
GGGTCAGGTAGCTGTAGGTCTTAGAAATGGCATCAAAGGTGGCCTTGGCGAAGTTGCCCAGGGTGGCAGTGCAGCC
CCGGGCTGAGGTGTAGCAGTCATCGATACCAGCCATCATGAG

13715.4

CTGGAATATAGACCCGTGATCGACAAAACTTTGAACGAGGCTGACTGTGCCACCGTCCCGCCAGCCATTCGCTCCT
ACTGATGAGACAAGATGTGGTGATGACAGAATCAGCTTTTGTAATTATGTATAATAGCTCATGCATGTGTCCATGT
CATAACTGTCTTCATACGCTTCTGCACTCTGGGGAAGAAGGAGTACATTGAAGGGAGATTGGCACCTAGTGGCTGG
GAGCTTGCCAGGAACCCAGTGGCCAGGGAGCGTGGCACTTACCTTTGTCCCTTGCTTCATTCTTGTGAGATGATAA
AACTGGGCACAGCTCTTAAATAAAATATAAATGAACA

13717.1&2

TGAATGGGGAGGAGCTGACCCAGGAAATGGAGCTTGNGGAGACCAGGCCTGCAGGGGATGGAACCTTCCAGAAGTG
GGCATCTGTGGTGGTGCCTCTTGGGAAGGAGCAGAAGTACACATGCCATGTGGAACATGAGGGGCTGCCTGAGCCC
CTCACCCTGAGATGGGGCAAGGAGGAGCCTCCTTCATCCACCAAGACTAACACAGTAATCATTGCTGTTCCGGTTG
TCCTTGGAGCTGTGGTCATCCTTGGAGCTGTGATGGCTTTTGTGATGAAGAGGAGGAGAAACACAGGTGGAAAAGG
AGGGGACTATGCTCTGGCTCCAGGCTCCAGAGCTCTGATATGTCTCTCCCAGATTGTAAAGTGTGAAGACAGCTG
CCTGGTGTGGACTTGGTGACAGACAATGTCTTCACACATCTCCTGTGACATCCAGAGACCTCAGTTCTCTTTAGTC
AAGTGTCTGATGTTCCCTGTGAGTCTGCGGGCTCAAAGTGAAGAACTGTGGAGCCCAGTCCACCCCTGCACACCAG
GACCCTATCCCTGCACTGCCCTGTGTTCCCTTCCACAGCCAACCTTGCTGCTCCAGCCAAACATTGGTGGACATCT
GCAGCCTGTCAGCTCCATGCTACCCTGACCTTCAACTCCTCACTTCCACACTGAGAATAATAATTTGAATGTGGGT
GGCTGGAGAGATGGCTCAGCGCTGACTGCTCTTCCAAAGGTCCTGAGTTCAAATCCCAGCAACCACATGGTGGCTC
ACAACCATCTGTAATGGGATCTAATACCCTCTTCTGCAGTGTCTGAAGACASCTACAGTGTACTTACATATAATAA
TAAATAAG

```
GGCCGGGCGCGCGCGCCCCCGCCACACGCACGCCGGGCGTGCCAGTTTATAAAGGGAGAGAGCAAGCAGCGAGTCT
TGAAGCTCTGTTTGGTGCTTTGGATCCATTTCCATCGGTCCTTACAGCCGCTCGTCAGACTCCAGCAGCCAAGATG
GTGAAGCAGATCGAGAGCAAGACTGCTTTTCAGGAAGCCTTGGACGCTGCAGGTGATAAACTTGTAGTAGTTGACT
TCTCAGCCACGTGGTGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAATGCATGCCAACATTC
CAGTTTTTTAAGAAGGGACAAAAGGTGGGTGAATTTTCTGGAGCCAATAAGGAAAAGCTTGAAGCCACCATTAATG
AATTAGTCTAATCATGTTTTCTGAAAATATAACCAGCCATTGGCTATTTAAAACTTGTAATTTTTTTAATTTACAA
AAATATAAAATATGAAGACATAAACCCMGTTGCCATCTGCGTGACAATAAAACATTAATGCTAACACTT
```

13721.1

```
TCACATAAGAAATTTAAGCAAGTTACRCTATCTTAAAAAACACAACGAATGCATTTTAATAGAGAAACCCTTCCCT
CCCTCCACCTCCCTCCCCCACCCTCCTCATGAATTAAGAATCTAAGAGAAGAAGTAACCATAAAACCAAGTTTTGT
GGAATCCATCATCCAGAGTGCTTACATGGTGATTAGGTTAATATTGCCTTCTTACAAAATTTCTATTTTAAAAAAA
ATTATAACCTTGATTGCTTATTACAAAAAAATTCAGTACAAAAGTTCAATATATTGAAAAATGCTTTTCCCCTCCC
TCACAGCACCGTTTTATATATAGCAGAGAATAATGAAGAGATTGCTAGTCTAGATGGGGCAATCTTCAAATTACAC
CAAGACGCACAGTGGTTTATTTACCCTCCCCTTCTCATAAG
```

13721.2

```
GGAAAGGATTCAAGAATTAGAGGACTTGCTTGCTRRAGAAAAAGACAACTCTCGTCGCATGCTGACAGACAAAGAG
AGAGAGATGGCGGAAATAAGGGATCAAATGCAGCAACAGCTGAATGACTATGAACAGCTTCTTGATGTAAAGTTAG
CCCTGGACATGGAAATCAGTGCTTACAGGAAACTCTTAGAAGGCGAAGAAGAGAGGTTGAAGCTGTCTCCAAGCCC
TTCTTCCCGTGTGACAGTATCCCGAGCATCCTCAAGTCGTAGTGTACCGTACAACTAGAGGAAAGCGGAAGAGGGT
TGATGTGGAAGAATCAGAGGCGAAGTAGTAGTGTTAGCATCTCTCATTCCGCCTCAACCACTGGAAATGTTTGCAT
CGAAGAAATTGATGTTGATGGGAAATTTATCCCGCTTGAAGAACACTTCTGAACAGGATCAACCAATGGGAAGGCT
TGGGAGATGATCAGAAAAATTGGAGACACATCAGTCAGTTATAAATATACCTCAA
```

13723.1

```
CATGGGTTTCACCAGGTTGGCCAGGCTGCTCTTGAACTSCTGACCTCAGGTGATCCACCCGCCTCGGCCTCCCAAA
GTGCTGGGATTACAGGCGTGAGCCACCACGCCCGGCCCCCAAAGCTGTTTCTTTTGTCTTTAGCGTAAAGCTCTCC
TGCCATGCAGTATCTACATAACTGACGTGACTGCCAGCAAGCTCAGTCACTCCGTGGTCTTTTTCTCTTTCCAGTT
CTTCTCTCTCTCTTCAAGTTCTGCCTCAGTGAAAGCTGCAGGTCCCCAGTTAAGTGATCAGGTGAGGGTTCTTTGA
ACCTGGTTCTATCAGTCGAATTAATCCTTCATGATGG
```

GATGTGTTGGACCCTCTGTGTCAAAAAAAACCTCACAAAGAATCCCCTGCTCATTACAGAAGAAGATGCATTTAAA
ATATGGGTTATTTTCAACTTTTTTATCTGAGGACAAGTATCCATTAATTATTGTGTCAGAAGAGATTGAATACCTGC
TTAAGAAGCTTACAGAAGCTATGGGAGGAGGTTGGCAGCAAGAACAATTTGAACATTATAAAATCAACTTTGATGA
CAGTAAAAATGGCCTTTCTGCATGGGAACTTATTGAGCTTATTGGAAATGGACAGTTTAGCAAAGGCATGGACCGG
CAGACTGTGTCTATGGCAATTAATGAAGTCTTTAATGAACTTATATTAGATGTGTTAAAGCAGGGTTACATGATGA
AAAAGGGCCACAGACGGAAAAACTGGACTGAAAGATGGTTTGTACTAAAACCCAACATAATTTCTTACTATGTGAG
TGAGGATCTGAAGGATAAGAAAGGAGACATTCTCTTGGATGAAAATTGCTGTGTAGAAGTCCTTGCCTGACAAAAG
ATGGAAAGAAATGCCTTTT 13725.1

GACTGGTTCTTTATTTCAAAAAGACACTTGTCAATATTCAGTRTCAAAACAGTTGCACTATTGATTTCTCTTTCTC
CCAATCGGCCCCAAAGAGACCACATAAAAGGAGAGTACATTTTAAGCCAATAAGCTGCAGGATGTACACCTAACAG
ACCTCCTAGAAACCTTACCAGAAAATGGGGACTGGGTAGGGAAGGAAACTTAAAAGATCAACAAACTGCCAGCCCA
CGGACTGCAGAGGCTGTCACAGCCAGATGGGGTGGCCAGGGTGCCACAAACCCAAAGCAAAGTTTCAAAATAATAT
AAAATTTAAAAAGTTTTGTACATAAGCTATTCAAGATTTCTCCAGCACTGACTGATACAAAGCACAATTGAGATGG
CACTTCTAGAGACAGCAGCTTCAAACCCAGAAAAGGGTGATGAGATGAAGTTTCACATGGCTAAATCAGTGGCAAA
AACACAGTCTTCTTTCTTTCTTTCTTTCAAGGANGCAGGAAAGCAATTAAGTGGTCACCTTAACATAAGGGGGAC 13725.2

TGGGTGGGCACCATGGCTGGGATCACCACCATCGAGGCGGTGAAGCGCAAGATCCAGGTTCTGCAGCAGCAGGCAG
ATGATGCAGAGGAGCGAGCTGAGCGCCTCCAGCGAGAAGTTGAGGGAGAAAGGCGGGCCCGGGAACAGGCTGAGGC
TGAGGTGGCCTCCTTGAACCGTAGGATCCAGCTGGTTGAAGAAGAGCTGGACCGTGCTCAGGAGCGCCTGGCCACT
GCCCTGCAAAAGCTGGAAGAAGCTGAAAAAGCTGCTGATGAGAGTGAGAGAGGTATGAAGGTTATTGAAAACCGGG
CCTTAAAAGATGAAGAAAAGATGGAACTCCAGGAAATCCAACTCAAAGAAGCTAAGCACATTGCAGAAGAGGCAGA
TAGGAAGTATGAAGAGGTGGCTCGTAAGTTGGTGATCATTGAAGGAGACTTGGAACCGCACAGAAGGAACGAGCTT
GAGCTTGGCAAAAGTCCCGTTGCCCAGAGATGGGATGAACCAGATTAGACTGATGGACCANAACC 13726.1&2

AGGGGCNGCGGGTGCGTGGGCCACTGGGTGACCGACTTAGCCTGGCCAGACTCTCAGCACCTGGAAGCGCCCCGAG
AGTGACAGCGTGAGGCTGGGAGGGAGGACTTGGCTTGAGCTTGTTAAACTCTGCTCTGAGCCTCCTTGTCGCCTGC
ATTTAGATGGCTCCCGCAAAGAAGGGTGGCGAGAAGAAAAAGGGCCGTTCTGCCATCAACGAAGTGGTAACCCGAG
AATACACCATCAACATTCACAAGCGCATCCATGGAGTGGGCTTCAAGAAGCGTGCACCTCGGGCACTCAAAGAGAT
TCGGAAATTTGCCATGAAGGAGATGGGAACTCCAGATGTGCGCATTGACACCAGGCTCAACAAAGCTGTCTGGGCC
AAAGGAATAAGGAATGTGCCATACCGAATCCGGTGTGCGGCTGTCCAGAAAACGTAATGAGGATGAAGATTCACCA
AATAAGCTATATACTTTGGTTACCTATGTACCTGTTACCACTTTCAAAAATCTACAGACAGTCAATGTGGATGAGA
ACTAATCGCTGATCGTCAGATCAAATAAAGTTATAAAAT

```
TCGGGAGCCACACTTGGCCCTCTTCCTCTCCAAAGSGCCAGAACCTCCTTCTCTTTGGAGAATGGGGAGGCCTCTT
GGAGACACAGAGGGTTTCACCTTGGATGACCTCTAGAGAAATTGCCCAAGAAGCCCACCTTCTGGTCCCAACCTGC
AGACCCCACAGCAGTCAGTTGGTCAGGCCCTGCTGTAGAAGGTCACTTGGCTCCATTGCCTGCTTCCAACCAATGG
GCAGGAGAGAAGGCCTTTATTTCTCGCCCACCCATTCCTCCTGTACCAGCACCTCCGTTTTCAGTCAGTGTTGTCC
AGCAACGGTACCGTTTACACAGTCACCTCAGACACACCATTTCACCTCCCTTGCCAAGCTGTTAGCCTTAGAGTGA
TTGCAGTGAACACTGTTTACACACCGTGAATCCATTCCCATCAGTCCATTCCAGTTGGCACCAGCCTGAACCATTT
GGTACCTGGTGTTAACTGGAGTCCTGTTTACAAGGTGGAGTCGGGGCTTGCTGACTTCTCTTCATTTGAGGGCAC
```

13727.2

```
ACCTAGACAGAAGGTGGGTGAGGGAGGACTGGTAGGAGGCTGAGGCAATTCCTTGGTAGTTTGTCCTGAAACCCTA
CTGGAGAAGTCAGCATGAGGCACCTACTGAGAGAAGTGCCCAGAAACTGCTGACTGCATCTGTTAAGAGTTAACAG
TAAAGAGGTAGAAGTGTGTTTCTGAATCAGAGTGGAAGCGTCTCAAGGGTCCCACAGTGGAGGTCCCTGAGCTACC
TCCCTTCCGTGAGTGGGAAGAGTGAAGCCCATGAAGAACTGAGATGAAGCAAGGATGGGGTTCCTGGGCTCCAGGC
AAGGGCTGTGCTCTCTGCAGCAGGGAGCCCCACGAGTCAGAAGAAAAGAACTAATCATTTGTTGCAAGAAACCTTG
CCCGGATACTAGCGGAAAACTGGAGGCGGNGGTGGGGGCACAGGAAAGTGGAAGTGATTTGATGGAGAGCAGAGAA
GCCTATGCACAGTGGCCGAGTCCACTTGTAAAGTG
```

13728.1&2

```
TTCAAGCAATTGTAACAAGTATATGTAGATTAGAGTGAGCAAAATCATATACAATTTTCATTTCCAGTTGCTATTT
TCCAAATTGTTCTGTAATGTCGTTAAAATTACTTAAAAATTAACAAAGCCAAAAATTATATTTATGACAAGAAAGC
CATCCCTACATTAATCTTACTTTTCCACTCACCGGCCCATCTCCTTCCTCTTTTTCCTAACTATGCCATTAAAACT
GTTCTACTGGGCCGGGCGTGTGGCTCATGCCTGTAATCCCAGCATTTTGGGAGGCCAAGGCAGGCGGATCATGAGG
TCAAGAGATTGAGACCATCCTGGCCAACATGGTGAAACCCCGCCTCGACTAAGAATACAAAAATTAGCTGGGCATG
GTGGCGCATGCCTGTAGTCTCAGCTACTCGGGAGGCTGAGGCAGAAGAATCGCTTGAACCCGGGAGGCAGAGGATG
CAGTGAGCCCCGATCGCGCCACTGCACTCTAGCCTGGGCGACAGACTGAGACTCTGCTC
```

13731.1&2

```
TGTGCCAGTCTACAGGCCTATCAGCAGCGACTCCTTCAGCAACAGATGGGGTCCCCTGTTCAGCCCAACCCCATGA
GCCCCCAGCAGCATATGCTCCCAAATCAGGCCCAGTCCCCACACCTACAAGGCCAGCAGATCCCTAATTCTCTCTC
CAATCAAGTGCGCTCTCCCCAGCCTGTCCCTTCTCCACGGCCACAGTCCCAGCCCCCCACTCCAGTCCTTCCCCA
AGGATGCAGCCTCAGCCTTCTCCACACCACGTTTCCCCACAGACAAGTTCCCCACATCCTGGACTGGTAGTTGCCC
AGGCCAACCCCATGGAACAAGGGCATTTTGCCAGCC
```

TGTAAAAACTTGTTTTTAATTTTGTATAAAATAAAGGTGGTCCATGCCCACGGGGGCTGTAGGAAATCCAAGCAGACCA
GCTGGGGTGGGGGGATGTAGCCTACCTCGGGGGACTGTCTGTCCTCAAAACGGGCTGAGAAGGCCCGTCAGGGGCCCAG
GTCCCACAGAGAGGCCTGGGATACTCCCCCAACCCGAGGGGCAGACTGGGCAGTGGGCAGCCCCCATCGTGCCCCAGAG
GTGGCCACAGGCTGAAGGAGGGGCCTGAGGCACCGCAGCCTGCAACCCCCAGGGCTGCAGTCCACTAACTTTTTACAGA
ATAAAAGGAACATGGGGATGGGGAAAAAAAGCACCAGGTCAGGCAGGGCCCGAGGGCCCCAGATCCCAGGAGGGCCAGGA
CTCAGGATGCCAGCACCACCCTAGCAGCTCCCACAGCTCCTGGCACAGGAGGCCGCCACGGATTGGCACAGGCCGCTGC
TGGCCATCACGCCACATTTGGAGAACTTGTCCCGACAGAGGTCAGCTCGGAGGAGCTCCTCGTGGGCACACACTGTACG
AACACAGATCTCCTTGTTAATGACGTACACACGGCGGAGGCTGCGGGGACAGGGCACGGGAGGTCTCAGCCCCACTT 13736.2

ATGGCTGCTGGATTTAGGTGGTAATAGGGGCTGTGGGCCATAAATCTGAAGCCTTGAGAACCTTGGGTCTGGAGAGCCA
TGAAGAGGGAAGGAAAAGAGGGCAAGTCCTGAACCTAACCAATGACCTGATGGATTGCTCGACCAAGACACAGAAGTGA
AGTCTGTGTCTGTGCACTTCCCACAGACTGGAGTTTTTGGTGCTGAATAGAGCCAGTTGCTAAAAAATTGGGGGTTTGG
TGAAGAAATCTGATTGTTGTGTGTATTCAATGTGTGATTTTAAAAATAAACAGCAACAACAATAAAAACCCTGACTGGC
TGTTTTTTCCCTGTATTCTTTACAACTATTTTTTTGACCCTCTGAAAATTATTATACTTCACCTAAATGGAAGACTGCTG
TGTTTGTGGAAATTTTGTAATTTTTTAATTTATTTTATTCTCTCTCCTTTTTATTTTGCCTGCAGAATCCGTTGAGAGA
CTAATAAGGCTTAATATTTAATTGATTTGTTTAATATGTATATAAAT 13744.2-13696.2

GGCATGCGAGCGCACTCGGCGGACGCAAGGGCGGCGGGGAGCACACGGAGCACTGCAGGCGCCGGGTTGGGACAGCGTC
TTCGCTGCTGCTGGATAGTCGTGTTTTCGGGGATCGAGGATACTCACCAGAAACCGAAAATGCCGAAACCAATCAATGT
CCGAGTTACCACCATGGATGCAGAGCTGGAGTTTGCAATCCAGCCAAATACAACTGGAAAACAGCTTTTTGATCAGGTG
GTAAAGACTATCGGCCTCCGGGAAGTGTGGTACTTTGGCCTCCACTATGTGGATAATAAAGGATTTCCTACCTGGCTGA
AGCTGGATAAGAAGGTGTCTGCCCAGGAGGTCAGGAAGGAGAATCCCCTCCAGTTCAAGTTCCGGGCCAAaGTTCTACC
CTGAAGATGTGGCTGAGGAGCTCATCCAGGACATCACCCAGAAACTTTTCTTCCTTCAAGTGAAGGAAGGAATCCTTAG
CGATGAGATCTACTGCCCCCCCTTGARACTGCCGTGCTCTTGGGGTCCTACGCTTGTGCATGCCAAGTTTGGGGACTACC
ACCAAGAAG 13746.1&2-13720.1&2

GAAGGAGTCGGGATACTCAGCATTGATGCACCCCAATTTCAAAGCGGCATTCTTCGGCAGGTCTCTGGGACAATCTCTA
GGGTCACTACCTGGAAACTCGTTAGGGTACAACTGAATGCTGAAAGGAAAGAACACCTGCAGAACCGGACAGAAATTCA
CCCCGGCGATCAGCTGATTGATCTCGGTCGACCAGAAGTCATGGCTAAAGATGACGAGGACGTTGTCAATTCCCTGGGC
TTTTCGAAGTGAGTCCAGCAGCAGTCTGAGGTATTCGGGCCGGTTATGCACCTGGACCACCAGCACCAGCTCCGGGGGG
GCCCAGGTGCCAGCCTTATCTACATTCCTCAGGGTCTGATCAAAGTTCAGCTGGTACACCAGGGACCGGTACCGCAGCG
TCAGGTTGTCCGCTCGGGCTGGGGGACCGCCGGGACCAGGGAAGCCGCCGACACGTTGGAGACCCTGCGGATGCCCACA
GCCACAGAGGGGTGGTCCCCACCGCGGCCGCCGGCACCCGCGCGGGTTCGGCGTCCAGCAACGGTGGGGCGAGGGCCT
CGTTCTTCCTTTGTCGCCCATTGCTGCTCCAGAGGACGAAGCCGCAGGCGGCCACCACGAGCGTCAGGATTAGCACCTT
CCGTTTGTAGATGCGGAACCTCATGGTCTCCAGGGCCGGGAGCGCAGCTACAGCTCGAGCGTCGGCGCCGCCGCTAGGA
GCCGCGGCTCGGCTTCGTCTCCGTCCTCTCCATTCAGCACCACGGGTCCCGGAAAAAGCTCAGCCSCGGTCCCAACCGC
ACCCTAGCTTCGTTACCTGCGCCTCGCTTG

```
CAGATTTTTATTTGCAGTCGTCACTGGGGCCGTTTCTTGCTGCTTATTTGTCTGCTAGCCTGCTCTTCCAGCTGCA
TGGCCAGGCGCAAGGCCTTGATGACATCTCGCAGGGCTGAGAAATGCTTGGCTTGCTGGGCCAGAGCAGATTCCGC
TTTGTTCACAAAGGTCTCCAGGTCATAGTCTGGCTGCTCGGTCATCTCAGAGAGCTCAAGCCAGTCTGGTCCTTGC
TGTATGATCTCCTTGAGCTCTTCCATAGCCTTCTCCTCCAGCTCCCTGATCTGAGTCATGGCTTCGTTAAAGCTGG
ACATCTGGGAAGACAGTTCCTCCTCTTCCTTGGATAAATTGCCTGGAATCAGCGCCCCGTTAGAGCAGGCTTCCAT
CTCTTCTGTTTCCATTTGAATCAACTGCTCTCCACTGGGCCCACTGTGGGGGCTCAGCTCCTTGACCCTGCTGCAT
ATCTTAAGGGTGTTTAAAGGATATTCACAGGAGCTTATGCCTGGT
```

14347.2

```
CTCCTCTTGGTACATGAACCCAAGTTGAAAGTGGACTTAACAAAGTATCTGGAGAACCAAGCATTCTGCTTTGACT
TTGCATTTGATGAAACAGCTTCGAATGAAGTTGTCTACAGGTTCACAGCAAGGCCACTGGTACAGACAATCTTTGA
AGGTGGAAAAGCAACTTGTTTTGCATATGGCCAGACAGGAAGTGGCAAGACACATACTATGGGCGGAGACCTCTCT
GGGAAAGCCCAGAATGCATCCAAAGGGATCTATGCCATGGCCTTCCGGGACGTCTTCTTCTGAAGAATCAACCCTG
CTACCGGAAGTTGGGCCTGGAAGTCTATGTGACATTCTTCGAGATCTACAATGGGAAGCTGTTTGACCTGCTCAAC
AAGAAGGCCAAGCTTGCGCGTGCTGGAAGACGGCAAGCAACAGGTGCAAGTGGTGGGGGCTTGCAGGAACATCTGG
NTAACTCTGCTTGATGATGGCANTCAAGATGATCGACATGGGCAGCGCCTGCAGA
```

14348.2&14350.1&2

```
TCCCGAATTCAAGCGACAAATTGGAWAGTGAAATGGAAGATGCCTATCATGAACATCAGGCAAATCTTTTGCGCCA
AGATCTGATGAGACGACAGGAAGAATTAAGACGCATGGAAGAACTTCACAATCAAGAAATGCAGAAACGTAAAGAA
ATGCAATTGAGGCAAGAGGAGGAACGACGTAGAAGAGAGGAAGAGATGATGATTCGTCAACGTGAGATGGAAGAAC
AAATGAGGCGCCAAAGAGAGGAAAGTTACAGCCGAATGGGCTACATGGATCCACGGGAAAGAGACATGCGAATGGG
TGGCGGAGGAGCAATGAACATGGGAGATCCCTATGGTTCAGGAGGCCAGAAATTTCCACCTCTAGGAGGTGGTGGT
GGCATAGGTTATGAAGCTAATCCTGGCGTTCCACCAGCAACCATGAGTGGTTCCATGATGGGAAGTGACATGCGTA
CTGAGCGCTTTGGGCAGGGAGGTGCGGGGCCTGTGGGTGGACAGGGTCCTAGAGGAATGGGGCCTGGAACTCCAGC
AGGATATGGTAGAGGGAGAGAAGAGTACGAAGGC
```

14349.1&2

```
TTCGTGAAGACCCTGACTGGTAAGACCATCACTCTCGAAGTGGAGCCCGAGTGACACCATTGAGAATGTCAAGGCA
AAGATCCAAGACAAGGAAGGCATCCCTCCTGACCAGCAKAGGTTGATCTTTGCTGGGAAACAGCTGGAAGATGGAC
GCACCCTGTCTGACTACAACATCCAGAAAGAGTCCACCCTGCACCTGGTGCTCCGTCTCAGAGGTGGGATGCAAAT
CTTCGTGAAGACCCTGACTGGTAAGACCATCACCCTCGAGGTGGAGCCCAGTGACACCATCGAGAATGTCAAGGCA
AAGATCCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACTCTGCACTTGGTCCTGCGCTTGAGGGGGGGTGTCTAAGT
TTCCCCTTTTAAGGTTTCAACAAATTTCATTGCACTTTCCTTTTCAATAAAGTTGTTGCATTC
```

```
GCGCGGGTGCGTGGGCCACTGGGTGACCGACTTAGCCTGGCCAGACTCTCAGCACCTGGAAGCGCCCCGAGAGTGA
CAGCGTGAGGCTGGGAGGGAGGACTTGGCTTGAGCTTGTTAAACTCTGCTCTGAGCCTCCTTGTCGCCTGCATTTA
GATGGCTCCCGCAAAGAAGGGTGGCGAGAAGAAAAAGGGCCGTTCTGCCATCAACGAAGTGGTAACCCGAGAATAC
ACCATCAACATTCACAAGCGCATCCATGGAGTGGGCTTCAAGAAGCGTGCACCTCGGGCACTCAAAGAGATTCGGA
AATTTGCCATGAAGGAGATGGGAACTCCAGATGTGCGCATTGACACCAGGCTCAACAAAGCTGTCTGGGCCAAAGG
AATAAGGAATGTGCCATACCGAATCCGTGTGCGGCTGTCCAGAAAACGTAATGAGGATGAAGATTCACCAAATAAG
CTATATACTTTGGTTACCTATGTACCTGTTACCACTTTCAAAAATCTACAGACAGTCAATGTGGATGAGAACTAAT
CGCTGATCGT
```

14353.1

```
AATTCTTTATTTAAATCAACAAACTCATCTTCCTCAAGCCCCAGACCATGGTAGGCAGCCCTCCCTCTCCATCCCC
TCACCCCACCCCTTAGCCACAGTGAAGGGAATGGAAAATGAGAAGCCACGAGGGCCCCTGCCAGGGAAGGCTGCCC
CAGATGTGTGGTGAGCACAGTCAGTGCAGCTGTGGCTGGGGCAGCAGCTGCCACAGGCTCCTCCCTATAAATTAAG
TTCCTGCAGCCACAGCTGTGGGAGAAGCATACTTGTAGAAGCAAGGCCAGTCCAGCATCAGAAGGCAGAGGCAGCA
TCAGTGACTCCCAGCCATGGAATGAACGGAGGACACAGAGCTCAGAGACAGAACAGGCCAGGGGGAAGAAGGAGAG
ACAGAATAGGCCAGGGCATGGCGGTGAGGGA
```

14353.2

```
TGATGAATCTGGGTGGGCTGGCAGTAGCCCGAGATGATGGGCTCTTCTCTGGGGATCCCAACTGGTTCCCTAAGAA
ATCCAAGGAGAATCCTCGGAACTTCTCGGATAACCAGCTGCAAGAGGGCAAGAACGTGATCGGGTTACAGATGGGC
ACCAACCGCGGGGCGTCTCANGCAGGCATGACTGGCTACGGGATGCCACGCCAGATCCTCTGATCCCACCCCAGGC
CTTGCCCCTGCCCTCCCACGAATGGTTAATATATATGTAGATATATATTTTAGCAGTGACATTCCCAGAGAGCCCC
AGAGCTCTCAAGCTCCTTTCTGTCAGGGTGGGGGGTTCAAGCCTGTCCTGTCACCTCTGAAGTGCCTGCTGGCATC
CTCTCCCCCATGCTTACTAATACATTCCCTTCCCCATAGCC
```

17182.1&2

```
AGCGGAGCTCCCTCCCCTGGTGGCTACAACCCACACACGCCAGGCTCAGGCATCGAGCAGAACTCCAGCGACTGGG
TAACCACTGACATTCAGGTGAAGGTGCGGGACACCTACCTGGATACACAGGTGGTGGGACAGACAGGTGTCATCCG
CAGTGTCACGGGGGGCATGTGCTCTGTGTACCTGAAGGACAGTGAGAAGGTTGTCAGCATTTCCAGTGAGCACCTG
GAGCCTATCACCCCCACCAAGAACAACAAGGTGAAAGTGATCCTGGGCGAGGATCGGGAAGCCACGGGCGTCCTAC
TGAGCATTGATGGTGAGGATGGCATTGTCCGTATGGACCTTGATGAGCAGCTCAAGATCCTCAACCTCCGCTTCCT
GGGGAAGCTCCTGGAAGCCTGAAGCAGGCAGGGCCGGTGGACTTCGTCGGATGAAGAGTGATCCTCCTTCCTTCCC
TGGCCCTTGGCTGTGACACAAGATCCTCCTGCAGGGCTAGGCGGATTGTTCTGGATTTCCTTTTGTTTTTCCTTTT
AGGTTTCCATCTTTTCCCTCCCTGGTGCTCATTGGAATCTGAGTAGAGTCTGGGGGAGGGTCCCCACCTTCCTGTA
CCTCCTCCCCACAGCTTGCTTTTGTTGTACCGTCTTTCAATAAAAAGAAGCTGTTTGGTCTA
```

```
GGTTCACAGCACTGCTGCTTGTGTGTTGCCGGCCAGGAATTCCAGGCTCACAAGGCTATCTTAGCAGCTCGTTCTC
CGGTTTTTAGTGCCATGTTTGAACATGAAATGGAGGAGAGCAAAAAGAATCGAGTTGAAATCAATGATGTGGAGCC
TGAAGTTTTTAAGGAAATGATGTGCTTCATTTACACGGGGAAGGCTCCAAACCTCGACAAAATGGCTGATGATTTG
CTGGCAGCTGCTGACAAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAACTCAGGCAGTGGATTT
CATCAACTATCATGCTTCGGATGTCTTGGAGACCTCTTGGG
```

17186.1&2

```
TCGTAGCCATTTTTCTGCTTCTTTGGAGAATGACGCCACACTGACTGCTCATTGTCGTTGGTTCCATGCCAATTGG
TGAAATAGAACCTCATCCGGTAGTGGAGCCGGAGGGACATCTTGTCATCAACGGTGATGGTGCGATTTGGAGCATA
CCAGAGCTTGGTGTTCTCGCCATACAGGGCAAAGAGGTTGTGACAAAGAGGAGAGATACGGCATGCCTGTGCAGCC
CTGATGCACAGTTCCTCTGCTGTGTACTCTCCACTGCCCAGCCGGAGGGGCTCCCTGTCCGACAGATAGAAGATCA
CTTCCACCCCTGGCTTG
```

17187.1&2

```
TGGCACACTGCTCTTAAGAAACTATGAWGATCTGAGATTTTTTTGTGTATGTTTTTGACTCTTTTGAGTGGTAATC
ATATGTGTCTTTATAGATGTACATACCTCCTTGCACAAATGGAGGGGAATTCATTTTCATCACTGGGAGTGTCCTT
AGTGTATAAAAACCATGCTGGTATATGGCTTCAAGTTGTAAAAATGAAAGTGACTTTAAAAGAAAATAGGGGATGG
TCCAGGATCTCCACTGATAAGACTGTTTTTAAGTAACTTAAGGACCTTTGGGTCTACAAGTATATGTGAAAAAAAT
GAGACTTACTGGGTGAGGAAATTCATTGTTTAAAGATGGTCGTGTGTGTGTGTGTGTGTGTGTGTTGTGTTGTG
TTTTGTTTTTTAAGGGAGGGAATTTATTATTTACCGTTGCTTGAAATTACTGKGTAAATATATGTYTGATAATGAT
TTGCTYTTTGVCMACTAAAATTAGGVCTGTATAAGTWCTARATGCMTCCCTGGGKGTTGATYTTCCMAGATATTGA
TGATAMCCCTTAAAATTGTAACCYGCCTTTTTCCCTTTGCTYTCMATTAAAGTCTATTCMAAAG
```

17191.1&89.1

```
GGGGGTAGGCTCTTTATTAGACGGTTATTGCTGTACTACAGGGTCAGAGTGCAGTGTAAGCAGTGTCAGAGGCCCG
CGTTCAGCCCAAGAATGTGGATTTTCTCTCCCTATTGATCACAGTGGGTGGGTTTCTTCAGAAAAGCCCCAGAGGC
AGGGACCAGTGAGCTCCAAGGTTAGAAGTGGAACTGGAAGGCTTCAGTCACATGCTGCTTCCACGCTTCCAGGCTG
GGCAGCAAGGAGGAGATGCCCATGACGTGCCAGGTCTCCCCATCTGACACCAGTGAAGTCTGGTAGGACAGCAGCC
GCACGCCTGCCTCTGCCAGGAGGCCAATCATGGTAGGCAGCATTGCAGGGTCAGAGGTCTGAGTCCGGAATAGGAG
CAGGGGCAGGTCCCTGCGGAGAGGCACTTCTGGCCTGAAGACAGCTCCATTGAGCCCCTGCAGTACAGGYGTAGTG
CCTTGGACCAAGCCCACAGCCTGGTAAGGGGCGCCTGCCAGGGCCACGGCCAGGAGGCA
```

TAATTTCTTAGTCGTTTGGAATCCTTAAGCATGCAAAAGCTTTGAACAGAAGGGTTCACAAAGGAACCAGGGTTGT
CTTATGGCATCCAGTTAAGCCAGAGCTGGGAATGCCTCTGGGTCATCCACATCAGGAGCAGAAGCACTTGACTTGT
CGGTCCTGCTGCCACGGTTTGGGCGCCCACCACGCCCACGTCCACCTCGTCCTCCCCTGCCGCCACGTCCTGGGCG
GCCAAGGTCTCCAAAATTGATCTCCAGCTGAGACGTTATATCATTTGCTGGCTTCCGGAAATGATGGTCCATAACC
GAATCTTCAGCATGAGCCTCTTCACTCTTTGATTTATGAAGAACAAATCCCTTCTTCCACTGCCCATCAGCACCTT
CATTTGGTTTTCGGATATTAAATTCTACTTTTGCCCGGTCCTTATTTTGAATAGCCTTCCACTCATCCAAAGTCAT
CTCTTTTGGACCCTCCTCTTTTACCTCTTCAACTTCATTCTCCTTATTTTCAGTGTCTGCCACTGGATGATGTTCT
TCACCTTCAGGTGTTTCCTCAGTCACATTTGATTGATCCAAGTCAGTTAATTCGTCTTTGACAGTTCCCCAGTTGT
GAGATCCGCTACCTCCACGTTTGTCCTCGTGCTTCAGGCCAGATCTATCACTTCCACTATGCCTATCAAATTCACG
TTTGCCACGAGAATCAAATCCATCTCCTCGGCCCATTCCACGTCCACGGCCCCCTCGACCTCTTCCAAGACCACCA
CGACCTCGAATAGGTCGGTCAATAATCGGTCTATCAACTGAAAATTCGCCTCCTTCACCCTTTTCTTCAAGTGGCT
TTTCGAATCTTCGTTCACGAGGTGGTCGCCTTTCTGGTCTTCTATCAATTATTTTCCCTTCACCCTGAAGTTGTTG
ATCAGGTCTTCTTCCAACTCGTGC

17193

AAGCGGATGGACCTGAGTCAGCCGAATCCTAGCCCCTTCCCTTGGGCCTGCTGTGGTGCTCGACATCAGTGACAGA
CGGAAGCAGCAGACCATCAAGGCTACGGGAGGCCCGGGGCGCTTGCGAAGATGAAGTTTGGCTGCCTCTCCTTCCG
GCAGCCTTATGCTGGCTTTGTCTTAAATGGAATCAAGACTGTGGAGACGCGCTGGCGTCCTCTGCTGAGCAGCCAG
CGGAACTGTACCATCGCCGTCCACATTGCTCACAGGGACTGGGAAGGCGATGCCTGTCGGGAGCTGCTGGTGGAGA
GACTCGGGATGACTCCTGCTCAGATTCAGGCCTTGCTCAGGAAAGGGGAAAAGTTTGGTCGAGGAGTGATAGCGGG
ACTCGTTGACATTGGGGAAACTTTGCAATGCCCCGAAGACTTAACTCCCGATGAGGTTGTGGAACTAGAAAATCAA
GCTGCACTGACCAACCTGAAGCAGAAGTACCTGACTGTGATTTCAAACCCCAGGTGGTTACTGGAGCCCATACCTA
GGAAAGGAGGCAAGGATGTATTCCAGGTAGACATCCCAGAGCACCTGATCCCTTTGGGGCATGAAGTGTGACAAGT
GTGGGCTCCTGAAAGGAATGTTCCRGAGAAACCAGCTAAATCATGGCACCTTCAATTTGCCATCGTGACGCAGACC
TGTATAAATTAGGTTAAAGATGAATTTCCACTGCTTTGGAGAGTCCCACCCACTAAGCACTGTGCATGTAAACAGG
TTCCTTTGCTCAGATGAAGGAAGTAGGGGGTGGGGCTTTCCTTGTGTGATGCCTCCTTAGGCACACAGGCAATGTC
TCAAGTACTTTGACCTTAGGGTAGAAGGCAAAGCTGCCAGTAAATGTCTCAGCATTGCTGCTAATTTTGGTCCTGC
TAGTTTCTGGATTGTACAAATAAATGTGTTGTAGATGA

*Fig. 15U*

16443.1.edit

```
TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTGGCATTATGCACCTCC
ACGCCGTCCACGTACCAATTGAACTTGACCTCAGGGTCTTCGTGGCTCACGTCCACCACCACGCATGTAACCTCAA
ANCTCGGNCGCGANCACGC
```

16443.2.edit

```
AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACA
TCGCCCGTGGAGTGGGAGAGCAATGGGCAGCCGGAGAACAACTACAAGACCACGCCTCCCGTGCTGGACTCCGACA
CCTGCCGGGCGGCCGCTCGA
```

16444.2.edit

```
AGCGTGGTTNCGGCCGAGGTCCCAACCAAGGCTGCANCCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGNCGCTCGA
```

16445.1.edit

```
AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGCCGCTCGA
```

*Fig. 15V*

16445.2.edit

```
TCGAGCGGTCGCCCGGGCAGGTCCACATCGGCAGGGTCGGAGCCCTGGCCGCCATACTCGAACTGGAATCCATCGG
NCATGCTCTCGCCGAACCAGACATGCCTCTTGNCCTTGGGGTTCTTGCTGATGTACCAGNTCTTCTGGGCCACACT
GGGCTGAGTGGGGTACACGCAGGTCTCACCANTCTCCATGTTGCANAAGACTTTGATGGCATCCAGGTTGCAGCCT
TGGTTGGGGTCAATCCAGTACTCTCCACTCTTCCAGACAGAGTGGCACATCTTGAGGTCACGGCAGGTGCGGGCGG
GGTTCTTGACCTCGGTCGCGACCACGCT
```

16446.1.edit

```
TCGAGCGGCCGCCCGGGCAGGTCCTCCTCAGAGCGGTAGCTGTTCTTATTGCCCCGGCAGCCTCCATAGATNAAGT
TATTGCANGAGTTCCTCTCCACGTCAAAGTACCAGCGTGGGAAGGATGCACGGCAAGGCCCAGTGACTGCGTTGGC
GGTGCAGTATTCTTCATAGTTGAACATATCGCTGGAGTGGACTTCAGAATCCTGCCTTCTGGGAGCACTTGGGACA
GAGGAATCCGCTGCATTCCTGCTGGTGGACCTCGGCCGCGACCACGCT
```

16446.2.edit

```
AGCGTGGTCGCGGCCGAGGTCCACCAGCAGGAATGCAGCGGATTCCTCTGTCCCAAGTGCTCCCAGAAGGCAGGAT
TCTGAAGACCACTCCAGCGATATGTTCAACTATGAAGAATACTGCACCGCCAACGCAGTCACTGGGCCTTGCCGTG
CATCCTTCCCACGCTGGTACTTTGACGTGGAGAGGAACTCCTGCAATAACTTCATCTATGGAGGCTGCCGGGGCAA
TAAGAACAGCTACCGCTCTGAGGAGGACCTGCCCGGGCGGCCGCTCGA
```

16447.1.edit

```
TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGCCAGAATGGCACATCTTGAGGTCACGGCANGTGCGGGCGG
GGTTCTTGACCTCGGCCGCGACCACGCT
```

*Fig. 15W*

16447.2.edit
```
AGCGTGGTCGCGGCCGAGGTCAAGAAACCCCGCCCGCACCTGCCGTGACCTCAAGATGTGCCACTCTGGCTGGAAG
AGTGGAGAGTACTGGATTGACCCCAACCAAGGCTGCAACCTGGATGCCATCAAAGTCTTCTGCAACATGGAGACTG
GTGAGACCTGCGTGTACCCCACTCAGCCCAGTGTGGCCCAGAAGAACTGGTACATCAGCAAGAACCCCAAGGACAA
GAGGCATGTCTGGCTCGGCGAGAGCATGACCGATGGATTCCAGTTCGAGTATGGCGGCCAGGGCTCCGACCCTGCC
GATGTGGACCTGCCCGGGCGGCCGCTCGA
```

16449.1.edit
```
AGCGTGGTCGCGGCCGAGGTCCTGTCAGAGTGGCACTGGTAGAAGNTCCAGGAACCCTGAACTGTAAGGGTTCTTC
ATCAGTGCCAACAGGATGACATGAAATGATGTACTCAGAAGTGTCCTGNAATGGGGCCCATGANATGGTTGNCTGA
GAGAGAGCTTCTTGTCCTACATTCGGCGGGTATGGTCTTGGCCTATGCCTTATGGGGGTGGCCGTTGNGGGCGGTG
NGGTCCGCCTAAAACCATGTTCCTCAAAGATCATTTGTTGCCCAACACTGGGTTGCTGACCANAAGTGCCAGGAAG
CTGAATACCATTTCCAGTGTCATACCCAGGGTGGGTGACGAAAGGGGTCTTTTGAACTGTGGAAGGAACATCCAAG
ATCTCTGNTCCATGAAGATTGGGGTGTGGAAGGGTTACCAGTTGGGGAAGCTCGCTGTCTTTTTCCTTCCAATCAN
GGGCTCGCTCTTCTGAATATTCTTCAGGGCAATGACATAAATTGTATATTCGGTTCCCGGTTCCAGGCCAG
```

16450.1.edit
```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGANGAACATGGNTTT
AGGCGGACCACACCGGCCACAACGGGCACCCCCATAAGGCATAGGCCAAGAACATACCCGNCGAATGTAGGACAAG
AAGCTCTNTCTCANACAANCATCTCATGGGCCCCATTCCANGACACTTCTGAGTACATCANTTCATGGCATCCTGG
TGGCACTGATAAAAACCCTTACAGTTA
```

16450.2.edit
```
AGCGTGGTCGCGGGCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
NGGGCTCGCTCTTCTGATTATTCTTCAGGGCAATGACATAAATTGTATATTCGGNTCCCGGGTNCAGCCAATAATA
ATAACCCTCTGTGACACCANGGCGGGGCCGAAGGANCACT
```

*Fig. 15X*

16451.1.edit

```
AGCGTGGTCGCGGCCGAGGTCCTCACCAGAGGTACCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA
```

16451.2.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGNTGACAGAGTTGCCCACGGTAACAACCTCTTCCCGAACCTTATGCCTCTGCTGG
TCTTTCAGTGCCTCCACTATGATGTTGTAGGTGGTACCTCTGGTGAGGACCTCGGCCGCGACCACGCT
```

16452.1.edit

```
AGCGTGGCCGCGGCCGAGGTCCATTGGCTGGAACGGCATCAACTTGGAAGCCAGTGATCGTCTCAGCCTTGGTTCT
CCAGCTAATGGTGATGGNGGTCTCAGTAGCATCTGTCACACGAGCCCTTCTTGGTGGGCTGACATTCTCCAGAGTG
GTGACAACACCCTGAGCTGGTCTGCTTGTCAAAGTGTCCTTAAGAGCATAGACACTCACTTCATATTTGGCGNCCA
CCATAAGTCCTGATACAACCACGGAATGACCTGTCAGGAAC
```

16452.2.edit

```
TCGAGCGGCCGCCCGGGCAGGTCCTCAGACCGGGTTCTGAGTACACAGTCAGTGTGGTTGCCTTGCACGATGATAT
GGAGAGCCAGCCCCTGATTGGAACCCAGTCCACAGCTATTCCTGCACCAACTGACCTGAAGTTCACTCAGGTCACA
CCCACAAGCCTGAGCGCCCAGTGGACACCACCCAATGTTCAGCTCACTGGATATCGAGTGCGGGTGACCCCCAAGG
AGAAGACCGGACCAATGAAAGAAATCAACCTTGCTCCTGACAGCTCATCCGTGGTTGTATCAGGACTTATGGCGGC
CACCAAATATGAAGTGAGTGTCTATGCTCTTAAGGACACTTTGACAAGCAGACCAGCTCAGGGTGTTGTCACCACT
CTGGAGAATGTCAGCCCACCAAGAAGGGCTCGTGTGACAGATGCTACTGAGACCACCATCACCATTAGCTGGAGAA
CCAAGACTGAGACGATCACTGGCTTCCAAGTTGATGCCGTTCCAGCCAATGGACCTCGGCCGCGACCACGCTT
```

*Fig. 15Y*

16453.1.edit

AGCGTGGTCGCGGCCGAGGTCTGGCCGAACTGCCAGTGTACAGGGAAGATGTACATGTTATAGNTCTTCTCGAAGT
CCCGGGCCAGCAGCTCCACGGGGTGGTCTCCTGCCTCCAGGCGCTTCTCATTCTCATGGATCTTCTTCACCCGCAG
CTTCTGCTTCTCAGTCAGAAGGTTGTTGTCCTCATCCCTCTCATACAGGGTGACCAGGACGTTCTTGAGCCAGTCC
CGCATGCGCAGGGGGAATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCAGGAAGAGTCGAAGGT
CTTGTTGTCATTGCTGCACACCTTCTCAAACTCGCCAATGGGGGCTGGGCAGACCTGCCCGGGCGGCCGCTCGA

16453.2.edit

TCGAGCGGCCGCCCGGGCAGGTCTGCCCAGCCCCCATTGGCGAGTTTGAGAAGGNGTGCAGCAATGACAACAAGAC
CTTCGACTCTTCCTGCCACTTCTTTGCCACAAAGTGCACCCTGGAGGGCACCAAGAAGGGCCACAAGCTCCACCTG
GACTACATCGGGCCTTGCAAATACATCCCCCCTTGCCTGGACTCTGAGCTGACCGAATTCCCCCTGCGCATGCGGG
ACTGGCTCAAGAACGTCCTGGTCACCCTGTATGAGAGGGATGAGGACAACAACCTTCTGACTGAGAAGCANAAGCT
GCGGGTGAAGAANATCCATGAGAATGANAAGCGCCTGNAGGCANGAGACCACCCCGTGGAGCTGCTGGCCCGGGAC
TTCGAGAAGAACTATAACATGTACATCTTCCCTGTACACTGGCAGTTCGGCCAGACCTCGGCCGCGACCACGCT

16454.1.edit

AGCGTGGNTGCGGACGACGCCCACAAAGCCATTGTATGTAGTTTTANTTCAGCTGCAAANAATACCNCCAGCATCC
ACCTTACTAACCAGCATATGCAGACA

16454.2.edit

TCGAGCGGTCGCCCGGGCAGGTCTGGGCGGATAGCACCGGGCATATTTTGGAATGGATGAGGTCTGGCACCCTGAG
CAGCCCAGCGAGGACTTGGTCTTAGTTGAGCAATTTGGCTAGGAGGATAGTATGCAGCACGGTTCTGAGTCTGTGG
GATAGCTGCCATGAAGNAACCTGAAGGAGGCGCTGGCTGGTANGGGTTGATTACAGGGCTGGGAACAGCTCGTACA
CTTGCCATTCTCTGCATATACTGGNTAGTGAGGCGAGCCTGGCGCTCTTCTTTGCGCTGAGCTAAAGCTACATACA
ATGGCTTTGNGGACCTCGGCCGCGACCACGCTT

*Fig. 15Z*

16455.1.edit

```
TCGAGCGGCCGCCCGGGCAGGTCCATTTTCTCCCTGACGGTCCCACTTCTCTCCAATCTTGTAGTTCACACCATTG
TCATGACACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAAGTTGCCCACGGTAACAACCTCTTCCCGAACCTTATGCCTCTGCTG
GTCTTTCAAGTGCCTCCACTATGATGTTGTAGGTGGCACCTCTGGTGAGGACCTCGGCCGCGACCACGCT
```

16455.2.edit

```
AGCGTGGTTTGCGGCCGAGGTCCTCACCANAGGTGCCACCTACAACATCATAGTGGAGGCACTGAAAGACCAGCAG
AGGCATAAGGTTCGGGAAGAGGTTGTTACCGTGGGCAACTCTGTCAACGAAGGCTTGAACCAACCTACGGATGACT
CGTGCTTTGACCCCTACACAGNTTCCCATTATGCCGTTGGAGATGAGTGGGAACGAATGTCTGAATCAGGCTTTAA
ACTGTTGTGCCAGTGCTTANGCTTTGGAAGTGGTCATTTCAGATGTGATTCATCTANATGGTGTCATGACAATGGT
GNGAACTACAAGATTGGAGAGAAGTGGNACCGTCAGGGGANAAAATGGACCTGCCCGGGCGGCNCGCTCGA
```

16456.1.edit

```
AGCGTGGTCGCGGCCGAGGTCTGGCTTNCTGCTCANGTGATTATCCTGAACCATCCAGGCCAAATAAGCGCCGGCT
ATGCCCCTGNATTGGATTGCCACACGGCTCACATTGCATGCAAGTTTGCTGAGCTGAAGGAAAAGATTGATC
```

16456.2.edit

```
TCGAGCGGCCGCCCGGGCAGGTCCAATTGAAACAAACAGTTCTGAGACCGTTCTTCCACCACTGATTAAGAGTGGG
GNGGCGGGTATTAGGGATAATATTCATTTAGCCTTCTGAGCTTTCTGGGCAGACTTGGTGACCTTGCCAGCTCCAG
CAGCCTTCTGGTCCACTGCTTTGATGACACCCACCGCAACTGTCTGTCTCATATCACGAACAGCAAAGCGACCCAA
AGGTGGATAGTCTGAGAAGCTCTCAACACACATGGGCTTGCCAGGAACCATATCAACAATGGGCAGCATCACCAGA
CTTCAAGAATTTAAGGGCCATCTTCCAGCTTTTTACCAGAACGGCGATCAATCTTTTCCTTCAGCTCAGCAAACTT
GCATGCAATGTGAGCCG
```

*Fig. 15A-1*

16459.1.edit

```
TCGAGCGGCCGCCCGGGCAGGTCCAGAGGGCTGTGCTGAAGTTTGCTGCTGCCACTGGAGCCACTCCAATTGCTGG
CCGCTTCACTCCTGGAACCTTCACTAACCAGATCCAGGCAGCCTTCCGGGAGCCACGGCTTCTTGTGGNTACTGAC
CCCAGGGCTGACCACCAGCCTCTCACGGAGGCATCTTATGTTAACCTACCTACCATTGCGCTGTGTAACACAGATT
CTCCTCTGCGCTATGTGGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGNCATGCCTGATCTGGA
CTTCTACAGAGATCCTGAAGAGATTGAAAAAGAAGAACAGGCTGNTTGCTGANAAAGCAAGTGACCAAGGANGAAA
TTTCANGGGTGAAANGGACTGCTCCCGCTCCTGAATTCACTGCTACTCAACCTGANGNTGCAGACTGGTCTTGAAG
GNGNACANGGGCCCTCTGGGCCTATTTAAGCANCTTCGGTCGCGAACACGNT
```

16459.2.edit

```
AGCGTGNGTCGCGGCCGAGGTGCTGAATAGGCACAGAGGGCACCTGTACACCTTCAGACCAGTCTGCAACCTCAGG
CTGAGTAGCAGTGAACTCAGGAGCGGGAGCAGTCCATTCACCCTGAAATTCCTCCTTGGNCACTGCCTTCTCAGCA
GCAGCCTGCTCTTCTTTTTCAATCTCTTCAGGATCTCTGTAGAAGTACAGATCAGGCATGACCTCCCATGGGTGTT
CACGGGAAATGGTGCCACGCATGCGCAGAACTTCCCGAGCCAGCATCCACCACATCAAACCCACTGAGTGAGCTCC
CTTGTTGTTGCATGGGATGGGCAATGTCCACATAGCGCAGAGGAGAATCTGTGTTACACAGCGCAATGGTAGGTAG
GTTAACATAAGATGCCTCCGCGAGAAGCTGGTGGTCAGCCCTGGGGTCAAGTAACCACAAGAAGCCGTGGCTCCCG
GAAGGCTGCCTGGATCTGGTTAGTGAAGGNTCCAGGAGTGAAGCGGCCAACAATTGGAGTGGCTTCAGTGGCAAGC
AGCAAACTTCAGCACAAGCCCTCTGGACCTGCCCGGCGGCCGCTCGA
```

16460.1.edit

```
TCGAGCGGCCGCCCGGGCAGGTCCATTTTCTCCCTGACGGNCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCNTCCCCGAACCTTATGCCTCTGCTG
GGCTTTCAGNGCCTCCACTATGATGNTGTAGGGGGGCACCTCTGGNGANGACCTCGGCCGCGACCACGCT
```

16460.2.edit

```
AGCGTGGTCGCGGCCGAGGTCCTCACCAGAGGTGCCACCTACAACATCATAGTGGAGGCACTGAAAGACCAGCAGA
GGCATAAGGCTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGGTCATTTCAGATGTGATTCATCTAGATGGTGCCATGACAATGGN
GNGAACTACAAGATTGGAGAGAAGTGGNACCGNCAGGGAGAAAATGGACCTGCCCGGGCGGCCGCTCGA
```

*Fig. 15B-1*

16461.1.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGNTGCAACCTTG
GTTGGGGTCAATCCAGTACTCTCCACTCTTCCAGCCAGAGTGGCACATCTTGAGGTCACGGCAGGTGCGGNCGGGG
GNTTTTGCGGCTGCCCTCTGGNCTTCGGNTGTNCTCNATCTGCTGGCTCA
```

16461.2.edit

```
TCGAGCGGCCGCCCGGGCAGGTCTCGCGGTCGCACTGGTGATGCTGGTCCTGTTGGTCCCCCCGGCCCTCCTGGAC
CTCCTGGCCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGNCGCAAGAACCCCGCCCGCACCTGCCGTG
ACCTCAAGATGTGCCACTCTGACTGGAAGAGTGGAGAGTACTGGATTGACCCCAACCAAGCTGCAACCTGGATGCC
ATCAAAGTCTTCTGCAACATGGAGACTGGTGAGACCTGCGTGTACCCCACTCAGCCCAGTGTGGCCCAAAAGAACT
GGTACATCAGCAAGAACCCCAAGGACAAGAAGCATGTCTGGTTCGGCGAGAACATGACCGATGGATTCCAGTTCGA
GTATGGCGGGCAGGGCTCCGACCCTGCCGATGGGGACCTTGGCCGCGAACACGCT
```

16463.1.edit

```
AGCGTGGNNGCGGCCGAGGTATAAATATCCAGNCCATATCCTCCCTCCACACGCTGANAGATGAAGCTGTNCAAAG
ATCTCAGGGTGGANAAAACCAT
```

16463.2.edit

```
TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT
```

*Fig. 15C-1*

16464.1.edit

```
CGAGCGGGCGACCGGGCAGGTNCAGACTCCAATCCANANAACCATCAAGCCAGATGTCAGAAGCTACACCATCACA
GGTTTACAACCAGGCACTGACTACAAGANCTACCTGCACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGTACATCATCNAGTATGANAAGCCTGGGCCTCCTCCCAGAGAAGNGG
TCCCTCGGCCCCGCCCTGNTGTCCCANAGGNTACTATTACTGNGCCNGCAACCGGCAACCGATATCNATTTTGNCA
TTGGCCTTCAACAATAATTA
```

16464.2.edit

```
AGCGTGGTTCGCGGCCGANGTCCTGTCAGAGTGGCACTGGTAGAAGTTCCAGGAACCCTGAACTGTAAGGGTTCTT
CATCAGNGCCAACAGGATGACATGAAATGATGTACTCAGAAGTGTCCTGGAATGGGGCCCATGAGATGGTTGTCTG
AGAGAGAGCTTCTTGNCCTGTCTTTTTCCTTCCAATCAGGGGCTCGCTCTTCTGATTATTCTTCAGGGCAATGACA
TAAATTGTATATTCGGGTCCCGGNTCCAGGCCAGTAATAGTANCCTCTGTGACACCAGGGCGGNGCCGAGGGACCA
CTTCTCTGGGAGGAGACCCAGGCTTCTCATACTTGATGATGTAACCGGTAATCCTGGCACGTGGCGGCTGCCATGA
TACCAGCAAGGAATTGGGGTGTGGTGGCCAGGAAACGCAGGTTGGATGGNGCATCAATGGCAGTGGAGGCCGTCGA
TGACCACAGGGGGAGCTCCGACATTGTCATTCAAGGTG
```

16465.1.edit

```
AGCGTGGNCGCGGCCGAGGTGCAGCGCGGGCTGTGCCACCTTCTGCTCTCTGCCCAACGATAAGGAGGGTNCCTGC
CCCCAGGAGAACATTAACTNTCCCCAGCTCGGCCTCTGCCGG
```

16465.2.edit

```
TCGAGCGGCCGCCCGGGCAGGTTTTTTTTTGCTGAAAGTGGNTACTTTATTGGNTGGGAAAGGGAGAAGCTGTGGTC
AGCCCAAGAGGGAATACAGAGNCCCGAAAAAGGGGAGGGCAGGTGGGCTGGAACCAGACGCAGGGCCAGGCAGAAA
CTTTCTCTCCTCACTGCTCAGCCTGGTGGTGGCTGGAGCTCANAAATTGGGAGTGACACAGGACACCTTCCCACAG
CCATTGCGGCGGCATTTCATCTGGCCAGGACACTGGCTGTCCACCTGGCACTGGTCCCGACAGAAGCCCGAGCTGG
GGAAAGTTAATGTTCACCTGGGGGCAGGAACCCTCCTTATCATTGNGCAGAGAGCAGAAGGTGGCACAGCCCGCGC
TGCACCTCGGCCGCGACCACGCT
```

16466.2.edit

```
TCGAGCGGCCGCCCGGGCAGGTCCACCATAAGTCCTGATACAACCACGGATGAGCTGTCAGGAGCAAGGTTGATTT
CTTTCATTGGTCCGGNCTTCTCCTTGGGGGNCACCCGCACTCGATATCCAGTGAGCTGAACATTGGGTGGCGTCCA
CTGGGCGCTCAGGCT
```

16467.2.edit

```
TCGAGCGGTTCGCCCGGGCAGGTCCACCACACCCAATTCCTTGCTGGTATCATGGCAGCCGCCACGTGCCAGGATT
ACCGGCTACATCATCAAGTATGAGAAGCCTGGGTCTCCTCCCAGAGAAGCGGTCCCTCGGCCCCGCCCTGGTGTCA
CAGAGGCTACTATTACTGGCCTGGAACCGGGAACCGAATATACAATTTATGTCATTGNCCTGAAGAATAATCANNA
ANAGCGANCCCCTGATTGGAAGGA
```

*Fig. 15D-1*

01_16469.edit

AGCGTGGTCGCGGCCGAGGTTGTACAAGCTTTTTTTTTTTTTTTTTTTTTTTTTTTTTTTTTTTTTTTTTTTTTTTT
TTTTTTTTTTTTTTTT

02_16469.edit

TCGAGCGGNCGCCCGGGCAGGTCTGCCAACACCAAGATTGGCCCCCGCCGCATCCACACAGTCCGTGTGCGGGGAG
GTAACAAGAAATACCGTGCCCTGAGGTTGGACGTGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATCGACAGCACACCGTACCGACAGTGGTACGAGTCCCACTATGCGCTGCCCCTGGGCCGCAAGAAGGGAG
CCAAGCTGACTCCTGAGGAAGAAGAGATTTTAAACAAAAAACGATCTAANAAAAAAAAAAACAAT

03_16470.edit

AGCGTGGTCGCGGCCGAGGTGAAATGGTATTCAGCTTCCTGGCACTTCTGGTCAGCAACCCAGTGTTGGGCAACAA
ATGATCTTTGAGGAACATGGTTTTAGGCGGACCACACCGCCCACAACGGCCACCCCCATAAGGCATAGGCCAAGAC
CATACCCGCCGAATGTAGGACAAGAAGCTCTCTCTCAGACAACCATCTCATGGGCCCCATTCCAGGACACTTCTGA
GTACATCATTTCATGTCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGACTCGTACCACTGTCGGT
ACGGTGTGCTGTCGATGAGCACGATGCAATTCTTCACCAGGGTCTTGGTACGAACCAGCTCGTTATTAGATGCATT
GTAGACAACATCGATGATCCTTGTTTTACGAGTACAACACTCTGAGCCCCAGGAGAAATTCCCCACGTCCAACCTC
AGGGCACGGTATTTCTTGTTACCTCCCCGCACACGGACTGTGTGGATGCGGCGGGGGCCAAGCTGACTCCTGAGGA
AGAAGAGATTTTAAACAAAAAACGATCTAAAAAAAATTCAGAAGAAATATGATGAAAGGAAAAAGAATGCCAAAATC
AGCAGTCTCCTGGAGGAGCAGTTCCAGCAGGGCAAGCTTCTTGCGTGCATCGCTTCAAGGCCGGGACAGTGTGACC
GAGCAGATGGCTATGTGCTAGAGGGCAAAGAAGTGGAGTTCTATCTTAAGAAAATCAGGGCCCAGAATGGTGNGTC
TTCAACTAATCCAAAGGGGAGTTTCAGACCAGTGCAATCAGCAAAAACATTGATACTGNTGGCCAAATTTATTGGT
GCAGGGCTTGCACANTANGANNGGCTGGGTCTTGGGGCTTGGATTGGNACAAGCTTTGGCAGCCTTTTCTTTGGTT
TTGCCAAAAACCTTTTGNTGAAGANGANACCTNGGGCGGACCCCTTAACCGATTCCACNCCNGGNGGCGTTCTANG
GNCCCNCTTG

*Fig. 15E-1*

06_16471.edit

```
AGCGTGGTCGCGGCCGAGGTCTGCTGCTTCAGCGAAGGGTTTCTGGCATAACCAATGATAAGGCTGCCAAAGACTG
TTCCAATACCAGCACCAGAACCAGCCACTCCTACTGTTGCAGCACCTGCACCAATAAATTTGGCAGCAGTATCAAT
GTCTCTGCTGATTGCACTGGTCTGAAACTCCCTTTGGATTAGCTGAGACACACCATTCTGGGCCCTGATTTTCCTA
AGATAGAACTCCAACTCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTTTTTCCTTTCATCATA
TTTCTTCTGAATTTTTTTAGATCGTTTTTTTGTTTAAAATCTCTTCTTCCTCAGGAGTCAGCTTGGCCCCCGCCGCA
TCCACACAGTCCGTGTGCGGGGAGGTAACAAGAAATACCGTGCCCTGAGGTTGGACGTGGGGAATTTCTCCTGGGG
CTCAGAGTGGTGTACTCGTAAAACAAGGATCATCGATGGTGNCTACAATGCATCTAATAACGAGCTGGGTCGGACC
CAAAGAACCTGGNGAANAAATGGATCGNCTCATCGACAGGACACCGTACCCGACAGGGGNACGANTCCCACTATGC
GCTTGCCCCTGGGCCGCAANAAAGGAAAACTGCCCGGGCGGCCNTCGAAAGCCCAATTNTGGAAAAAATCCATCAC
ACTGGGNGGCCNGTCGAGCATGCATNTANAGGGGCCCATTCCCCCTNANN
```

07_16472.edit

```
TCGAGCGGCCGCCCGGGCAGGTCCCCAACCAAGGCTGCAACCTGGATGCCATCAAAGTCTTCTGCAACATGGAGAC
TGGTGAGACCTGCGTGTACCCCACTCAGCCCAGTGTGGCCCAGAAGAACTGGTACATCAGCAAGAACCCCAAGGAC
AAGAGGCATGTCTGGTTCGGCGAGAGCATGACCGATGGATTCCAGTTCGAGTATGGCGGCCAGGGCTCCGACCCTG
CCGATGTGGACCTCGGCCGCGACCACGCT
```

08_16472.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGACCTGCCCGGGCGGCCGCTCGA
```

09_16473.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGNTTT
AGGCGGACCACACCGCCCACAACGGCCACCCCCATAAGGCATAGGCCAAGACCATACCCGCCGAATGTAGGACAAG
AAGCTNTNTNTCANACACCATNTNATGGGCCCCATTCCAGGACACTTCTGAGTACATCATTTATGNCATCTGTGGC
ACTTGATGAAAACCCTTACAGTTCAGGGTTCTGGAACTTTTTACCAGGCCTNTTACAGGACTNGGCCGGACNCCTTA
AGCCNATTNCACCCTGGGGCGTTCTANGGTCCCACTCGNNCACTGGNGAAAATGGCTACTGTN
```

*Fig. 15F-1*

11_16474.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGNGAAACTCCNAGGACANGAGGGCTAAATTCCATGAAGTTTGTGGATGGCCTGATGATCCACAAT
CGGAGACCCTGTTAACTACTACCGTCTNACCNCCTGCTGTNCNCCCCCNTTTCTGCTNAANACATNGGGNTNNTNC
TTGNCCNTCCTTGGGTNGAANATNNAATNGCCTNCCCNTTCNTANCNCTACTNGNTCCANANTTGGCCTTTAAANA
ATCCNCCTTGCCTTNNNCACTGTTCANNTNTTTNNTCGTAAACCCTATNANTTNNATTANATNNTNNNNNNCTCAC
CCCCCTCNTCATTNANCCNATANGCTNNNAANTCCTTNANNCCTCCCNCCCNNTNCNCTCNTACTNANTNCTTCTN
NCCCATTACNNAGCTCTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAATTNCNNANTTCCNCNTTCCNNCNTTT
CGGNTNNTCCCATNCTTTCCANNNCTTCANTCTANCNCNCTNCAACTTATTTTCCTNTCATCCCTTNTTCTTTACA
NNCCCCCTNNTCTACTCNNCNNTTNCATTANATTTGAAACTNCCACNNCTANTTNCCTCNCTCTACNNTTTTATTT
TNCGNTCNCTCTACNTAATANTTTAATNANTTNTCN
```

12_16474.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAAGCAGTGTCAACGTAGTAAGTTAACAGGGTCTCCGCTGTGGATCA
TCAGGCCATCCACAAACTTCATGGATTTAGCCCTCTGTCCTCGGAGTTTCCCAGACACCACAACCTCGCAGCCTTT
GGCCCCACTCTCCATGATGAACCGCAGCACACCATAGCAGGCCCTCCGCACAAGCAAGCCCTCCTAAGAATTTGTA
ACGCANANACTCTGCTGGCAATGGCACACAAACCTCTAGTGGACCTCGGNCGCGACCACGC
```

13_16475.edit

```
TCGAGCGGCCGCCCGGGCAGGTCTGGTCCAGGATAGCCTGCGAGTCCTCCTACTGCTACTCCAGACTTGACATCAT
ATGAATCATACTGGGGAGAATAGTTCTGAGGACCAGTAGGGCATGATTCACAGATTCCAGGGGGGCCAGGAGAACC
AGGGGACCCTGGTTGTCCTGGAATACCAGGGTCACCATTTCTCCCAGGAATACCAGGAGGGCCTGGATCTCCCTTG
GGGCCTTGAGGTCCTTGACCATTAGGAGGGCGAGTAGGAGCAGTTGGAGGCTGTGGGCAAACTGCACAACATTCTC
CAAATGGAATTTCTGGGTTGGGGCAGTCTAATTCTTGATCCGTCACATATTATGTCATCGCAGAGAACGGATCCTG
AGTCACAGACACATATTTGGCATGGTTCTGGCTTCCAGACATCTCTATCCGNCATAGGACTGACCAAGATGGGAAC
ATCCTCCTTCAACAAGCTTNCTGTTGTGCCAAAAATAATAGTGGGATGAAGCAGACCGAGAAGTANCCAGCTCCCC
TTTTTGCACAAAGCNTCATCATGTCTAAATATCAGACATGAGACTTCTTTGGGCAAAAAAGGAGAAAAAGAAAAAG
CAGTTCAAAGTANCCNCCATCAAGTTGGTTCCTTGCCCNTTCAGCACCCGGGCCCCGTTATAAAACACCTNGGGCC
GGACCCCCCTT
```

*Fig. 15G-1*

14_16475.edit

```
AGCGTGGTCGCGGCCGAGGTGTTTTATGACGGGCCCGGTGCTGAAGGGCAGGGAACAACTTGATGGTGCTACTTTG
AACTGCTTTTCTTTTCTCCTTTTTGCACAAAGAGTCTCATGTCTGATATTTAGACATGATGAGCTTTGTGCAAAAG
GGGAGCTGGCTACTTCTCGCTCTGCTTCATCCCACTATTATTTTGGCACAACAGGAAGCTGTTGAAGGAGGATGTT
CCCATCTTGGTCAGTCCTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAAATTCCATTTGGAGAA
TGTTGTGCAGTTTGCCCACAGCCTCCAACTGCTCCTACTCGCCCTCCTAATGGTCAAGGACCTCAAGGCCCCAAGG
GAGATCCAGGCCCTCCTGGTATTCCTGGGAGAAATGGTGACCCTGGTATTCCAGGACAACCAGGGTCCCCTGGTTC
TCCTGGCCCCCCTGGAATCNGGNGAATCATGCCCTACTGGTCCTCAAACTATTCTCCCANATGATTCATATGATGT
CAAGTCTGGGATAGCNAGTANGGANGGACTCGCAGGCTATTCTGGACCANACCTGCCGGGGGGGCGTTCGAAAGCC
CGAATCTGCANANNTNCNTTCACACTGGCGGCCGTCGAGCTGCTTTAAAAGGGGCCATTCCNCCTTTAGNGNGGGGG
ANTACAATTACTNGGCGGCGTTTTANANCGCGNGNCTGGGAAAT
```

15_16476.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAGGCTCTTGAGGGTGGTGTCCACCTCGA
GGTCACGGTCACGAACCACATTGGCATCATCAGCCCGGTAGTAGCGGCCACCATCGTGAGCCTTCTCTTGANGTGG
CTGGGGCAGGAACTGAAGTCGAAACCAGCGCTGGGAGGACCAGGGGGACCAANAGGTCCAGGAAGGGCCCGGGGGG
GACCAACAGGACCAGCATCACCAAGTGCGACCCGCGAGAACCTGCCCGGCCGNCCGCTCGAA
```

16_16476.edit

```
TCGAGCGNNCGCCCGGGCAGGTCTCGCGGTCGCACTGGTGATGCTGGTCCTGTTGGTCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGCCGCAAGAACCCCGCCCGCACCTGCCGTG
ACCTCAAGATGTGCCACTCTGACTGGAAGAGTGGAGAGTACTGGATTGACCCCAACCAAGGCTGCAACCTGGATGC
CATCAAAGTCTTCTGCAACATGGAGACTGGTGAGACCTGCGTGTACCCCACTCAGCCCAGTGTGGCCCAGAAGAAC
TGGTACATCAGCAAGAACCCCAAGGACAAGAGGCATGTCTGGTTCGGCGAGAGCATGACCGATGGATTCCAGTTCG
AGTATGGCGGCCAGGGCTCCCACCCTGCCGATGTGGACCTCCGGCCGCGACCACCCTT
```

*Fig. 15H-1*

17_16477.edit

```
TNGAGCGGCCGCCCGGGCAGGNTGNNAACGCTGGTCCTGCTGGTCCTCCTGGCAAGGCTGGTGAAGATGGTCACCC
TGGAAAACCCGGACGACCTGGTGAGAGAGGAGTTGTTGGACCACAGGGTGCTCGTGGTTTCCCTGGAACTCCTGGA
CTTCCTGGCTTCAAAGGCATTAGGGGACACAATGGTCTGGATGGATTGAAGGGACAGCCCGGTGCTCCTGGTGTGA
AGGGTGAACCTGGTGCCCCTGGTGAAAATGGAACTCCAGGTCAAACAGGAGCCCGTGGGCTTCCTGGTGAGAGAGG
ACCGTGTTGGTGCCCCTGGCCCANACCTCGGCCGCGACCACGCTAAGCCCGAATTTCCAGCACACTGGNGGCCGTT
ACTANTGGATCCGAGCTCGGTACCAAGCTTGGCGTAATCATGGTCATAGCTGTTTCCTGNGTGAAATTGTTATCCG
CTCACAATTTCACACANCATACGAAGCCGGAAAGCATAAAGTGTAAAGCCTTGGGGTGCTAATGAGTGAGCTAACT
CNCATTAAATTGCGTTGCGCTCACTGCCCGCTTTTCCANNNGGGAAACCNTGGCNTNGCCNGCTTGCNTTAANTGA
AATCCGCCNACCCCCGGGGAAAAGNCGGTTTGCNGTATTGGGGCNCTTTTTCCCTTTCCTCGGNTTACTTGANTTA
NTGGGCTTTGGNCGNTTCGGGTTGNGGCGANCNGGTTCAACNTCACNCCAAAGGNGGNAANACGGTTTTCCCANAA
TCCGGGGGNTANCCCAANGNAAAACATNNGNCNAANGGGCT
```

18_16477.edit

```
AGCGTGGTTNGCGGCCGAGGTCTGGGCCAGGGGCACCAACACGTCCTCTCTCACCAGGAAGCCCACGGGCTCCTGT
TTGACCTGGAGTTCCATTTTCACCAGGGGCACCAGGTTCACCCTTCACACCAGGAGCACCGGGCTGTCCCTTCAAT
CCATNCAGACCATTGTGNCCCCTAATGCCTTTGAAGCCAGGAAGTCCAGGAGTTCCAGGGAAACCACCGAGCACCC
TGTGGTCCAACAACTCCTCTCTCACCAGGTCGTCCGGGTTTTCCAGGGTGACCATCTTCACCAGCCTTGCCAGGAG
GACCAGCAGGACCAGCGTTACCAACCTGCCCGGGCGGCCGCTCGA
```

21_16479.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT
```

22_16479.edit

```
AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAAGATGTGATTCATCTAGATGGTGCCATGACAATGGT
GTGAACTACAAGATTGGAGAGAAGTGGGACCGTCAGGGAGAAAATGGACCTGCCCGGGCCGGCCGCTCGA
```

*Fig. 15I-1*

24_16480.edit

```
TCGAGCGNNCGCCCGGGCAGGTCCAGTAGTGCCTTCGGGACTGGGTTCACCCCCAGGTCTGCGGCAGTTGTCACAG
CGCCAGCCCCGCTGGCCTCCAAAGCATGTGCAGGAGCAAATGGCACCGAGATATTCCTTCTGCCACTGTTCTCCTA
CGTGGTATGTCTTCCCATCATCGTAACACGTTGCCTCATGAGGGTCACACTTGAATTCTCCTTTTCCGTTCCCAAG
ACATGTGCAGCTCATTTGGCTGGCTCTATAGTTTGGGGAAAGTTTGTTGAAACTGTGCCACTGACCTTTACTTCCT
CCTTCTCTACTGGAGCTTTCGTACCTTCCACTTCTGCTGTTGGTAAAATGGTGGATCTTCTATCAATTTCATTGAC
AGTACCCACTTCTCCCAAACATCCAGGGAAATAGTGATTTCAGAGCGATTAGGAGAACCAAATTATGGGGCAGAAA
TAAGGGGCTTTTCCACAGGTTTTCCTTTGGAGGAAGATTTCAGTGGTGACTTTAAAAGAATACTCAACAGTGTCTT
CATCCCCATAGCAAAAGAAGAAACNGTAAATGATGGAANGCTTCTGGAGATGCCNNCATTTAAGGGACNCCCAGAA
CTTCACCATCTACAGGACCTACTTCAGTTTACANNAAGNCACATANTCTGACTCANAAAGGACCCAAGTAGCNCCA
TGGNCAGCACTTTNAGCCTTTCCCCTGGGGAAAANNTTACNTTCTTAAAANCCTNGGCCNNGACCCCCTTAAGNCCA
AATTNTGGAAAANTTCCNTNCNNCTGGGGGGCNGTTCNACATGCNTTTNAAGGGCCCAATTNCCCCNT
```

25_16481.edit

```
TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTGGCATTATGCACCTCC
ACGCCGTCCACGTACCAGTTGAACTTGACCTCAGGGTCTTCGTGGCTCACGTCCACCACCACGCATGTAACCTCAG
ACCTCGGCCGCGACCACGCT
```

26_16481.edit

```
AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACA
CCTGCCCGGGCGGCCGCTCGA
```

27_16482.edit

```
TCGAGCGGCCGCCCGGGCAGGTTGAATGGCTCCTCGCTGACCACCCCGGTGCTGGTGGTGGGTACAGAGCTCCGAT
GGGTGAAACCATTGACATAGAGACTGTCCCTGTCCAGGGTGTAGGGGCCCAGCTCAGTGATGCCGTGGGTCAGCTG
GCTCAGCTTCCAGTACAGCCGCTCTCTGTCCAGTCCAGGGCTTTTGGGGTCAGGACGATGGGTGCAGACAGCATCC
ACTCTGGTGGCTGCCCCATCCTTCTCAGGCCTGAGCAAGGTCAGTCTGCAACCAGAGTACAGAGAGCTGACACTGG
TGTTCTTGAACAAGGGCATAAGCAGACCCTGAAGGACACCTCGGCCGCGACCACGCT
```

*Fig. 15J-1*

28_16482.edit

```
AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA
```

29_16483.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTCCCGGTTCCAGGCCAGTAATA
GTAGCCTCTGTGACACCAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNGGACCTGCCCGGCGGCCG
TTCNAAAGCCCAATTCCACACACTTGGNGGCCGTACTATGGATCCCACTCNGTCCAACTTGGNGGAATATGGCATA
ACTTTT
```

31_16484.edit

```
TCGAGCGGCCGCCCGGGCAGGTCCTTGACCTTTTCAGCAAGTGGGAAGGTGTAATCCGTCTCCACAGACAAGGCCA
GGACTCGTTTGTACCCGTTGATGATAGAATGGGGTACTGATGCAACAGTTGGGTAGCCAATCTGCAGACAGACACT
GGCAACATTGCGGACACCCTCCAGGAAGCGAGAATGCAGAGTTTCCTCTGTGATATCAAGCACTTCAGGGTTGTAG
ATGCTGCCATTGTCGAACACCTGCTGGATGACCAGCCCAAAGGAGAAGGGGGAGATGTTGAGCATGTTCAGCAGCG
TGGCTTCGCTGGCTCCCACTTTGTCTCCAGTCTTGATCAGACCTCGGCCGCGACCACGCT
```

37_16487.edit

```
AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCG
```

*Fig. 15K-1*

38_16487.edit

CGAGCGGCCGCCCGGGCAGGTTTGGAAGGGGGATGCGGGGGAAGAGGAAGACTGACGGTCCCCCCAGGAGTTCAGG
TGCTGGGCACGGTGGGCATGTGTGAGTTTTGTCACAAGATTTGGGCTCAACTCTCTTGTCCACCTTGGTGTTGCTG
GGCTTGTGATCTACGTTGCAGGTGTAGGTCTGGGTGCCGAAGTTGCTGGAGGGCACGGTCACCACGCTGCTGAGGG
AGTAGAGTCCTGAGGACTGTAGGACAGACCTCGGCCGCGACCACGCT

39_16488.edit

NGGNNGGTCCGGNCNGNCAGGACCACTCNTCTTCGAAATA

41_16489.edit

AGCGTGGTCGCGGCCGAGGTCCTCACTTGCCTCCTGCAAAGCACCGATAGCTGCGCTCTGGAAGCGCAGATCTGTT
TTAAAGTCCTGAGCAATTTCTCGCACCAGACGCTGGAAGGGAAGTTTGCGAATCAGAAGTTCAGTGGACTTCTGAT
AACGTCTAATTTCACGGAGCGCCACAGTACCAGGACCTGCCCGGGCGGCCGCTCGA

42_16489.edit

TCGAGCGGCCGCCCGGGCAGGTCCTGGTACTGNGGCGCTCCGTGAAATTAGACGTTATCAGAAGTCCACTGAACTT
CTGATTCGCAAACTTCCCTTCCAGCGTCTGGTGCGAGAAATTGCTCAGGACTTTAAAACAGATCTGCGCTTCCAGA
GCGCAGCTATCGGTGCTTTGCAGGAGGCAAGTGAGGACCTCGGCCGCGACCACGCT

45_16491.edit

TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT

*Fig. 15L-1*

46_16491.edit

```
GTGGGNTTGAACCCNTTTNANCTCCGCTTGGTACCGAGCTCGGATCCACTAGTAACGGCCGCCAGTGTGCTGGAAT
TCGGCTTAGCGTGGTCGCGGCCGAGGTCAAGAACCCCGCCCGCACCTGCCGTGACCTCAAGATGTGCCACTCTGAC
TGGAAGAGTGGAGAGTACTGGATTGACCCCAACCAAGGCTGCAACCTGGATGCCATCAAAGTCTTCTGCAACATGG
AGACTGGTGAGACCTGCGTGTACCCCACTCAGCCCAGTGTGGCCCAGAAGAACTGGTACATCAGCAAGAACCCCAA
GGACAAGAGGCATGTCTGGTTCGGCGAGAGCATGACCGATGGATTCCAGTTCGAGTATGGCGGCCAGGGCTCCGAC
CCTGCCGATGTGGACCTGCCCGGGCGGCCGCTCGA
```

47_16492.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAAGTGT
CTATGCTCAGAATCCAAGCGGAGAGAAGTCAGCCTCTGGTTCAGACTGNAAGTAACCAACATTGATCGCCTAAAGG
ACTGGCATTCACTGATGNGGATGCCGATTCCATCAAAATTGNTTGGGAAAACCCACAGGGGCAAGTTTNCANGTCN
AGGNGGACCTACTCGAGCCCTGAGGATGGAATCCTTGACTNTTCCTTNNCCTGATGGGGAAAAAAAACCTTNAAAA
CTTGAAGGACCTGCCCGGGCGGCCGTNCAAAACCCAATTCCACCCCCTTGGGGGCGTTCTATGGGNCCCACTCGGA
CCAAACTTGGGGTAAN
```

48_16492.edit

```
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGGCATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAGTTTTTGTTGGTCCTGGTCCATTTTTGGGAGTGGTGGTTACTCTGT
AACCAGTAACAGGGGAACTTGAAGGCAGCCACTTGACACTAATGCTGTTGTCCTGAACATCGGTCACTTGCATCTG
GGATGGTTTGTCAATTTCTGTTCGGTAATTAATGGAAATTGGCTTGCTGCTTGCGGGGCTTGTCTCCACGGCCAGT
GACAGCATACACAGTGATGGTATAATCAACTCCAGGTTTAAGCCGCTGATGGTAGCTGAAACTTTGCTCCAGGCAC
AAGTGAACTCCTGACAGGGCTATTTCCTNCTGTTCTCCGTAAGTGATCCTGTAATATCTCACTGGGACAGCAGGAN
GCATTCCAAAACTTCGGGCGNGACCCCCTAAGCCGAATTNTGCAATATNCATCACACTGGCGGGCGCTCGANCATT
CATTAAAAGGCCCAATCNCCCCTATAGGGAGTNTANTACAATTNG
```

*Fig. 15M-1*

49_16493.edit

```
TCGAGCGGCCGCCCGGGCAGGTCACTTTTGGTTTTTTGGTCATGTTCGGTTGGTCAAAGATAAAAACTAAGTTTGAG
AGATGAATGCAAAGGAAAAAAATATTTTCCAAAGTCCATGTGAAATTGTCTCCCATTTTTTTGGCTTTTGAGGGGG
TTCAGTTTGGGTTGCTTGTCTGTTTCCGGGTTGGGGGGAAAGTTGGTTGGGTGGGAGGGAGCCAGGTTGGGATGGA
GGGAGTTTACAGGAAGCAGACAGGGCCAACGTCG
```

55_16496.edit

```
AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA
```

56_16496.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT
```

59_16498.edit

```
TCGAGCGGCCGCCCGGGCAGGTCCACCATAAGTCCTGATACAACCACGGATGAGCTGTCAGGAGCAAGGTTGATTT
CTTTCATTGGTCCGGTCTTCTCCTTGGGGGTCACCCGCACTCGATATCCAGTGAGCTGAACATTGGGTGGTGTCCA
CTGGGCGCTCAGGCTTGTGGGTGTGACCTGAGTGAACTTCAGGTCAGTTGGTGCAGGAATAGTGGTTACTGCAGTC
TGAACCAGAGGCTGACTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCATTTTTGGGAGTGGT
GGTTACTCTGTAACCAGTAACAGGGGAACTTGAAGGCAGCCACTTGACACTAATGCTGTTGTCCTGAACATCGGTC
ACTTGCATCTGGGATGGTTTGNCAATTTCTGTTCGGTAATTAATGGAAATTGGCTTGCTGCTTGCGGGGCTGTCTC
CACGGCCAGTGACAGCATACACAGNGATGGNATNATCAACTCCAAGTTTAAGGCCCTGATGGTAACTTTAAACTTG
CTCCCAGCCAGNGAACTTCCGGACAGGGTATTTCTTCTGGTTTTCCGAAAGNGANCCTGGAATNNTCTCCTTGGAN
CAGAAGGANCNTCCAAAACTTGGGCCGGAACCCCTT
```

*Fig. 15N-1*

60_16473.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTTCCCGGTTCCAGGCCAGTAAT
AGTAGCCTCTTGTGACACCAGGCGGGGCCCANGGACCACTTCTCTGGGANGAGACCCAGCTTCTCATACTTGATGA
TGTAACCCGGTAATCCTGCACGTGGCGGCTGNCATGATACCANCAAGGAATTGGGTGNGGNGGACCTGCCCGGCGG
CCCTCNA
```

60_16498.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAGTGTC
TATGCTCAGAATCCAAGCGGAGAGAGTCAGCCTCTGGTTCAGACTGCAGTAACCACTATTCCTGCACCAACTGACC
TGAAGTTCACTCAGGTCACACCCACAAGCCTGAGCCGCCAGTGGACACCACCCAATGTTCACTCACTGGATATCGA
GTGCGGGTGACCCCCAAGGAGAAGACCCGGACCCATGAAAGAAATCAACCTTGCTCCTGACAGCTCATCCGNGGGT
GTATCAGGACTTATGGGGGACTGCCCCGGCNGGCCGNTCGAAANCGAATTNTGAAATTTCCTTCNCACTGGGNGGC
GNTTCGAGCTTNCTTNTANANGGCCCAATTCNCCTNTAGNGGGTCGTN
```

61_16499.edit

```
AGCGTGGTCGCGGCCGAGGTCNAGG
```

62_16483.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGTTTT
AGGCGGACCACACCGCCCACAACGGGCACCCCCATAAGGNATAGGCCAAGACCATACCCCGCCGAATGTAGGACAA
GAAGCTCTNTCTCAACAACCATCTCATGGGCCCCATTCCAGGACACTTCTGAGTACATCATTTCATGTCATCCTGG
TGGGCACTTGATGAANAACCCTTACAGTTCAGGGTTCCTGGAACTTCTACCAGNGCCACTTCTGACAGGANCTTGG
GCGNGACCACCCT
```

*Fig. 150-1*

63_16500.edit

AGCGTGGTCGCGGCCGAGGTCCATTTTCTCCCTGACGGTCCCACTTCTCTCCAATCTTGTAGTTCACACCATTGTC
ATGGCACCATCTAGATGAATCACATCTGAAATGACCACTTCCAAAGCCTAAGCACTGGCACAACAGTTTAAAGCCT
GATTCAGACATTCGTTCCCACTCATCTCCAACGGCATAATGGGAAACTGTGTAGGGGTCAAAGCACGAGTCATCCG
TAGGTTGGTTCAAGCCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTGCCCGGGCGGCCCGCTCGA

64_16493.edit

AGCGTGGTCGCGGCCGAGGTGTGCCCCAGACCAGGAATTCGGCTTCGACGTTGGCCCTGTCTGCTTCCTGTAAACT
CCCTCCATCCCAACCTGGCTCCCTCCCACCCAACCAACTTTCCCCCCAACCCGGAAACAGACAAGCAACCCAAACT
GAACCCCCTCAAAAGCCAAAAAAATGGGAGACAATTTCACATGGACTTTGGAAAATATTTTTTTTCCTTTGCATTCA
TCTCTCAAACTTAGTTTTTATCTTTGACCAACCGAACATGACCAAAAACCAAAAGTGACCTGCCCGGGCGGCCGCT
CGA

64_16500.edit

TCGAGCGGCCGCCCGGGCAGGTCCTCACCAGAGGTGCCACCTACAACATCATAGTGGAGGCACTGAAAGACCAGCA
GAGGCATAAGGTTCGGGAAGAGGTTGTTACCGTGGGCAACTCTGTCAACGAAGGCTTGAACCAACCTACGGATGAC
TCGTGCTTTGACCCCTACACAGTTTCCCATTATGCCGTTGGAGATGAGTGGGAACGAATGTCTGAATCAGGCTTTA
AACTGTTGTGCCAGTGCTTAGGCTTTGGAAGTGGTCATTTCAGATGTGATTCATCTAGATGGTGCCATGACAATGG
TGTGAACTACAAGATTGGAGAGAAGTGGGACCGTCAGGGAGAAAATGGACCTCGGCCGCGACCACGCT

*Fig. 15P-1*

16501.edit

```
TCGAGCGGCCGCCCGGGCAGGTACCGGGGTGGTCAGCGAGGAGCCATTCACACTGAACTTCACCATCAACAACCTG
CGGTATGAGGAGAACATGCAGCACCCTGGCTCCAGGAAGTTCAACACCACGGAGAGGGTCCTTCAGGGCCTGCTCA
GGTCCCTGTTCAAGAGCACCAGTGTTGGCCCTCTGTACTCTGGCTGCAGACTGACTTTGCTCAGACCTGAGAAACA
TGGGGCAGCCACTGGAGTGGACGCCATCTGCACCCTCCGCCTTGATCCCACTGGTNCTGGACTGGACANANAGCGG
CTATACTTGGGAGCTGANCCNAACCTTTGGCGGNGACNCCNCTT
```

16501.2.edit

```
GAGGACTGGCTCAGCTCCCAGTATAGCCGCTCTCTGTCCAGTCCAGGACCAGTGGGATCAAGGCGGAGGGTGCAGA
TGGCGTCCACTCCAGTGGCTGCCCCATGTTTCTCAAGTCTGAGCAAAGNCAGTCTGCAGCCAGAGTACAGAGGGCC
AACACTGGTGCTCTTGAACAGGGACCTGAGCAGGCCCTGAAGGACCCTCTCCGTGGTGTTGAACTTCCTGGAGCCA
GGGTGCTGCATGTTCTCCTCATACCGCAGGTTGTTGATGGTGAAGTTCAGTGTGAATGGCTCCTCGCTGACCACCC
```

16502.1.edit

```
AGCGTGGTCGCGGCCGAGGTCCACCACACCCAATTCCTTGCTGGTATCATGGCAGCCGCCACGTGCCAGGATTACC
GGCTACATCATCAAGTATGAGAAGCCTGGGTCTCCTCCCAGAGAAGTGGTCCCTCGGCCCCGCCCTGGTGTCACAG
AGGCTACTATTACTGGCCTGGAACCGGGAACCGAATATACAATTTATGTCATTGCCCTGAAGAATAATCAGAAGAG
CGAGCCCCTGATTGGAAGGAAAAAGACAGACGAGCTTCCCCAACTGGTAACCCTTCCACACCCCAATCTTCATGGA
CCANANANCTTGGATNGTCCTTTCACNGGTTNAAAAAAACCCTTTTCGCCCCCCCACCTTGGGGATTAACCTTGGGA
AANGGGGATTTNACCNTTCC
```

16502.2.edit

```
TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCCAGTGTCATACCCAGGGNGGGTGACCAAAGGGGGTCNTTTNGACCTGGNGAAAGGAACCA
TCCAAAANCTCTGNCCCATG
```

*Fig. 15Q-1*

16503.1.edit

```
AGCGTGGNCGCGGCCGAGGTCTGAGGATGTAAACTCTTCCCAGGGGAAGGCTGAAGTGCTGACCATGGTGCTACTG
GGTCCTTCTGAGTCAGATATGTGACTGATGNGAACTGAAGTAGGTACTGTAGATGGTGAAGTCTGGGTGTCCCTAA
ATGCTGCATCTCCAGAGCCTTCCATCATTACCGTTTCTTCTTTTGCTATGGGATGAGACACTGTTGAGTATTCTCT
AAAGTCACCACTGAAATCTTCCTCCAAAGGAAAAACCTGTGGAAAAGCCCCTTATTTCTGCCCCATAATTTGGTTCT
CCTAATCNCTCTGAAATCACTATTTCCCTGGAANGTTTGGGAAAAAANNGGGCNACCTGNCANTGGAAANTGGATAN
AAAGATCCCACCATTTTACCCAACNAGCAGAAAGTGGGAANGGTACCGAAAAGCTCCAAGTAANAAAAAGGAGGGA
AGTAAAGGTCAAGTGGGCACCAGTTTCAAACAAAACTTTCCCCAAACTATANAACCCA
```

16503.2.edit

```
AAGCGGCCGCCCGGGCAGGNNCAGNAGTGCCTTCGGGACTGGGNTCACCCCCAGGTCTGCGGCAGTTGTCACAGCG
CCAGCCCCGCTGGCCTCCAAAGCATGTGCAGGAGCAAATGGCACCGAGATATTCCTTCTGCCACTGTTCTCCTACG
TGGTATGTCTTCCCATCATCGTAACACGTTGCCTCATGAGGGTCACACTTGAATTCTCCTTTTCCGTTCCCAAGAC
ATGTGCAGCTCATTTGGCTGGCTCTATAGTTTGGGGAAAGTTTGTTGAAACTGTGCCACTGACCTTTACTTCCTCC
TTCTCTACTGGAGCTTTCCGTACCTTCCACTTCTGCTGNTGGNAAAAAGGGNGGAACNTCTTATCAATTTCATTGG
ACAGTANCCCNCTTTCTNCCCAAAACATNCAAGGGAAAATATTGATTNCNAGAGCGGATTAAGGAACAACCCNAAT
TATGGGGGCCAGAAATAAAGGGGGCTTTTCCACAGGTNTTTTCCT
```

16504.1.edit

```
TCGAGCGGCCGCCCGGGCAGGTCTGCAGGCTATTGTAAGTGTTCTGAGCACATATGAGATAACCTGGGCCAAGCTA
TGATGTTCGATACGTTAGGTGTATTAAATGCACTTTTGACTGCCATCTCAGTGGATGACAGCCTTCTCACTGACAG
CAGAGATCTTCCTCACTGTGCCAGTGGGCAGGAGAAAGAGCATGCTGCGACTGGACCTCGGCCGCGACCACGCT
```

16504.2.edit

```
AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA
```

*Fig. 15R-1*

16505.1.edit

```
CGAGCGGCCGCCCGGGCAGGTCCAGACTCCAATCCAGAGAACCACCAAGCCAGATGTCAGAAGCTACACCATCACA
GGTTTACAACCAGGCACTGACTACAAGATCTACCTGTACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGCTACATCATCAAGTATGAGAAGCCTGGGTCTCCTCCCAGAGAAGTG
GTCCCTCGGCCCCGCCCTGGTGNCACAGAAGCTACTATTACTGGCCTGGAACCGGGAACCGAATATACAATTTATG
TCATTGCCCTGAAGAATAATCANAAGAGCGAGCCCCTGATTGGAAGG
```

16505.2.edit

```
AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTGTCTTTTTCCTTCCAATCAGGGGCTCGCTCTTCTGATTATTCTTCAGGGCAATGACAT
AAATTGTATATTCGGTTCCCGGTTCCAGGCCAGTAATAGTAGCCTCTGTGACACCAGGGCGGGGCCGAGGGACCAC
TTCTCTGGGAGGAGACCCAGGCTTCTCATACTTGATGATGTANCCGGTAATCCTGGCACCGTGGCGGCTGCCATGA
TACCAGCAAGGAATTGGGTGTGGTGGCCAAGAAACGCAGGTTGGATGGTGCATCAATGGCAGTGGAGGCGTCGATN
ACCACAGGGGAGCTCCGANCATTGTCATTCAAGGTGGACAGGTAGAATCTTGTAATCAGGTGCCTGGTTTGTAAAC
CTG
```

16506.1.edit

```
TCGAGCGGCCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCAAGAACC
CCAAGGACAAGAAGCATGTCTGGTTCGGCGAAAGCATGACCGATGGATTCCAGTTCGAGTATGGCGGCCAGGGCTC
CGACCCTGCCGATGTGGACCTCGGCCGCGACCACGCTAAGCCCGAATTCCAGCACACTGGCGGCCGTTACTAGTGG
GATCCGAGCTTCGGTACCAAGCTTGGCGTAATCATGGGNCATAGCTGTTTCCTGNGTGAAAATGGTATTCCGCTTC
ACAATTTCCCAC
```

16506.2.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAAGCTCTTGAAGGGTGGTGTCCACCTCG
AGGTCACGGTCACGAAACCTGCCCGGGCGGCCGCTCGA
```

*Fig. 15S-1*

16507.1.edit

```
AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGNGCCGGNCCGCTCGAAAAGCCCNAATTTCCAGNCACACTTGGCCGGCCGTTACTACTG
```

16507.2.edit

```
TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT
```

16508.1.edit

```
CGAGCGGCCGCCCGGGCAGGTCCCCCCCCCTTTTTTTTTTTTTTTTTTTTTTTTTTTTTTTTTTTTTTTTTTTTTT
TTTTTTTTTTTTTTTTTT
```

16508.2.edit

```
AGCGTGGTCGCGGCCGAGGTCTGGCATTCCTTCGACTTCTCTCCAGCCGAGCTTCCCAGAACATCACATATCACTG
CAAAAATAGCATTGCATACATGGATCAGGCCAGTGGAAATGTAAAGAAGGCCCTGAAGCTGATGGGGTCAAATGAA
GGTGAATTCAAGGCTGAAGGAAATAGCAAATTCACCTACACAGTTCTGGAGGATGGTTGCACGAAACACACTGGGG
AATGGAGCAAAACAGTCTTTGAATATCGAACACGCAAGGCTGTGAGACTACCTATTGTAGATATTGCACCCTATGA
CATTGGTGGTCCTGATCAAGAATTTGGTGTGGACGTTGGCCCTGTTTGCTTTTTATAAACCAAACTCTATCTGAAA
TCCCAACAAAAAAAATTTAACTCCATATGTGNTCCTCTTGTTCTAATCTTGGCAACCAGTGCAAGTGACCGACAAA
ATTCCAGTTATTTATTTCCAAAATGTTTGGAAACAGTATAATTTGACAAAGAAAAAAGGATACTTCTCTTTTTTTG
GCTGGTCCACCAAATACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT
```

*Fig. 15T-1*

16509.1.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAAGTAACCACCACTCCCAAAAATGGACCAGGACCAACAAAAA
CTAAAACTGCAGGTCCAGATCAAACAGAAAATGGACTATTGAAGGCTTGCAGCCCACAGTGGAAGTATGTGGNTAG
GNGTCTATGCTCAGAATCCCAAGCCGGAGAAAGTCAGCCTTCTGGTTTAGACTGCAGTAACCAACATTGATCGCCC
TAAAGGACTGGNCATTCACTTGGATGGTGGATGTCCAATTC
```

16509.2.edit

```
TCGAGCGGCCGCCCGGGCAGGTCCTTGCAGCTCTGCAGNGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGNGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGGTGGTCCTGNCCCATTTTTGGGAAGTGGGGGGTTACTC
TGTAACCAGTAACAGGGGAACTTGAAGGCAGCCACTTGACACTAATGCTGTTGTCCTGAACATCGGTCACTTGCAT
CTGGGGATGGTTTTGACAATTTCTGGTTCGGCAAATTAATGGAAATTGGCTTGCTGCTTGGCGGGGCTGNCTCCAC
GGGCCAGTGACAGCATAC
```

16510.1.edit

```
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGTTGGNCCTGNNCCATTTTTGGGGAAGGGGTGGTTACTC
TTGTAACCAGTAACAGGGGAACTTGAAGCAGCCACTTGACACTAATGCTGGTGGCCTGAACATCGGTCACTTGCAT
CTGGGGATGGTTTGGTCAATTTCTGTTCGGTAATTAATGGGAAATTGGCTTACTGGCTTGCGGGGGCTGTCTCCACG
GNCAGTGACAAGCATACACAGGNGATGGGTATAATCAACTCCAGGTTTAAGGCCNCTGATGGTA
```

16510.2.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGTAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGGACCAGGACCAACAAAAA
ACTAAAACTGCANGGTCCAGATCAAACAGAAATGACTATTGAAGGCTTGCAGCCCACAGTGGAGTATGTGGGTTAG
TGTCTATGCTCAGAATNCCAAGCGGAGAGAGTCAGCCTCTGGTTCAGACT
```

*Fig. 15U-1*

16511.1.edit

```
TCGAGCGGCCGCCCGGGCAGGTCAGCGCTCTCAGGACGTCACCACCATGGCCTGGGCTCTGCTCCTCCTCACCCTC
CTCACTCAGGGCACAGGGTCCTGGGCCCAGTCTGCCCTGACTCAGCCTCCCTCCGCGTCCGGGTCTCCTGGACAGT
CAGTCACCATCTCCTGCACTGGAACCAGCAGTGACGTTGGTGCTTATGAATTTGTCTCCTGGTACCAACAACACCC
AGGCAAGGCCCCCAAACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATTATTACTGGAAGCTCA
TATGCAGGCAACAACAATTGGGTGTTCGGCGGAAGGGACCAAGCTGACCGTNCTAAGGTCAAGCCCAAGGCTTGCC
CCCCTCGGTCACTCTGTTCCCACCCTCCTCTGAAGAAGCTTTCAAGCCAACAANGNCACACTGGGTGTGTCTCATA
AGTGGACTTTCTACCC
```

16511.2.edit

```
AGCGTGGTCGCGGCCGAGGTCTGTAGCTTCTGTGGGACTTCCACTGCTCAGGCGTCAGGCTCAGGTAGCTGCTGGC
CGCGTACTTGTTGTTGCTTTGNTTGGAGGGTGTGGTGGTCTCCACTCCCGCCTTGACGGGGCTGCTATCTGCCTTC
CAGGCCACTGTCACGGCTCCCGGGTAGAAGTCACTTATGAGACACACCAGTGTGGCCTTGTTGGCTTGAAGCTCCT
CAGAGGAGGGTGGGAACAGAGTGACCGAGGGGGCAGCCTTGGGCTGACCTAGGACGGTCAGCTTGGTCCCTCCGCC
GAACACCCAATTGTTGTTGCCTGCATATGAGCTGCAGTAATAATCAGCCTCATCCTCAGCCTGGAGCCCAGAGACN
GTCAAGGGAGGCCCGTGTTTGCCAAGACTTGGAAGCCAGANAAGCGATCAGGGACCCCTGAGGGCCGCTTTACNGA
CCTCAAAAAATCATGAATTTGGGGGGCCTTTGCCTGGGNGTTGGTTGGTNACCAGNAAAACAAAATTTCATAAAGC
ACCAACGTCACTGCTGGTTTCCAGTGCANGAANATGGTGAACTGAANTGTCC
```

16512.1.edit

```
AGCGTGGTCGCGGCCGAGGTCCAGCATCAGGAGCCCCGCCTTGCCGGCTCTGGTCATCGCCTTTCTTTTTGTGGCC
TGAAACGATGTCATCAATTCGCAGTAGCAGAACTGCCGTCTCCACTGCTGTCTTATAAGTCTGCAGCTTCACAGCC
AATGGCTCCCATATGCCCAGTTCCTTCATGTCCACCAAAGTACCCGTCTCACCATTTACACCCCAGGTCTCACAGT
TCTCCTGGGTGTGCTTGGCCCGAAGGGAGGTAAGTANACGGATGGTGCTGGTCCCACAGTTCTGGATCAGGGTACG
AGGAATGACCTCTAGGGCCTGGGCNACAAGCCCTGTATGGACCTGCCCGGGCGGGCCCGCTCGA
```

16512.2.edit

```
TCGAGCGGCCGCCCGGGCAGGTCCATACAGGGCTGTTGCCCAGGCCCTAGAGGNCATTCCTTGTACCCTGATCCAG
AACTGTGGGACCAGCACCATCCGTCTACTTACCTCCCTTCGGGCCAAGCACACCCAGGAGAACTGTGAGACCTGGG
GTGTAAATGGNGAGACGGGTACTTTGGTGGACATGAAGGAACTGGGCATATGGGAGCCATTGGCTGNGAAGCTGCA
NACTTATAAGACAGCAGTGGAGACGGCAGTTCTGCTACTGCGAATTGATGACATCGTTTCAGGCCACAAAAAGAAA
GGCGATGACCANAGCCGGCAAGGCGGGGCTTCCTGATGCTGGACCTCGGCCGCCGACCACGCTT
```

*Fig. 15V-1*

16514.1.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTCTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTGACCACGTGAACCATTT
GTGNGAACCCCAAGATGAANATACTTGCCCACCACCCCCCATTC
```

16514.2.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAGTGTCAACGTAGTAGTTAACAGGGTCTCCGCTGTGGATCATC
AGGCCATCCACAAACTTCATGGATTTAGCCCTCTGTCCTCGGAGTTTCCCAAAACACCACAACCTCGCCAGCCTTT
GGGCCCCACTTCTTCATGAATGAAACCGCAGCACACCATTANCAAGGCCCTTCCGCACAGGNAAGCCCTTCCTAAG
GAGTTTTGTAAACGCAAAAAACTCTTGCCTGGGGCAAATGGGCACACAGACCTNTANTNGGACCTTGGNCCGCGAA
CCACCGCTT
```

16515.1.edit

```
AGCGTGGTCGCGGCCGAGGTCTGGCCCTCCTGGCAAGGCTGGTGAAGATGGTCACCCTGGAAAACCCGGACGACCT
GGTGAGAGAGGAGTTGTTGGACCACAGGGTGCTCGTGGTTTCCCTGGAACTCCTGGACTTCCTGGCTTCAAAGGCA
TTAGGGGACACAATGGTCTGGATGGATTGAAGGGACAGCCCGGTGCTCCTGGTGTGAAGGGTGAACCTGGNGCCCC
TGGTGAAAATGGAACTCCAGGTCAAACAGGAGCCCGNGGGCTTCCTGGNGAGAGAGGACGTGTTGGTGCCCCTGGC
CCANACCTGCCCGGGCGGCCGCTCNAAAAGCCGAAATCCAGNACACTGGCGGCCGNTACTANTGGAATCCGAACTT
CGGTACCAAAGCTTGGCCGTAATCATGGCCATAGCTTGTTCCCTGGGGNGGAAATTGGTATTCCGCTNCCAATTCC
ACACAACATACCGAACCCGGAAAGCATTAAAGTGTAAAAGCCCTGGGGGGGCCTAAATGANGTGAGCNTAACTCNC
ATTTAATTGGCGTTGCGCTTCACTGCCCCGCTTTTCCAGTCCGGGNA
```

16515.2.edit

```
TCGAGCGGCCGCCCGGGCAGGTCTGGGCCAGGGGCACCAACACGTCCTCTCTCACCAGGAAGCCCACGGGCTCCTG
TTTGACCTGGAGTTCCATTTTCACCAGGGGCACCAGGTTCACCCTTCACACCAGGAGCACCGGGCTGTCCCTTCAA
TCCATCCAGACCATTGTGNCCCCTAATGCCTTTGAAGCCAGGAAGTCCAGGAGTTCCAGGGAAACCACGAGCACCC
TGTGGTCCAACAACTCCTCTCTCACCAGGTCGTCCGGGTTTTCCAGGGTGACCATCTTCACCAGCCTTGCCAGGAG
GGCCAGACCTCGGCCGCGACCACGCT
```

*Fig. 15W-1*

16516.1.edit

ANCGTGGTCGCGGCCGAGGTCCTCACCAGAGGTGNCACCTACAACATCATAGTGGAGGCACTGAAAGACCANCAGA
GGCATAAGGTTCGGGAAGAGG

16516.2.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGTCCACGGTAACAACCTCTTCCCGAACCTTATGCCTCTGCTGG
TCTTTCAGTGCCTCCACTATGATGTTGTAGGTGGCACCTCTGGTGAGGACCTCNGNCCNGAACAACGCTTAAGCCC
GNATTCTGCAGAATAATCCCATCACACTTGGCGGCCGCTTCGANCATGCATCNTAAAAGGGGCCCCAATTTCCCCC
TTATAAGNGAANCCGTATTTNCCAATTTCACTGGNCCCGCCGNTTTTTACAAACGNCGGTGAACTGGGGAAAAACCC
TGGCGGTTACCCAACTTTAATCGCCNTTGGCAGCACAATCCCCCCTTTTCGNCCANCNTGGGCGTAAATAACCGAA
AA

16517.1.edit

ANCGNGGTCGCGGCCGANGTNTTTTTTCTTNTTTTTTT

16518.1.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GGGNGGTCAGCGTCCTCACCGTCCTGCACCAGAATTGGTTGAATGGCAAGGAGTACAAGNGCAAGGTTTCCAACAA
AGCCNTCCCAGCCCCCNTCGAAAAAACCATTTCCAAAGCCAAAGGGCAGCCCCGAGAACCACAGGTGTACACCCTG
CCCCCATCCCGGGAGGAAAAGANCAANAACCNGGTTCAGCCTTAACTTGCTTGGTCNAANGCTTTTTATCCCAACG
NACTTCCCCCNTGGAANTGGGAAAAACCAATGGGCCAANCCGAAAAACAATTACAANAACCCC

16518.2.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGAACACCTGGGGTTCTCGGGGCTTGCCCTTTGGTTTTGAANATGGTTTTC
TCGATGGGGGCTGGAAGGGCTTTGTTGNAAACCTTGCACTTGACTCCTTGCCATTCACCCAGNCCTGGNGCAGGAC
GGNGAGGACNCTNACCACACGGAACCGGGCTGGTGGACTGCTCC

*Fig. 15X-1*

16519.1.edit

```
AGCGTGGTCGCGGACGANGTCCTGTCAGAGTGGNACTGGTAGAAGTTCCANGAACCCTGAACTGTAAGGGTTCTTC
ATCAGTGCCAACAGGATGACATGAAATGATGTACTCAGAAGNGNCCTGGAATGGGGCCCATGANATGGTTGCC
```

16519.2.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGGGTATGAACCTGGGAA
AANGGNANTTAANCTTTCCTGGCA
```

16520.1.edit

```
AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGGTNCCCTGGTACTGGGTTACAGANTAACCACCACTCCCAAAAATGGACCAGGAACCACAAAAA
CTTAAACTGCAGGGTCCAGATCAAAACAGAAATGACTATTGAANGCTTGCAGCCCACAGTGGGAGTATGNGGGTAG
TGNCTATGCTTCAGAATCCAAGCGGAAAAANGTCAAGCCTTNTGGGTTCAA
```

16520.2.edit

```
TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGNCTGAACCAGAGG
CTGACTCTCTCCGCTTGGATTCTGAGCATAGACACTAACCACATACTCCACTGTGGGCTGCAANCCTTCAATAANN
CATTTCTGTTTGATCTGGACC
```

16521.2.edit

```
TCGAGCGGCCGCCCGGGCAGGTCTGGTGGGGTCCTGGCACACGCACATGGGGGNGTTGNTCTNATCCAGCTGCCCA
GCCCCCATTGGCGAGTTTGAGAAGGTGTGCAGCAATGACAACAANACCTTCGACTCTTCCTGCCACTTCTTTGCCA
CAAAGTGCACCCTGGAGGGCACCAAGAAGGGCCACAAGCTCCACCTGGACTACATCGGGCCTTGCAAATACATCCC
CCCTTGCCTGGACTCTGAGCTGACCGAATTCCCCCTTGCGCATGCGGGACTGGCTCAAGAACCGTCCTGGCACCCT
TGTATGANAGGGATGAAGACACNACCC
```

*Fig. 15Y-1*

16522.1.edit

```
AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTCTGGGGGGAAATTGGTA
TCCNGTTTACAATTCCCNCACAACATACGAGCCGGAAGCATAAAAGNGTAAAAGCCTGGGGGNGGCCTANTGAAGT
GAAGCTAAACTCACATTAATTNGCGTTGCCGCTCACTGGCCCGCTTTTCCAGC
```

16522.2.edit

```
TCGAGCGGCCGCCCGGGCAGGTTTGGAAGGGGGATGCGGGGGAAGAGGAAGACTGACGGTCCCCCCAGGAGTTCAG
GTGCTGGGCACGGTGGGCATGTGTGAGTTTTGTCACAAGATTTGGGCTCAACTCTCTTGTCCACCTTGGTGTTGCT
GGGCTTGTGATCTACGTTGCAGGTGTAGGTCTGGGNGCCGAAGTTGCTGGAGGGCACGGTCACCACGCTGCTGAGG
GAGTAGAGTCCTGAGGACTGTANGACAGACCTCGGCCGNGACCACGCTAAGCCGAATTCTGCAGATATCCATCACA
CTGGCGGCCGCTCCGAGCATGCATTTTAGAGG
```

16523.1.edit

```
AGCGTGGNCGCGGACGANGACAACAACCCC
```

16523.2.edit

```
TCGAGCGGCCGCCCGGGCAGGNCCACATCGGCAGGGTCGGAGCCCTGGCCGCCATACTCGAACTGGAATCCATCGG
TCATGCTCTTGCCGAACCAGACATGCCTCTTGTCCTTGGGGTTCTTGCTGATGNACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCT
```

16524.1.edit

```
AGCGTGGTCGCGGCCGAGGTCCAGCCTGGAGATAANGGTGAAGGTGGTGCCCCCGGACTTCCAGGTATAGCTGGAC
CTCGTGGTAGCCCTGGTGAGAGAGGTGAAACTGGCCCTCCAGGACCTGCTGGTTTCCCTGGTGCTCCTGGACAGAA
TGGTGAACCTGGNGGTAAAGGAGAAAGAGGGGCTCCGGNTGANAAAGGTGAAGGAGGCCCTCCTGNATTGGCAGGG
GCCCCANGACTTAGAGGTGGAGCTGGCCCCCCTGGCCCCGAAGGAGGAAAGGGTGCTGCTGGTCCTCCTGGGCCAC
CTGG
```

*Fig. 15Z-1*

16524.2.edit

TCGAGCGGCCGCCCGGGCAGGTCTGGGCCAGGAGGACCAATAGGACCAGTAGGACCCCTTGGGCCATCTTTCCCTG
GGACACCATCAGCACCTGGACCGCCTGGTTCACCCTTGTCACCCTTTGGACCAGGACTTCCAAGACCTCCTCTTTC
TCCAGGCATTCCTTGCAGACCAGGAGTACCANCAGCACCAGGTGGCCCAGGAGGACCAGCAGCACCCTTTCCTCCT
TCGGGACCAGGGGGACCAGCTCCACCTCTAAGTCCTGGGGCCCCTGCCAATCCAGGAGGGCCTCCTTCACCTTTCT
CACCCGGAGCCCCTCTTTCT 16526.1.edit TCGAGCGGCCGCCCGGGCAGGTCCACCGGGATATTCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGACAACCGGAG
GCTGGAGAGCAAAATCCGGGAGCACTTGGAGAAGAAGGGACCCCAGGTCAGAGACTGGAGCCATTACTTCAAGATC
ATCGAGGACCTGAGGGCTCANATCTTCGCAAATACTGCNGACAATGCCCG 16526.2.edit ATGCGNGGTCGCGGCCGANGACCANCTCTGGCTCATACTTGACTCTAAAGNCNTCACCAGNANTTACGGNCATTGC
CAATCTGCAGAACGATGCGGGCATTGTCCGCANTATTTGCGAAGATCTGAGCCCTCAGGNCCTCGATGATCTTGAA
GTAANGGCTCCAGTCTCTGACCTGGGGTCCCTTCTTCTCCAAGTGCTCCCGGATTTTGCTCTCCAGCCTCCGGTTC
TCGGTCTCCAAGNCTTCTCACTCTGTCCAGGAAAAGAGGCCAGGCGGNCGATCAGGGCTTTTGCATGGACT 16527.1.edit AGCGTGGTCGCGGCCGAGGTTGTACAAGCTTTTTTTTTTTTTTTTTTTTTTTTTTTTTTTTTTTTTTTTTTTTTTT
TTTTTTTTTTTTTTTTTTTTTTTT 16527.2.edit TCGAGCGGCCGCCCGGGCAGGTCTGCCAACACCAAGATTGGCCCCCGCCGCATCCACACAGTTNGTGTGCGGGGAG
GTAACAAGAAATACCGTGCCCTGAGGNTGGACGNGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATNGACAGCACACCGTACCGACAGTGGGTACCGAAGTCCCACTATGCNCCT

*Fig. 15A-2*

16528.1.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAG
```

16528.2.edit

```
AGCGTGNTCNCGGCCGAGGATGGGGAAGCTCGNCTGTCTTTTTCCTTCCAATCAGGGGCTNNNTCTTCTGATTATT
CTTCAGGGCAANGACATAAATTGTATATTCGGNTCCCGGTTCCAGNCCAGTAATAGTAGCCTCTGTGACACCAGGG
CGGGGCCGAGGGACCACTTCTCTGGGAGGAGACCCAGGCTTCTCATACTTGATGATGAAGCCGGTAATCCTGGCAC
GTGGGCGGCTGCCATGATACCACCAANGAATTGGGTGTGGTGGACCTGCCCGGGCGGGCCGCTCGAAAANCCGAAT
TCNTGCAAGAATATCCATCACACTTGGGCGGGCCGNTCGAACCATGCATCNTAAAAGGGCCCCAATTTCCCCCCTA
TTAGGNGAAGCCNCATTTAACAAATTCCACTTGG
```

16529.1.edit

```
TCGAGCGGCCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTTGAGCCAGCAGAATCGAAAACATTCGGAACCCAAGAAGGGCAAGCCCGCAAAGAAACCCGCCCGCAC
CTGGCCGNGAACCTCCAAGAANGTGCCCACNTCTTGACTGGGAAAAAAAGGGAAAANTACTTGGAATTGGAC
```

16529.2.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAAGTGGCACATCTTGAGGTCACGGCAGGGTGCGGGCGG
GGTTCTTGCGGGCTGCCCTTCTGGGCTCCCGGAATGTTCTNNGAACTTGCTGG
```

*Fig. 15B-2*

16530.1.edit
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTTGCTTGTGCGCCACGTGTTGCTCANACANGGGTGGGCTGGGCATCAAG
GNG

16530.2.edit
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAAGTGTCAACGTAAGTAAGTTAACAGGGTCTCCGCTGTGGATC
ATCAGGCCATCCACAAACTTCATGGATTTAACCCTCTGTCCTCGGAG

16531.1.edit
TCGAGCGGCCGCCCGGGCAGGTGTTTCAGAGGTTCCAAGGTCCACTGTGGAGGTCCCAGGAGTGCTGGTGGTGGGC
ACAGAGGTCCGATGGGTGAAACCATTGACATAGAGACTGTTCCTGTCCAGGGTGTAGGGGCCCAGCTCTTTGATGC
CATTGGCCAGTTGGCTCAGCTCCCAGTACAGCCGCTCTCTGTTGAGTCCAGGGCTTTTGGGGTCAAGATGATGGAT
GCAGATGGCATCCACTCCAGTGGCTGCTCCATCCTTCTCGGACCTGAGAGAGGTCAGTCTGCAGCCAGAGTACAGA
GGGCCAACACTGGTGTTCTTTGAATA

16531.2.edit
AGCGTGGTCGCGGCCGAGGTCTGTACTGGGAGCTAAGCAAACTGACCAATGACATTGAAGAGCTGGGCCCCTACAC
CCTGGACAGGAACAGTCTCTATGTCAATGGTTTCACCCATCAGAGCTCTGTGNCCACCACCAGCACTCCTGGGACC
TCCACAGTGGATTTCAGAACCTCAGGGACTCCATCCTCCCTCTCCAGCCCCACAATTATGGCTGCTGGCCCTCTCC
TGGTACCATTCACCCTCAACTTCACCATCACCAACCTGCAGTATGGGGAGGACATGGGTCACCCTGNCTCCAGGAA
GTTCAACACCACA

16532.1.edit
TCGAGCGGCCGCCCGGACAGGTCTGGGCGGATAGCACCGGGCATATTTTGGAATGGATGAGGTCTGGCACCCTGAG
CAGTCCAGCGAGGACTTGGTCTTAGTTGAGCAATTTGGCTAGGAGGATAGTATGCAGCACGGNTCTGAGNCTGTGG
GATAGCTGCCATGAAGTAACCTGAAGGAGGTGCTGGCTGGTANGGGTTGATTACAGGGTTGGGAACAGCTCGTACA
CTTGCCATTCTCTGCATATACTGGTTAGTGAGGTGAGCCTGGCCCTCTTCTTTTG

*Fig. 15C-2*

01_16558.3.edit

AGCGTGGTCGCGGCCGAGGTGAGCCACAGGTGACCGGGGCTGAAGCTGGGGCTGCTGGNCCTGCTGGTCCTG

02_16558.4.edit

CAGCNGCTCCNACGGGGCCTGNGGGACCAACAACACCGTTTTCACCCTTAGGCCCTTTGGCTCCTCTTTCTCCTTT
AGCACCAGGTTGACCAGCAGCNCCANCAGGACCAGCAAATCCATTGGGGCCAGCAGGACCGACCTCACCACGTTCA
CCAGGGCTTCCCCGAGGACCAGCAGGACCAGCAGGACCAGCAGCCCCAGCTTCGCCCCGGTCACCTGTGGCTCACC
TCGGCCGCGACCACGCT

03_16535.1.edit

TCGAGCGGTCGCCCGGGCAGGTCCACCGGGATAGCCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGANAACCGGAG
GCTGGANAGCAAAATCCGGGAGCACTTGGAGAAGAAGGGACCCCAGGTCAAGAGACTGGAGCCATTACTTCAAGAT
CATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCATTGTCA
ATCTGCAGAACGATGCGGGCATTGTCCGCAGTATTTGCGAAGATCTGAGCCCTCAGGTCCTCGATGATCTTGAAGT
AATGGCTCCAGTCTCTGACCTGGGGTCCCTTCTTCTCCAAGTGCTCCCGGATTTTGCTCTCCAGCCTCCGGTTCTC
GGTCTCCAGGCTCCTCACTCTGTCCAGGTAAGAAGGCCCAGGCGGTCGTTCAGGCTTTGCATGGTCTCCTTCTCGT
TCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 15D-2*

07_16537.1.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACCGCAGGTCTCACCAGTCTCCATGTTGCAGAAGACTTTGATGGCATCCAGGTTGCAGCCTT
GGTTGGGGTCAATCCAGTACTCTCCACTCTTCCAGTCAGAAGTGGGCACATCTTGAGGTCACCGGCAGGTGCCGGG
CCGGGGGTTCTTGCGGCTTGCCCTCTGGGCTCCGGATGTTCTCGATCTGCTTGGCTCAGGCTCTTGAGGGTGGGTG
TCCACCTCGAGGTCACGGTCACCGAAACCTGCCCGGGCGGCCCGCTCGA
```

08_16537.2.edit

```
TCGAGCGGTCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGGCCCAGAAGAAACTGGTACATCAGCAAGGA
ACCCCAAGGACAAGAGGCATTGTCTTGGTTCGGCGAGNAGCATGACCCGATGGATTCCAGTTTCGAGTATTGGCGG
CCAGGGCTTCCCGACCCTTGCCGATGTGGACCTCGGCCGCGACCACCGCT
```

*Fig. 15E-2*

O8E Surface Expression

■ B305D/HEK stained with anti-O8E antibody
O8E/HEK stained with anti-O8E antibody
O8E/HEK stained with an irrelevant antibody O8E expression in HEK293 Cells
(probed with anti-O8E rabbit polyclonal sera #2333L)

| Antigen on Plate | Sera Sample | Antibody Dilutions | | | | | | | | | | |
|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| 08E (#632-24) | Preimmune sera (#2576L):11/10/99 | 0.13 | 0.09 | 0.08 | 0.07 | 0.07 | 0.07 | 0.07 | 0.06 | 0.07 | 0.07 | 0.07 | 0.07 |
| | | 0.10 | 0.08 | 0.07 | 0.07 | 0.07 | 0.07 | 0.07 | 0.06 | 0.06 | 0.07 | 0.06 | 0.07 |
| | Average | 0.11 | 0.08 | 0.07 | 0.07 | 0.07 | 0.07 | 0.07 | 0.06 | 0.07 | 0.07 | 0.06 | 0.07 |
| | α-08E (#2576K):1/11/2000 | 2.92 | 2.81 | 2.74 | 2.70 | 2.58 | 2.08 | 1.61 | 1.01 | 0.68 | 0.40 | 0.24 | 0.15 |
| | | 2.93 | 2.77 | 2.74 | 2.69 | 2.48 | 2.08 | 1.57 | 1.00 | 0.66 | 0.40 | 0.23 | 0.16 |
| | Average | 2.93 | 2.79 | 2.74 | 2.69 | 2.53 | 2.08 | 1.59 | 1.00 | 0.67 | 0.40 | 0.23 | 0.16 |
| | Preimmune sera (#2333L):11/10/99 | 0.09 | 0.07 | 0.06 | 0.06 | 0.07 | 0.07 | 0.07 | 0.07 | 0.07 | 0.07 | 0.07 | 0.07 |
| | | 0.08 | 0.07 | 0.06 | 0.07 | 0.10 | 0.07 | 0.07 | 0.07 | 0.07 | 0.07 | 0.07 | 0.07 |
| | Average | 0.08 | 0.07 | 0.06 | 0.06 | 0.08 | 0.07 | 0.07 | 0.07 | 0.07 | 0.07 | 0.07 | 0.07 |
| | α-08E (#2333L):1/11/2000 | 2.73 | 2.75 | 2.64 | 2.48 | 2.30 | 1.78 | 1.41 | 0.92 | 0.58 | 0.32 | 0.20 | 0.14 |
| | | 2.73 | 2.76 | 2.51 | 2.60 | 2.37 | 1.93 | 1.44 | 0.88 | 0.58 | 0.35 | 0.20 | 0.14 |
| | Average | 2.73 | 2.76 | 2.57 | 2.54 | 2.33 | 1.85 | 1.43 | 0.90 | 0.58 | 0.33 | 0.20 | 0.14 |

Fig. 23

| Antibody Name | O8E polyclonal | Date: 5/2/2000 |
|---|---|---|
| Rabbit #, Bleed Date | 2576L, 1/11/2000 | |
| Purification Method | affinity | |
| Buffer | PBS | |
| Notebook | #705, p150 | |
| lot # | 739.87A | 739.87B |
| Antibody Concentration | 1.4mg/ml | 1.7mg/ml |
| Initial Amount | 18mg | 3mg |

| Antigen on Plate | Sera Sample | Antibody Dilutions | | | | | | | | | | |
|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E #632-24 | preimmune sera (2576L) | 0.15 | 0.11 | 0.09 | 0.08 | 0.08 | 0.07 | 0.07 | 0.07 | 0.07 | 0.08 | 0.07 | 0.08 |
| | | 0.14 | 0.10 | 0.09 | 0.08 | 0.07 | 0.07 | 0.07 | 0.07 | 0.07 | 0.07 | 0.07 | 0.07 |
| | Average | 0.14 | 0.10 | 0.09 | 0.08 | 0.07 | 0.07 | 0.07 | 0.07 | 0.07 | 0.08 | 0.07 | 0.08 |
| | α-O8E (2576K):2/8/2000 | 2.74 | 2.71 | 2.63 | 2.49 | 2.29 | 1.87 | 1.39 | 0.92 | 0.57 | 0.33 | 0.20 | 0.14 |
| | | 2.72 | 2.68 | 2.64 | 2.47 | 2.26 | 1.93 | 1.42 | 0.94 | 0.57 | 0.34 | 0.21 | 0.14 |
| | Average | 2.73 | 2.70 | 2.63 | 2.48 | 2.27 | 1.90 | 1.41 | 0.93 | 0.57 | 0.34 | 0.21 | 0.14 |
| | affinity pure α-O8E poly salt peak 739-87A | 2.69 | 2.60 | 2.50 | 2.21 | 1.83 | 1.34 | 0.99 | 0.64 | 0.38 | 0.22 | 0.15 | 0.11 |
| | | 2.59 | 2.48 | 2.38 | 2.21 | 1.82 | 1.33 | 1.00 | 0.62 | 0.37 | 0.22 | 0.14 | 0.11 |
| | Average | 2.64 | 2.54 | 2.44 | 2.21 | 1.83 | 1.34 | 1.00 | 0.63 | 0.37 | 0.22 | 0.15 | 0.11 |
| | affinity pure α-O8E poly acid peak 739-67B | 2.46 | 2.39 | 2.40 | 2.34 | 2.08 | 1.73 | 1.29 | 0.81 | 0.49 | 0.29 | 0.19 | 0.13 |
| | | 2.65 | 2.66 | 2.61 | 2.45 | 2.14 | 1.76 | 1.30 | 0.82 | 0.48 | 0.29 | 0.19 | 0.13 |
| | Average | 2.56 | 2.53 | 2.51 | 2.39 | 2.11 | 1.74 | 1.30 | 0.81 | 0.49 | 0.29 | 0.19 | 0.13 |

Fig. 24

SEQUENCE LISTING

```
<160> NUMBER OF SEQ ID NOS: 455

<210> SEQ ID NO 1
<211> LENGTH: 461
<212> TYPE: DNA
<213> ORGANISM: Homo sapien

<400> SEQUENCE: 1
ttagagaggc acagaaggaa gaagagttaa aagcagcaaa gccgggtttt tttgttttgt       60
tttgttttgt tttgttttga gatggagtct cactctgttg cccaagctgg agtacaacgg      120
catgatctca gctcgctgca acctccgcct cccacgttca agtgattctc ctgcctcagc      180
ctcccaagta gctgggatta caggcgcccg ccaccacgct cagctaattt ttttgtatt       240 tttagtagag acagggtttc accaggttgg ccaggctgct cttgaactcc tgacctcagg      300
tgatccaccc gcctcggcct cccaaagtgc tgggattaca ggcgtgagcc accacgcccg      360
gcccccaaag ctgtttcttt tgtctttagc gtaaagctct cctgccatgc agtatctaca      420
taactgacgt gactgccagc aagctcagtc actccgtggt c                          461

<210> SEQ ID NO 2
<211> LENGTH: 540
<212> TYPE: DNA
<213> ORGANISM: Homo sapien

<400> SEQUENCE: 2
taggatgtgt tggaccctct gtgtcaaaaa aaacctcaca aagaatcccc tgctcattac       60
agaagaagat gcatttaaaa tatgggttat tttcaacttt ttatctgagg acaagtatcc      120
attaattatt gtgtcagaag agattgaata cctgcttaag aagcttacag aagctatggg      180
aggaggttgg cagcaagaac aatttgaaca ttataaaatc aactttgatg acagtaaaaa      240
tggcctttct gcatgggaac ttattgagct tattggaaat ggacagttta gcaaaggcat      300
ggaccggcag actgtgtcta tggcaattaa tgaagtcttt aatgaactta tattagatgt      360
gttaaagcag ggttacatga tgaaaaaggg ccacagacgg aaaaactgga ctgaaagatg      420
gtttgtacta aaacccaaca taatttctta ctatgtgagt gaggatctga aggataagaa      480
aggagacatt ctcttggatg aaaattgctg tgtagagtcc ttgcctgaca agatggaaa       540

<210> SEQ ID NO 3
<211> LENGTH: 461
<212> TYPE: DNA
<213> ORGANISM: Homo sapien
```

<400> SEQUENCE: 3

```
ttagagaggc acagaaggaa gaagagttaa aagcagcaaa gccgggtttt tttgttttgt      60
tttgttttgt tttgttttga gatggagtct cactctgttg cccaagctgg agtacaacgg     120
catgatctca gctcgctgca acctccgcct cccacgttca agtgattctc ctgcctcagc     180
ctcccaagta gctgggatta caggcgcccg ccaccacgct cagctaattt ttttgtatt     240
tttagtagag acagggtttc accaggttgg ccaggctgct cttgaactcc tgacctcagg     300
tgatccaccc gcctcggcct cccaaagtgc tgggattaca ggcgtgagcc accacgcccg     360
gcccccaaag ctgtttcttt tgtctttagc gtaaagctct cctgccatgc agtatctaca     420
taactgacgt gactgccagc aagctcagtc actccgtggt c                         461
```

<210> SEQ ID NO 4
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 4

```
tcttttcttt tcgatttcct tcaatttgtc acgtttgatt ttatgaagtt gttcaagggc      60
taactgctgt gtattatagc tttctctgag ttccttcagc tgattgttaa atgaatccat     120
ttctgagagc ttagatgcag tttcttttc aagagcatct aattgttctt taagtctttg     180
gcataattct tccttttctg atgactttt atgaagtaaa ctgatccctg aatcaggtgt     240
gttactgagc tgcatgtttt taattctttc gtttaatagc tgcttctcag ggaccagata     300
gataagctta ttttgatatt ccttaagctc ttgttgaagt tgtttgattt ccataatttc     360
caggtcacac tgtttatcca aaacttctag ctcagtcttt tgtgtttgct ttctgatttg     420
gacatcttgt agtctgcctg agatctgctg atgntttcca ttcactgctt ccagttccag     480
gtggagactt tncttctgg agctcagcct gacaatgcct tcttgntccc t              531
```

<210> SEQ ID NO 5
<211> LENGTH: 531
<212> TYPE: DNA
<213> ORGANISM: Homo sapien

<400> SEQUENCE: 5

```
agccagatgg ctgagagctg caagaagaag tcaggatcat gatggctcag tttcccacag      60
cgatgaatgg agggccaaat atgtgggcta ttacatctga agaacgtact aagcatgata     120
aacagtttga taacctcaaa ccttcaggag gttacataac aggtgatcaa gcccgtactt     180
ttttcctaca gtcaggtctg ccggcccggg ttttagctga aatatgggcc ttatcagatc     240
tgaacaagga tgggaagatg gaccagcaag agttctctat agctatgaaa ctcatcaagt     300
taaagttgca gggccaacag ctgcctgtag tcctccctcc tatcatgaaa caaccccta     360
tgttctctcc actaatctct gctcgttttg ggatgggaag catgcccaat ctgtccattc     420
atcagccatt gcctccagtt gcacctatag caacacccett gtcttctgct acttcaggga     480
ccagtattcc tcccctaatg atgcctgctc ccctagtgcc ttctgttagt a              531
```

<210> SEQ ID NO 6
<211> LENGTH: 531
<212> TYPE: DNA

<213> ORGANISM: Homo sapien

<400> SEQUENCE: 6

| | | | | |
|---|---|---|---|---|
| aatagattta | atgcagagtg | tcaacttcaa | ttgattgata gtggctgcct agagtgctgt | 60 |
| gttgagtagg | tttctgagga | tgcaccctgg | cttgaagaga aagactggca ggattaacaa | 120 |
| tatctaaaat | ctcacttgta | ggagaaacca | caggcaccag agctgccact ggtgctggca | 180 |
| ccagctccac | caaggccagc | gaagagccca | atgtgagag tggcggtcag ctggcacca | 240 |
| gcactgaagc | caccactggt | gctggcactg | gcactggcac tgttattggt actggtactg | 300 |
| gcaccagtgc | tggcactgcc | actctcttgg | gctttggctt tagcttctgc tcccgcctgg | 360 |
| atccgggctt | tggcccaggg | tccgatatca | gcttcgtccc agttgcaggg cccggcagca | 420 |
| ttctccgagc | cgagcccaat | gcccattcga | gctctaatct cggccctagc cttggcttca | 480 |
| gctgcagcct | cagctgcagc | cttcaaatcc | gcttccatcg cctctcggta c | 531 |

<210> SEQ ID NO 7
<211> LENGTH: 531
<212> TYPE: DNA
<213> ORGANISM: Homo sapien

<400> SEQUENCE: 7

| | | | | |
|---|---|---|---|---|
| gccaagaaag | cccgaaaggt | gaagcatctg | gatggggaag aggatggcag cagtgatcag | 60 |
| agtcaggctt | ctggaaccac | aggtggccga | agggtctcaa aggccctaat ggcctcaatg | 120 |
| gcccgcaggg | cttcaagggg | tcccatagcc | ttttgggccc gcaggcatc aaggactcgg | 180 |
| ttggctgctt | gggcccggag | agccttgctc | tccctgagat cacctaaagc ccgtaggggc | 240 |
| aaggctcgcc | gtagagctgc | caagctccag | tcatcccaag agcctgaagc accaccacct | 300 |
| cgggatgtgg | ccctttttgca | agggagggca | aatgatttgg tgaagtacct tttggctaaa | 360 |
| gaccagacga | agattcccat | caagcgctcg | gacatgctga aggacatcat caaagaatac | 420 |
| actgatgtgt | accccgaaat | cattgaacga | gcaggctatt ccttggagaa ggtatttggg | 480 |
| attcaattga | aggaaattga | taagaatgac | cacttgtaca ttcttctcag c | 531 |

<210> SEQ ID NO 8
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 8

| | | | | |
|---|---|---|---|---|
| gaggtctcac | tatgttgccc | aggctgttct | tgaactcctg ggatcaagca atccacccat | 60 |
| gttggtctcc | aaaagtgctg | ggatcatagg | cgtgagccac ctcacccagc caccaatttt | 120 |
| caatcaggaa | gacttttttcc | ttcttcaaga | agtgaagggt ttccagagta tagctacact | 180 |
| attgcttgcc | tgagggtgac | tacaaaattg | cttgctaaaa ggttaggatg ggtaaagaat | 240 |
| tagattttct | gaatgcaaaa | ataaaatgtg | aactaatgaa ctttaggtaa tacatattca | 300 |
| taaaataatt | attcacatat | ttcctgattt | atcacagaaa taatgtatga aatgctttga | 360 |
| gtttcttgga | gtaaactcca | ttactcatcc | caagaaacca tattataagt atcactgata | 420 |
| ataagaacaa | caggaccttg | tcataaaattc | tggataagag aaatagtctc tgggtgtttg | 480 |
| ntcttaattg | ataaaattta | cttgtccatc | ttttagttca gaatcacaaa a | 531 |

```
<210> SEQ ID NO 9
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 9
aagcggaaat gagaaaggag ggaaaatcat gtggtattga gcggaaaact gctggatgac      60
agggctcagt cctgttggag aactctgggt ggtgctgtag aacagggcca ctcacagtgg     120
ggtgcacaga ccagcacggc tctgtgacct gtttgttaca ggtccatgat gaggtaaaca     180
atacactgag tataagggtt ggtttagaaa ctcttacagc aatttgacaa agtaatcttc     240
tgtgcagtga atctaagaaa aaaattgggg ctgtatttgt atgttccttt ttttcatttc     300
atgttctgag ttacctattt ttattgcatt ttacaaaagc atccttccat gaaggaccgg     360
aagttaaaaa caaagcaggt cctttatcac agcactgtcg tagaacacag ttcagagtta     420
tccacccaag gagccaggga gctgggctaa accaaagaat tttgcttttg gttaatcatc     480
aggtacttga gttggaattg ttttaatccc atcattacca ggctggangt g              531

<210> SEQ ID NO 10
<211> LENGTH: 861
<212> TYPE: DNA
<213> ORGANISM: Homo sapien

<400> SEQUENCE: 10
ccgcggctcc tgtccagacc ctgaccctcc ctcccaaggc tcaaccgtcc cccaacaacc      60
gccagccttg tactgatgtc ggctgcgaga gcctgtgctt aagtaagaat caggccttat     120
tggagacatt caagcaaagg ttggacaact acttttccag aacagaaagg aaactcatgc     180
atcagaaaag gtgactaata aaggtaccag aagaatatgg ctgcacaaat accagaatct     240
gatcagataa aacagtttaa ggaatttctg gggacctaca ataaacttac agagacctgc     300
tttttggact gtgttagaga cttcacaaca agagaagtaa aacctgaaga gaccacctgt     360
tcagaacatt gcttacagaa atatttaaaa atgacacaaa gaatatccat gagatttcag     420
gaatatcata ttcagcagaa tgaagccctg gcagccaaag caggactcct tggccaacca     480
cgatagagaa gtcctgatgg atgaactttt gatgaaagat tgccaacagc tgctttattg     540
gaaatgagga ctcatctgat agaatcccct gaaagcagta gccaccatgt tcaaccatct     600
gtcatgactg tttggcaaat ggaaaccgct ggagaaacaa aattgctatt taccaggaat     660
aatcacaata gaaggtctta tgttcagtg aaataataag atgcaacatt tgttgaggcc      720
ttatgattca gcagcttggt cacttgatta gaaaataaa ccattgtttc ttcaattgtg      780
actgttaatt taaagcaac ttatgtgttc gatcatgtat gagatagaaa aattttttatt     840
actcaaagta aaataaatgg a                                               861

<210> SEQ ID NO 11
<211> LENGTH: 541
<212> TYPE: DNA
<213> ORGANISM: Homo sapien

<400> SEQUENCE: 11
gaaaaaaaat ataaaacaca cttttgcgaa aacggtggcc ctaaaagagg aaaagaattt      60
caccaatata aatccaattt tatgaaaact gacaatttaa tccaagaatc acttttgtaa     120
```

-continued

| | |
|---|---|
| atgaagctag caagtgatga tatgataaaa taaacgtgga ggaaataaaa acacaagact | 180 |
| tggcataaga tatatccact tttgatatta aacttgtgaa gcatattctt cgacaaattg | 240 |
| tgaaagcgtt cctgatcttg cttgttctcc atttcaaata aggaggcata tcacatccca | 300 |
| agagtaacag aaaaagaaaa aagacatttt tgcattttga gatgaaccaa agacacaaaa | 360 |
| caaaacgaac aaagtgtcat gtctaattct agcctctgaa ataaaccttg aacatctcct | 420 |
| acaaggcacc gtgattttttg taattctaac ctgaagaaat gtgatgactt tgtggacat | 480 |
| gaaaatcaga tgagaaaact gtggtctttc caaagcctga actcccctga aaacctttgc | 540 |
| a | 541 |

<210> SEQ ID NO 12
<211> LENGTH: 541
<212> TYPE: DNA
<213> ORGANISM: Homo sapien

<400> SEQUENCE: 12

| | |
|---|---|
| ctgggatcat ttctcttgat gtcataaaag actcttcttc ttcctcttca tcctcttctt | 60 |
| catcctcttc tgtacagtgc tgccgggtac aacggctatc tttgtcttta tcctgagatg | 120 |
| aagatgatgc ttctgtttct cctaccataa ctgaagaaat ttcgctggaa gtcgtttgac | 180 |
| tggctgtttc tctgacttca ccttctttgt caaacctgag tcttttttacc tcatgcccct | 240 |
| cagcttccac agcatcttca tctggatgtt tattttttcaa agggctcact gaggaaactt | 300 |
| ctgattcaga ggtcgaagag tcactgtgat tttttctcctc attttgctgc aaatttgcct | 360 |
| ctttgctgtc tgtgctctca ggcaacccat ttgttgtcat gggggctgac aaagaaacct | 420 |
| ttggtcgatt aagtggcctg ggtgtcccag gcccatttat attagacctc tcagtatagc | 480 |
| ttggtgaatt tccaggaaac ataacaccat tcattcgatt taaactattg gaattggttt | 540 |
| t | 541 |

<210> SEQ ID NO 13
<211> LENGTH: 441
<212> TYPE: DNA
<213> ORGANISM: Homo sapien

<400> SEQUENCE: 13

| | |
|---|---|
| gagggttggt ggtagcggct tggggaggtg ctcgctctgt cggtcttgct ctctcgcacg | 60 |
| cttccccccgg ctcccttcgt ttccccccccc cggtcgcctg cgtgccggag tgtgtgcgag | 120 |
| ggaggggggag ggcgtcgggg gggtgggggg aggcgttccg gtccccaaga gacccgcgga | 180 |
| gggaggcgga ggctgtgagg gactccggga agccatggac gtcgagaggc tccaggaggc | 240 |
| gctgaaagat tttgagaaga gggggaaaaa ggaagtttgt cctgtcctgg atcagtttct | 300 |
| ttgtcatgta gccaagactg gagaaacaat gattcagtgg tcccaattta aaggctatttt | 360 |
| tattttttcaaa ctgagaaag tgatggatga tttcagaact tcagctcctg agccaagagg | 420 |
| tcctcccaac cctaatgtcg a | 441 |

<210> SEQ ID NO 14
<211> LENGTH: 131
<212> TYPE: DNA
<213> ORGANISM: Homo sapien
<220> FEATURE:
<221> NAME/KEY: misc_feature
<222> LOCATION: (1)...(131)
<223> OTHER INFORMATION: n = A,T,C or G

<400> SEQUENCE: 14

| | |
|---|---|
| aagcaggcgg ctcccgcgct cgcagggccg tgccacctgc ccgcccgccc gctcgctcgc | 60 |
| tcgcccgccg cgccgcgctg ccgaccgcca gcatgctgcc gagagtgggc tgccccgcgc | 120 |
| tgccgntgcc g | 131 |

<210> SEQ ID NO 15
<211> LENGTH: 692
<212> TYPE: DNA
<213> ORGANISM: Homo sapien

<400> SEQUENCE: 15

| | |
|---|---|
| atctcttgta tgccaaatat ttaatataaa tctttgaaac aagttcagat gaaataaaaa | 60 |
| tcaaagtttg caaaaacgtg aagattaact taattgtcaa atattcctca ttgccccaaa | 120 |
| tcagtatttt ttttatttct atgcaaaagt atgccttcaa actgcttaaa tgatatatga | 180 |
| tatgatacac aaaccagttt tcaaatagta agccagtca tcttgcaatt gtaagaaata | 240 |
| ggtaaaagat tataagacac cttacacaca cacacacaca cacacgtg tgcacgccaa | 300 |
| tgacaaaaaa caatttggcc tctcctaaaa taagaacatg aagaccctta attgctgcca | 360 |
| ggagggaaca ctgtgtcacc cctccctaca atccaggtag tttcctttaa tccaatagca | 420 |
| aatctgggca tatttgagag gagtgattct gacagccacg ttgaaatcct gtggggaacc | 480 |
| attcatgtcc acccactggt gccctgaaaa atgccaata atttttcgct cccacttctg | 540 |
| ctgctgtctc ttccacatcc tcacatagac cccagacccg ctggcccctg gctgggcatc | 600 |
| gcattgctgg tagagcaagt cataggtctc gtctttgacg tcacagaagc gatacaccaa | 660 |
| attgcctggt cggtcattgt cataaccaga ga | 692 |

<210> SEQ ID NO 16
<211> LENGTH: 728
<212> TYPE: DNA
<213> ORGANISM: Homo sapien

<400> SEQUENCE: 16

| | |
|---|---|
| cagacggggt ttcactatgt tggctaggct ggtcttgaac tcctgacttc aggtgatctg | 60 |
| cctgccttgg cctcccaaag tgctgggatt acaggcataa gccactgcgc ccggctgatc | 120 |
| tgatggtttc ataaggcttt tcccccttt gctcagcact tctccttcct gccgccatgt | 180 |
| gaagaaggac atgtttgctt ccccttccac cacgattgta agttgtttcc tgaggcctcc | 240 |
| ccggccatgc tgaactgtga gtcaattaaa cctctttcct ttataaatta tccagttttg | 300 |
| ggtatgtctt tattagtaga atgagaacag actaatacaa cccttaaagg agactgacgg | 360 |
| agaggattct tcctggatcc cagcacttcc tctgaatgct actgacattc ttcttgagga | 420 |
| ctttaaactg ggagatagaa aacagattcc atggctcagc agcctgagag cagggaggga | 480 |
| gccaagctat agatgacatg ggcagcctcc cctgaggcca ggtgtggccg aacctgggca | 540 |
| gtgctgccac ccaccccacc agggccaagt cctgtccttg gagagccaag cctcaatcac | 600 |
| tgctagcctc aagtgtcccc aagccacagt ggctaggggg actcagggaa cagttcccag | 660 |
| tctgccctac ttctcttacc tttacccctc atacctccaa agtagaccat gttcatgagg | 720 |
| tccaaagg | 728 |

<210> SEQ ID NO 17
<211> LENGTH: 531
<212> TYPE: DNA
<213> ORGANISM: Homo sapien
<220> FEATURE:

<221> NAME/KEY: misc_feature
<222> LOCATION: (1)...(531)
<223> OTHER INFORMATION: n = A,T,C or G

<400> SEQUENCE: 17

```
aagcgaggaa gccactgcgg ctcctggctg aaaagcggcg ccaggctcgg gaacagaggg      60
aacgcgaaga acaggagcgg aagctgcagg ctgaaaggga caagcgaatg cgagaggagc     120
agctggcccg ggaggctgaa gcccgggctg aacgtgaggc cgaggcgcgg agacgggagg     180
agcaggaggc tcgagagaag cgcaggctg agcaggagga gcaggagcga ctgcagaagc      240
agaaagagga agccgaagcc cggtcccggg aagaagctga gcgccagcgc caggagcggg     300
aaaagcactt tcagaaggag gaacaggaga gacaagagcg aagaaagcgg ctggaggaga     360
taatgaagag gactcggaaa tcagaagccg ccgaaaccaa gaagcaggat gcaaaggaga     420
ccgcagctaa caattccggc ccagacccct gtgaaagctg tagagactcg gccctctggg     480
cttccagaaa ggattctatt gcagaaagga aggagctngg cccccangg a               531
```

<210> SEQ ID NO 18
<211> LENGTH: 1041
<212> TYPE: DNA
<213> ORGANISM: Homo sapien
<220> FEATURE:
<221> NAME/KEY: misc_feature
<222> LOCATION: (1)...(1041)
<223> OTHER INFORMATION: n = A,T,C or G

<400> SEQUENCE: 18

```
ctctgtggaa aactgatgag gaatgaattt accattaccc atgttctcat ccccaagcaa      60
agtgctgggt ctgattactg caacacagag aacgaagaag aacttttcct catacaggat     120
cagcagggcc tcatcacact gggctggatt catactcacc ccacacagac cgcgtttctc     180
tccagtgtcg acctacacac tcactgctct taccagatga tgttgccaga gtcagtagcc     240
attgtttgct cccccaagtt ccaggaaact ggattcttta aactaactga ccatggacta     300
gaggagattt cttcctgtcg ccagaaagga tttcatccac acagcaagga tccacctctg     360
ttctgtagct gcagccacgt gactgttgtg gacagagcag tgaccatcac agaccttcga     420
tgagcgtttg agtccaacac cttccaagaa caacaaaacc atatcagtgt actgtagccc     480
cttaatttaa gctttctaga aagctttgga agttttgta gatagtagaa aggggggcat      540
cacntgagaa agagctgatt ttgtatttca ggtttgaaaa gaataactg aacatatttt      600
ttaggcaagt cagaaagaga acatggtcac ccaaaagcaa ctgtaactca gaaattaagt     660
tactcagaaa ttaagtagct cagaaattaa gaaagaatgg tataatgaac ccccatatac     720
ccttccttct ggattcacca attgttaaca tttttttcct ctcagctatc cttctaattt     780
ctctctaatt tcaatttgtt tatatttacc tctgggctca ataagggcat ctgtgcagaa     840
atttggaagc catttagaaa atcttttgga tttttcctgtg gtttatggca atatgaatgg     900
agcttattac tggggtgagg gacagcttac tccatttgac cagattgttt ggctaacaca     960
tcccgaagaa tgattttgtc aggaattatt gttatttaat aaatatttca ggatattttt    1020
cctctacaat aaagtaacaa t                                               1041
```

<210> SEQ ID NO 19
<211> LENGTH: 1043
<212> TYPE: DNA
<213> ORGANISM: Homo sapien

<400> SEQUENCE: 19

```
ctctgtggaa aactgatgag gaatgaattt accattaccc atgttctcat ccccaagcaa      60
agtgctgggt ctgattactg caacacagag aacgaagaag aacttttcct catacaggat     120
cagcagggcc tcatcacact gggctggatt catactcacc ccacacagac cgcgtttctc     180
tccagtgtcg acctacacac tcactgctct taccagatga tgttgccaga gtcagtagcc     240
attgtttgct cccccaagtt ccaggaaact ggattcttta aactaactga ccatggacta     300
gaggagattt cttcctgtcg ccagaaagga tttcatccac acagcaagga tccacctctg     360
ttctgtagct gcagccacgt gactgttgtg gacagagcag tgaccatcac agaccttcga     420
tgagcgtttg agtccaacac cttccaagaa caacaaaacc atatcagtgt actgtagccc     480
cttaatttaa gctttctaga aagctttgga agttttgta gatagtagaa agggggggcat     540
cacctgagaa agagctgatt ttgtatttca ggtttgaaaa gaataactg aacatatttt      600
ttaggcaagt cagaaagaga acatggtcac ccaaaagcaa ctgtaactca gaattaagt      660
tactcagaaa ttaagtagct cagaaattaa gaagaatgg tataatgaac ccccatatac      720
ccttccttct ggattcacca attgttaaca tttttttcct ctcagctatc cttctaattt      780
ctctctaatt tcaatttgtt tatatttacc tctgggctca ataagggcat ctgtgcagaa     840
atttggaagc catttagaaa atcttttgga ttttcctgtg gtttatggca atatgaatgg     900
agcttattac tggggtgagg acagcttac tccatttgac cagattgttt ggctaacaca      960
tcccgaagaa tgattttgtc aggaattatt gttatttaat aaatatttca ggatatttt     1020
cctctacaat aaagtaacaa tta                                            1043
```

```
<210> SEQ ID NO 20
<211> LENGTH: 448
<212> TYPE: DNA
<213> ORGANISM: Homo sapien

<400> SEQUENCE: 20
ggacgacaag gccatggcga tatcggatcc gaattcaagc ctttggaatt aaataaacct      60
ggaacaggga aggtgaaagt tggagtgaga tgtcttccat atctatacct ttgtgcacag     120
ttgaatggga actgtttggg tttagggcat cttagagttg attgatggaa aaagcagaca     180
ggaactggtg ggaggtcaag tggggaagtt ggtgaatgtg gaataactta cctttgtgct     240
ccacttaaac cagatgtgtt gcagctttcc tgacatgcaa ggatctactt taattccaca     300
ctctcattaa taaattgaat aaaagggaat gttttggcac ctgatataat ctgccaggct     360
atgtgacagt aggaaggaat ggtttcccct aacaagccca atgcactggt ctgactttat     420
aaattattta ataaaatgaa ctattatc                                        448
```

```
<210> SEQ ID NO 21
<211> LENGTH: 411
<212> TYPE: DNA
<213> ORGANISM: Homo sapien

<400> SEQUENCE: 21
ggcagtgaca ttcaccatca tgggaaccac cttccctttt cttcaggatt ctctgtagtg      60
gaagagagca cccagtgttg ggctgaaaac atctgaaagt agggagaaga acctaaaata     120
atcagtatct cagagggctc taaggtgcca agaagtctca ctggacattt aagtgccaac     180
aaaggcatac tttcggaatc gccaagtcaa aactttctaa cttctgtctc tctcagagac     240
aagtgagact caagagtcta ctgctttagt ggcaactaca gaaaactggt gttacccaga     300
```

-continued

| | | |
|---|---|---|
| aaaacaggag caattagaaa tggttccaat atttcaaagc tccgcaaaca ggatgtgctt | 360 | |
| tcctttgccc atttagggtt tcttctcttt cctttctctt tattaaccac t | 411 | |

<210> SEQ ID NO 22
<211> LENGTH: 896
<212> TYPE: DNA
<213> ORGANISM: Homo sapien
<220> FEATURE:
<221> NAME/KEY: misc_feature
<222> LOCATION: (1)...(896)
<223> OTHER INFORMATION: n = A,T,C or G

<400> SEQUENCE: 22

| | |
|---|---|
| tgcgctgaaa acaacggcct cctttactgt taaaatgcag ccacaggtgc ttagccgtgg | 60 |
| gcatctcaac caccagcctc tgtgggggc aggtgggcgt ccctgtgggc ctctgggccc | 120 |
| acgtccagcc tctgtcctct gccttccgtt cttcgacagt gttcccggca tccctggtca | 180 |
| cttggtactt ggcgtgggcc tcctgtgctg ctccagcagc tcctccaggn ggtcggcccg | 240 |
| cttcaccgca gcctcatgtt gtgtccgag gctgctcacg gcctcctcct tcctcgcgag | 300 |
| ggctgtcttc accctccggn gcacctcctc cagctccagc tgctggcggg cctgcagcgt | 360 |
| ggccagctcg gccttggcct gccgcgtctc ctcctcarag gctgccagcc ggtcctcgaa | 420 |
| ctcctggcgg atcacctggg ccaggttgct gcgctcgcta gaaagctgct cgttcaccgc | 480 |
| ctgcgcatcc tccagcgccc gctccttctg ccgcacaagg ccctgcagac gcagattctc | 540 |
| gccctcggcc tccccaagct ggcccttcag ctccgagcac cgctcctgaa gcttccgctc | 600 |
| cgactgctcc agctcggaga gctcggcctc gtacttgtcc cgtaagcgct tgatgcggct | 660 |
| ctcggcagcc ttctcactct cctccttggc cagcgccatg tcggcctcca gccggtgaat | 720 |
| gaccagctca atctccttgt cccggccttt ccggatttct tccctcagct cctgttcccg | 780 |
| gttcagcagc cacgcctcct ccttcctggt gcggccggcc tccacgcct gcctctccag | 840 |
| ctccagctgc tgcttcaggg tattcagctc catctggcgg gcctgcagcg tggcca | 896 |

<210> SEQ ID NO 23
<211> LENGTH: 111
<212> TYPE: DNA
<213> ORGANISM: Homo sapien

<400> SEQUENCE: 23

| | |
|---|---|
| caacttatta cttgaaatta taatatagcc tgtccgtttg ctgtttccag gctgtgatat | 60 |
| attttcctag tggtttgact ttaaaaataa ataaggttta attttctccc c | 111 |

<210> SEQ ID NO 24
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 24

| | |
|---|---|
| tgcaagtcac gggagtttat ttatttaatt tttttcccca gatggagact ctgtcgccca | 60 |
| ggctggagtg caatggtgtg atcttggctc actgcaacct ccacctcctg ggttcaagcg | 120 |
| attctcctgc cacagcctcc cgagtagctg ggattacagg tgccgccac cacacccagc | 180 |
| taatttttat attttagta aagacagggt ttccccatgt tggccaggct ggtcttgaac | 240 |
| ttctgacctc aggtgatcca cctgcctcgg cctcccaaag tgttgggatt acaggcgtga | 300 |

```
gctacccgtg cctggccagc cactggagtt taaaggacag tcatgttggc tccagcctaa    360
ggcggcattt tccccatca gaaagcccgc ggctcctgta cctcaaaata gggcacctgt    420
aaagtcagtc agtgaagtct ctgctctaac tggccacccg gggccattgg cntctgacac    480
agccttgcca ggangcctgc atctgcaaaa gaaaagttca cttcctttcc g             531
```

<210> SEQ ID NO 25
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 25

```
cagagaatct kagaaagatg tcgcgttttc ttttaatgaa tgagagaagc ccatttgtat     60
ccctgaatca ttgagaaaag gcggcggtgg cgacagcggc gacctaggga tcgatctgga    120
gggacttggg gagcgtgcag agacctctag ctcgagcgcg agggacctcc cgccgggatg    180
cctggggagc agatggaccc tactggaagt cagttggatt cagatttctc tcagcaagat    240
actccttgcc tgataattga agattctcag cctgaaagcc aggttctaga ggatgattct    300
ggttctcact tcagtatgct atctcgacac cttcctaatc tccagacgca caagaaaat    360 cctgtgttgg atgttgngtc caatccttga acaaacagct ggagaagaac gaggagaccg    420
gtaatagtgg gttcaatgaa catttgaaag aaaaccaggt tgcagaccct g             471
```

<210> SEQ ID NO 26
<211> LENGTH: 541
<212> TYPE: DNA
<213> ORGANISM: Homo sapien

<400> SEQUENCE: 26

```
gactgtcctg aacaagggac ctctgaccag agagctgcag gagatgcaga gtggtggcag     60
gagtggaagc caaagaacac ccaccttcct cccttgaagg agtagagcaa ccatcagaag    120
atactgtttt attgctctgg tcaaacaagt cttcctgagt tgacaaaacc tcaggctctg    180
gtgacttctg aatctgcagt ccactttcca taagttcttg tgcagacaac tgttcttttg    240
cttccatagc agcaacagat gctttggggc taaaaggcat gtcctctgac cttgcaggtg    300
gtggattttg ctcttttaca acatgtacat ccttactggg ctgtgctgtc acaggatgt    360 ccttgctgga ctgttctgct atggggatat cttcgttgga ctgttcttca tgcttaattg    420
cagtattagc atccacatca gacagcctgg tataaccaga gttggtggtt actgattgta    480
gctgctcttt gtccacttca tatggcacaa gtattttcct caacatcctg gctctgggaa    540
g                                                                    541
```

<210> SEQ ID NO 27
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 27

```
gaaatgtata tttaatcatt ctcttgaacg atcagaactc traaatcagt tttctataac     60
```

-continued

| | |
|---|---|
| arcatgtaat acagtcaccg tggctccaag gtccaggaag gcagtggtta acacatgaag | 120 |
| agtgtgggaa gggggctgga aacaaagtat tcttttcctt caaagcttca ttcctcaagg | 180 |
| cctcaattca agcagtcatt gtccttgctt tcaaaagtct gtgtgtgctt catggaaggt | 240 |
| atatgtttgt tgccttaatt tgaattgtgg ccaggaaggg tctggagatc taaattcaga | 300 |
| gtaagaaaac ctgagctaga actcaggcat ttctcttaca gaacttggct tgcagggtag | 360 |
| aatgaangga aagaaactta aagctcaac aagctgaaga taatcccatc aggcatttcc | 420 |
| cataggcctt gcaactctgt tcactgagag atgttatcct g | 461 |

<210> SEQ ID NO 28
<211> LENGTH: 541
<212> TYPE: DNA
<213> ORGANISM: Homo sapien

<400> SEQUENCE: 28

| | |
|---|---|
| agtctggagt gagcaaacaa gagcaagaaa caarragaag ccaaaagcag aaggctccaa | 60 |
| tatgaacaag ataaatctat cttcaaagac atattagaag ttgggaaaat aattcatgtg | 120 |
| aactagacaa gtgtgttaag agtgataagt aaaatgcacg tggagacaag tgcatcccca | 180 |
| gatctcaggg acctcccct gcctgtcacc tggggagtga gaggacagga tagtgcatgt | 240 |
| tctttgtctc tgaattttta gttatatgtg ctgtaatgtt gctctgagga agcccctgga | 300 |
| aagtctatcc caacatatcc acatcttata ttccacaaat taagctgtag tatgtaccct | 360 |
| aagacgctgc taattgactg ccacttcgca actcaggggc ggctgcattt tagtaatggg | 420 |
| tcaaatgatt cactttttat gatgcttccc aaggtgcctt ggcttctctt cccaactgac | 480 |
| aaatgcccaa gttgagaaaa atgatcataa ttttagcata aaccgagcaa tcggcgaccc | 540 |
| c | 541 |

<210> SEQ ID NO 29
<211> LENGTH: 411
<212> TYPE: DNA
<213> ORGANISM: Homo sapien

<400> SEQUENCE: 29

| | |
|---|---|
| tagctgtctt cctccactctt atggcaatga ccccatatct taatggatta agataatgaa | 60 |
| agtgtatttc ttacactctg tatctatcac cagaagctga ggtgatagcc cgcttgtcat | 120 |
| tgtcatccat attctgggac tcaggcggga actttctgga atattgccag ggagcatggc | 180 |
| agagggcac agtgcattct gggggaatgc acattggctc agcctgggta atgagtgata | 240 |
| tacattacct ctgttcacaa ctcattgccc agcaccagtc acaaggcccc accaaatacc | 300 |
| agagcccaag aaatgtagtc ctgttgatat ggttttgctg tgtcccaacc caaatctcat | 360 |
| cttgaattgt aagctcccat aattcccatg tgttgtggga gggacctggt g | 411 |

<210> SEQ ID NO 30
<211> LENGTH: 511
<212> TYPE: DNA
<213> ORGANISM: Homo sapien

<400> SEQUENCE: 30

| | |
|---|---|
| atcatgagga tgttaccaaa gggatggtac taaaccattt gtattcgtct gttttcacac | 60 |
| tgctttgaag atactacctg agactgggta atttataaac aaaagagatt taattgactc | 120 |
| acagttctgc atggctgaag aggcctcagg aaacttacag tcatggtgga aggcaaagga | 180 |
| ggagcaaggc atgtcttaca tgtcagtagg agagagagcg agagcaggag aacctgccac | 240 |

```
ttataaacca ttcagatctc ataactccct atcatgagaa aaacatggag gaaaccaccc      300
tcatgatcca atcacctccc gccaggtccc tccctcgaca cgtggggatt ataattcagg      360
attagaggga cacagagaca aaccatatca tcattcatga gaaatccacc ctcatagtcc      420
aatcagctcc taccaggccc cacctccaac actggggatt gcaattcaac atgagatttg      480
gatggggaca cagattcaaa ccatatcata c                                    511
```

<210> SEQ ID NO 31
<211> LENGTH: 827
<212> TYPE: DNA
<213> ORGANISM: Homo sapien

<400> SEQUENCE: 31

```
catggccttt ctccttagag gccagaggtg ctgccctggc tgggagtgaa gctccaggca       60
ctaccagctt tcctgatttt cccgtttggt ccatgtgaag agctaccacg agccccagcc      120
tcacagtgtc cactcaaggg cagcttggtc ctcttgtcct gcagaggcag gctggtgtga      180
ccctgggaac ttgacccggg aacaacaggt ggcccagagt gagtgtggcc tggcccctca      240
acctagtgtc cgtcctcctc tctcctggag ccagtcttga gtttaaaggc attaagtgtt      300
agatacaagc tccttgtggc tggaaaaaca cccctctgct gataaagctc agggggcact      360
gaggaagcag aggcccttg ggggtgccct cctgaagaga gcgtcaggcc atcagctctg       420
tccctctggt gctcccacgt ctgttcctca ccctccatct ctgggagcag ctgcacctga      480
ctggccacgc gggggcagtg gaggcacagg ctcaggtgg ccgggctacc tggcacccta       540
tggcttacaa agtagagttg gcccagtttc cttccacctg aggggagcac tctgactcct      600
aacagtcttc cttgccctgc catcatctgg ggtggctggc tgtcaagaaa ggccgggcat      660
gctttctaaa cacagccaca ggaggcttgt agggcatctt ccaggtgggg aaacagtctt      720
agataagtaa ggtgacttgc ctaaggcctc ccagcaccct tgatcttgga gtctcacagc      780
agactgcatg tsaacaactg gaaccgaaaa catgcctcag tataaaa                    827
```

<210> SEQ ID NO 32
<211> LENGTH: 291
<212> TYPE: DNA
<213> ORGANISM: Homo sapien

<400> SEQUENCE: 32

```
ccagaacctc cttctctttg gagaatgggg aggcctcttg gagacacaga gggtttcacc       60
ttggatgacc tctagagaaa ttgcccaaga agcccacctt ctggtcccaa cctgcagacc      120
ccacagcagt cagttggtca ggccctgctg tagaaggtca cttggctcca ttgcctgctt      180
ccaaccaatg ggcaggagag aaggccttta tttctcgccc acccattctc ctgtaccagc      240
acctccgttt tcagtcagyg ttgtccagca acggtaccgt ttacacagtc a              291
```

<210> SEQ ID NO 33
<211> LENGTH: 491
<212> TYPE: DNA
<213> ORGANISM: Homo sapien

<400> SEQUENCE: 33

```
tgcatgtagt tttatttatg tgttttsgtc tggaaaacca agtgtcccag cagcatgact       60
gaacatcact cacttcccct acttgatcta caaggccaac gccgagagcc cagaccagga      120
ttccaaacac actgcacgag aatattgtgg atccgctgtc aggtaagtgt ccgtcactga      180
```

```
cccaracgct gttacgtggc acatgactgt acagtgccac gtaacagcac tgtacttttc      240
tcccatgaac agttacctgc catgtatcta catgattcag aacattttga acagttaatt      300
ctgacacttg aataatccca tcaaaaaccg taaaatcact ttgatgtttg taacgacaac      360
atagcatcac tttacgacag aatcatctgg aaaaacagaa caacgaatac atacatctta      420
aaaaatgctg gggtgggcca ggcacagctt cacgcctgta atcccagcac tttgggaggc      480
ttaagcgggt g                                                           491
```

<210> SEQ ID NO 34
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 34

```
tggggcggaa agaagccaag gccaaggagc tggtgcggca gctgcagctg gaggccgagg       60
agcagaggaa gcagaagaag cggcagagtg tgtcgggcct gcacagatac cttcacttgc      120
tggatggaaa tgaaaattac ccgtgtcttg tggatgcaga cggtgatgtg atttccttcc      180
caccaataac caacagtgag aagacaaagg ttaagaaaac gacttctgat ttgttttgg       240 aagtaacaag tgccaccagt ctgcagattt gcaaggatgt catggatgcc ctcattctga      300
aaatggcaag aaatgaaaaa gtacacttta gaaaataaag aggaaggatc actctcagat      360
actgaagccg atgcagtctc tggacaactt ccagatccca caacgaatcc cagtgctgga      420
aaggacgggc ccttccttct ggtggtggaa cangtcccgg tggtggatct tggaanggaa      480
cctgaangtg gtgtaccccg tccaaggccg accttggcca c                          521
```

<210> SEQ ID NO 35
<211> LENGTH: 161
<212> TYPE: DNA
<213> ORGANISM: Homo sapien
<220> FEATURE:
<221> NAME/KEY: misc_feature
<222> LOCATION: (1)...(161)
<223> OTHER INFORMATION: n = A,T,C or G

<400> SEQUENCE: 35

```
tcccgcgctc gcagggcncg tgccacctgc cygtccgccc gctcgctcgc tcgcccgccg       60
cgccgcgctg ccgaccgyca gcatgctgcc gagagtgggc tgccccgcgc tgccgctgcc      120
gccgccgccg ctgctgccgc tgctgccgct gctgctgctg c                          161
```

<210> SEQ ID NO 36
<211> LENGTH: 341
<212> TYPE: DNA
<213> ORGANISM: Homo sapien

<400> SEQUENCE: 36

```
ggcgggtagg catggaactg agaagaacga agaagctttc agactacgtg gggaagaatg       60
aaaaaaccaa aattatcgcc aagattcagc aaagggggaca gggagctcca gcccgagagc      120
ctattattag cagtgaggag cagaagcagc tgatgctgta ctatcacaga agacaagagg      180
agctcaagag attggaagaa aatgatgatg atgcctattt aaactcacca tgggcggata      240
acactgcttt gaaaagacat tttcatggag tgaaagacat aaagtggaga ccaagatgaa      300
gttcaccagc tgatgacact tccaaagaga ttagctcacc t                          341
```

<210> SEQ ID NO 37
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 37

```
tctgaaggtt aaatgtttca tctaaatagg gataatgrta aacacctata gcatagagtt      60
gtttgagatt aaatgagata atacatgtaa aattatgtgc ctggcataca gcaagattgt     120
tgttgttgtt gatgatgatg atgatgatga taatatttt  ctatccccag tgcacaactg     180
cttgaaccta ttagataatc aatacatgtt tcttgaactg agatcaattt ccccatgttg     240
tctgactgat gaagccctac attttcttct agaggagatg acatttgagc aagatcttaa     300
agaaaatcag atgccttcac ctgaccactg cttggtgatc ccatggcact ttgtacatct     360
ctccattagc tctcatctca ccagcccatc attattgtat gtgctgcctt ctgaagcttg     420
cagctggcta ccatcmggta gaataaaaat catcctttca taaaatagtg accctccttt     480
tttatttgca tttcccaaag ccaagcaccg tgggangta  g                         521
```

<210> SEQ ID NO 38
<211> LENGTH: 461
<212> TYPE: DNA
<213> ORGANISM: Homo sapien

<400> SEQUENCE: 38

```
tatgaagaag ggaaaagaag ataatttgtg aaagaaatgg gtccagttac tagtctttga      60
aaagggtcag tctgtagctc ttcttaatga gaataggcag cttctcagttg ctcagggtca    120
gatttcctta gtggtgtatc taatcacagg aaacatctgt ggttccctcc agtctctttc     180
tgggggactt gggcccactt ctcatttcat ttaattagag gaaatagaac tcaaagtaca     240
atttactgtt gtttaacaat gccacaaaga catggttggg agctatttct tgatttgtgt     300
aaaatgctgt ttttgtgtgc tcataatggt tccaaaaatt gggtgctggc caaagagaga     360
tactgttaca gaagccagca agaagacctc tgttcattca cacccccggg gatatcagga     420
attgactcca gtgtgtgcaa atccagtttg gcctatcttc t                         461
```

<210> SEQ ID NO 39
<211> LENGTH: 769
<212> TYPE: DNA
<213> ORGANISM: Homo sapien

<400> SEQUENCE: 39

```
tgagggactg attggtttgc tctctgctat tcaattcccc aagcccactt gttcctgcag      60
cgtcctcctt ctcattccct ttagttgtac cctctctttc atctgagacc tttccttctt     120
gatgtcgcct tttcttcttc ttgcttttt  tgatgttctg ctcagcatgt tctgggtgct     180
tctcatctgc atcattcctt tcagatgctg tagcttcttc ctcctctttc tgcctccttt     240
tcttttttctt ttttttggg  ggcttgctct ctgactgcag ttgaggggcc ccagggtcct    300
ggcctttgag acgagccagg aaggcctgct cctgggcctc taggcgagca agcttggcct     360
tcattgtgat cccaagacgg gcagccttgt gtgctgttcg cccctcacag gcttggagca     420
gcatctcatc agtcagaatc tttggggact tggacccctg gttgtcgtca tcactgcagc     480
```

-continued

| | |
|---|---|
| tctccaagtc tttgtttggc ttctctccac ctgaagtcaa tgtagccatc ttcacaaact | 540 |
| tctgatacag caagttgggc ttgggatgat tataacgggt ggtctcctta gaaaggctcc | 600 |
| ttatctgtac tccatcctgc ccagtttcca ctaccaagtt ggccgcagtc ttgttgaaga | 660 |
| gctcattcca ccagtggttt gtgaactcct tggcagggtc atgtcctacc ccatgagtgt | 720 |
| cttgcttcag ygtcaccctg agagcctgag tgataccatt ctccttccg | 769 |

<210> SEQ ID NO 40
<211> LENGTH: 292
<212> TYPE: DNA
<213> ORGANISM: Homo sapien

<400> SEQUENCE: 40

| | |
|---|---|
| gacaacatga ataaatcct agaggacaaa attaaactca atagagtgta gtctagttaa | 60 |
| aaactcgaaa atgagcaag tctggtggga gtggaggaag ggctatacta taaatccaag | 120 |
| tgggcctcct gatcttaaca agccatgctc attatacaca tctctgaact ggacatacca | 180 |
| cctttacgca ggaaacaggg cttggaactt ctaagggaaa ttaacatgca ccacccacat | 240 |
| ctaacctacc tgccgggtag gtaccatccc tgcttcgctg aaatcagtgc tc | 292 |

<210> SEQ ID NO 41
<211> LENGTH: 406
<212> TYPE: DNA
<213> ORGANISM: Homo sapien

<400> SEQUENCE: 41

| | |
|---|---|
| ttggaattaa ataaacctgg aacagggaag gtgaaagttg gagtgagatg tcttccatat | 60 |
| ctataccttt gtgcacagtt gaatgggaac tgtttgggtt tagggcatct tagagttgat | 120 |
| tgatggaaaa agcagacagg aactggtggg aggtcaagtg gggaagttgg tgaatgtgga | 180 |
| ataacttacc tttgtgctcc acttaaacca gatgtgttgc agctttcctg acatgcaagg | 240 |
| atctacttta attccacact ctcattaata aattgaataa aagggaatgt tttggcacct | 300 |
| gatataatct gccaggctat gtgacagtag gaaggaatgt tttcccctaa caagcccaat | 360 |
| gcactggtct gactttataa attatttaat aaaatgaact attatc | 406 |

<210> SEQ ID NO 42
<211> LENGTH: 381
<212> TYPE: DNA
<213> ORGANISM: Homo sapien

<400> SEQUENCE: 42

| | |
|---|---|
| aaactggacc tgcaacaggg acatgaattt actgcarggt ctgagcaagc tcagcccctc | 60 |
| tacctcaggg ccccacagcc atgactacct cccccaggag cgggagggtg aaggggggcct | 120 |
| gtctctgcaa gtggagccag agtggaggaa tgagctctga agacacagca cccagccttc | 180 |
| tcgcaccagc caagccttaa ctgcctgcct gaccctgaac cagaacccag ctgaactgcc | 240 |
| cctccaaggg acaggaaggc tgggggaggg agtttacaac ccaagccatt ccaccccctc | 300 |
| ccctgctggg gagaatgaca catcaagctg ctaacaattg ggggaagggg aaggaagaaa | 360 |
| actctgaaaa caaaatcttg t | 381 |

<210> SEQ ID NO 43
<211> LENGTH: 451
<212> TYPE: DNA
<213> ORGANISM: Homo sapien

<400> SEQUENCE: 43

```
catgcgtttc accactgttg gccaggctgg tctcgaactc ctggcctcaa gcaatccacc    60
cgcctcagcc tccaaaagtg ctgggattac agatgtgagc catggcacca tgccaaaagg   120
ctatattcct ggctctgtgt ttccgagact gcttttaatc ccaacttctc tacatttaga   180
ttaaaaaata ttttattcat ggtcaatctg aacataatt actgcatctt aagtttccac    240
tgatgtatat agaaggctaa aggcacaatt tttatcaaat ctagtagagt aaccaaacat   300
aaaatcatta attactttca acttaataac taattgacat tcctcaaaag agctgttttc   360
aatcctgata ggttctttat tttttcaaaa tatatttgcc atgggatgct aatttgcaat   420
aaggcgcata atgagaatac cccaaactgg a                                   451
```

<210> SEQ ID NO 44
<211> LENGTH: 521
<212> TYPE: DNA
<213> ORGANISM: Homo sapien

<400> SEQUENCE: 44

```
gttggacccc cagggactgg aaagacactt cttgcccgag ctgtggcggg agaagctgat    60
gttcctttt attatgcttc tggatccgaa tttgatgaga tgtttgtggg tgtgggagcc    120
agccgtatca gaaatctttt tagggaagca aaggcgaatg ctccttgtgt tatatttatt   180
gatgaattag attctgttgg tgggaagaga attgaatctc caatgcatcc atattcaagg   240
cagaccataa atcaacttct tgctgaaatg gatggtttta aacccaatga aggagttatc   300
ataataggag ccacaaaactt cccagaggca ttagataatg ccttaatacc gtcctggtcg   360
ttttgacatg caagttacag ttccaaggcc agatgtaaaa ggtcgaacag aaattttgaa    420
atggtatctc aataaaataa agtttgatca atcccgttga tccagaaatt atagcctcga   480
ggtactggtg gcttttccgg aagcagagtt gggagaatct t                        521
```

<210> SEQ ID NO 45
<211> LENGTH: 585
<212> TYPE: DNA
<213> ORGANISM: Homo sapien

<400> SEQUENCE: 45

```
gcctacaaca tccagaaaga gtctaccctg cacctggtgc tscgtctcag aggtgggatg    60
cagatcttcg tgaagaccct gactggtaag accatcactc tcgaagtgga gccgagtgac   120
accatygaga acgtcaaagc aaagatccar gacaaggaag gcrtycctcc tgaccagcag   180
aggttgatct tgccggaaa gcagctggaa gatggdcgca ccctgtctga ctacaacatc   240
cagaaagagt cyaccctgca cctggtgctc cgtctcagag gtgggatgca ratcttcgtg   300
aagaccctga ctggtaagac catcaccctc gaggtggagc ccagtgacac catcgagaat   360
gtcaaggcaa agatccaaga taaggaaggc atccctcctg atcagcagag gttgatcttt   420
gctgggaaac agctggaaga tggacgcacc ctgtctgact acaacatcca gaaagagtcc   480
actctgcact tggtcctgcg cttgaggggg ggtgtctaag tttcccctt taaggtttcm   540
acaaatttca ttgcactttc ctttcaataa agttgttgca ttccc                    585
```

<210> SEQ ID NO 46
<211> LENGTH: 481
<212> TYPE: DNA
<213> ORGANISM: Homo sapien

<400> SEQUENCE: 46

-continued

| | | |
|---|---|---|
| gaactgggcc ctgagcccaa gtcatgcctt gtgtccgcat ctgccgtgtc acctctgtkc | 60 |
| ctgcccctca ccctccctc ctggtcttct gagccagcac catctccaaa tagcctattc | 120 |
| cttcctgcaa atcacacaca catgcgggcc acacatacct gctgccctgg agatggggaa | 180 |
| gtaggagaga tgaatagagg cccatacatt gtacagaagg aggggcaggt gcagataaaa | 240 |
| gcagcagacc cagcggcagc tgaggtgcat ggagcacggt tggggccggc attgggctga | 300 |
| gcacctgatg ggcctcatct cgtgaatcct cgaggcagcg ccacagcaga ggagttaagt | 360 |
| ggcacctggg ccgagcagag caggagactg agggtcagag tggaggctaa gctgccctgg | 420 |
| aactcctcaa tcttgcctgc ccctagtat gaagccccct tcctgcccct acaattcctg | 480 |
| a | 481 |

<210> SEQ ID NO 47
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 47

| | | |
|---|---|---|
| atggatctta ctttgccacc caggttggag tgcagtgctg caatcttggc tcactgcagc | 60 |
| cttaacctcc caggctcaag ctatcctcct gccaaagcct tccacatagc tgggactaca | 120 |
| ggtacacngc caccacaccc agctaaaatt tttgtatttt ttgtagagac gggatctcgc | 180 |
| cacgttgccc aggctggtcc catcctgacc tcaagcagat ctgcccacct cagcccccca | 240 |
| acgtgctagg attacaggcg tgagccaccg cacccagcct ttgttttgct tttaatggaa | 300 |
| tcaccagttc ccctccgtgt ctcagcagca gctgtgagaa atgctttgca tctgtgacct | 360 |
| ttatgaaggg gaacttccat gctgaatgag ggtaggatta catgctcctg tttccgggg | 420 |
| gtcaagaaag cctcagactc cagcatgata agcagggtga g | 461 |

<210> SEQ ID NO 48
<211> LENGTH: 571
<212> TYPE: DNA
<213> ORGANISM: Homo sapien

<400> SEQUENCE: 48

| | | |
|---|---|---|
| atagggctt taaggaggga attcaggttc aatgaggtcg taaggccagg gctcttatcc | 60 |
| agtaagactg gggtccttag atgagaaaga cacaccgag gtccttctct ctgccgtgtg | 120 |
| aggatgcatc aagaaggcgg ccgtctgcaa gcgaaggaga ggccgcacca gaaaccgaca | 180 |
| ccttcatctt ggacttgcag cctctagaac tgagaaaata actgtctgtt ggttaagcca | 240 |
| cccagtttgt agtattctct tatggcttcc taagcagact aacaaacaaa cacccaaaat | 300 |
| taactgatgg cttcgctgtc ttctgtaaaa attgctatga gagaactttt cactcactgt | 360 |
| tttgcagttt ctccctcagt ccctggttct ttcttctcac ataatcccaa tttcaattta | 420 |
| tagttcatgg cccaggcaga gtcattcatc acggcatctc ctgagctaaa ccagcacctg | 480 |
| ctctgctcac ttcttgactg gctgctcatc atcagccctc ttgcagagat ttcatttcct | 540 |
| cccgtgccag gtacttcacg caccaagctc a | 571 |

<210> SEQ ID NO 49
<211> LENGTH: 511
<212> TYPE: DNA
<213> ORGANISM: Homo sapien

<400> SEQUENCE: 49

```
ggataatgaa gttgttttat ttagcttgga caaaaaggca tattcctcta ttttcttata    60
caacaaatat ccccaaaata aagcaagcat atatatcttg aatgtgtaat aatccagtga   120
taaacaagag cagtacttta aaagaaaaaa aaatatgtat ttctgtcagg ttaaaatgag   180
aatcaaaacc atttactctg ctaactcatt atttttttgct ttcttttttgg ttaagagagg   240
caatgcaata cactgaaaaa ggttttttatc ttatctggca ttggaattag acatattcaa   300
accccagccc ccatttccaa actttaagac cacaaacaag taatttactt ttctgaacat   360
tggttttttc tggaaaatgg gaattataaa atagactttg cagactctta tgagattaaa   420
taagataatg tatgaaattc tttcttcttt tttacttctt tttcctttttt gagatggagt   480
ctcaccccgt cacccaggct ggagtacagt g                                  511
```

<210> SEQ ID NO 50
<211> LENGTH: 561
<212> TYPE: DNA
<213> ORGANISM: Homo sapien

<400> SEQUENCE: 50

```
ccactgcact ccagcctggg tgacggagtg agactctgtc tcaaaaaaac aaacaaacaa    60
acaaacaaaa aactgaaaag gaaatagagt tcctctttcc tcatatatga atatattatt   120
tcaacagatt gttgatcacc taccatatgc ttggtattgt tctaattgct ggggatacag   180
caagaggttc tgcagaactt catggagcat gaaagtaaat aaacaaagtt aatttcaagg   240
ccaggcatgg ttgctcacac ctttagtccc agcactttgg gaggctgagg caggtggatc   300
acttgggccc aggagttcaa ggctgcagtg agccaagatt gtgccactac tctccaggct   360
gggcaacaga gcaagaccct gtctcagggg aacaaaaag ttaatttcag attttgttaa   420
gtgctgtaaa ggaagtaaat aggttgatat tcaagagagc acctgaaggc caggcgtggt   480
ggctcacgcc tgtggtctaa cgctttggga agcccgagcg gcggatcac aaggtcagga   540
gaattttggc caggcatggt g                                             561
```

<210> SEQ ID NO 51
<211> LENGTH: 451
<212> TYPE: DNA
<213> ORGANISM: Homo sapien

<400> SEQUENCE: 51

```
agaatccatt tattgggttt taaactagtt acacaactga aatcagtttg gcactacttt    60
atacagggat tacgcctgtg tatgccgaca cttaaatact gtaccaggac cactgctgtg   120
cttaggtctg tattcagtca ttcagcatgt agatactaaa aatatactgt agtgttcctt   180
taaggaagac tgtacagggt gtgttgcaag atgacattca ccaatttgtg aattatttca   240
acccagaaga tacctttcac tctataaact tgtcataggc aaacatgtgg tgttagcatt   300
gagagatgca cacaaaaatg ttacataaaa gttcagacat tctaatgata agtgaactga   360
aaaaaaaaaa aaccccacat ctcaattttt gtaacaagat aagaaaata atttaaaaac   420
acaaaaaatg gcattcagtg ggtacaaagc c                                  451
```

<210> SEQ ID NO 52
<211> LENGTH: 682
<212> TYPE: DNA
<213> ORGANISM: Homo sapien -continued

```
<400> SEQUENCE: 52
caaatattta atataaatct ttgaaacaag ttcagakgaa ataaaaatca aagtttgcaa      60
aaacgtgaag attaacttaa ttgtcaaata ttcctcattg ccccaaatca gtattttttt     120
tatttctatg caaaagtatg ccttcaaact gcttaaatga tatatgatat gatacacaaa    180
ccagttttca aatagtaaag ccagtcatct tgcaattgta agaaataggt aaaagattat    240
aagacacctt acacacacac acacacacac acacacacgt gtgcaccgcc aatgacaaaa    300
aacaatttgg cctctcctaa aataagaaca tgaagaccct taattgctgc caggagggaa    360
cactgtgtca cccctcccta caatccaggt agtttccttt aatccaatag caaatctggg    420
catatttgag aggagtgatt ctgacagcca csgttgaaat cctgtgggga accattcatg    480
tccacccact ggtgccctga aaaaatgcca ataattttc gctcccactt ctgctgctgt     540
ctcttccaca tcctcacata gaccccgac ccgctggccc ctggctgggc atcgcattgc    600
tggtagagca agtcataggt ctcgtctttg acgtcacaga agcgatacac caaattgcct    660
ggtcggtcat tgtcataacc ag                                             682

<210> SEQ ID NO 53
<211> LENGTH: 311
<212> TYPE: DNA
<213> ORGANISM: Homo sapien
<220> FEATURE:
<221> NAME/KEY: misc_feature
<222> LOCATION: (1)...(311)
<223> OTHER INFORMATION: n = A,T,C or G

<400> SEQUENCE: 53
tttgacttta gtagggggtct gaactatta ttttactttg ccmgtaatat ttaraccyta     60
tatatctttc attatgccat cttatcttct aatgbcaagg gaacagwtgc taamctggct    120
tctgcattwa tcacattaaa aatggctttc ttggaaaatc ttcttgatat gaataaagga    180
tcttttavag ccatcattta aagcmggntt ctctccaaca cgagtctgct sasggggggk    240
gagctgtgaa ctctggctga aggctttccc atacacactg caatgacmtg gtttctgacc    300
agbgtgagtt a                                                         311

<210> SEQ ID NO 54
<211> LENGTH: 561
<212> TYPE: DNA
<213> ORGANISM: Homo sapien

<400> SEQUENCE: 54
agagaagccc cataaatgca atcagtgtgg gaaggccttc agtcagagct caagcctttt     60
cctccatcat cgggttcata ctggagagaa accctatgta tgtaatgaat gcggcagagc    120
ctttggtttt aactctcatc ttactgaaca cgtaaggatt cacacaggag aaaaacccta    180
tgtttgtaat gagtgcggca aagcctttcg tcggagttcc actcttgttc agcatcgaag    240
agttcacact ggggagaagc cctaccagtg cgttgaatgt gggaaagctt tcagccagag    300
ctcccagctc accctacatc agccgagttc acactggaga gaagccctat gactgtggtg    360
actgtgggaa ggccttcagc cggaggtcaa ccctcattca gcatcagaaa gttcacagcg    420
gagagactcg taagtgcaga aaacatggtc cagcctttgt tcatggctcc agcctcacag    480
cagatggaca gattcccact ggagagaagc acggcagaac ctttaaccat ggtgcaaatc    540
tcattctgcg ctggacagtt c                                              561
```

<210> SEQ ID NO 55
<211> LENGTH: 811
<212> TYPE: DNA
<213> ORGANISM: Homo sapien

<400> SEQUENCE: 55

| | | | | | |
|---|---|---|---|---|---|
| gagacagggt | ctcactttgt | cacccaggct | ggaatgcagt | ggtgcgatct | tacgtagctc | 60 |
| actgcagccc | tgacctcctg | gactcaaaca | attctcctgc | ctcagccctg | caagtagctg | 120 |
| ggactgtggg | tgcatgccac | catgcctggc | taacttttgt | agttttttgta | aagatggggt | 180 |
| tttgccatgt | tgcacatgct | ggtcttgaac | tcctgagctc | aaacgatctg | cccacctcgg | 240 |
| cctcccagaa | tgttgggatt | acaggggtaa | accaccacgc | ctggccccat | tagggtattc | 300 |
| ttagcatcca | cttgctcact | gagattaatc | ataagagatg | ataagcactg | gaagaaaaaa | 360 |
| attttacta | ggctttggat | attttttttcc | tttttcagct | ttatacagag | gattggatct | 420 |
| ttagttttcc | tttaactgat | aataaaacat | tgaaaggaaa | taagtttacc | tgagattcac | 480 |
| agagataacc | ggcatcactc | ccttgctcaa | ttccagtctt | taccacatca | attattttca | 540 |
| gaggtgcagg | ataaaggcct | ttagtctgct | ttcgcacttt | ttcttccact | tttttgtaaa | 600 |
| cctgttgcct | gacaaatgga | attgacagcg | tatgccatga | ctattccatt | tgtcaggcat | 660 |
| acgctgtcaa | ttttttccacc | aatcccttgt | ctctcttттgg | agagatcttc | ttatcagcta | 720 |
| gtcctttggc | aaaagtaatt | gcaacttctt | ctaggtattc | tattgtccgt | tccactggtg | 780 |
| gaacccctgg | gaccaggact | aaaacctcca | g | | | 811 |

<210> SEQ ID NO 56
<211> LENGTH: 591
<212> TYPE: DNA
<213> ORGANISM: Homo sapien
<220> FEATURE:
<221> NAME/KEY: misc_feature
<222> LOCATION: (1)...(591)
<223> OTHER INFORMATION: n = A,T,C or G

<400> SEQUENCE: 56

| | | | | | |
|---|---|---|---|---|---|
| atctcatata | tatatttctt | cctgacttta | tttgcttgct | tctgncacgc | atttaaaata | 60 |
| tcacagagac | caaaatagag | cggctttctg | gtggaacgca | tggcagtcac | aggacaaaat | 120 |
| acaaaactag | ggggctctgt | cttctcatac | atcatacaat | tttcaagtat | tttttttatg | 180 |
| tacaaagagc | tactctatct | gaaaaaaaat | taaaaaataa | atgagacaag | atagtttatg | 240 |
| catcctagga | agaaagaatg | ggaagaaaga | acggggcagt | tgggtacaga | ttcctgtccc | 300 |
| ctgttcccag | ggaccactac | cttcctgcca | ctgagttccc | ccacagcctc | acccatcatg | 360 |
| tcacagggca | agtgccaggg | taggtgggga | ccagtggaga | caggaaccag | caacatactt | 420 |
| tggcctggaa | gataaggaga | aagtctcaga | aacacactgg | tgggaagcaa | tcccacnggc | 480 |
| cgtgccccan | gagcttccca | cctgctgctg | gctccctggg | tggctttggg | aacagcttgg | 540 |
| gcaggccctt | ttgggtgggg | nccaactggg | cctttgggcc | cgtgtggaaa | g | 591 |

<210> SEQ ID NO 57
<211> LENGTH: 481
<212> TYPE: DNA
<213> ORGANISM: Homo sapien

<400> SEQUENCE: 57

| | | | | | |
|---|---|---|---|---|---|
| aaacattgag | atggaatgat | agggtttccc | agaatcaggt | ccatatttta | actaaatgaa | 60 |
| aattatgatt | tatagccttc | tcaaatacct | gccatacttg | atatctcaac | cagagctaat | 120 |

```
tttacctctt tacaaattaa ataagcaagt aactggatcc acaatttata atacctgtca    180
attttttctg tattaaacct ctatcatagt ttaagcctat tagggtactt aatccttaca    240
aataaacagg tttaaaatca cctcaatagg caactgccct tctggttttc ttctttgact    300
aaacaatctg aatgcttaag attttccact ttgggtgcta gcagtacaca gtgttacact    360
ctgtattcca gacttcttaa attatagaaa aaggaatgta cacttttttgt attctttctg   420 agcagggccg ggaggcaaca tcatctacca tggtagggac ttgtatgcat ggactacttt    480
a                                                                   481

<210> SEQ ID NO 58
<211> LENGTH: 141
<212> TYPE: DNA
<213> ORGANISM: Homo sapien

<400> SEQUENCE: 58
actctgtcgc ccaggctgga gcccabtggm gcgatctcga ctccctgcaa gctmcgcctc     60
acaggwtcat gccattctcc tgcctcagca tctggagtag ctgggactac aggcgccagc    120
caccatgccc agctaattttt t                                             141

<210> SEQ ID NO 59
<211> LENGTH: 191
<212> TYPE: DNA
<213> ORGANISM: Homo sapien

<400> SEQUENCE: 59
accttaaaga cataggagaa tttatactgg gagagaaagc ttacaaatgt aaggtttctg     60
acaagacttg ggagtgattc acacctggaa caacatactg gacttcacac tggabagaaa   120
ccttacaagt gtaatgagtg tggcaaagcc tttggcaagc agtcaacact tattcaccat    180
caggcaattc a                                                        191

<210> SEQ ID NO 60
<211> LENGTH: 480
<212> TYPE: DNA
<213> ORGANISM: Homo sapien

<400> SEQUENCE: 60
agtcaggatc atgatggctc agtttcccac agcgatgaat ggagggccaa atatgtgggc    60
tattacatct gaagaacgta ctaagcatga taaacagttt gataacctca aaccttcagg   120
aggttacata acaggtgatc aagcccgtac ttttttccta cagtcaggtc tgccggcccc   180
ggttttagct gaaatatggg ccttatcaga tctgaacaag gatgggaaga tggaccagca   240
agagttctct atagctatga aactcatcaa gttaaagttg cagggccaac agctgcctgt   300
agtcctccct cctatcatga acaaccccc tatgttctct ccactaatct ctgctcgttt    360
tgggatggga agcatgccca atctgtccat tcatcagcca ttgcctccag ttgcacctat   420
agcaacaccc ttgtcttctg ctacttcagg gaccagtatt cctccctaat gatgcctgct   480

<210> SEQ ID NO 61
<211> LENGTH: 381
<212> TYPE: DNA
<213> ORGANISM: Homo sapien

<400> SEQUENCE: 61
ctttcgattt ccttcaattt gtcacgtttg attttatgaa gttgttcaag ggctaactgc     60
tgtgtattat agctttctct gagttccttc agctgattgt taaatgaatc catttctgag   120
```

```
agcttagatg cagtttcttt ttcaagagca tctaattgtt ctttaagtct ttggcataat    180 tcttccttt  ctgatgactt tctatgaagt aaactgatcc ctgaatcagg tgtgttactg    240
agctgcatgt ttttaattct ttcgtttaat agctgcttct cagggaccag atagataagc    300
ttattttgat attccttaag ctcttggtga agttgttcga tttccataat ttccaggtca    360
cactggttat cccaaacttc t                                              381

<210> SEQ ID NO 62
<211> LENGTH: 906
<212> TYPE: DNA
<213> ORGANISM: Homo sapien

<400> SEQUENCE: 62
gtggaggtga aacggaggca agaaaggggg ctacctcagg agcgagggac aaaggggcg     60 tgaggcacct aggccgcggc accccggcga caggaagccg tcctgaaccg ggctaccggg    120 tagggaagg  gcccgcgtag tcctcgcagg gccccagagc tggagtcggc tccacagccc    180
cgggccgtcg gcttctcact tcctggacct ccccggcgcc cggcctgag  gactggctcg    240 gcggagggag aagaggaaac agacttgagc agctccccgt tgtctcgcaa ctccactgcc    300
gaggaactct catttcttcc ctcgctcctt cacccccac  ctcatgtaga aaggtgctga    360
agcgtccgga gggaagaaga acctgggcta ccgtcctggc cttcccmccc ccttcccggg    420
gcgctttggt gggcgtggag ttgggttgg  gggggtgggt gggggttctt ttttggagtg    480
ctggggaact ttttccctt cttcaggtca ggggaaaggg aatgcccaat tcagagagac    540 atggggcaa  gaaggacggg agtggaggag cttctggaac tttgcagccg tcatcgggag    600
gcggcagctc taacagcaga gagcgtcacc gcttggtatc gaagcacaag cggcataagt    660
ccaaacactc caaagacatg gggttggtga ccccgaagc  agcatccctg ggcacagtta    720 tcaaacctt  ggtggagtat gatgatatca gctctgattc cgacaccttc tccgatgaca    780
tggccttcaa actagaccga agggagaacg acgaacgtcg tggatcagat cggagcgacc    840
gcctgcacaa acatcgtcac caccagcaca ggcgttcccg ggacttacta aaagctaaac    900
agaccg                                                              906

<210> SEQ ID NO 63
<211> LENGTH: 491
<212> TYPE: DNA
<213> ORGANISM: Homo sapien

<400> SEQUENCE: 63
gacatgtttg cctgcagggg accagagaca atgggattag ccagtgctca ctgttcttta     60
tgcttccaga gaggatgggg acagctctca ggtcagaatc caggctgaga aggccatgct    120
ggttgggggc cccggaagc  acggtccgga tcctccctgg catcagcgta gacccgctgc    180
tcaggcttgg ggtaccaaac tcatgctctg tactgttttg gccccatgcg gtgagaggaa    240
aacctagaaa aagattggtc gtgctaagga atcagctgcc cctcatcct  ccgcatccaa    300 tgctggtgac aacatattcc ctctcccagg acacagactc ggtgactcca cactgggctg    360
agtggcctct ggaggctcgt ggcctaaggc agggctccgt aaggctgatc ggctgaactg    420
ggtggggtga gggtttctga cccttcgctt cccatcccat aaccgctgtc aatgagctca    480
cactgtggtc a                                                        491

<210> SEQ ID NO 64
```

<210> SEQ ID NO 64
<211> LENGTH: 511
<212> TYPE: DNA
<213> ORGANISM: Homo sapien

<400> SEQUENCE: 64

```
gatggcatgg tcgttgctaa tgtgcctgct gggatggagc acttcctcct gtgagcccag      60
gggacccgcc tgtccctgga gcttggggca aggagggaag agtgatacca ggaaggtggg     120
gctgcagcca ggggccagag tcagttcagg gagtggtcct cggccctcaa agctcctccg     180
gggactgctc aggagtgatg gtgccctgga gtttgcccca acttccctgg ccaccctgga     240
aggtgcctgg ctgctccagg cctctaggct gggctgatgg gtttctccag gacacaagta     300
tcattaaagc caccctctcc tcagcttgtc aggccgcaca tgtgggacag gctgtgctca     360
caacccctc gcctgccctg ccctccatca ggaggagcca gtggaacctt cggaaagctc      420
ccagcatctc agcagccctc aaaagtcgtc ctggggcaag ctctggttct cctgactgga     480
ggtcatctgg gcttggcctg ctctctctcg c                                     511
```

<210> SEQ ID NO 65
<211> LENGTH: 394
<212> TYPE: DNA
<213> ORGANISM: Homo sapien

<400> SEQUENCE: 65

```
taaaaaagtg taacaaaggt ttatttagac tttcttcatg cccccagatc caggatgtct      60
atgtaaaccg ttatcttaca agaaagcac aatatttggt ataaactaag tcagtgactt      120
gcttaactga aatagcgtcc atccaaaagt gggtttaagg taaaactacc tgacgatatt     180
ggcggggatc ctgcagtttg gactgcttgc cgggtttgtc cagggttccg ggtctgttct     240
tggcactcat ggggacaggc atcctgctcg tctgtggggc cccgctggag cccttacgtg      300
aagctgaagg tatcgaccst agggggctct agggcagtgg gaccttcatc cggaactaac      360
aagggtcggg gagaggcctc ttgggctatg tggg                                  394
```

<210> SEQ ID NO 66
<211> LENGTH: 359
<212> TYPE: DNA
<213> ORGANISM: Homo sapien

<400> SEQUENCE: 66

```
caagcgttcc tttatggatg taaattcaaa cagtcatgct gagccatccc gggctgacag      60
tcacgttwaa gacactaggt cgggcgccac agtgccaccc aaggagaaga agaatttgga     120
atttttccat gaagatgtac ggaaatctga tgttgaatat gaaaatggcc cccaaatgga     180
attccaaaag gttaccacag gggctgtaag acctagtgac cctcctaagt gggaaagagg     240
aatggagaat agtatttctg atgcatcaag aacatcagaa tataaaactg agatcataat      300
gaaggaaaat tccatatcca atatgagttt actcagagac agtagaaact attcccagg      359
```

<210> SEQ ID NO 67
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 67

```
taggaataac aaatgtttat tcagaaatgg ataagtaata cataatcacc cttcatctct      60
```

```
taatgcccct tcctctcctt ctgcacagga gacacagatg ggtaacatag aggcatggga    120
agtggaggag gacacaggac tagcccacca ccttctcttc ccggtctccc aagatgactg    180
cttatagagt ggaggaggca aacaggtccc ctcaatgtac cagatggtca cctatagcac    240
cagctccaga tggccacgtg gttgcagctg gactcaatga aactctgtga caaccagaag    300
atacctgctt tgggatgaga gggaggataa agccatgcag ggaggatatt taccatccct    360
accctaagca cagtgcaagc agtgagcccc cggctcccag tacctgaaaa accaaggcct    420 actgncttt ggatgctctc ttgggccacg                                       450

<210> SEQ ID NO 68
<211> LENGTH: 511
<212> TYPE: DNA
<213> ORGANISM: Homo sapien

<400> SEQUENCE: 68
aagcctcctg ccctggaaat ctggagcccc ttggagctga gctggacggg gcagggaggg     60
gctgagaggc aagaccgtct ccctcctgct gcagctgctt ccccagcagc cactgctggg    120
cacagcagaa acgccagcag agaaaatggg agccgagagt ccttagccct ggagctgagg    180
ctgcctctgg gctgacccgc tggctgtacg tggccagaac tggggttggc atctggcatc    240
catttgaggc cagggtggag gaaagggagg ccaacagagg aaaacctatt cctgctgtga    300
caacacagcc cttgtcccac gcagcctaag tgcagggagc gtgatgaagt caggcagcca    360
gtcggggagg acgaggtaac tcagcagcaa tgtcaccttg tagcctatgc gctcaatggc    420
ccggaggggc agcaaccccc cgcacacgtc agccaacagc agtgcctctg caggcaccaa    480
gagagcgatg atggacttga gcgccgtgtt c                                   511

<210> SEQ ID NO 69
<211> LENGTH: 511
<212> TYPE: DNA
<213> ORGANISM: Homo sapien

<400> SEQUENCE: 69
gtttggcaga agacatgttt aataacattt tcatatttaa aaaatacagc aacaattctc     60
tatctgtcca ccatcttgcc ttgcccttcc tggggctgag gcagacaaag gaaaggtaat    120
gaggttaggg ccccccaggcg ggctaagtgc tattggcctg ctcctgctca agagagcca    180 tagccagctg ggcacggccc cctagcccct ccaggttgct gaggcggcag cggtggtaga    240
gttcttcact gagccgtggg ctgcagtctc gcagggagaa cttctgcacc agccctggct    300
ctacggcccg aaagaggtgg agccctgaga accggaggaa aacatccatc acctccagcc    360 cctccaggggc ttcctcctct tcctggcctg ccagttcacc tgccagccgg gctcgggccg    420
ccaggtagtc agcgttgtag aagcagccct ccgcagaagc ctgccggtca aatctccccg    480
ctataggagc cccccgggag gggtcagcac c                                   511

<210> SEQ ID NO 70
<211> LENGTH: 511
<212> TYPE: DNA
<213> ORGANISM: Homo sapien

<400> SEQUENCE: 70
caagttgaac gtcaggcttg gcagaggtgg agtgtagatg aaaacaaagg tgtgattatg     60
aagaggatgt gagtcctttg ggtgtaggag agaaaggctg ttgagcttct atttcaagat    120
```

-continued

```
acttttacct gtgcaaaaag cacattttcc acctccttct catggcattt gtgtaaggtg      180
agtatgattc ctattccatc tgcattttag aggtgaagaa taacgtacaa gggattcagt      240
gattagcaag ggacccctca ctaagtgttg atggagttag acagagctc agctgtttga       300 atctcagagc ccaggcagct ggagctgggt aggatcctgg agctggcact aatgtgaggt      360
gcattccctc caacccaggc tcagatccgg aacctgaccg tgctgacccc cgaaggggag      420
gcagggctga gctggcccgt tgggctccct gctcctttca caccacactc tcgctttgag      480
gtgctgggct gggactactt cacagagcag c                                      511
```

<210> SEQ ID NO 71
<211> LENGTH: 511
<212> TYPE: DNA
<213> ORGANISM: Homo sapien

<400> SEQUENCE: 71

```
tggcctgggc aggattggga gagaggtagc tacccggatg cagtcctttg ggatgaagac       60
tatagggtat gacccatca tttccccaga ggtctcggcc tcctttggtg ttcagcagct       120 gccctggag gagatctggc ctctctgtga tttcatcact gtgcacactc ctctcctgcc       180
ctccacgaca ggcttgctga atgacaaac ctttgcccag tgcaagaagg gggtgcgtgt       240
ggtgaactgt gcccgtggag ggatcgtgga cgaaggcgcc ctgctccggg ccctgcagtc       300
tggccagtgt gccggggctg cactggacgt gtttacggaa gagccgccac gggaccgggc      360
cttggtggac catgagaatg tcatcagctg tccccacctg ggtgccagca ccaaggaggc      420
tcagagccgc tgtggggagg aaattgctgt tcagttcgtg gacatggtga aggggaaatc      480
tctcacgggg gttgtgaatg cccaggccct t                                      511
```

<210> SEQ ID NO 72
<211> LENGTH: 2017
<212> TYPE: DNA
<213> ORGANISM: Homo sapien

<400> SEQUENCE: 72

```
agccagatgg ctgagagctg caagaagaag tcaggatcat gatggctcag tttcccacag        60
cgatgaatgg agggccaaat atgtgggcta ttacatctga agaacgtact aagcatgata       120
aacagtttga taacctcaaa ccttcaggag gttacataac aggtgatcaa gcccgtactt       180
ttttcctaca gtcaggtctg ccggccccgg ttttagctga aatatgggcc ttatcagatc       240
tgaacaagga tgggaagatg gaccagcaag agttctctat agctatgaaa ctcatcaagt       300
taaagttgca gggccaacag ctgcctgtag tcctccctcc tatcatgaaa caaccccta       360 tgttctctcc actaatctct gctcgttttg ggatgggaag catgcccaat ctgtccattc       420
atcagccatt gcctccagtt gcacctatag caacaccctt gtcttctgct acttcaggga       480
ccagtattcc tcccctaatg atgcctgctc ccctagtgcc ttctgttagt acatcctcat       540
taccaaatgg aactgccagt ctcattcagc ctttatccat tccttattct tcttcaacat       600
tgcctcatgc atcatcttac agcctgatga tgggaggatt tggtggtgct agtatccaga       660
aggcccagtc tctgattgat ttaggatcta gtagctcaac ttcctcaact gcttccctct       720
cagggaactc acctaagaca gggacctcag agtgggcagt tcctcagcct tcaagattaa       780
agtatcggca aaaatttaat agtctagaca aggcatgag cggatacctc tcaggttttc       840
aagctagaaa tgcccttctt cagtcaaatc tctctcaaac tcagctagct actatttgga       900
ctctggctga catcgatggt gacggacagt tgaaagctga agaatttatt ctggcgatgc       960
```

```
acctcactga catggccaaa gctggacagc cactaccact gacgttgcct cccgagcttg    1020
tccctccatc tttcagaggg ggaaagcaag ttgattctgt taatggaact ctgccttcat    1080
atcagaaaac acaagaagaa gagcctcaga agaaactgcc agttactttt gaggacaaac    1140
ggaaagccaa ctatgaacga ggaaacatgg agctggagaa gcgacgccaa gtgttgatgg    1200
agcagcagca gagggaggct gaacgcaaag cccagaaaga gaaggaagag tgggagcgga    1260
aacagagaga actgcaagag caagaatgga agaagcagct ggagttggag aaacgcttgg    1320
agaaacagag agagctggag agacagcggg aggaagagag gagaaaggag atagaaagac    1380
gagaggcagc aaaacaggag cttgagagac aacgccgttt agaatgggaa agactccgtc    1440
ggcaggagct gctcagtcag aagaccaggg aacaagaaga cattgtcagg ctgagctcca    1500
gaaagaaaag tctccacctg gaactggaag cagtgaatgg aaaacatcag cagatctcag    1560
gcagactaca agatgtccaa atcagaaagc aaacacaaaa gactgagcta gaagttttgg    1620
ataaacagtg tgacctggaa attatggaaa tcaaacaact tcaacaagag cttaaggaat    1680
atcaaaataa gcttatctat ctggtccctg agaagcagct attaaacgaa agaattaaaa    1740
acatgcagct cagtaacaca cctgattcag ggatcagttt acttcataaa aagtcatcag    1800
aaaaggaaga attatgccaa agacttaaag aacaattaga tgctcttgaa aaagaaactg    1860
catctaagct ctcagaaatg gattcattta acaatcagct gaaggaactc agagaaagct    1920
ataatacaca gcagttagcc cttgaacaac ttcataaaat caaacgtgac aaattgaagg    1980
aaatcgaaag aaaaagatta gagcaaaaaa aaaaaaa                              2017

<210> SEQ ID NO 73
<211> LENGTH: 414
<212> TYPE: DNA
<213> ORGANISM: Homo sapien

<400> SEQUENCE: 73
atggcagtga cattcaccat catgggaacc accttcccctt tcttcagga ttctctgtag      60 tggaagagag cacccagtgt tgggctgaaa acatctgaaa gtagggagaa gaacctaaaa     120
taatcagtat ctcagagggc tctaaggtgc aagaagtct cactggacat ttaagtgcca     180
acaaaggcat actttcggaa tcgccaagtc aaaactttct aacttctgtc tctctcagag     240
acaagtgaga ctcaagagtc tactgcttta gtggcaacta cagaaaactg gtgttaccca     300
gaaaaacagg agcaattaga aatggttcca atatttcaaa gctccgcaaa caggatgtgc     360
tttcctttgc ccatttaggg tttcttctct ttcctttctc tttattaacc acta           414

<210> SEQ ID NO 74
<211> LENGTH: 1567
<212> TYPE: DNA
<213> ORGANISM: Homo sapien

<400> SEQUENCE: 74
atatctagaa gtctggagtg agcaaacaag agcaagaaac aaaagaagc caaaagcaga       60 aggctccaat atgaacaaga taaatctatc ttcaaagaca tattagaagt tgggaaaata     120
attcatgtga actagacaag tgtgttaaga gtgataagta aaatgcacgt ggagacaagt     180
gcatccccag atctcaggga cctccccctg cctgtcacct ggggagtgag aggacaggat     240
agtgcatgtt ctttgtctct gaattttag ttatatgtgc tgtaatgttg ctctgaggaa      300
gcccctggaa agtctatccc aacatatcca catcttatat tccacaaatt aagctgtagt     360
```

```
atgtaccctaagacgctgctaattgactgccacttcgcaactcaggggcggctgcatttt        420 agtaatgggtcaaatgattcactttttatgatgcttccaaaggtgccttggcttctcttc        480 ccaactgacaaatgccaaagttgagaaaaatgatcataatttagcataaacagagcagt        540 cggcgacaccgattttataaataaactgagcaccttctttttaaacaaacaaatgcgggt        600 ttatttctcagatgatgttcatccgtgaatggtccagggaaggacctttcaccttgacta        660 tatggcattatgtcatcacaagctctgaggcttctccttt ccatcctgcgtggacagcta     720 agacctcagttttcaatagcatctagagcagtgggactcagctggggtgatttcgccccc        780 catctccgggggaatgtctgaagacaatttgttacctcaatgagggagtggaggaggat        840 acagtgctactaccaactagtggataaaggccagggatgctgctcaacctcctaccatgt        900 acaggacgtctcccattacaactacccaatccgaagtgtcaactgtgtcaggactaaga        960 aaccctggttttgagtagaaaagggcctggaaagaggggagccaacaaatctgtctgctt       1020 cctcacattagtcattggcaaataagcattctgtctctttggctgctgcctcagcacaga       1080 gagccagaactctatcggccaccaggataacatctctcagtgaacagagttgacaaggcc       1140 tatgggaaatgcctgatgggattatcttcagcttgttgagcttctaagttctttcccctt       1200 cattctaccctgcaagccaagttctgtaagagaaatgcctgagttctagctcaggttttc       1260 ttactctgaatttagatctccagacccttcctggccacaattcaaattaaggcaacaaac       1320 atataccttccatgaagcacacacagacttttgaaagcaaggacaatgactgcttgaatt       1380 gaggccttgaggaatgaagctttgaaggaaaagaatacttgtttccagccccttccca        1440 cactcttcatgtgttaaccactgccttcctggaccttggagccacggtgactgtattaca       1500 tgttgttatagaaaactgattttagagttctgatcgttcaagagaatgattaaatataca      1560 tttccta                                                          1567

<210> SEQ ID NO 75
<211> LENGTH: 240
<212> TYPE: DNA
<213> ORGANISM: Homo sapien

<400> SEQUENCE: 75 tcgagcggccgcccgggcaggtccttcagacttggactgtgtcacactgccaggcttcca         60 gggctccaacttgcagacggcctgttgtgggacagtctctgtaatcgcgaaagcaaccat        120 ggaagacctgggggaaaacaccatggttttatccaccctgagatctttgaacaacttcat        180 ctctcagcgtgcggagggaggctctggactggatatttctacctcggccgcgaccacgct        240

<210> SEQ ID NO 76
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 76 tagcgyggtcgcggccgaggyctgcttytctgtccagcccagggcctgtggggtcagggc         60 ggtgggtgcagatggcatccactccggtggcttccccatctttctctggcctgagcaagg       120 tcagcctgcagccagagtacagagggccaacactggtgttcttgaacaagggccttagca       180 ggccctgaaggrccctctctgtagtgttgaacttcctggagccaggccacatgttctcct       240 cataccgcaggytagygatggtgaagttgagggtgaaatagtattmangragatggctgg       300
```

```
caracctgcc cgggcggccg ctcsaaatcc                                      330
```

<210> SEQ ID NO 77
<211> LENGTH: 361
<212> TYPE: DNA
<213> ORGANISM: Homo sapien

<400> SEQUENCE: 77

```
agcgtggtcg cggccgaggt gtccttcagg gtctgcttat gcccttgttc aagaacacca     60
gtgtcagctc tctgtactct ggttgcagac tgaccttgct caggcctgag aaggatgggg    120
cagccaccag agtggatgct gtctgcaccc atcgtcctga ccccaaaagc cctggactgg    180
acagagagcg gctgtactgg aagctgagcc agctgaccca cggcatcact gagctgggcc    240
cctacaccct ggacagggac agtctctatg tcaatggttt cacccatcgg agctctgtac    300
ccaccaccag caccggggtg gtcagcgagg agccattcaa cctgcccggg cggccgctcg    360
a                                                                    361
```

<210> SEQ ID NO 78
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 78

```
ttggggnttt mgagcggccg cccgggcagg taccggggtg gtcagcgagg agccattcac     60
actgaacttc accatcaaca acctgcggta tgaggagaac atgcagcacc ctggctccag    120
gaagttcaac accacggaga gggtccttca gggcctgctc aggtccctgt tcaagagcac    180
cagtgttggc cctctgtact ctggctgcag actgactttg ctcagacttg agaaacatgg    240
ggcagccact ggagtggacg ccatctgcac cctccgcctt gatcccactg gtcctggact    300
ggacagagag cggctatact gggagctgag ccagtcctct ggcggngacn ccnctt        356
```

<210> SEQ ID NO 79
<211> LENGTH: 226
<212> TYPE: DNA
<213> ORGANISM: Homo sapien

<400> SEQUENCE: 79

```
agcgtggtcg cggccgaggt ccagtcgcag catgctcttt ctcctgccca ctggcacagt     60
gaggaagatc tctgctgtca gtgagaaggc tgtcatccac tgagatggca gtcaaaagtg    120
catttaatac acctaacgta tcgaacatca tagcttggcc caggttatct catatgtgct    180
cagaacactt acaatagcct gcagacctgc ccgggcggcc gctcga                   226
```

<210> SEQ ID NO 80
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 80

```
tgtggtgttg aacttcctgg agncagggtg acccatgtcc tccccatact gcaggttggt     60
```

```
gatggtgaag ttgagggtga atggtaccag gagagggcca gcagccataa ttgtsgrgck    120
gsmgmssgag gmwggwgtyy cwgaggttcy rarrtccact gtggaggtcc caggagtgct    180
ggtggtgggc acagagstcy gatgggtgaa accattgaca tagagactgt tcctgtccag    240
ggtgtagggg cccagctctt yratgycatt ggycagttkg ctyagctccc agtacagccr    300
ctctckgyyg mgwccagsgc ttttggggtc aagatgatgg atgcagatgg catccactcc    360
agtggctgct ccatccttct cggacctgag agaggtcagt ctgcagccag agtacagagg    420
gccaacactg gtgttctttg aata                                           444
```

<210> SEQ ID NO 81
<211> LENGTH: 310
<212> TYPE: DNA
<213> ORGANISM: Homo sapien

<400> SEQUENCE: 81

```
tcgagcggcc gcccgggcag gtcaggaagc acattggtct tagagccact gcctcctgga     60
ttccacctgt gctgcggaca tctccaggga gtgcagaagg gaagcaggtc aaactgctca    120
gatcagtcag actggctgtt ctcagttctc acctgagcaa ggtcagtctg cagccagagt    180
acagagggcc aacactggtg ttcttgaaca agggcttgag cagaccctgc agaaccctct    240
tccgtggtgt tgaacttcct ggaaaccagg gtgttgcatg ttttcctca taatgcaagg     300 ttggtgatgg                                                           310
```

<210> SEQ ID NO 82
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 82

```
acggtttcaa tggacacttt tattgtttac ttaatggatc atcaattttg tctcactacc     60
tacaaatgga atttcatctt gtttccatgc tgagtagtga acagtgaca aagctaatca    120 taataaccta catcaaaaga gaactaagct aacactgctc actttctttt taacaggcaa    180
aatataaata tatgcactct anaatgcaca atggtttagt cactaaaaaa ttcaaatggg    240
atcttgaaga atgtatgcaa atccagggtg cagtgaagat gagctgagat gctgtgcaac    300
tgtttaaggg ttcctggcac tgcatctctt ggccactagc tgaatcttga catggaaggt    360
tttagctaat gccaagtgga gatgcagaaa atgctaagtt gacttagggg ctgtgcacag    420
gaactaaaag gcaggaaagt actaaatatt gctgagagca tccaccccag gaaggacttt    480
accttccagg agctccaaac tggcaccacc cccagtgctc acatggctga ctttatcctc    540
cgtgttccat ttggcacagc aagtggcagt g                                   571
```

<210> SEQ ID NO 83
<211> LENGTH: 551
<212> TYPE: DNA
<213> ORGANISM: Homo sapien

<400> SEQUENCE: 83

```
aaggctggtg ggtttttgat cctgctggag aacctccgct ttcatgtgga ggaagaaggg     60
aagggaaaag atgcttctgg gaacaaggtt aaagccgagc cagccaaaat agaagctttc    120
cgagcttcac tttccaagct aggggatgtc tatgtcaatg atgctttggg cactgctcac    180
```

```
agagcccaca gctccatggt aggagtcaat ctgccacaga aggctggtgg gttttttgatg      240 aagaaggagc tgaactactt tgcaaaggcc ttggagagcc cagagcgacc cttcctggcc      300
atcctgggcg gagctaaagt tgcagacaag atccagctca tcaataatat gctggacaaa      360
gtcaatgaga tgattattgg tggtggaatg gcttttacct tccttaaggt gctcaacaac      420
atggagattg gcacttctct gtttgatgaa gagggagcca agattgtcaa agacctaatg      480
tccaaagctg agaagaatgg tgtgaagatt accttgcctg ttgactttgt cactgctgac      540
aagtttgatg a                                                          551

<210> SEQ ID NO 84
<211> LENGTH: 571
<212> TYPE: DNA
<213> ORGANISM: Homo sapien

<400> SEQUENCE: 84
tttgttcctt acatttttct aaagagttac ttaaatcagt caactggtct ttgagactct      60
taagttctga ttccaactta gctaattcat tctgagaact gtggtatagg tggcgtgtct     120
cttctagctg gacaaaagt tctttgtttt ccccctgtag agtatcacag accttctgct      180
gaagctggac ctctgtctgg gccttggact cccaaatctg cttgtcatgt tcaagcctgg      240
aaatgttaat ctttaattct tccatatgga tggacatctg tctaagttga tcctttagaa      300
cactgcaatt atcttctttg agtctaattt cttcttcttt gctttgaatc gcatcactaa      360
acttcctctc ccatttctta gcttcatcta tcaccctgtc acgatcatcc tggagggaag      420
acatgctctt agtaaaggct gcaagctggg tcacagtact gtccaagttt tcctgaagtt      480
gctgaacttc cttgtctttc ttgttcaaag taacctgaat ctctccaatt gtctcttcca      540
agtggacttt tctctgcgc aaagcatcca g                                     571

<210> SEQ ID NO 85
<211> LENGTH: 561
<212> TYPE: DNA
<213> ORGANISM: Homo sapien

<400> SEQUENCE: 85
tcattgcctg tgatggcatc tggaatgtga tgagcagcca ggaagttgta gatttcattc      60
aatcaaagga ttcagcatgt ggtggaagct gtgaggcaag agaaacaaga actgtatggc     120
aagttaagaa gcacagaggc aaacaagaag gagacagaaa agcagttgca ggaagctgag     180
caagaaatgg aggaaatgaa agaaagatg agaaagtttg ctaaatctaa acagcagaaa     240
atcctagagc tggaagaaga gaatgaccgg cttagggcag aggtgcaccc tgcaggagat     300
acagctaaag agtgtatgga aacacttctt tcttccaatg ccagcatgaa ggaagaactt     360
gaaagggtca aaatggagta tgaaaccctt tctaagaagt ttcagtcttt aatgtctgag     420
aaagactctc taagtgaaga ggttcaagat ttaaagcatc agatagaagg taatgtatct     480
aaacaagcta acctagaggc caccgagaaa catgataacc aaacgaatgt cactgaagag     540
ggaacacagt ctataccagg t                                               561

<210> SEQ ID NO 86
<211> LENGTH: 795
<212> TYPE: DNA
<213> ORGANISM: Homo sapien

<400> SEQUENCE: 86
```

-continued

```
aagccaataa tcaccattta ttacttaata tatgccaacc actgtacttg gcagttcaca      60
aattctcacc gttacaacaa ccccatgagg tatttattcc cattctatag atagggaaac     120
cacagctcaa gtaagttagg aaactgagcc aagtatacac agaatacgaa gtggcaaaac     180
tagaaggaaa gactgacact gctatctgct ggcctccagt gtcctggctc ttttcacacg     240
ggttcaatgt ctccagcgct gctgctgctg ctgcattacc atgccctcat tgttttttctt    300 cctctggtgt tcaactgcat ccttcaaaga atctaactca ttccagagac cacttatttc     360
tttctctctt tctgaaatta cttttaataa ttccttcatga gggggaaaag aagatgcctg    420
ttggtagttt tgttgtttaa gctgctcaat ttgggactta aacaatttgt tttcatcttg     480
tacatcctgt aacagctgtg ttttgctaga agatcactc tccctctctt ttagcatggc      540
ttctaacctc ttcaattcat tttccttttc tttcaacaca atctcaagtt cttcaaactg     600
tgatgcagaa gaggcctctt tcaagttatg ttgtgctact tcctgaacat gtgcttttaa     660
agattcattt tcttcttgaa gatcctgtaa ccacttccct gtattggcta ggtctttctc     720
tttctcttcc aaaacagcct tcatggtatt catctgttcc tcttttcctt ttaataagtt     780
caggagcttc agaac                                                      795

<210> SEQ ID NO 87
<211> LENGTH: 594
<212> TYPE: DNA
<213> ORGANISM: Homo sapien

<400> SEQUENCE: 87 caagctttt ttttttttt aaaaagtgtt agcattaatg ttttattgtc acgcagatgg        60
caactgggtt tatgtcttca tattttatat ttttgtaaat taaaaaaatt acaagtttta    120
aatagccaat ggctggttat attttcagaa aacatgatta gactaattca ttaatggtgg    180
cttcaagctt ttccttattg gctccagaaa attcacccac cttttgtccc ttcttaaaaa    240
actggaatgt tggcatgcat ttgacttcac actctgaagc aacatcctga cagtcatcca    300
catctacttc aaggaatatc acgttggaat acttttcaga gagggaatga agaaaggct     360 tgatcatttt gcaaggccca caccacgtgg ctgagaagtc aactactaca agtttatcac    420
ctgcagcgtc caaggcttcc tgaaaagcag tcttgctctc gatctgcttc accatcttgg    480
ctgctggagt ctgacgagcg gctgtaagga ccgatggaaa tggatccaaa gcaccaaaca    540
gagcttcaag actcgctgct tggcttgaat tcggatccga tatcgccatg gcct           594

<210> SEQ ID NO 88
<211> LENGTH: 557
<212> TYPE: DNA
<213> ORGANISM: Homo sapien

<400> SEQUENCE: 88
aagtgttagc attaatgttt tattgtcacg cagatggcaa ctgggtttat gtcttcatat     60
tttatatttt tgtaaattaa aaaaattmca agttttaaat agccaatggc tggttatatt    120
ttcagaaaac atgattagac taattcatta atggtggctt caagcttttc cttattggct    180
ccagaaaatt cacccacctt ttgtcccttc ttaaaaaact ggaatgttgg catgcatttg    240
acttcacact ctgaagcaac atcctgacag tcatccacat ctacttcaag gaatatcacg    300
ttggaatact tttcagagag ggaatgaag aaaggcttga tcattttgca aggcccacac    360
cacgtggctg agaagtcaac tactacaagt ttatcacctg cagcgtccaa ggcttcctga    420
aaagcagtct tgctctcgat ctgcttcacc atcttggctg ctggagtctg acgagcggct    480
```

```
gtaaggaccg atggaaatgg atccaaagca ccaaacagag cttcaagact cgctgcttgg    540
catgaattcg gatccga                                                   557
```

```
<210> SEQ ID NO 89
<211> LENGTH: 561
<212> TYPE: DNA
<213> ORGANISM: Homo sapien
<220> FEATURE:
<221> NAME/KEY: misc_feature
<222> LOCATION: (1)...(561)
<223> OTHER INFORMATION: n = A,T,C or G

<400> SEQUENCE: 89
tacaaacttt attgaaacgc acacgcgcac acacacaaac acccctgtgg atagggaaaa     60
gcacctggcc acagggtcca ctgaaacggg gaggggatgg cagcttgtaa tgtggctttt    120
gccacaaccc ccttctgaca gggaaggcct tagattgagg ccccacctcc catggtgatg    180
gggagctcag aatggggtcc aggagaatt tggttagggg gaggtgctag ggaggcatga     240
gcagagggca ccctccgagt ggggtcccga ggctgcaga gtcttcagta ctgtccctca     300
cagcagctgt ctcaaggctg gtccctcaa aggggcgtcc cagcgcgggg cctccctgcg    360
caaacacttg gtaccctgg ctgcgcagcg gaagccagca ggacagcagt ggcgccgatc    420
agcacaacag acgccctggc ggtagggaca gcaggcccag ccctgtcggt tgtctcggca   480
gcaggtctgg ttatcatggc agaagtgtcc ttcccacact tcacgtcctt cacacccacg    540
tganggctac nggccaggaa g                                              561
```

```
<210> SEQ ID NO 90
<211> LENGTH: 561
<212> TYPE: DNA
<213> ORGANISM: Homo sapien

<400> SEQUENCE: 90
cccgtgggtg ccatccacgg agttgttacc tgatctttgg aagcaggatc gcccgtctgc    60
actgcagtgg aagccccgtg ggcagcagtg atggccatcc ccgcatgcca cggcctctgg   120
gaaggggcag caactggaag tccctgagac ggtaaagatg caggagtggc cggcagagca   180
gtgggcatca acctggcagg ggccacccag atgcctgctc agtgttgtgg gccatttgtc    240
cagaagggga cggcagcagc tgtagctggc cctccggggg tccaggcagc aggccacagg    300
gcagaactga ccatctgggc accgcgttcc agccaccagc cctgctgtta aggccaccca    360
gctcaccagg gtccacatgg tctgcctgcg tccgactccg cggtccttgg gccctgatgg   420
ttctacctgc tgtgagctgc ccagtgggaa gtatggctgc tgccaatgcc caacgccacc    480
tgctgctccg atcacctgca ctgctgcccc aagacactgt gtgtgacctg atccagagta    540
agtgcctctc caaggagaac g                                              561
```

```
<210> SEQ ID NO 91
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 91
gaatcacctt tctggtttag ctagtacttt gtacagaaca atgaggtttc ccacagcgga    60
```

-continued

```
gtctccctgg gctctgtttg gctctcggta aggcaggcct acaccttttc ctctcctcta      120
tggagagggg aatatgcatt aaggtgaaaa gtcaccttcc aaaagtgaga aagggattcg      180
attgctgctt caggactgtg gaattatttg gaatgtttta caaatggttg ctacaaaaca      240
acaaaaaagg taattacaaa atgtgtacat cacaacatgc ttttaaaga cattatgcat       300 tgtgctcaca ttcccttaaa tgttgtttcc aaaggtgctc agcctctagc ccagctggat      360
tctccgggaa gaggcagaga cagtttggcg aaaaagacac agggaaggag ggggtggtga      420
aaggagaaag cagccttcca gttaaagatc agccctcagt taaaggtcag cttcccgcan      480
gctggcctca ngcggagtct gggtcagagg gaggagcagc agcagggtgg gactggggcg      540
t                                                                    541
```

<210> SEQ ID NO 92
<211> LENGTH: 551
<212> TYPE: DNA
<213> ORGANISM: Homo sapien

<400> SEQUENCE: 92

```
aaccggagcg cgagcagtag ctgggtgggc accatggctg ggatcaccac catcgaggcg       60
gtgaagcgca agatccaggt tctgcagcag caggcagatg atgcagagga gcgagctgag      120
cgcctccagc gagaagttga gggagaaagg cgggcccggg aacaggctga ggctgaggtg      180
gcctccttga accgtaggat ccagctggtt gaagaagagc tggaccgtgc tcaggagcgc      240
ctggccactg ccctgcaaaa gctggaagaa gctgaaaaag ctgctgatga gagtgagaga      300
ggtatgaagg ttattgaaaa ccgggcctta aagatgaag aaaagatgga actccaggaa       360
atccaactca aagaagctaa gcacattgca gaagaggcag ataggaagta tgaagaggtg      420
gctcgtaagt tggtgatcat tgaaggagac ttggaacgca cagaggaacg agctgagctg      480
gcagagtccc gttgccgaga gatggatgag cagattagac tgatggacca gaacctgaag      540
tgtctgagtg c                                                         551
```

<210> SEQ ID NO 93
<211> LENGTH: 531
<212> TYPE: DNA
<213> ORGANISM: Homo sapien

<400> SEQUENCE: 93

```
gagaacttgg cctttattgt gggcccagga gggcacaaag gtcaggaggc ccaagggagg       60
gatctggttt tctggatagc caggtcatag catgggtatc agtaggaatc cgctgtagct      120
gcacaggcct cacttgctgc agttccgggg agaacacctg cactgcatgg cgttgatgac      180
ctcgtggtac acgacagagc cattggtgca gtgcaagggc acgcgcatgg gctccgtcct      240
cgagggcagg cagcaggagc attgctcctg cacatcctcg atgtcaatgg agtacacagc      300
tttgctggca cactttccct ggcagtaatg aatgtccact tcctcttggg acttacaatc      360
tcccactttg atgtactgca ccttggctgt gatgtctttg caatcaggct cctcacatgt      420
gtcacagcag gtgcctggaa ttttcacgat tttgcctcct cagccagac acttgtgttc      480 atcaaatggt gggcagcccg tgaccctctt ctcccagatg tactctcctc t              531
```

<210> SEQ ID NO 94
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 94

```
gcctggacct tgccggatca gtgccacaca gtgacttgct tggcaaatgg ccagaccttg    60
ctgcagagtc atcgtgtcaa ttgtgaccat ggaccccggc cttcatgtgc caacagccag   120
tctcctgttc gggtggagga gacgtgtggc tgccgctgga cctgcccttg tgtgtgcacg   180
ggcagttcca ctcggcacat cgtcaccttc gatgggcaga atttcaagct tactggtagc   240
tgctcctatg tcatctttca aaacaaggag caggacctgg aagtgctcct ccacaatggg   300
gcctgcagcc ccggggcaaa acaagcctgc atgaagtcca ttgagattaa gcatgctggc   360
gtctctgctg agctgcacag taacatggag atggcagtgg atgggagact ggtccttgcc   420
ccgtacgttg gtgaaaacat ggaagtcagc atctacggcg ctatcatgta tgaagtcagg   480
tttacccatc ttggccacat cctcacatac accgccncaa acaacgagt t             531
```

<210> SEQ ID NO 95
<211> LENGTH: 605
<212> TYPE: DNA
<213> ORGANISM: Homo sapien

<400> SEQUENCE: 95

```
agatcaacct ctgctggtca ggaggaatgc cttccttgtc ttggatcttt gctttgacgt    60
tctcgatagt rwcaactkkr ytsramskma agkgyratgr wmttksywgw rasyktmwwm   120
rsgraraytt agacaycccm cctcwgagac gsagkaccar gtgcagaggt ggactctttc   180
tggatgttgt agtcagacag ggtgcgtcca tcttccagct gtttcccagc aaagatcaac   240
ctctgctgat caggagggat gccttcctta tcttggatct ttgccttgac attctcgatg   300
gtgtcactgg gctccacctc gagggtgatg gtcttaccag tcagggtctt cacgaagaty   360
tgcatcccac ctctgagacg gagcaccagg tgcagggtrg actctttctg gatgttgtag   420
tcagacaggt gcgyccatc ttccagctgc tttccsagca aagatcaacc tctgctggtc   480
aggaggratg ccttccttgt cytggatctt tgcyttgacr ttctcratgg tgtcactcgg   540
ctccacttcg agagtgatgg tcttaccagt cagggtcttc acgaagatct gcatcccacc   600
tctaa                                                                605
```

<210> SEQ ID NO 96
<211> LENGTH: 531
<212> TYPE: DNA
<213> ORGANISM: Homo sapien

<400> SEQUENCE: 96

```
aagtcacaaa cagacaaaga ttattaccag ctgcaagcta tattagaagc tgaacgaaga    60
gacagaggtc atgattctga gatgattgga gaccttcaag ctcgaattac atctttacaa   120
gaggaggtga agcatctcaa acataatctc gaaaagtgg aaggagaaag aaaagaggct   180
caagacatgc ttaatcactc agaaaaggaa agaataatt tagagataga tttaaactac   240
aaacttaaat cattacaaca acggttagaa caagaggtaa atgaacacaa agtaaccaaa   300
gctcgtttaa ctgacaaaca tcaatctatt gaagaggcaa agtctgtggc aatgtgtgag   360
atggaaaaaa agctgaaaga agaaagagaa gctcgagaga aggctgaaaa tcgggttgtt   420
cagattgaga aacagtgttc catgctagac gttgatctga agcaatctca gcagaaacta   480
gaacatttga ctggaaataa agaaaggatg gaggatgaag ttaagaatct a             531
```

<210> SEQ ID NO 97
<211> LENGTH: 1017
<212> TYPE: DNA
<213> ORGANISM: Homo sapien
<220> FEATURE:
<221> NAME/KEY: misc_feature
<222> LOCATION: (1)...(1017)
<223> OTHER INFORMATION: n = A,T,C or G

<400> SEQUENCE: 97

```
cgcctccacc atgtccatca gggtgaccca gaagtcctac aaggtgtcca cctctggccc      60
ccgggccttc agcagccgct cctacacgag tgggcccggt tcccgcatca gctcctcgag     120
cttctcccga gtgggcagca gcaactttcg cggtggcctg gcggcggct atggtggggc      180
cagcggcatg ggaggcatca ccgcagttac ggtcaaccag agcctgctga ccccccttgt     240
cctggaggtg gaccccaaca tccaggccgt gcgcacccag gagaaggagc agatcaagac     300
cctcaacaac aagtttgcct ccttcataga caaggtacgg ttcctggagc agcagaacaa     360
gatgctggag accaagtgga gcctcctgca gcagcagaag acggctcgaa gcaacatgga     420
caacatgttc gagagctaca tcaacarcct taggcggcag ctggagactc tgggccagga     480
gaagctgaag ctggaggcgg agcttggcaa catgcagggg ctggtggagg acttcaagaa     540
caagtatgag gatgagatca ataagcgtac agagatggag aacgaatttg tcctcatcaa     600
gaaggatgtg gatgaagctt acatgaacaa ggtagagctg gagtctcgcc tggaagggct     660
gaccgacgag atcaacttcc tcaggcagct gtatgaagag gagatccggg agctgcagtc     720
ccagatctcg gacacatctg tggtgctgtc catggacaac agccgctccc tggacatgga     780
cagcatcatt gctgaggtca aggcacagta cgaggatatt gccaaccgca gccgggctga     840
ggctgagagc atgtaccagg tcaagtatga ggagctgcag agcctggctg ggaagcacgg     900
ggatgacctg cggcgcacaa agactgagat ctctgagatg aacccggaac atcagcccgg     960
ctncaggctg agattgaggg cctcaaaggc caganggctt ncctggangn ccgccat       1017
```

<210> SEQ ID NO 98
<211> LENGTH: 561
<212> TYPE: DNA
<213> ORGANISM: Homo sapien

<400> SEQUENCE: 98

```
cccggagcca gccaacgagc ggaaaatggc agacaatttt tcgctccatg atgcgttatc      60
tgggtctgga aacccaaacc ctcaaggatg gcctggcgca tgggggaacc agcctgctgg     120
ggcaggggc tacccagggg cttcctatcc tggggcctac cccgggcagg cacccccagg      180
ggcttatcct ggacaggcac ctccaggcgc ctaccctgga gcacctggag cttatcccgg     240
agcacctgca cctggagtct acccaggcc acccagcggc cctggggcct acccatcttc      300
tggacagcca agtgccaccg gagcctaccc tgccactggc ccctatggcg ccctgctgg      360
gccactgatt gtgccttata acctgccttt gcctggggga gtggtgcctc gcatgctgat     420
aacaattctg ggcacggtga agcccaatgc aaacagaatt gctttagatt tccaaagagg     480
gaatgatgtt gccttccact ttaacccacg cttcaatgag aacaacagga gagtcattgg     540
ttgcaataca aagctggata a                                               561
```

<210> SEQ ID NO 99
<211> LENGTH: 636
<212> TYPE: DNA
<213> ORGANISM: Homo sapien

<400> SEQUENCE: 99

```
gggaatgcaa caactttatt gaaaggaaag tgcaatgaaa tttgttgaaa ccttaaaagg      60
ggaaacttag acaccccccc tcragcgmag kaccargtgc araggtggac tctttctgga     120
tgttgtagtc agacagggtr cgwccatctt ccagctgttt yccrgcaaag atcaacctct     180
gctgatcagg aggratgcct tccttatctt ggatctttgc cttgacattc tcgatggtgt     240
cactgggctc cacctcgagg gtgatggtct taccagtcag ggtcttcacg aagatytgca     300
tcccacctct gagacggagc accaggtgca ggtrgactc tttctggatg ttgtagtcag      360
acagggtgcg yccatcttcc agctgctttc csagcaaaga tcaacctctg ctggtcagga    420
ggratgcctt ccttgtcytg gatctttgcy ttgacrttct caatggtgtc actcggctcc    480
acttcgagag tgatggtctt accagtcagg gtcttcacga agatctgcat cccacctcta    540
agacggagca ccaggtgcag gtggactct ttctggatgg ttgtagtcag acagggtgcg     600
tccatcttcc agctgtttcc cagcaaagat caacct                              636
```

<210> SEQ ID NO 100
<211> LENGTH: 697
<212> TYPE: DNA
<213> ORGANISM: Homo sapien

<400> SEQUENCE: 100

```
aggttgatct tgctgggaa acagctggaa gatggacgca ccctgtctga ctacaaccat      60
ccagaaagag tccaccctgc acctggtgct ccgtcttaga ggtgggatgc agatcttcgt    120
gaagaccctg actggtaaga ccatcactct cgaagtggag ccgagtgaca ccattgagaa    180
ygtcaargca aagatccarg acaaggaagg catycctcct gaccagcaga ggttgatctt   240
tgctsggaaa gcagctggaa gatggrcgca ccctgtctga ctacaacatc cagaaagagt    300
cyaccctgca cctggtgctc cgtctcagag gtgggatgca ratcttcgtg aagaccctga    360
ctggtaagac catcaccctc gaggtggagc ccagtgacac catcgagaat gtcaaggcaa    420
agatccaaga taaggaaggc atccctcctg atcagcagag gttgatcttt gctgggaaac   480
agctggaaga tggacgcacc ctgtctgact acaacatcca gaaagagtcc acctytgcac    540
ytggtmctbc gtctyagagg kgggrtgcaa atctwmgtkw agacactcac tkkyaagryy    600
atcamcmwtg akktcgakys castkwcact wtcrakaamg tyrwwgcawa gatccmagac    660
aaggaaggca ttcctcctga ccagcagagg ttgatct                              697
```

<210> SEQ ID NO 101
<211> LENGTH: 451
<212> TYPE: DNA
<213> ORGANISM: Homo sapien

<400> SEQUENCE: 101

```
atggagtctc actctgtcga ccaggctgga gcgctgtggt gcgatatcgg ctcactgcag      60
tctccacttc ctgggttcaa gcgatcctcc tgcctcagcc tcccgagtag ctgggactac    120
aggcaggcgt caccataatt tttgtatttt tagtagagac atggtttcgc catgttggct    180
gggctggtct cgaactcctg acctcaagtg atctgtcctg cctcccaaa gtgttgggat     240
tacaggcgaa agccaacgct cccggccagg gaacaacttt agaatgaagg aaatatgcaa    300
aagaacatca catcaaggat caattaatta ccatctatta attactatat gtgggtaatt    360
atgactattt cccaagcatt ctacgttgac tgcttgagaa gatgtttgtc ctgcatggtg    420
```

```
gagagtggag aagggccagg attcttaggt t                                  451
```

<210> SEQ ID NO 102
<211> LENGTH: 571
<212> TYPE: DNA
<213> ORGANISM: Homo sapien

<400> SEQUENCE: 102

```
agcgcggtct tccggcgcga gaaagctgaa ggtgatgtgg ccgccctcaa ccgacgcatc     60
cagctcgttg aggaggagtt ggacagggct caggaacgac tggccacggc cctgcagaag    120
ctggaggagg cagaaaaagc tgcagatgag agtgagagag gaatgaaggt gatagaaaac    180
cgggccatga aggatgagga gaagatggag attcaggaga tgcagctcaa agaggccaag    240
cacattgcgg aagaggctga ccgcaaatac gaggaggtag ctcgtaagct ggtcatcctg    300
gagggtgagc tggagagggc agaggagcgt gcggaggtgt ctgaactaaa atgtggtgac    360
ctggaagaag aactcaagaa tgttactaac aatctgaaat ctctggaggc tgcatctgaa    420
aagtattctg aaaaggagga caaatatgaa gaagaaatta aacttctgtc tgacaaactg    480
aaagaggctg agacccgtgc tgaatttgca gagagaacgg ttgcaaaact ggaaaagaca    540
attgatgacc tggaagagaa acttgcccag c                                  571
```

<210> SEQ ID NO 103
<211> LENGTH: 451
<212> TYPE: DNA
<213> ORGANISM: Homo sapien

<400> SEQUENCE: 103

```
gtgcacaggt cccatttatt gtagaaaata ataataatta cagtgatgaa tagctcttct     60
taaattacaa aacagaaacc acaaagaagg aagaggaaaa accccaggac ttccaagggt    120
gaagctgtcc cctcctccct gccaccctcc caggctcatt agtgtccttg aaggggcag     180
aggactcaga ggggatcagt ctccaggggc cctgggctga agcgggtgag cagagagtc     240
ctgaggccac agagctgggc aacctgagcc gcctctctgg cccctcccc caccactgcc     300
caaacctgtt tacagcacct tcgcccctcc cctctaaacc cgtccatcca ctctgcactt    360
cccaggcagg tgggtgggcc aggcctcagc catactcctg ggcgcgggtt tcggtgagca    420
aggcacagtc ccagaggtga tatcaaggcc t                                  451
```

<210> SEQ ID NO 104
<211> LENGTH: 441
<212> TYPE: DNA
<213> ORGANISM: Homo sapien

<400> SEQUENCE: 104

```
gcaaggaact ggtctgctca cacttgctgg cttgcgcatc aggactggct ttatctcctg     60
actcacggtg caaaggtgca ctctgcgaac gttaagtccg tccccagcgc ttggaatcct    120
acggccccca cagccggatc ccctcagcct tccaggtcct caactcccgt ggacgctgaa    180
caatggcctc catgggcta caggtaatgg gcatcgcgct ggccgtcctg ggctggctgg     240
ccgtcatgct gtgctgcgcg ctgcccatgt ggcgcgtgac ggccttcatc ggcagcaaca    300
ttgtcacctc gcagaccatc tgggagggcc tatggatgaa ctgcgtggtg cagagcaccg    360
gccagatgca gtgcaaggtg tacgactcgc tgctggcact gccgcaggac ctgcaggcgg    420
cccgcgccct cgtcatcatc a                                             441
```

-continued

```
<210> SEQ ID NO 105
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 105
tgcaaaaggg acacagggt tcaaaaataa aaatttctct tccccctccc caaacctgta      60
ccccagctcc ccgaccacaa ccccctttcct ccccgggga aagcaagaag gagcaggtgt    120
ggcatctgca gctgggaaga gagaggccgg ggaggtgccg agctcggtgc tggtctcttt    180
ccaaatataa atacntgtgt cagaactgga aaatcctcca gcacccacca cccaagcact    240
ctccgttttc tgccggtgtt tggagagggg cggggggcag gggcgccagg caccggctgg    300
ctgcggtcta ctgcatccgc tgggtgtgca ccccgcgagc ctcctgctgc tcattgtaga    360
agagatgaca ctcggggtcc ccccggatgg tggggctcc ctggatcagc ttccggtgt     420 tggggttcac acaccagcac tccccacgct gcccgttcag agacatcttg cactgtttga    480
ggttgtacag gccatgcttg tcacagttg                                     509

<210> SEQ ID NO 106
<211> LENGTH: 571
<212> TYPE: DNA
<213> ORGANISM: Homo sapien

<400> SEQUENCE: 106
gggttggagg gactggttct ttatttcaaa aagacacttg tcaatattca gtatcaaaac    60
agttgcacta ttgatttctc tttctcccaa tcggccccaa agagaccaca taaaaggaga    120
gtacatttta agccaataag ctgcaggatg tacacctaac agacctccta gaaaccttac    180
cagaaaatgg ggactgggta gggaaggaaa cttaaaagat caacaaactg ccagcccacg    240
gactgcagag gctgtcacag ccagatgggg tggccaggt gccacaaacc caaagcaaag    300
tttcaaaata atataaaatt taaaaagttt tgtacataag ctattcaaga tttctccagc    360
actgactgat acaaagcaca attgagatgg cacttctaga gacagcagct tcaaacccag    420
aaaagggtga tgagatgagt ttcacatggc taaatcagtg gcaaaaacac agtcttcttt    480
ctttctttct ttcaaggagg caggaaagca attaagtggt cacctcaaca taaggggggac    540 atgatccatt ctgtaagcag ttgtgaaggg g                                   571

<210> SEQ ID NO 107
<211> LENGTH: 555
<212> TYPE: DNA
<213> ORGANISM: Homo sapien

<400> SEQUENCE: 107
caggaaccgg agcgcgagca gtagctgggt gggcaccatg gctgggatca ccaccatcga    60
ggcggtgaag cgcaagatcc aggttctgca gcagcaggca gatgatgcag aggagcgagc    120
tgagcgcctc cagcgagaag ttgagggaga aggcgggcc cgggaacagg ctgaggctga    180
ggtggcctcc ttgaaccgta ggatccagct ggttgaagaa gagctggacc gtgctcagga    240
gcgcctggcc actgccctgc aaaagctgga agaagctgaa aaagctgctg atgagagtga    300
gagaggtatg aaggttattg aaaaccgggc cttaaaagat gaagaaaaga tggaactcca    360
ggaaatccaa ctcaaagaag ctaagcacat tgcagaagag gcagatagga agtatgaaga    420
```

-continued ggtggctcgt aagttggtga tcattgaagg agacttggaa cgcacagagg aacgagctga        480
gctggcagag tcccgttgcc gagagatgga tgagcagatt agactgatgg accagaacct        540
gaagtgtctg agtgc                                                          555

<210> SEQ ID NO 108
<211> LENGTH: 541
<212> TYPE: DNA
<213> ORGANISM: Homo sapien

<400> SEQUENCE: 108
atctacgtca tcaatcaggc tggagacacc atgttcaatc gagctaagct gctcaatatt         60
ggctttcaag aggccttgaa ggactatgat tacaactgct ttgtgttcag tgatgtggac        120
ctcattccga tggacgaccg taatgcctac aggtgttttt cgcagccacg gcacatttct        180
gttgcaatgg acaagttcgg gtttagcctg ccatatgttc agtattttgg aggtgtctct        240
gctctcagta acaacagtt tcttgccatc aatggattcc ctaataatta ttggggttgg        300
ggaggagaag atgacgacat ttttaacaga ttagttcata aaggcatgtc tatatcacgt        360
ccaaatgctg tagtagggag gtgtcgaatg atccggcatt caagagacaa gaaaaatgag        420
cccaatcctc agaggtttga ccggatcgca catacaaagg aaacgatgcg cttcgatggt        480
ttgaactcac ttacctacaa ggtgttggat gtcagagata cccgttatat acccaaatca        540
c                                                                         541

<210> SEQ ID NO 109
<211> LENGTH: 411
<212> TYPE: DNA
<213> ORGANISM: Homo sapien

<400> SEQUENCE: 109
ctagacctct aattaaaagg cacaatcatg ctggagaatg aacagtctga ccccgagggc         60
cacagcgaat tttagggaag gaggcaaaga ggtgagaagg gaaaggaaag aaggaaggaa        120
ggagaacaat aagaactgga gacgttgggt gggtcaggga gtgtggtgga ggctcggaga        180
gatggtaaac aaacctgact gctatgagtt ttcaaccca tagtctaggg ccatgagggc         240
gtcagttctt ggtggctgag ggtccttcca cccagcccac ctgggggagt ggagtgggga        300
gttctgccag gtaagcagat gttgtctccc aagttcctga cccagatgtc tggcaggata        360
acgctgacct gttccctcaa caagggacct gaaagtaatt ttgctcttta c                 411

<210> SEQ ID NO 110
<211> LENGTH: 451
<212> TYPE: DNA
<213> ORGANISM: Homo sapien

<400> SEQUENCE: 110
ccgaattcaa gcgtcaacga tccytcccott accatcaaat caattggcca ccaatggtac         60
tgaacctacg agtacaccga ctacgggcgg actaatcttc aactcctaca tacttccccc        120
attattccta gaaccaggcg acctgcgact ccttgacgtt gacaatcgag tagtactccc        180
gattgaagcc cccattcgta taataattac atcacaagac gtcttgcact catgagctgt        240
ccccacatta ggcttaaaaa cagatgcaat tcccggacgt ctaagccaaa ccactttcac        300
cgctacacga ccgggggtat actacggtca atgctctgaa atctgtggag caaaccacag        360
tttcatgccc atcgtcctag aattaattcc cctaaaaatc tttgaaatag ggcccgtatt        420
taccctatag caccccctct accccctcta g                                        451

<210> SEQ ID NO 111
<211> LENGTH: 541
<212> TYPE: DNA
<213> ORGANISM: Homo sapien

<400> SEQUENCE: 111

```
gctcttcaca cttttattgt taattctctt cacatggcag atacagagct gtcgtcttga      60
agaccaccac tgaccaggaa atgccacttt tacaaaatca tcccccttt tcatgattgg     120
aacagttttc ctgaccgtct gggagcgttg aagggtgacc agcacatttg cacatgcaaa    180
aaaggagtga ccccaaggcc tcaaccacac ttcccagagc tcaccatggg ctgcaggtga    240
cttgccaggt ttggggttcg tgagctttcc ttgctgctgc ggtggggagg ccctcaagaa    300
ctgagaggcc ggggtatgct tcatgagtgt taacatttac gggacaaaag cgcatcatta    360
ggataaggaa cagccacagc acttcatgct tgtgagggtt agctgtagga gcgggtgaaa    420
ggattccagt ttatgaaaat ttaaagcaaa aacggttttt tagctgggtg ggaaacagga    480
aaactgtgat gtcggccaat gaccaccatt tttctgccca tgtgaaggtc cccatgaaac    540
c                                                                     541
```

<210> SEQ ID NO 112
<211> LENGTH: 521
<212> TYPE: DNA
<213> ORGANISM: Homo sapien

<400> SEQUENCE: 112

```
caagcgcttg gcgtttggac ccagttcagt gaggttcttg ggttttgtgc ctttggggat     60
tttggtttga cccaggggtc agccttagga aggtcttcag gaggaggccg agttcccctt    120
cagtaccacc cctctctccc cactttccct ctcccggcaa catctctggg aatcaacagc    180
atattgacac gttggagccg agcctgaaca tgcccctcgg ccccagcaca tggaaaaccc    240
ccttccttgc ctaaggtgtc tgagtttctg gctcttgagg catttccaga cttgaaattc    300
tcatcagtcc attgctcttg agtctttgca gagaacctca gatcaggtgc acctgggaga    360
aagactttgt ccccacttac agatctatct cctcccttgg gaaggcagg gaatggggac    420
ggtgtatgga ggggaaggga tctcctgcgc ccttcattgc cacacttggt gggaccatga    480
acatctttag tgtctgagct tctcaaatta ctgcaatagg a                        521
```

<210> SEQ ID NO 113
<211> LENGTH: 568
<212> TYPE: DNA
<213> ORGANISM: Homo sapien

<400> SEQUENCE: 113

```
agcgtcaaat cagaatggaa aagactcaaa accatcatca acaccaagat caaaaggaca     60
agratccttc aagaaacagg aaaaaactcc taaacacca aaaggaccta gttctgtaga    120
agacattaaa gcaaaatgc aagcaagtat agaaaaaggt ggttctcttc ccaaagtgga    180
agccaaattc atcaattatg tgaagaattg cttccggatg actgaccaag aggctattca    240
agatctctgg cagtggagga agtctcttta agaaaatagt ttaaacaatt tgttaaaaaa    300
ttttccgtct tatttcattt ctgtaacagt tgatatctgg ctgtccttt tataatgcag    360
agtgagaact ttccctaccg tgtttgataa atgttgtcca ggttctattg ccaagaatgt    420
gttgtccaaa atgcctgttt agtttttaaa gatggaactc caccctttgc ttggttttaa    480
```

-continued

| | |
|---|---|
| gtatgtatgg aatgttatga taggacatag tagtagcggt ggtcagacat ggaaatggtg | 540 |
| ggsmgacaaa aatatacatg tgaaataa | 568 |

<210> SEQ ID NO 114
<211> LENGTH: 483
<212> TYPE: DNA
<213> ORGANISM: Homo sapien

<400> SEQUENCE: 114

| | |
|---|---|
| tccgaattcc aagcgaatta tggacaaacg attcctttta gaggattact ttttcaatt | 60 |
| tcggttttag taatctaggc tttgcctgta aagaatacaa cgatggattt taaatactgt | 120 |
| ttgtggaatg tgtttaaagg attgattcta gaacctttgt atatttgata gtatttctaa | 180 |
| cttcatttc tttactgttt gcagttaatg ttcatgttct gctatgcaat cgtttatatg | 240 |
| cacgtttctt taatttttt agattttcct ggatgtatag tttaaacaac aaaaagtcta | 300 |
| tttaaaactg tagcagtagt ttacagttct agcaaagagg aaagttgtgg ggttaaactt | 360 |
| tgtattttct ttcttataga ggcttctaaa aaggtatttt tatatgttct ttttaacaaa | 420 |
| tattgtgtac aacctttaaa acatcaatgt ttggatcaaa acaagaccca gcttattttc | 480 |
| tgc | 483 |

<210> SEQ ID NO 115
<211> LENGTH: 521
<212> TYPE: DNA
<213> ORGANISM: Homo sapien

<400> SEQUENCE: 115

| | |
|---|---|
| tgtggtggcg cgggctgagg tggaggccca ggactctgac cctgcccctg ccttcagcaa | 60 |
| ggccccccggc agcgccggcc actacgaact gccgtgggtt gaaaaatata ggccagtaaa | 120 |
| gctgaatgaa attgtcggga atgaagacac cgtgagcagg ctagaggtct ttgcaaggga | 180 |
| aggaaatgtg cccaacatca tcattgcggg ccctccagga accggcaaga ccacaagcat | 240 |
| tctgtgcttg gcccgggccc tgctgggccc agcactcaaa gatgccatgt tggaactcaa | 300 |
| tgcttcaaat gacaggggca ttgacgttgt gaggaataaa attaaaatgt ttgctcaaca | 360 |
| aaaagtcact cttcccaaag gccgacataa gatcatcatt ctggatgaag cagacagcat | 420 |
| gaccgacgga gcccagcaag ccttgaggag aaccatggaa atctactcta aaaccactcg | 480 |
| ttcgcccttg cttgtaatgc ttcggataag atcatcgagc c | 521 |

<210> SEQ ID NO 116
<211> LENGTH: 501
<212> TYPE: DNA
<213> ORGANISM: Homo sapien

<400> SEQUENCE: 116

| | |
|---|---|
| ctttgcaaag cttttatttc atgtctgcgg catggaatcc acctgcacat ggcatcttag | 60 |
| ctgtgaagga gaaagcagtg cacgagaagg aatgagtggg cggaaccaac ggcctccaca | 120 |
| agctgccttc cagcagcctg ccaaggccat ggcagagaga gactgcaaac aaacacaagc | 180 |
| aaacagagtc tcttcacagc tggagtctga aagctcatag tggcatgtgt gaatctgaca | 240 |
| aaattaaaag tgtgcatagt ccattacatg cataaaacac taataataat cctgtttaca | 300 |
| cgtgactgca gcaggcaggt ccagctccac cactgccctc ctgccacatc acatcaagtg | 360 |
| ccatggttta gagggttttt catatgtaat tcttttattc tgtaaaaggt aacaaaatat | 420 |
| acagaacaaa actttccctt tttaaaacta atgttacaaa tctgtattat cacttggata | 480 |

-continued

| taaatagtat ataagctgat c | 501 |

<210> SEQ ID NO 117
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 117

| caagggatat atgttgaggg tacrgrgtga cactgaacag atcacaaagc acgagaaaca | 60 |
| ttagttctct ccctccccag cgtctccttc gtctccctgg ttttccgatg tccacagagt | 120 |
| gagattgtcc ctaagtaact gcatgatcag agtgctgkct ttataagact cttcattcag | 180 |
| cgtatccaat tcagcaattg cttcatcaaa tgccgttttt gccaggctac aggccttttc | 240 |
| aggagagttt agaatctcat agtaaagac tgagaaattt agtgccagac caagacgaat | 300 |
| tgggtgtgta ggctgcattn ctttcttact aatttcaaat gcttcctggt aagcctgctg | 360 |
| ggagttcgac acaagtggtt tgtttgttgc tccagatgcc acttcagaaa gatacctaaa | 420 |
| ataatctcct ttcattttca aagtagaaca c | 451 |

<210> SEQ ID NO 118
<211> LENGTH: 501
<212> TYPE: DNA
<213> ORGANISM: Homo sapien

<400> SEQUENCE: 118

| tccggagccg gggtagtcgc cgccgccgcc gccggtgcag ccactgcagg caccgctgcc | 60 |
| gccgcctgag tagtgggctt aggaaggaag aggtcatctc gctcggagct tcgctcggaa | 120 |
| gggtctttgt tccctgcagc cctcccacgg gaatgacaat ggataaaagt gagctggtac | 180 |
| agaaagccaa actcgctgag caggctgagc gatatgatga tatggctgca gccatgaagg | 240 |
| cagtcacaga acagggcat gaactctcca acgaagagag aaatctgctc tctgttgcct | 300 |
| acaagaatgt ggtaaggccg cccgccgctc ttcctggcgt gtcatctcca gcattgagca | 360 |
| gaaaacagag aggaatgaga agaagcagca gatgggcaaa gagtaccgtg agaagataga | 420 |
| ggcagaactg caggacatct gcaatgatgt tctggagctt gttggacaaa tatcttattc | 480 |
| caatgctaca caacccagaa a | 501 |

<210> SEQ ID NO 119
<211> LENGTH: 391
<212> TYPE: DNA
<213> ORGANISM: Homo sapien

<400> SEQUENCE: 119

| aaaaagcagc argttcaaca caaaatagaa atctcaaatg taggatagaa caaaaccaag | 60 |
| tgtgtgaggg gggaagcaac agcaaaagga agaaatgaga tgttgcaaaa aagatggagg | 120 |
| agggttcccc tctcctctgg ggactgactc aaacactgat gtggcagtat acaccattcc | 180 |
| agagtcaggg gtgttcattc ttttttggga gtaagaaaag gtggggatta agaagacgtt | 240 |
| tctggaggct tagggaccaa ggctggtctc tttcccccct cccaaccccc ttgatccctt | 300 |
| tctctgatca ggggaaagga gctcgaatga gggaggtaga gttggaaagg gaaaggattc | 360 |
| cacttgacag aatgggacag actccttccc a | 391 |

<210> SEQ ID NO 120
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 120

```
tggcaatagc acagccatcc aggagctctt cargcgcatc tcggagcagt tcactgccat    60
gttccgccgg aaggccttcc tccactggta cacaggcgag ggcatggacg agatggagtt   120
caccgaggct gagagcaaca tgaacgacct cgtctctgag tatcaagcag taccaggatg   180
ccaccgcaga agaggaggag gatttcggtg aggaggccga agaggaggcc taaggcagag   240
cccccatcac ctcaggcttc tcagttccct tagccgtctt actcaactgc ccctttcctc   300
tccctcagaa tttgtgtttg ctgcctctat cttgtttttt gttttttctt ctgggggggt   360
ctagaacagt gcctggcaca tagtaggcgc tcaataaata cttggttgnt gaatgtctcc   420
t                                                                  421
```

<210> SEQ ID NO 121
<211> LENGTH: 206
<212> TYPE: DNA
<213> ORGANISM: Homo sapien

<400> SEQUENCE: 121

```
agctggcgct agggctcggt tgtgaaatac agcgtrgtca gcccttgcgc tcagtgtaga    60
aacccacgcc tgtaaggtcg gtcttcgtcc atctgctttt ttctgaaata cactaagagc   120
agccacaaaa ctgtaacctc aaggaaacca taaagcttgg agtgccttaa tttttaacca   180
gtttccaata aaacggttta ctacct                                       206
```

<210> SEQ ID NO 122
<211> LENGTH: 131
<212> TYPE: DNA
<213> ORGANISM: Homo sapien

<400> SEQUENCE: 122

```
ggagatgaag atgaggaagc tgagtcagct acgggcargc gggcagctga agatgatgag    60
gatgacgatg tcgataccaa gaagcagaag accgacgagg atgactagac agcaaaaaag   120
gaaaagttaa a                                                       131
```

<210> SEQ ID NO 123
<211> LENGTH: 231
<212> TYPE: DNA
<213> ORGANISM: Homo sapien
<220> FEATURE:
<221> NAME/KEY: misc_feature
<222> LOCATION: (1)...(231)
<223> OTHER INFORMATION: n = A,T,C or G

<400> SEQUENCE: 123

```
gatgaaaatt aaatacttaa attaatcaaa aggcactacg ataccaccta aaacctactg    60
cctcagtggc agtakgctaa kgaagatcaa gctacagsac atyatctaat atgaatgtta   120
gcaattacat akcargaagc atgtttgctt ccagaagac tatggnacaa tggtcattwg   180
ggcccaagag gatatttggc cnggaaagga tcaagataga tnaangtaaa g           231
```

<210> SEQ ID NO 124
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 124

| | | | | | |
|---|---|---|---|---|---|
| gagtagcaac | gcaaagcgct | tggtattgag | tctgtgggsg | acttcggttc | cggtctctgc | 60 |
| agcagccgtg | atcgcttagt | ggagtgctta | gggtagttgg | ccaggatgcc | gaatatcaaa | 120 |
| atcttcagca | ggcagctccc | accaggactt | atctcasaaa | attgctgacc | gcctgggcct | 180 |
| ggagctaggc | aaggtggtga | ctaagaaatt | cagcaaccag | gagacctgtg | tggaaattgg | 240 |
| tgaaagtgta | ccgtggagag | gatgtctaca | ttgttcagag | tggntgtggc | gaaatcaatg | 300 |
| acaatttaat | ggagcttttg | atcatgatta | atgcctgcaa | gattgcttca | gccagccggg | 360 |
| ttactgcagt | catcccatgc | ttcccttatg | ccccggcagg | ataagaaaga | tnagagccgg | 420 |
| gccgccaatc | tcagccaagc | ttggtgcaaa | tatgctatct | gtagcagtgc | agatcatatt | 480 |
| atcaccatgg | acctacatgc | ttctcaaatt | canggctttt | t | | 521 |

<210> SEQ ID NO 125
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 125

| | | | | | |
|---|---|---|---|---|---|
| atgcaaaagg | ggacacaggg | ggttcaaaaa | taaaaatttc | tcttcccct | ccccaaacct | 60 |
| gtacccccagc | tccccgacca | caaccccctt | cctccccgg | ggaaagcaag | aaggagcagg | 120 |
| tgtggcatct | gcagctggga | agagagaggc | cggggaggtg | ccgagctcgg | tgctggtctc | 180 |
| tttccaaata | taaatacgtg | tgtcagaact | ggaaaatcct | ccagcaccca | ccacccaagc | 240 |
| actctccgtt | ttctgccggt | gtttggagag | gggcggnggg | caggggcgcc | aggcaccggc | 300 |
| tggctgcggt | ctactgcatc | cgctgggtgt | gcaccccgcg | a | | 341 |

<210> SEQ ID NO 126
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 126

| | | | | | |
|---|---|---|---|---|---|
| aggttggaga | aggtcatgca | ggtgcagatt | gtccaggskc | agccacaggg | tcaagcccaa | 60 |
| caggcccaga | gtggcactgg | acagaccatg | caggtgatgc | agcagatcat | cactaacaca | 120 |
| ggagagatcc | agcagatccc | ggtgcagctg | aatgccggcc | agctgcagta | tatccgctta | 180 |
| gcccagcctg | tatcaggcac | tcaagttgtg | caggggacaga | tccagacact | tgccaccaat | 240 |
| gctcaacaga | ttacacagac | agaggtccag | caaggacagc | agcagttcaa | gccagttcac | 300 |
| aagatggaca | gcagctctac | cagatccagc | aagtcaccat | gcctgcgggc | cangacctcg | 360 |
| ccagcccatg | ttcatccagt | caagccaacc | agcccttcna | cgggcaggcc | cccaggtga | 420 |

| | |
|---|---|
| ccggcgactg aagggcctga gctggcaagg ccaangacac ccaacacaat ttttgccata | 480 |
| cagcccccag gcaatgggca cagcctttct tcccagagga c | 521 |

<210> SEQ ID NO 127
<211> LENGTH: 351
<212> TYPE: DNA
<213> ORGANISM: Homo sapien

<400> SEQUENCE: 127

| | |
|---|---|
| tgagatttat tgcatttcat gcagcttgaa gtccatgcaa aggrgactag cacagttttt | 60 |
| aatgcattta aaaaataaaa gggaggtggg cagcaaacac acaaagtcct agtttcctgg | 120 |
| gtccctggga gaaagagtg tggcaatgaa tccacccact ctccacaggg aataaatctg | 180 |
| tctcttaaat gcaaagaatg tttccatggc ctctggatgc aaatacacag agctctgggg | 240 |
| tcagagcaag ggatggggag aggaccacga gtgaaaaagc agctacacac attcacctaa | 300 |
| ttccatctga gggcaagaac aacgtggcaa gtcttggggg tagcagctgt t | 351 |

<210> SEQ ID NO 128
<211> LENGTH: 521
<212> TYPE: DNA
<213> ORGANISM: Homo sapien

<400> SEQUENCE: 128

| | |
|---|---|
| tccagacatg ctcctgtcct aggcggggag caggaaccag acctgctatg ggaagcagaa | 60 |
| agagttaagg gaaggtttcc tttcattcct gttccttctc ttttgctttt gaacagtttt | 120 |
| taaatatact aatagctaag tcatttgcca gccaggtccc ggtgaacagt agagaacaag | 180 |
| gagcttgcta agaattaatt ttgctgtttt tcacccatt caaacagagc tgccctgttc | 240 |
| cctgatggag ttccattcct gccagggcac ggctgagtaa cacgaagcca ttcaagaaag | 300 |
| gcgggtgtga atcactgcc accccatgga cagacccctc actcttcctt cttagccgca | 360 |
| gcgctactta ataaatatat ttatactttg aaattatgat aaccgatttt tcccatgcgg | 420 |
| catcctaagg gcacttgcca gctcttatcc ggacagtcaa gcactgttgt tggacaacag | 480 |
| ataaaggaaa agaaaaagaa gaaaacaacc gcaacttctg t | 521 |

<210> SEQ ID NO 129
<211> LENGTH: 521
<212> TYPE: DNA
<213> ORGANISM: Homo sapien

<400> SEQUENCE: 129

| | |
|---|---|
| tgagacggac cactggcctg gtcccccctc atktgctgtc gtaggacctg acatgaaacg | 60 |
| cagatctagt ggcagagagg aagatgatga ggaacttctg agacgtcggc agcttcaaga | 120 |
| agagcaatta atgaagctta actcaggcct gggacagttg atcttgaaag aagagatgga | 180 |
| gaaagagagc cgggaaaggt catctctgtt agccagtcgc tacgattctc ccatcaactc | 240 |
| agcttcacat attccatcat ctaaaactgc atctctccct ggctatggaa gaaatgggct | 300 |
| tcaccggcct gtttctaccg acttcgctca gtataacagc tatgggatg tcagcggggg | 360 |
| agtgcgagat taccagacac ttccagatgg ccacatgcct gcaatgagaa tggaccgagg | 420 |
| agtgtctatg cccaacatgt tggaaccaaa gatatttcca tatgaaatgc tcatggtgac | 480 |
| caacagaggg ccgaaaccaa atctcagaga ggtggacaga a | 521 |

<210> SEQ ID NO 130
<211> LENGTH: 270

```
<212> TYPE: DNA
<213> ORGANISM: Homo sapien

<400> SEQUENCE: 130
tcactttatt tttcttgtat aaaaacccta tgttgtagcc acagctggag cctgagtccg     60
ctgcacggag actctggtgt gggtcttgac gaggtggtca gtgaactcct gatagggaga   120
cttggtgaat acagtctcct tccagaggtc ggggtcagg tagctgtagg tcttagaaat   180
ggcatcaaag gtggccttgg cgaagttgcc cagggtggca gtgcagcccc gggctgaggt   240
gtagcagtca tcgataccag ccatcatgag                                    270

<210> SEQ ID NO 131
<211> LENGTH: 341
<212> TYPE: DNA
<213> ORGANISM: Homo sapien

<400> SEQUENCE: 131
ctggaatata gacccgtgat cgacaaaact ttgaacgagg ctgactgtgc caccgtcccg     60
ccagccattc gctcctactg atgagacaag atgtggtgat gacagaatca gcttttgtaa   120
ttatgtataa tagctcatgc atgtgtccat gtcataactg tcttcatacg cttctgcact   180
ctggggaaga aggagtacat tgaagggaga ttggcaccta gtggctggga gcttgccagg   240
aacccagtgg ccagggagcg tggcacttac ctttgtccct tgcttcattc ttgtgagatg   300
ataaaactgg gcacagctct taaataaaat ataaatgaac a                       341

<210> SEQ ID NO 132
<211> LENGTH: 844
<212> TYPE: DNA
<213> ORGANISM: Homo sapien
<220> FEATURE:
<221> NAME/KEY: misc_feature
<222> LOCATION: (1)...(844)
<223> OTHER INFORMATION: n = A,T,C or G

<400> SEQUENCE: 132
tgaatgggga ggagctgacc caggaaatgg agcttgngga gaccaggcct gcagggatg      60 gaaccttcca gaagtgggca tctgtggtgg tgcctcttgg gaaggagcag aagtacacat   120
gccatgtgga acatgagggg ctgcctgagc ccctcaccct gagatgggc aaggaggagc   180 ctccttcatc caccaagact aacacagtaa tcattgctgt tccggttgtc cttggagctg   240
tggtcatcct tggagctgtg atggctttg tgatgaagag gaggagaaac acaggtggaa   300
aggaggggga ctatgctctg gctccaggct cccagagctc tgatatgtct ctcccagatt   360
gtaaagtgtg aagacagctg cctggtgtgg acttggtgac agacaatgtc ttcacacatc   420
tcctgtgaca tccagagacc tcagttctct ttagtcaagt gtctgatgtt ccctgtgagt   480
ctgcgggctc aaagtgaaga actgtggagc ccagtccacc cctgcacacc aggaccctat   540
ccctgcactg ccctgtgttc ccttccacag ccaaccttgc tgctccagcc aaacattggt   600
ggacatctgc agcctgtcag ctccatgcta ccctgacctt caactcctca cttccacact   660
gagaataata atttgaatgt gggtggctgg agagatggct cagcgctgac tgctcttcca   720 aggtcctga gttcaaatcc cagcaaccac atggtggctc acaaccatct gtaatgggat   780 ctaatacccct cttctgcagt gtctgaagac asctacagtg tacttacata taataataaa   840
taag                                                                844

<210> SEQ ID NO 133
```

<211> LENGTH: 601
<212> TYPE: DNA
<213> ORGANISM: Homo sapien

<400> SEQUENCE: 133

```
ggccgggcgc gcgcgccccc gccacacgca cgccgggcgt gccagtttat aaagggagag      60
agcaagcagc gagtcttgaa gctctgtttg gtgctttgga tccatttcca tcggtccttta    120
cagccgctcg tcagactcca gcagccaaga tggtgaagca gatcgagagc aagactgctt    180
ttcaggaagc cttggacgct gcaggtgata aacttgtagt agttgacttc tcagccacgt    240
ggtgtgggcc ttgcaaaatg atcaagcctt tctttcattc cctctctgaa agtattcca    300
acgtgatatt ccttgaagta gatgtggatg actgtcagga tgttgcttca gagtgtgaag    360
tcaaatgcat gccaacattc cagttttta gaagggaca aaaggtgggt gaattttctg      420
gagccaataa ggaaaagctt gaagccacca ttaatgaatt agtctaatca tgttttctga    480
aaatataacc agccattggc tatttaaaac ttgtaatttt tttaatttac aaaaatataa    540
aatatgaaga cataaacccm gttgccatct gcgtgacaat aaaacattaa tgctaacact    600
t                                                                    601
```

<210> SEQ ID NO 134
<211> LENGTH: 421
<212> TYPE: DNA
<213> ORGANISM: Homo sapien

<400> SEQUENCE: 134

```
tcacataaga aatttaagca agttacrcta tcttaaaaaa cacaacgaat gcatttaat      60
agagaaaccc ttccctccct ccacctccct ccccacccct cctcatgaat taagaatcta    120
agagaagaag taaccataaa accaagtttt gtggaatcca tcatccagag tgcttacatg    180
gtgattaggt taatattgcc ttcttacaaa atttctattt taaaaaaaat tataaccttg    240
attgcttatt acaaaaaaat tcagtacaaa agttcaatat attgaaaaat gcttttcccc    300
tccctcacag caccgtttta tatatagcag agaataatga agagattgct agtctagatg    360
gggcaatctt caaattacac caagacgcac agtggtttat ttaccctccc cttctcataa    420
g                                                                    421
```

<210> SEQ ID NO 135
<211> LENGTH: 511
<212> TYPE: DNA
<213> ORGANISM: Homo sapien

<400> SEQUENCE: 135

```
ggaaaggatt caagaattag aggacttgct tgctrragaa aaagacaact ctcgtcgcat      60
gctgacagac aaagagagag agatggcgga aataagggat caaatgcagc aacagctgaa    120
tgactatgaa cagcttcttg atgtaaagtt agccctggac atggaaatca gtgcttacag    180
gaaactctta gaaggcgaag aagagaggtt gaagctgtct ccaagccctt cttcccgtgt    240
gacagtatcc cgagcatcct caagtcgtag tgtaccgtac aactagagga aagcggaaga    300
gggttgatgt ggaagaatca gaggcgaagt agtagtgtta gcatctctca ttccgcctca    360
accactggaa atgtttgcat cgaagaaatt gatgttgatg ggaaatttat cccgcttgaa    420
gaacacttct gaacaggatc aaccaatggg aaggcttggg agatgatcag aaaaattgga    480
gacacatcag tcagttataa atatacctca a                                   511
```

<210> SEQ ID NO 136
<211> LENGTH: 341
<212> TYPE: DNA
<213> ORGANISM: Homo sapien

<400> SEQUENCE: 136

| | | | | | |
|---|---|---|---|---|---|
| catgggtttc | accaggttgg | ccaggctgct | cttgaactsc | tgacctcagg | tgatccaccc | 60 |
| gcctcggcct | cccaaagtgc | tgggattaca | ggcgtgagcc | accacgcccg | gcccccaaag | 120 |
| ctgtttcttt | tgtctttagc | gtaaagctct | cctgccatgc | agtatctaca | taactgacgt | 180 |
| gactgccagc | aagctcagtc | actccgtggt | ctttttctct | ttccagttct | tctctctctc | 240 |
| ttcaagttct | gcctcagtga | aagctgcagg | tccccagtta | agtgatcagg | tgagggttct | 300 |
| ttgaacctgg | ttctatcagt | cgaattaatc | cttcatgatg | g | | 341 |

<210> SEQ ID NO 137
<211> LENGTH: 551
<212> TYPE: DNA
<213> ORGANISM: Homo sapien

<400> SEQUENCE: 137

| | | | | | |
|---|---|---|---|---|---|
| gatgtgttgg | accctctgtg | tcaaaaaaaa | cctcacaaag | aatcccctgc | tcattacaga | 60 |
| agaagatgca | tttaaaatat | gggttatttt | caactttta | tctgaggaca | agtatccatt | 120 |
| aattattgtg | tcagaagaga | ttgaatacct | gcttaagaag | cttacagaag | ctatgggagg | 180 |
| aggttggcag | caagaacaat | ttgaacatta | taaaatcaac | tttgatgaca | gtaaaaatgg | 240 |
| cctttctgca | tgggaactta | ttgagcttat | tggaaatgga | cagtttagca | aaggcatgga | 300 |
| ccggcagact | gtgtctatgg | caattaatga | agtctttaat | gaacttatat | tagatgtgtt | 360 |
| aaagcagggt | tacatgatga | aaaagggcca | cagacggaaa | aactggactg | aaagatggtt | 420 |
| tgtactaaaa | cccaacataa | tttcttacta | tgtgagtgag | gatctgaagg | ataagaaagg | 480 |
| agacattctc | ttggatgaaa | attgctgtgt | agaagtcctt | gcctgacaaa | agatggaaag | 540 |
| aaatgccttt | t | | | | | 551 |

<210> SEQ ID NO 138
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 138

| | | | | | |
|---|---|---|---|---|---|
| gactggttct | ttatttcaaa | aagacacttg | tcaatattca | gtrtcaaaac | agttgcacta | 60 |
| ttgatttctc | tttctcccaa | tcggccccaa | agagaccaca | taaaggaga | gtacatttta | 120 |
| agccaataag | ctgcaggatg | tacacctaac | agacctcta | gaaaccttac | cagaaaatgg | 180 |
| ggactgggta | gggaaggaaa | cttaaaagat | caacaaactg | ccagcccacg | gactgcagag | 240 |
| gctgtcacag | ccagatgggg | tggccaggt | gccacaaacc | caaagcaaag | tttcaaaata | 300 |
| atataaaatt | taaaaagttt | tgtacataag | ctattcaaga | tttctccagc | actgactgat | 360 |
| acaaagcaca | attgagatgg | cacttctaga | gacagcagct | tcaaacccag | aaaagggtga | 420 |
| tgagatgaag | tttcacatgg | ctaaatcagt | ggcaaaaaca | cagtcttctt | tctttcttc | 480 |
| tttcaaggan | gcaggaaagc | aattaagtgg | tcaccttaac | ataaggggga | c | 531 |

<210> SEQ ID NO 139

<210> SEQ ID NO 139
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 139

```
tgggtgggca ccatggctgg gatcaccacc atcgaggcgg tgaagcgcaa gatccaggtt      60
ctgcagcagc aggcagatga tgcagaggag cgagctgagc gcctccagcg agaagttgag     120
ggagaaaggc gggcccggga acaggctgag gctgaggtgg cctccttgaa ccgtaggatc     180
cagctggttg aagaagagct ggaccgtgct caggagcgcc tggccactgc cctgcaaaag     240
ctggaagaag ctgaaaaagc tgctgatgag agtgagagag gtatgaaggt tattgaaaac     300
cgggccttaa aagatgaaga aaagatgaaa ctccaggaaa tccaactcaa agaagctaag     360
cacattgcag aagaggcaga taggaagtat gaagaggtgg ctcgtaagtt ggtgatcatt     420
gaaggagact tggaaccgca cagaaggaac gagcttgagc ttggcaaaag tcccgttgcc     480
cagagatggg atgaaccaga ttagactgat ggaccanaac c                         521
```

<210> SEQ ID NO 140
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 140

```
aggggcngcg ggtgcgtggg ccactgggtg accgacttag cctggccaga ctctcagcac      60
ctggaagcgc cccgagagtg acagcgtgag gctgggaggg aggacttggc ttgagcttgt     120
taaactctgc tctgagcctc cttgtcgcct gcatttagat ggctcccgca agaagggtg      180
gcgagaagaa aaagggccgt tctgccatca acgaagtggt aacccgagaa tacaccatca     240
acattcacaa gcgcatccat ggagtgggct tcaagaagcg tgcacctcgg gcactcaaag     300
agattcggaa atttgccatg aaggagatgg gaactccaga tgtgcgcatt gacaccaggc     360
tcaacaaagc tgtctgggcc aaaggaataa ggaatgtgcc ataccgaatc cggtgtgcgg     420
ctgtccagaa aacgtaatga ggatgaagat tcaccaaata agctatatac tttggttacc     480
tatgtacctg ttaccacttt caaaaatcta cagacagtca atgtggatga gaactaatcg     540
ctgatcgtca gatcaaataa agttataaaa t                                   571
```

<210> SEQ ID NO 141
<211> LENGTH: 531
<212> TYPE: DNA
<213> ORGANISM: Homo sapien

<400> SEQUENCE: 141

```
tcgggagcca cacttggccc tcttcctctc caaagsgcca gaacctcctt ctctttggag      60
aatggggagg cctcttggag acacagaggg tttcaccttg gatgacctct agagaaattg     120
cccaagaagc ccaccttctg gtcccaacct gcagacccca cagcagtcag ttggtcaggc     180
cctgctgtag aaggtcactt ggctccattg cctgcttcca accatgggc aggagagaag     240
gcctttattt ctcgcccacc cattcctcct gtaccagcac ctccgttttc agtcagtgtt     300
gtccagcaac ggtaccgttt acacagtcac ctcagacaca ccatttcacc tcccttgcca     360
```

-continued

```
agctgttagc cttagagtga ttgcagtgaa cactgtttac acaccgtgaa tccattccca       420
tcagtccatt ccagttggca ccagcctgaa ccatttggta cctggtgtta actggagtcc       480
tgtttacaag gtggagtcgg ggcttgctga cttctcttca tttgagggca c               531
```

<210> SEQ ID NO 142
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 142

```
acctagacag aaggtgggtg agggaggact ggtaggaggc tgaggcaatt ccttggtagt        60
ttgtcctgaa accctactgg agaagtcagc atgaggcacc tactgagaga agtgcccaga      120
aactgctgac tgcatctgtt aagagttaac agtaaagagg tagaagtgtg tttctgaatc      180
agagtggaag cgtctcaagg gtcccacagt ggaggtccct gagctacctc ccttccgtga      240
gtgggaagag tgaagcccat gaagaactga gatgaagcaa ggatggggtt cctgggctcc      300
aggcaagggc tgtgctctct gcagcaggga gccccacgag tcagaagaaa gaactaatc      360 atttgttgca agaaaccttg cccggatact agcggaaaac tggaggcggn ggtgggggca      420
caggaaagtg gaagtgattt gatggagagc agagaagcct atgcacagtg gccgagtcca      480
cttgtaaagt g                                                           491
```

<210> SEQ ID NO 143
<211> LENGTH: 515
<212> TYPE: DNA
<213> ORGANISM: Homo sapien

<400> SEQUENCE: 143

```
ttcaagcaat tgtaacaagt atatgtagat tagagtgagc aaaatcatat acaattttca       60
tttccagttg ctattttcca aattgttctg taatgtcgtt aaaattactt aaaaattaac      120
aaagccaaaa attatattta tgacaagaaa gccatcccta cattaatctt acttttccac      180
tcaccggccc atctccttcc tctttttcct aactatgcca ttaaaactgt tctactgggc      240
cgggcgtgtg gctcatgcct gtaatcccag cattttggga ggccaaggca ggcggatcat      300
gaggtcaaga gattgagacc atcctggcca acatggtgaa accccgcctc gactaagaat      360
acaaaaatta gctgggcatg gtggcgcatg cctgtagtct cagctactcg ggaggctgag      420
gcagaagaat cgcttgaacc cgggaggcag aggatgcagt gagccccgat cgcgccactg      480
cactctagcc tgggcgacag actgagactc tgctc                                 515
```

<210> SEQ ID NO 144
<211> LENGTH: 340
<212> TYPE: DNA
<213> ORGANISM: Homo sapien

<400> SEQUENCE: 144

```
tgtgccagtc tacaggccta tcagcagcga ctccttcagc aacagatggg gtccctgtt        60 cagcccaacc ccatgagccc ccagcagcat atgctcccaa atcaggccca gtccccacac     120
ctacaaggcc agcagatccc taattctctc tccaatcaag tgcgctctcc ccagcctgtc     180
ccttctccac ggccacagtc ccagcccccc cactccagtc cttccccaag gatgcagcct     240
```

-continued

```
cagccttctc cacaccacgt tcccccacag acaagttccc cacatcctgg actggtagtt    300
gcccaggcca accccatgga acaagggcat tttgccagcc                          340
```

<210> SEQ ID NO 145
<211> LENGTH: 630
<212> TYPE: DNA
<213> ORGANISM: Homo sapien

<400> SEQUENCE: 145

```
tgtaaaaact tgtttttaat tttgtataaa ataaaggtgg tccatgccca cgggggctgt    60
aggaaatcca agcagaccag ctggggtggg gggatgtagc ctacctcggg ggactgtctg    120
tcctcaaaac gggctgagaa ggcccgtcag gggcccaggt cccacagaga ggcctgggat    180
actcccccaa cccgagaggc agactgggca gtggggagcc cccatcgtgc cccagaggtg    240
gccacaggct gaaggagggg cctgaggcac cgcagcctgc aacccccagg gctgcagtcc    300
actaactttt tacagaataa aggaacatg  gggatgggga aaaaagcacc aggtcaggca    360
gggcccgagg gccccagatc ccaggagggc caggactcag gatgccagca ccaccctagc    420
agctcccaca gctcctggca caggaggccg ccacggattg gcacaggccg ctgctggcca    480
tcacgccaca tttggagaac ttgtcccgac agaggtcagc tcggaggagc tcctcgtggg    540
cacacactgt acgaacacag atctccttgt taatgacgta cacacggcgg aggctgcggg    600
gacagggcac gggaggtctc agccccactt                                     630
```

<210> SEQ ID NO 146
<211> LENGTH: 521
<212> TYPE: DNA
<213> ORGANISM: Homo sapien

<400> SEQUENCE: 146

```
atggctgctg gatttaggtg gtaataggg  ctgtgggcca taaatctgaa gccttgagaa    60
ccttgggtct ggagagccat gaagagggaa ggaaaagagg gcaagtcctg aacctaacca    120
atgacctgat ggattgctcg accaagacac agaagtgaag tctgtgtctg tgcacttccc    180
acagactgga gttttggtg ctgaatagag ccagttgcta aaaaattggg ggtttggtga    240
agaaatctga ttgttgtgtg tattcaatgt gtgattttaa aataaacag caacaacaat    300 aaaaaccctg actggctgtt ttttcccctgt attctttaca actatttttt gaccctctga    360
aaattattat acttcaccta aatggaagac tgctgtgttt gtggaaattt tgtaattttt    420
taatttattt tattctctct ccttttttatt ttgcctgcag aatccgttga gagactaata    480
aggcttaata tttaattgat ttgtttaata tgtatataaa t                        521
```

<210> SEQ ID NO 147
<211> LENGTH: 562
<212> TYPE: DNA
<213> ORGANISM: Homo sapien

<400> SEQUENCE: 147

```
ggcatgcgag cgcactcggc ggacgcaagg gcggcgggga gcacacggag cactgcaggc    60
gccgggttgg gacagcgtct tcgctgctgc tggatagtcg tgttttcggg gatcgaggat    120
actcaccaga aaccgaaaat gccgaaacca atcaatgtcc gagttaccac catggatgca    180
gagctggagt ttgcaatcca gccaaataca actggaaaac agcttttga tcaggtggta    240 aagactatcg gcctccggga agtgtggtac tttggcctcc actatgtgga aataaagga    300 tttcctacct ggctgaagct ggataagaag gtgtctgccc aggaggtcag gaaggagaat    360
```

```
cccctccagt tcaagttccg ggccaaagtt ctaccctgaa gatgtggctg aggagctcat    420
ccaggacatc acccagaaac ttttcttcct tcaagtgaag gaaggaatcc ttagcgatga    480
gatctactgc ccccttgar actgccgtgc tcttggggtc ctacgcttgt gcatgccaag    540
tttggggact accaccaaga ag                                            562
```

<210> SEQ ID NO 148
<211> LENGTH: 820
<212> TYPE: DNA
<213> ORGANISM: Homo sapien

<400> SEQUENCE: 148

```
gaaggagtcg ggatactcag cattgatgca ccccaatttc aaagcggcat tcttcggcag     60
gtctctggga caatctctag ggtcactacc tggaaactcg ttagggtaca actgaatgct    120
gaaaggaaag aacacctgca gaaccggaca gaaattcacc ccggcgatca gctgattgat    180
ctcggtcgac cagaagtcat ggctaaagat gacgaggacg ttgtcaattc cctgggcttt    240
tcgaagtgag tccagcagca gtctgaggta ttcgggccgg ttatgcacct ggaccaccag    300
caccagctcc cggggggccc aggtgccagc cttatctaca ttcctcaggg tctgatcaaa    360
gttcagctgg tacaccaggg accggtaccg cagcgtcagg ttgtccgctc gggctggggg    420
accgccggga ccagggaagc cgccgacacg ttggagaccc tgcggatgcc cacagccaca    480 gagggtggt ccccaccgcg gccgccggca ccccgcgcgg gttcggcgtc cagcaacggt    540
ggggcgaggg cctcgttctt cctttgtcgc ccattgctgc tccagaggac gaagccgcag    600
gcggccacca cgagcgtcag gattagcacc ttccgtttgt agatgcggaa cctcatggtc    660
tccagggccg ggagcgcagc tacagctcga gcgtcggcgc cgccgctagg agccgcggct    720
cggcttcgtc tccgtcctct ccattcagca ccacgggtcc cggaaaaagc tcagccscgg    780
tcccaaccgc accctagctt cgttacctgc gcctcgcttg                        820
```

<210> SEQ ID NO 149
<211> LENGTH: 501
<212> TYPE: DNA
<213> ORGANISM: Homo sapien

<400> SEQUENCE: 149

```
cagattttta tttgcagtcg tcactggggc cgtttcttgc tgcttatttg tctgctagcc     60
tgctcttcca gctgcatggc caggcgcaag gccttgatga catctcgcag ggctgagaaa    120
tgcttggctt gctgggccag agcagattcc gctttgttca caaaggtctc caggtcatag    180
tctggctgct cggtcatctc agagagctca agccagtctg gtccttgctg tatgatctcc    240
ttgagctctt ccatagcctt ctcctccagc tccctgatct gagtcatggc ttcgttaaag    300
ctggacatct gggaagacag ttcctcctct tccttggata aattgcctgg aatcagcgcc    360
ccgttagagc aggcttccat ctcttctgtt tccatttgaa tcaactgctc tccactgggc    420
ccactgtggg ggctcagctc cttgaccctg ctgcatatct taagggtgtt taaaggatat    480
tcacaggagc ttatgcctgg t                                            501
```

<210> SEQ ID NO 150
<211> LENGTH: 511
<212> TYPE: DNA
<213> ORGANISM: Homo sapien
<220> FEATURE:
<221> NAME/KEY: misc_feature
<222> LOCATION: (1)...(511)

<223> OTHER INFORMATION: n = A,T,C or G

<400> SEQUENCE: 150

| | | | | | |
|---|---|---|---|---|---|
| ctcctcttgg | tacatgaacc | caagttgaaa | gtggacttaa | caaagtatct | ggagaaccaa | 60 |
| gcattctgct | ttgactttgc | atttgatgaa | acagcttcga | atgaagttgt | ctacaggttc | 120 |
| acagcaaggc | cactggtaca | gacaatcttt | gaaggtggaa | aagcaacttg | ttttgcatat | 180 |
| ggccagacag | gaagtggcaa | gacacatact | atgggcggag | acctctctgg | gaaagcccag | 240 |
| aatgcatcca | aagggatcta | tgccatggcc | ttccgggacg | tcttcttctg | aagaatcaac | 300 |
| cctgctaccg | gaagttgggc | ctggaagtct | atgtgacatt | cttcgagatc | tacaatggga | 360 |
| agctgtttga | cctgctcaac | aagaaggcca | agcttgcgcg | tgctggaaga | cggcaagcaa | 420 |
| caggtgcaag | tggtggggc | ttgcaggaac | atctggntaa | ctctgcttga | tgatggcant | 480 |
| caagatgatc | gacatgggca | gcgcctgcag | a | | | 511 |

<210> SEQ ID NO 151
<211> LENGTH: 566
<212> TYPE: DNA
<213> ORGANISM: Homo sapien

<400> SEQUENCE: 151

| | | | | | |
|---|---|---|---|---|---|
| tcccgaattc | aagcgacaaa | ttggawagtg | aaatggaaga | tgcctatcat | gaacatcagg | 60 |
| caaatctttt | gcgccaagat | ctgatgagac | gacaggaaga | attaagacgc | atggaagaac | 120 |
| ttcacaatca | agaaatgcag | aaacgtaaag | aaatgcaatt | gaggcaagag | gaggaacgac | 180 |
| gtagaagaga | ggaagagatg | atgattcgtc | aacgtgagat | ggaagaacaa | atgaggcgcc | 240 |
| aaagagagga | aagttacagc | cgaatgggct | acatggatcc | acgggaaaga | gacatgcgaa | 300 |
| tgggtggcgg | aggagcaatg | aacatggagg | atccctatgg | ttcaggaggc | cagaaatttc | 360 |
| cacctctagg | agtggtggt | ggcataggtt | atgaagctaa | tcctggcgtt | ccaccagcaa | 420 |
| ccatgagtgg | ttccatgatg | ggaagtgaca | tgcgtactga | gcgctttggg | cagggaggtg | 480 |
| cggggcctgt | gggtggacag | ggtcctagag | gaatggggcc | tggaactcca | gcaggatatg | 540 |
| gtagagggag | agaagagtac | gaaggc | | | | 566 |

<210> SEQ ID NO 152
<211> LENGTH: 518
<212> TYPE: DNA
<213> ORGANISM: Homo sapien

<400> SEQUENCE: 152

| | | | | | |
|---|---|---|---|---|---|
| ttcgtgaaga | ccctgactgg | taagaccatc | actctcgaag | tggagcccga | gtgacaccat | 60 |
| tgagaatgtc | aaggcaaaga | tccaagacaa | ggaaggcatc | cctcctgacc | agcakaggtt | 120 |
| gatctttgct | gggaaacagc | tggaagatgg | acgcaccctg | tctgactaca | acatccagaa | 180 |
| agagtccacc | ctgcacctgg | tgctccgtct | cagaggtggg | atgcaaatct | tcgtgaagac | 240 |
| cctgactggt | aagaccatca | ccctcgaggt | ggagcccagt | gacaccatcg | agaatgtcaa | 300 |
| ggcaaagatc | caagataagg | aaggcatccc | tcctgatcag | cagaggttga | tctttgctgg | 360 |
| gaaacagctg | gaagatggac | gcaccctgtc | tgactacaac | atccagaaag | agtccactct | 420 |
| gcacttggtc | ctgcgcttga | gggggggtgt | ctaagtttcc | ccttttaagg | tttcaacaaa | 480 |
| tttcattgca | ctttccttc | aataaagttg | ttgcattc | | | 518 |

<210> SEQ ID NO 153
<211> LENGTH: 542

<212> TYPE: DNA
<213> ORGANISM: Homo sapien

<400> SEQUENCE: 153

| | | | | | |
|---|---|---|---|---|---|
| gcgcgggtgc | gtgggccact | gggtgaccga | cttagcctgg | ccagactctc | agcacctgga | 60 |
| agcgccccga | gagtgacagc | gtgaggctgg | gagggaggac | ttggcttgag | cttgttaaac | 120 |
| tctgctctga | gcctccttgt | cgcctgcatt | tagatggctc | ccgcaaagaa | gggtggcgag | 180 |
| aagaaaaagg | gccgttctgc | catcaacgaa | gtggtaaccc | gagaatacac | catcaacatt | 240 |
| cacaagcgca | tccatggagt | gggcttcaag | aagcgtgcac | ctcgggcact | caaagagatt | 300 |
| cggaaatttg | ccatgaagga | gatgggaact | ccagatgtgc | gcattgacac | caggctcaac | 360 |
| aaagctgtct | gggccaaagg | aataaggaat | gtgccatacc | gaatccgtgt | gcggctgtcc | 420 |
| agaaaacgta | atgaggatga | agattcacca | aataagctat | atactttggt | tacctatgta | 480 |
| cctgttacca | ctttcaaaaa | tctacagaca | gtcaatgtgg | atgagaacta | atcgctgatc | 540 |
| gt | | | | | | 542 |

<210> SEQ ID NO 154
<211> LENGTH: 411
<212> TYPE: DNA
<213> ORGANISM: Homo sapien

<400> SEQUENCE: 154

| | | | | | |
|---|---|---|---|---|---|
| aattctttat | ttaaatcaac | aaactcatct | tcctcaagcc | ccagaccatg | gtaggcagcc | 60 |
| ctccctctcc | atccctcac | cccacccctt | agccacagtg | aagggaatgg | aaaatgagaa | 120 |
| gccacgaggg | cccctgccag | ggaaggctgc | cccagatgtg | tggtgagcac | agtcagtgca | 180 |
| gctgtggctg | gggcagcagc | tgccacaggc | tcctccctat | aaattaagtt | cctgcagcca | 240 |
| cagctgtggg | agaagcatac | ttgtagaagc | aaggccagtc | cagcatcaga | aggcagaggc | 300 |
| agcatcagtg | actcccagcc | atggaatgaa | cggaggacac | agagctcaga | gacagaacag | 360 |
| gccaggggga | agaaggagag | acagaatagg | ccagggcatg | gcggtgaggg | a | 411 |

<210> SEQ ID NO 155
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 155

| | | | | | |
|---|---|---|---|---|---|
| tgatgaatct | gggtgggctg | gcagtagccc | gagatgatgg | gctcttctct | ggggatccca | 60 |
| actggttccc | taagaaatcc | aaggagaatc | ctcggaactt | ctcggataac | cagctgcaag | 120 |
| agggcaagaa | cgtgatcggg | ttacagatgg | gcaccaaccg | cggggcgtct | cangcaggca | 180 |
| tgactggcta | cgggatgcca | cgccagatcc | tctgatccca | ccccaggcct | gcccctgcc | 240 |
| ctcccacgaa | tggttaatat | atatgtagat | atatatttta | gcagtgacat | tcccagagag | 300 |
| ccccagagct | ctcaagctcc | tttctgtcag | ggtgggggt | tcaagcctgt | cctgtcacct | 360 |
| ctgaagtgcc | tgctggcatc | ctctcccca | tgcttactaa | tacattccct | tccccatagc | 420 |
| c | | | | | | 421 |

<210> SEQ ID NO 156
<211> LENGTH: 670
<212> TYPE: DNA

<210> SEQ ID NO 156
<211> LENGTH: 670
<212> TYPE: DNA
<213> ORGANISM: Homo sapien

<400> SEQUENCE: 156

| | | | | | |
|---|---|---|---|---|---|
| agcggagctc | cctcccctgg | tggctacaac | ccacacacgc | caggctcagg | catcgagcag | 60 |
| aactccagcg | actgggtaac | cactgacatt | caggtgaagg | tgcgggacac | ctacctggat | 120 |
| acacaggtgg | tgggacagac | agtgtgtcatc | cgcagtgtca | cggggggcat | gtgctctgtg | 180 |
| tacctgaagg | acagtgagaa | ggttgtcagc | atttccagtg | agcacctgga | gcctatcacc | 240 |
| cccaccaaga | caacaaggt | gaaagtgatc | ctgggcgagg | atcgggaagc | cacgggcgtc | 300 |
| ctactgagca | ttgatggtga | ggatggcatt | gtccgtatgg | accttgatga | gcagctcaag | 360 |
| atcctcaacc | tccgcttcct | ggggaagctc | ctggaagcct | gaagcaggca | gggccggtgg | 420 |
| acttcgtcgg | atgaagagtg | atcctccttc | cttccctggc | ccttggctgt | gacacaagat | 480 |
| cctcctgcag | ggctaggcgg | attgttctgg | atttcctttt | gtttttcctt | ttaggtttcc | 540 |
| atcttttccc | tccctggtgc | tcattggaat | ctgagtagag | tctgggggag | ggtccccacc | 600 |
| ttcctgtacc | tcctccccac | agcttgcttt | tgttgtaccg | tctttcaata | aaaagaagct | 660 |
| gtttggtcta | | | | | | 670 |

<210> SEQ ID NO 157
<211> LENGTH: 421
<212> TYPE: DNA
<213> ORGANISM: Homo sapien

<400> SEQUENCE: 157

| | | | | | |
|---|---|---|---|---|---|
| ggttcacagc | actgctgctt | gtgtgttgcc | ggccaggaat | tccaggctca | caaggctatc | 60 |
| ttagcagctc | gttctccggt | ttttagtgcc | atgtttgaac | atgaaatgga | ggagagcaaa | 120 |
| aagaatcgag | ttgaaatcaa | tgatgtggag | cctgaagttt | ttaaggaaat | gatgtgcttc | 180 |
| atttacacgg | ggaaggctcc | aaacctcgac | aaaatggctg | atgatttgct | ggcagctgct | 240 |
| gacaagtatg | ccctggagcg | cttaaaggtc | atgtgtgagg | atgccctctg | cagtaacctg | 300 |
| tccgtggaga | acgctgcaga | aattctcatc | ctggccgacc | tccacagtgc | agatcagttg | 360 |
| aaaactcagg | cagtggattt | catcaactat | catgcttcgg | atgtcttgga | gacctcttgg | 420 |
| g | | | | | | 421 |

<210> SEQ ID NO 158
<211> LENGTH: 321
<212> TYPE: DNA
<213> ORGANISM: Homo sapien

<400> SEQUENCE: 158

| | | | | | |
|---|---|---|---|---|---|
| tcgtagccat | ttttctgctt | ctttggagaa | tgacgccaca | ctgactgctc | attgtcgttg | 60 |
| gttccatgcc | aattggtgaa | atagaacctc | atccggtagt | ggagccggag | ggacatcttg | 120 |
| tcatcaacgg | tgatggtgcg | atttggagca | taccagagct | tggtgttctc | gccatacagg | 180 |
| gcaaagaggt | tgtgacaaag | aggagagata | cggcatgcct | gtgcagccct | gatgcacagt | 240 |
| tcctctgctg | tgtactctcc | actgcccagc | cggagggggct | ccctgtccga | cagatagaag | 300 |
| atcacttcca | ccctggctt | g | | | | 321 |

<210> SEQ ID NO 159
<211> LENGTH: 596
<212> TYPE: DNA
<213> ORGANISM: Homo sapien

<400> SEQUENCE: 159

```
tggcacactg ctcttaagaa actatgawga tctgagattt ttttgtgtat gttttttgact      60 cttttgagtg gtaatcatat gtgtctttat agatgtacat acctccttgc acaaatggag     120
gggaattcat tttcatcact gggagtgtcc ttagtgtata aaaaccatgc tggtatatgg     180
cttcaagttg taaaaatgaa agtgacttta aagaaaata ggggatggtc caggatctcc      240
actgataaga ctgtttttaa gtaacttaag gacctttggg tctacaagta tatgtgaaaa     300
aaatgagact tactgggtga ggaaattcat tgtttaaaga tggtcgtgtg tgtgtgtgtg     360
tgtgtgtgtg ttgtgttgtg ttttgttttt taagggaggg aatttattat ttaccgttgc     420
ttgaaattac tgkgtaaata tatgtytgat aatgatttgc tytttgvcma ctaaaattag     480
gvctgtataa gtwctaratg cmtccctggg kgttgatytt ccmagatatt gatgatamcc     540
cttaaaattg taaccygcct ttttcccttt gctytcmatt aaagtctatt cmaaag         596

<210> SEQ ID NO 160
<211> LENGTH: 515
<212> TYPE: DNA
<213> ORGANISM: Homo sapien

<400> SEQUENCE: 160
gggggtaggc tctttattag acggttattg ctgtactaca gggtcagagt gcagtgtaag      60
cagtgtcaga ggcccgcgtt cagcccaaga atgtggattt tctctcccta ttgatcacag     120
tgggtgggtt tcttcagaaa agccccagag gcagggacca gtgagctcca aggttagaag     180
tggaactgga aggcttcagt cacatgctgc ttccacgctt ccaggctggg cagcaaggag     240
gagatgccca tgacgtgcca ggtctcccca tctgacacca gtgaagtctg gtaggacagc     300
agccgcacgc ctgcctctgc caggaggcca atcatggtag gcagcattgc agggtcagag     360
gtctgagtcc ggaataggag caggggcagg tccctgcgga gaggcacttc tggcctgaag     420
acagctccat tgagcccctg cagtacaggy gtagtgcctt ggaccaagcc cacagcctgg     480 taagggcgc ctgccagggc cacggccagg aggca                                 515

<210> SEQ ID NO 161
<211> LENGTH: 936
<212> TYPE: DNA
<213> ORGANISM: Homo sapien

<400> SEQUENCE: 161
taatttctta gtcgtttgga atccttaagc atgcaaaagc tttgaacaga agggttcaca      60
aaggaaccag ggttgtctta tggcatccag ttaagccaga gctgggaatg cctctgggtc     120
atccacatca ggagcagaag cacttgactt gtcggtcctg ctgccacggt ttgggcgccc     180
accacgccca cgtccacctc gtcctcccct gccgccacgt cctgggcggc caaggtctcc     240
aaaattgatc tccagctgag acgttatatc atttgctggc ttccggaaat gatggtccat     300
aaccgaatct tcagcatgag cctcttcact ctttgattta tgaagaacaa atcccttctt     360
ccactgccca tcagcacctt catttggttt tcggatatta aattctactt ttgcccggtc     420
cttattttga atagccttcc actcatccaa agtcatctct tttggacccct cctcttttac     480 ctcttcaact tcattctcct tattttcagt gtctgccact ggatgatgtt cttcaccttc     540
aggtgtttcc tcagtcacat ttgattgatc caagtcagtt aattcgtctt tgacagttcc     600
ccagttgtga gatccgctac ctccacgttt gtcctcgtgt ttcaggccag atctatcact     660
tccactatgc ctatcaaatt cacgtttgcc acagaaatca aatccatctc ctcggcccat     720
```

-continued

| | |
|---|---|
| tccacgtcca cggcccctc gacctcttcc aagaccacca cgacctcgaa taggtcggtc | 780 |
| aataatcggt ctatcaactg aaaattcgcc tccttcaccc ttttcttcaa gtggcttttc | 840 |
| gaatcttcgt tcacgaggtg gtcgccttc tggtcttcta tcaattattt tcccttcacc | 900 |
| ctgaagttgt tgatcaggtc ttcttccaac tcgtgc | 936 |

<210> SEQ ID NO 162
<211> LENGTH: 950
<212> TYPE: DNA
<213> ORGANISM: Homo sapien

<400> SEQUENCE: 162

| | |
|---|---|
| aagcggatgg acctgagtca gccgaatcct agcccttcc cttgggcctg ctgtggtgct | 60 |
| cgacatcagt gacagacgga agcagcagac catcaaggct acgggaggcc cggggcgctt | 120 |
| gcgaagatga agtttggctg cctctccttc cggcagcctt atgctggctt tgtcttaaat | 180 |
| ggaatcaaga ctgtggagac cgctggcgt cctctgctga gcagccagcg gaactgtacc | 240 |
| atcgccgtcc acattgctca cagggactgg gaaggcgatg cctgtcggga gctgctggtg | 300 |
| gagagactcg ggatgactcc tgctcagatt caggccttgc tcaggaaagg ggaaaagttt | 360 |
| ggtcgaggag tgatagcggg actcgttgac attggggaaa cttttgcaatg ccccgaagac | 420 |
| ttaactcccg atgaggttgt ggaactagaa atcaagctg cactgaccaa cctgaagcag | 480 |
| aagtacctga ctgtgatttc aaaccccagg tggttactgg agcccatacc taggaaagga | 540 |
| ggcaaggatg tattccaggt agacatccca gagcacctga tcccttttggg gcatgaagtg | 600 |
| tgacaagtgt gggctcctga aaggaatgtt ccrgagaaac cagctaaatc atggcacctt | 660 |
| caatttgcca tcgtgacgca gacctgtata aattaggtta aagatgaatt tccactgctt | 720 |
| tggagagtcc cacccactaa gcactgtgca tgtaaacagg ttccttttgct cagatgaagg | 780 |
| aagtaggggg tggggctttc cttgtgtgat gcctccttag gcacacaggc aatgtctcaa | 840 |
| gtactttgac cttagggtag aaggcaaagc tgccagtaaa tgtctcagca ttgctgctaa | 900 |
| ttttggtcct gctagtttct ggattgtaca aataaatgtg ttgtagatga | 950 |

<210> SEQ ID NO 163
<211> LENGTH: 475
<212> TYPE: DNA
<213> ORGANISM: Homo sapien
<220> FEATURE:
<221> NAME/KEY: misc_feature
<222> LOCATION: (1)...(475)
<223> OTHER INFORMATION: n = A,T,C or G

<400> SEQUENCE: 163

| | |
|---|---|
| tcgagcggcc gcccgggcag gtgtcggagt ccagcacggg aggcgtggtc ttgtagttgt | 60 |
| tctccggctg cccattgctc tcccactcca cggcgatgtc gctgggatag aagcctttga | 120 |
| ccaggcaggt caggctgacc tggttcttgg tcatctcctc ccgggatggg ggcagggtgt | 180 |
| acacctgtgg ttctcgggc tgccctttgg ctttggagat ggttttctcg atggggctg | 240 |
| ggagggcttt gttggagacc ttgcacttgt actccttgcc attcaaccag tcctggtgca | 300 |
| ngacggtgag gacgctnacc acacggtacg ngctggtgta ctgctcctcc cgcggctttg | 360 |
| tcttggcatt atgcacctcc acgccgtcca cgtaccaatt gaacttgacc tcagggtctt | 420 |
| cgtggctcac gtccaccacc acgcatgtaa cctcaaanct cggncgcgan cacgc | 475 |

<210> SEQ ID NO 164
<211> LENGTH: 476

<212> TYPE: DNA
<213> ORGANISM: Homo sapien

<400> SEQUENCE: 164
agcgtggtcg cggccgaggt ctgaggttac atgcgtggtg gtggacgtga gccacgaaga    60
ccctgaggtc aagttcaact ggtacgtgga cggcgtggag gtgcataatg ccaagacaaa    120
gccgcgggag gagcagtaca acagcacgta ccgtgtggtc agcgtcctca ccgtcctgca    180
ccaggactgg ctgaatggca aggagtacaa gtgcaaggtc tccaacaaag ccctcccagc    240
ccccatcgag aaaaccatct ccaaagccaa agggcagccc cgagaaccac aggtgtacac    300
cctgccccca tcccgggagg agatgaccaa gaaccaggtc agcctgacct gcctggtcaa    360
aggcttctat cccagcgaca tcgcccgtgg agtgggagag caatgggcag ccggagaaca    420
actacaagac cacgcctccc gtgctggact ccgacacctg ccgggcggcc gctcga    476

<210> SEQ ID NO 165
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 165
agcgtggttn cggccgaggt cccaaccaag gctgcancct ggatgccatc aaagtcttct    60
gcaacatgga gactggtgag acctgcgtgt accccactca gcccagtgtg gcccagaaga    120
actggtacat cagcaagaac cccaaggaca agaggcatgt ctggttcggc gagagcatga    180
ccgatggatt ccagttcgag tatggcggcc agggctccga ccctgccgat gtggacctgc    240
ccgggcggnc gctcga    256

<210> SEQ ID NO 166
<211> LENGTH: 332
<212> TYPE: DNA
<213> ORGANISM: Homo sapien

<400> SEQUENCE: 166
agcgtggtcg cggccgaggt caagaacccc gcccgcacct gccgtgacct caagatgtgc    60
cactctgact ggaagagtgg agagtactgg attgaccccca accaaggctg caacctggat    120
gccatcaaag tcttctgcaa catggagact ggtgagacct cgtgtaccc cactcagccc    180 agtgtggccc agaagaactg gtacatcagc aagaacccca aggacaagag gcatgtctgg    240
ttcggcgaga gcatgaccga tggattccag ttcgagtatg gcggccaggg ctccgaccct    300
gccgatgtgg acctgcccgg gcggccgctc ga    332

<210> SEQ ID NO 167
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 167
tcgagcggtc gcccgggcag gtccacatcg gcagggtcgg agccctggcc gccatactcg    60
aactggaatc catcggncat gctctcgccg aaccagacat gcctcttgnc cttggggttc    120

```
ttgctgatgt accagntctt ctgggccaca ctgggctgag tggggtacac gcaggtctca    180
ccantctcca tgttgcanaa gactttgatg gcatccaggt tgcagccttg gttggggtca    240
atccagtact ctccactctt ccagacagag tggcacatct tgaggtcacg gcaggtgcgg    300
gcggggttct tgacctcggt cgcgaccacg ct                                  332
```

<210> SEQ ID NO 168
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 168

```
tcgagcggcc gcccgggcag gtcctcctca gagcggtagc tgttcttatt gccccggcag     60
cctccataga tnaagttatt gcangagttc ctctccacgt caaagtacca gcgtgggaag    120
gatgcacggc aaggcccagt gactgcgttg gcggtgcagt attcttcata gttgaacata    180
tcgctggagt ggacttcaga atcctgcctt ctgggagcac ttgggacaga ggaatccgct    240
gcattcctgc tggtggacct cggccgcgac cacgct                              276
```

<210> SEQ ID NO 169
<211> LENGTH: 276
<212> TYPE: DNA
<213> ORGANISM: Homo sapien

<400> SEQUENCE: 169

```
agcgtggtcg cggccgaggt ccaccagcag gaatgcagcg gattcctctg tcccaagtgc     60
tcccagaagg caggattctg aagaccactc cagcgatatg ttcaactatg aagaatactg    120
caccgccaac gcagtcactg ggccttgccg tgcatccttc ccacgctggt actttgacgt    180
ggagaggaac tcctgcaata acttcatcta tggaggctgc cggggcaata agaacagcta    240
ccgctctgag gaggacctgc ccgggcggcc gctcga                              276
```

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170

```
tcgagcggcc gcccgggcag gtccacatcg gcaggtcgg agccctggcc gccatactcg      60
aactggaatc catcggtcat gctctcgccg aaccagacat gcctcttgtc cttgggttc    120 ttgctgatgt accagttctt ctgggccaca ctgggctgag tggggtacac gcaggtctca    180
ccagtctcca tgttgcagaa gactttgatg gcatccaggt tgcagccttg gttggggtca    240
atccagtact ctccactctt ccagccagaa tggcacatct tgaggtcacg gcangtgcgg    300
gcggggttct tgacctcggc cgcgaccacg ct                                  332
```

<210> SEQ ID NO 171
<211> LENGTH: 333
<212> TYPE: DNA
<213> ORGANISM: Homo sapien

<400> SEQUENCE: 171

```
agcgtggtcg cggccgaggt caagaaaccc cgcccgcacc tgccgtgacc tcaagatgtg      60
ccactctggc tggaagagtg gagagtactg gattgacccc aaccaaggct gcaacctgga     120
tgccatcaaa gtcttctgca acatggagac tggtgagacc tgcgtgtacc ccactcagcc     180
cagtgtggcc cagaagaact ggtacatcag caagaaccc aaggacaaga ggcatgtctg      240
gctcggcgag agcatgaccg atggattcca gttcgagtat ggcggccagg ctccgaccc     300 tgccgatgtg gacctgcccg ggcggccgct cga                                  333
```

<210> SEQ ID NO 172
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 172

```
agcgtggtcg cggccgaggt cctgtcagag tggcactggt agaagntcca ggaaccctga      60
actgtaaggg ttcttcatca gtgccaacag gatgacatga aatgatgtac tcagaagtgt     120
cctgnaatgg ggcccatgan atggttgnct gagagagagc ttcttgtcct acattcggcg     180
ggtatggtct tggcctatgc cttatggggg tggccgttgn gggcggtgng gtccgcctaa     240
aaccatgttc ctcaaagatc atttgttgcc caacactggg ttgctgacca naagtgccag     300
gaagctgaat accatttcca gtgtcatacc cagggtgggt gacgaaaggg gtcttttgaa     360
ctgtggaagg aacatccaag atctctgntc catgaagatt ggggtgtgga agggttacca     420
gttggggaag ctcgctgtct ttttccttcc aatcangggc tcgctcttct gaatattctt     480
cagggcaatg acataaattg tatattcggt tcccggttcc aggccag                   527
```

<210> SEQ ID NO 173
<211> LENGTH: 635
<212> TYPE: DNA
<213> ORGANISM: Homo sapien
<220> FEATURE:
<221> NAME/KEY: misc_feature
<222> LOCATION: (1)...(635)
<223> OTHER INFORMATION: n = A,T,C or G

<400> SEQUENCE: 173

```
tcgagcggcc gcccgggcag gtccaccaca cccaattcct tgctggtatc atggcagccg      60
ccacgtgcca ggattaccgg ctacatcatc aagtatgaga agcctgggtc tcctcccaga     120
gaagtggtcc ctcggccccg ccctggtgtc acagaggcta ctattactgg cctggaaccg     180
ggaaccgaat atacaattta tgtcattgcc ctgaagaata atcagaagag cgagcccctg     240
attggaagga aaagacaga cgagcttccc caactggtaa cccttccaca ccccaatctt     300
catggaccag agatcttgga tgttccttcc acagttcaaa agacccctt cgtcacccac      360 cctgggtatg acactggaaa tggtattcag cttcctgcca cttctggtca gcaacccagt     420
gttgggcaac aaatgatctt tgangaacat ggntttaggc ggaccacacc ggccacaacg     480 ggcacccccta taaggcatag gccaagaaca tacccgncga atgtaggaca agaagctctn    540
tctcanacaa ncatctcatg ggccccattc cangacactt ctgagtacat canttcatgg     600
catcctggtg gcactgataa aaaccttac agtta                                 635
```

<210> SEQ ID NO 174

<211> LENGTH: 572
<212> TYPE: DNA
<213> ORGANISM: Homo sapien
<220> FEATURE:
<221> NAME/KEY: misc_feature
<222> LOCATION: (1)...(572)
<223> OTHER INFORMATION: n = A,T,C or G

<400> SEQUENCE: 174

```
agcgtggtcg cgggcgaggt cctgtcagag tggcactggt agaagttcca ggaaccctga      60
actgtaaggg ttcttcatca gtgccaacag gatgacatga aatgatgtac tcagaagtgt     120
cctggaatgg ggcccatgag atggttgtct gagagagagc ttcttgtcct acattcggcg     180
ggtatggtct tggcctatgc cttatggggg tggccgttgt gggcggtgtg gtccgcctaa     240
aaccatgttc ctcaaagatc atttgttgcc caacactggg ttgctgacca gaagtgccag     300
gaagctgaat accatttcca gtgtcatacc cagggtgggt gacgaaaggg gtctttttgaa    360
ctgtggaagg aacatccaag atctctggtc catgaagatt ggggtgtgga agggttacca     420
gttggggaag ctcgtctgtc ttttttcctttc caatcanggg ctcgctcttc tgattattct   480
tcagggcaat gacataaatt gtatattcgg ntcccgggtn cagccaataa taataaccct    540
ctgtgacacc anggcggggc cgaaggganca ct                                  572
```

<210> SEQ ID NO 175
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 175

```
agcgtggtcg cggccgaggt cctcaccaga ggtaccacct acaacatcat agtggaggca      60
ctgaaagacc agcagaggca taaggttcgg gaagaggttg ttaccgtggg caactctgtc     120
aacgaaggct tgaaccaacc tacgatgac tcgtgctttg acccctacac agtttcccat      180
tatgccgttg gagatgagtg ggaacgaatg tctgaatcag gctttaaact gttgtgccag     240
tgcttangct ttggaagtgg tcatttcaga tgtgattcat ctagatggtg ccatgacaat     300
ggtgtgaact acaagattgg agagaagtgg gaccgtcagg gagaaaatgg acctgcccgg     360
gcggccgctc ga                                                         372
```

<210> SEQ ID NO 176
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 176

```
tcgagcggcc gcccgggcag gtccattttc tccctgacgg tcccacttct ctccaatctt      60
gtagttcaca ccattgtcat ggcaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ntgacagagt tgcccacggt aacaacctct tcccgaacct tatgcctctg     300
ctggtctttc agtgcctcca ctatgatgtt gtaggtggta cctctggtga ggacctcggc     360
```

```
cgcgaccacg ct                                                             372

<210> SEQ ID NO 177
<211> LENGTH: 269
<212> TYPE: DNA
<213> ORGANISM: Homo sapien
<220> FEATURE:
<221> NAME/KEY: misc_feature
<222> LOCATION: (1)...(269)
<223> OTHER INFORMATION: n = A,T,C or G

<400> SEQUENCE: 177
agcgtggccg cggccgaggt ccattggctg gaacggcatc aacttggaag ccagtgatcg    60
tctcagcctt ggttctccag ctaatggtga tggnggtctc agtagcatct gtcacacgag   120
cccttcttgg tgggctgaca ttctccagag tggtgacaac ccctgagct ggtctgcttg    180
tcaaagtgtc cttaagagca tagacactca cttcatattt ggcgnccacc ataagtcctg   240
atacaaccac ggaatgacct gtcaggaac                                      269

<210> SEQ ID NO 178
<211> LENGTH: 529
<212> TYPE: DNA
<213> ORGANISM: Homo sapien

<400> SEQUENCE: 178
tcgagcggcc gcccgggcag gtcctcagac cgggttctga gtacacagtc agtgtggttg    60
ccttgcacga tgatatggag agccagcccc tgattggaac ccagtccaca gctattcctg   120
caccaactga cctgaagttc actcaggtca cacccacaag cctgagcgcc cagtggacac   180
cacccaatgt tcagctcact ggatatcgag tgcgggtgac ccccaaggag aagaccggac   240
caatgaaaga aatcaacctt gctcctgaca gctcatccgt ggttgtatca ggacttatgg   300
cggccaccaa atatgaagtg agtgtctatg ctcttaagga cactttgaca agcagaccag   360
ctcagggtgt tgtcaccact ctggagaatg tcagcccacc aagaagggct cgtgtgacag   420
atgctactga gaccaccatc accattagct ggagaaccaa gactgagacg atcactggct   480
tccaagttga tgccgttcca gccaatggac ctcggccgcg accacgctt                529

<210> SEQ ID NO 179
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 179
agcgtggtcg cggccgaggt ctggccgaac tgccagtgta cagggaagat gtacatgtta    60
tagntcttct cgaagtcccg ggccagcagc tccacggggt ggtctcctgc ctccaggcgc   120
ttctcattct catggatctt cttcacccgc agcttctgct tctcagtcag aaggttgttg   180
tcctcatccc tctcatacag ggtgaccagg acgttcttga gccagtcccg catgcgcagg   240
gggaattcgg tcagctcaga gtccaggcaa gggggggatg atttgcaagg cccgatgtag   300
tccaagtgga gcttgtggcc cttcttggtg ccctccaagg tgcactttgt ggcaaagaag   360
tggcaggaag agtcgaaggt cttgttgtca ttgctgcaca ccttctcaaa ctcgccaatg   420
ggggctgggc agacctgccc gggcggccgc tcga                                454
```

<210> SEQ ID NO 180
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 180

| | |
|---|---|
| tcgagcggcc gcccgggcag gtctgcccag cccccattgg cgagtttgag aaggngtgca | 60 |
| gcaatgacaa caagaccttc gactcttcct gccacttctt tgccacaaag tgcaccctgg | 120 |
| agggcaccaa gaagggccac aagctccacc tggactacat cgggccttgc aaatacatcc | 180 |
| ccccttgcct ggactctgag ctgaccgaat tccccctgcg catgcgggac tggctcaaga | 240 |
| acgtcctggt caccctgtat gagagggatg aggacaacaa ccttctgact gagaagcana | 300 |
| agctgcgggt gaagaanatc catgagaatg anaagcgcct gnaggcanga gaccaccccg | 360 |
| tggagctgct ggcccgggac ttcgagaaga actataacat gtacatcttc cctgtacact | 420 |
| ggcagttcgg ccagacctcg gccgcgacca cgct | 454 |

<210> SEQ ID NO 181
<211> LENGTH: 102
<212> TYPE: DNA
<213> ORGANISM: Homo sapien
<220> FEATURE:
<221> NAME/KEY: misc_feature
<222> LOCATION: (1)...(102)
<223> OTHER INFORMATION: n = A,T,C or G

<400> SEQUENCE: 181

| | |
|---|---|
| agcgtggntg cggacgacgc ccacaaagcc attgtatgta gttttanttc agctgcaaan | 60 |
| aataccncca gcatccacct tactaaccag catatgcaga ca | 102 |

<210> SEQ ID NO 182
<211> LENGTH: 337
<212> TYPE: DNA
<213> ORGANISM: Homo sapien
<220> FEATURE:
<221> NAME/KEY: misc_feature
<222> LOCATION: (1)...(337)
<223> OTHER INFORMATION: n = A,T,C or G

<400> SEQUENCE: 182

| | |
|---|---|
| tcgagcggtc gcccgggcag gtctgggcgg atagcaccgg gcatattttg gaatggatga | 60 |
| ggtctggcac cctgagcagc ccagcgagga cttggtctta gttgagcaat ttggctagga | 120 |
| ggatagtatg cagcacggtt ctgagtctgt gggatagctg ccatgaagna acctgaagga | 180 |
| ggcgctggct ggtangggtt gattacaggg ctgggaacag ctcgtacact tgccattctc | 240 |
| tgcatatact ggntagtgag cgagcctggc gctcttctt tgcgctgagc taaagctaca | 300 |
| tacaatggct ttgnggacct cggccgcgac cacgctt | 337 |

<210> SEQ ID NO 183
<211> LENGTH: 374
<212> TYPE: DNA
<213> ORGANISM: Homo sapien

<400> SEQUENCE: 183

| | |
|---|---|
| tcgagcggcc gcccgggcag gtccattttc tccctgacgg tcccacttct ctccaatctt | 60 |
| gtagttcaca ccattgtcat gacaccatct agatgaatca catctgaaat gaccacttcc | 120 |

```
aaagcctaag cactggcaca acagtttaaa gcctgattca gacattcgtt cccactcatc      180
tccaacggca taatgggaaa ctgtgtaggg gtcaaagcac gagtcatccg taggttggtt      240
caagccttcg ttgacagaag ttgcccacgg taacaacctc ttcccgaacc ttatgcctct      300
gctggtcttt caagtgcctc cactatgatg ttgtaggtgg cacctctggt gaggacctcg      360
gccgcgacca cgct                                                        374
```

```
<210> SEQ ID NO 184
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G

<400> SEQUENCE: 184
```

```
agcgtggttt gcggccgagg tcctcaccan aggtgccacc tacaacatca tagtggaggc       60
actgaaagac cagcagaggc ataaggttcg ggaagaggtt gttaccgtgg caactctgt       120 caacgaaggc ttgaaccaac ctacggatga ctcgtgcttt gacccctaca cagnttccca      180
ttatgccgtt ggagatgagt gggaacgaat gtctgaatca ggctttaaac tgttgtgcca      240
gtgcttangc tttggaagtg gtcatttcag atgtgattca tctanatggt gtcatgacaa      300
tggtgngaac tacaagattg gagagaagtg gnaccgtcag ggganaaaat ggacctgccc      360
gggcggcncg ctcga                                                       375
```

```
<210> SEQ ID NO 185
<211> LENGTH: 148
<212> TYPE: DNA
<213> ORGANISM: Homo sapien
<220> FEATURE:
<221> NAME/KEY: misc_feature
<222> LOCATION: (1)...(148)
<223> OTHER INFORMATION: n = A,T,C or G

<400> SEQUENCE: 185
```

```
agcgtggtcg cggccgaggt ctggcttnct gctcangtga ttatcctgaa ccatccaggc       60
caaataagcg ccggctatgc ccctgnattg gattgccaca cggctcacat tgcatgcaag      120
tttgctgagc tgaaggaaaa gattgatc                                         148
```

```
<210> SEQ ID NO 186
<211> LENGTH: 397
<212> TYPE: DNA
<213> ORGANISM: Homo sapien
<220> FEATURE:
<221> NAME/KEY: misc_feature
<222> LOCATION: (1)...(397)
<223> OTHER INFORMATION: n = A,T,C or G

<400> SEQUENCE: 186
```

```
tcgagcggcc gcccgggcag gtccaattga acaaacagt tctgagaccg ttcttccacc        60
actgattaag agtggggngg cgggtattag ggataatatt catttagcct tctgagcttt      120
ctgggcagac ttggtgacct tgccagctcc agcagccttc tggtccactg ctttgatgac      180
acccaccgca actgtctgtc tcatatcacg aacagcaaag cgacccaaag gtggatagtc      240
tgagaagctc tcaacacaca tgggcttgcc aggaaccata tcaacaatgg gcagcatcac      300
cagacttcaa gaatttaagg gccatcttcc agcttttac cagaacggcg atcaatcttt       360
```
tccttcagct cagcaaactt gcatgcaatg tgagccg        397

<210> SEQ ID NO 187
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 187
tcgagcggcc gcccgggcag gtccagaggg ctgtgctgaa gtttgctgct gccactggag        60
ccactccaat tgctggccgc ttcactcctg gaaccttcac taaccagatc caggcagcct      120
tccgggagcc acggcttctt gtggntactg accccagggc tgaccaccag cctctcacgg      180
aggcatctta tgttaaccta cctaccattg cgctgtgtaa cacagattct cctctgcgct      240
atgtggacat tgccatccca tgcaacaaca agggagctca ctcagngggg tttgatgtgg      300
tggatgctgg ctcgggaagt tctgcgcatg cgtggcacca tttcccgtga acacccatgg      360
gangncatgc ctgatctgga cttctacaga gatcctgaag agattgaaaa agaagaacag      420
gctgnttgct ganaaagcaa gtgaccaagg angaaatttc angggtgaaa nggactgctc      480
ccgctcctga attcactgct actcaacctg angntgcaga ctggtcttga aggngnacan      540
gggccctctg ggcctattta agcancttcg gtcgcgaaca cgnt                       584

<210> SEQ ID NO 188
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 188
agcgtgngtc gcggccgagg tgctgaatag gcacagaggg cacctgtaca ccttcagacc        60
agtctgcaac ctcaggctga gtagcagtga actcaggagc gggagcagtc cattcaccct      120
gaaattcctc cttggncact gccttctcag cagcagcctg ctcttctttt tcaatctctt      180
caggatctct gtagaagtac agatcaggca tgacctccca tgggtgttca cgggaaatgg      240
tgccacgcat gcgcagaact tcccgagcca gcatccacca catcaaaccc actgagtgag      300
ctcccttgtt gttgcatggg atgggcaatg tccacatagc gcagaggaga atctgtgtta      360
cacagcgcaa tggtaggtag gttaacataa gatgcctccg cgagaagctg gtggtcagcc      420
ctggggtcaa gtaaccacaa gaagccgtgg ctcccggaag gctgcctgga tctggttagt      480
gaaggntcca ggagtgaagc ggccaacaat tggagtggct tcagtggcaa gcagcaaact      540
tcagcacaag ccctctggac ctgcccggcg gccgctcga                             579

<210> SEQ ID NO 189
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 189
tcgagcggcc gcccgggcag gtccattttc tccctgacgg ncccacttct ctccaatctt        60

-continued

| | |
|---|---|
| gtagttcaca ccattgtcat ggcaccatct agatgaatca catctgaaat gaccacttcc | 120 |
| aaagcctaag cactggcaca acagtttaaa gcctgattca gacattcgtt cccactcatc | 180 |
| tccaacggca taatgggaaa ctgtgtaggg gtcaaagcac gagtcatccg taggttggtt | 240 |
| caagccttcg ttgacagagt tgcccacggt aacaacctcn tccccgaacc ttatgcctct | 300 |
| gctgggcttt cagngcctcc actatgatgn tgtaggggggg cacctctggn gangacctcg | 360 |
| gccgcgacca cgct | 374 |

<210> SEQ ID NO 190
<211> LENGTH: 373
<212> TYPE: DNA
<213> ORGANISM: Homo sapien
<220> FEATURE:
<221> NAME/KEY: misc_feature
<222> LOCATION: (1)...(373)
<223> OTHER INFORMATION: n = A,T,C or G

<400> SEQUENCE: 190

| | |
|---|---|
| agcgtggtcg cggccgaggt cctcaccaga ggtgccacct acaacatcat agtggaggca | 60 |
| ctgaaagacc agcagaggca taaggctcgg gaagaggttg ttaccgtggg caactctgtc | 120 |
| aacgaaggct tgaaccaacc tacgatgac tcgtgctttg acccctacac agtttcccat | 180 |
| tatgccgttg gagatgagtg ggaacgaatg tctgaatcag gctttaaact gttgtgccag | 240 |
| tgcttangct ttggaagtgg gtcatttcag atgtgattca tctagatggt gccatgacaa | 300 |
| tggngngaac tacaagattg gagagaagtg gnaccgncag ggagaaaatg gacctgcccg | 360 |
| ggcggccgct cga | 373 |

<210> SEQ ID NO 191
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 191

| | |
|---|---|
| agcgtggtcg cggccgaggt ccacatcggc agggtcggag ccctggccgc catactcgaa | 60 |
| ctggaatcca tcggtcatgc tctcgccgaa ccagacatgc ctcttgtcct tggggttctt | 120 |
| gctgatgtac cagttcttct gggccacact gggctgagtg gggtacacgc aggtctcacc | 180 |
| agtctccatg ttgcagaaga ctttgatggc atccaggntg caaccttggt tgggggtcaat | 240 |
| ccagtactct ccactcttcc agccagagtg gcacatcttg aggtcacggc aggtgcggnc | 300 |
| gggggntttt gcggctgccc tctggncttc ggntgtnctc natctgctgg ctca | 354 |

<210> SEQ ID NO 192
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 192

| | |
|---|---|
| tcgagcggcc gcccgggcag gtctcgcggt cgcactggtg atgctggtcc tgttggtccc | 60 |
| cccggccctc ctggacctcc tggccccct ggtcctccca gcgctggttt cgacttcagc | 120 |

```
ttcctgcccc agccacctca agagaaggct cacgatggtg gccgctacta ccgggctgat      180
gatgccaatg tggttcgtga ccgtgacctc gaggtggaca ccaccctcaa gagcctgagc      240
cagcagatcg agaacatccg gagcccagag ggcagncgca agaacccgc ccgcacctgc      300 cgtgacctca agatgtgcca ctctgactgg aagagtggag agtactggat tgaccccaac      360
caagctgcaa cctggatgcc atcaaagtct tctgcaacat ggagactggt gagacctgcg      420
tgtaccccac tcagcccagt gtggcccaaa agaactggta catcagcaag aaccccaagg      480
acaagaagca tgtctggttc ggcgagaaca tgaccgatgg attccagttc gagtatggcg      540
ggcagggctc cgaccctgcc gatggggacc ttggccgcga acacgct                    587
```

<210> SEQ ID NO 193
<211> LENGTH: 98
<212> TYPE: DNA
<213> ORGANISM: Homo sapien
<220> FEATURE:
<221> NAME/KEY: misc_feature
<222> LOCATION: (1)...(98)
<223> OTHER INFORMATION: n = A,T,C or G

<400> SEQUENCE: 193

```
agcgtggnng cggccgaggt ataaatatcc agnccatatc ctccctccac acgctganag      60
atgaagctgt ncaaagatct cagggtggan aaaaccat                              98
```

<210> SEQ ID NO 194
<211> LENGTH: 240
<212> TYPE: DNA
<213> ORGANISM: Homo sapien

<400> SEQUENCE: 194

```
tcgagcggcc gcccgggcag gtccttcaga cttggactgt gtcacactgc caggcttcca      60
gggctccaac ttgcagacgg cctgttgtgg gacagtctct gtaatcgcga aagcaaccat     120
ggaagacctg ggggaaaaca ccatggtttt atccaccctg agatctttga acaacttcat     180
ctctcagcgt gcggagggag gctctggact ggatatttct acctcggccg cgaccacgct     240
```

<210> SEQ ID NO 195
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 195

```
cgagcgggcg accgggcagg tncagactcc aatccanana accatcaagc cagatgtcag      60
aagctacacc atcacaggtt tacaaccagg cactgactac aaganctacc tgcacacctt     120
gaatgacaat gctcggagct cccctgtggt catcgacgcc tccactgcca ttgatgcacc     180
atccaacctg cgtttcctgg ccaccacacc caattccttg ctggtatcat ggcagccgcc     240
acgtgccagg attaccggta catcatcnag tatganaagc ctgggcctcc tcccagagaa     300
gnggtccctc ggccccgccc tgntgtccca naggntacta ttactgngcc ngcaaccggc     360
aaccgatatc nattttgnca ttggccttca acaataatta                           400
```

<210> SEQ ID NO 196
<211> LENGTH: 494
<212> TYPE: DNA
<213> ORGANISM: Homo sapien

```
<220> FEATURE:
<221> NAME/KEY: misc_feature
<222> LOCATION: (1)...(494)
<223> OTHER INFORMATION: n = A,T,C or G

<400> SEQUENCE: 196
agcgtggttc gcggccgang tcctgtcaga gtggcactgg tagaagttcc aggaaccctg      60
aactgtaagg gttcttcatc agngccaaca ggatgacatg aaatgatgta ctcagaagtg     120
tcctggaatg gggcccatga gatggttgtc tgagagagag cttcttgncc tgtcttttc     180 cttccaatca ggggctcgct cttctgatta ttcttcaggg caatgacata aattgtatat     240
tcgggtcccg gntccaggcc agtaatagta ncctctgtga caccagggcg gngccgaggg     300
accacttctc tgggaggaga cccaggcttc tcatacttga tgatgtaacc ggtaatcctg     360
gcacgtggcg gctgccatga taccagcaag gaattggggt gtggtggcca ggaaacgcag     420
gttggatggn gcatcaatgg cagtggaggc cgtcgatgac cacaggggga gctccgacat     480
tgtcattcaa ggtg                                                      494

<210> SEQ ID NO 197
<211> LENGTH: 118
<212> TYPE: DNA
<213> ORGANISM: Homo sapien
<220> FEATURE:
<221> NAME/KEY: misc_feature
<222> LOCATION: (1)...(118)
<223> OTHER INFORMATION: n = A,T,C or G

<400> SEQUENCE: 197
agcgtggncg cggccgaggt gcagcgcggg ctgtgccacc ttctgctctc tgcccaacga      60
taaggagggt ncctgccccc aggagaacat taactntccc cagctcggcc tctgccgg     118

<210> SEQ ID NO 198
<211> LENGTH: 403
<212> TYPE: DNA
<213> ORGANISM: Homo sapien
<220> FEATURE:
<221> NAME/KEY: misc_feature
<222> LOCATION: (1)...(403)
<223> OTHER INFORMATION: n = A,T,C or G

<400> SEQUENCE: 198
tcgagcggcc gcccgggcag gttttttttg ctgaaagtgg ntactttatt ggntgggaaa      60
gggagaagct gtggtcagcc caagagggaa tacagagncc cgaaaaaggg gagggcaggt     120
gggctggaac cagacgcagg gccaggcaga aactttctct cctcactgct cagcctggtg     180
gtggctggag ctcanaaatt gggagtgaca caggacacct tcccacagcc attgcggcgg     240
catttcatct ggccaggaca ctggctgtcc acctggcact ggtcccgaca gaagcccgag     300
ctggggaaag ttaatgttca cctggggca ggaaccctcc ttatcattgn gcagagagca     360
gaaggtggca cagcccgcgc tgcacctcgg ccgcgaccac gct                      403

<210> SEQ ID NO 199
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 199
```

```
tcgagcggcc gcccgggcag gtccaccata agtcctgata caaccacgga tgagctgtca    60
ggagcaaggt tgatttcttt cattggtccg gncttctcct tgggggncac ccgcactcga   120
tatccagtga gctgaacatt gggtggcgtc cactgggcgc tcaggct                 167

<210> SEQ ID NO 200
<211> LENGTH: 252
<212> TYPE: DNA
<213> ORGANISM: Homo sapien
<220> FEATURE:
<221> NAME/KEY: misc_feature
<222> LOCATION: (1)...(252)
<223> OTHER INFORMATION: n = A,T,C or G

<400> SEQUENCE: 200
tcgagcggtt cgcccgggca ggtccaccac acccaattcc ttgctggtat catggcagcc    60
gccacgtgcc aggattaccg gctacatcat caagtatgag aagcctgggt ctcctcccag   120
agaagcggtc cctcggcccc gccctggtgt cacagaggct actattactg gcctggaacc   180
gggaaccgaa tatacaattt atgtcattgn cctgaagaat aatcannaan agcgancccc   240
tgattggaag ga                                                       252

<210> SEQ ID NO 201
<211> LENGTH: 91
<212> TYPE: DNA
<213> ORGANISM: Homo sapien

<400> SEQUENCE: 201
agcgtggtcg cggccgaggt tgtacaagct tttttttttt tttttttttt tttttttttt    60
tttttttttt tttttttttt tttttttttt t                                   91

<210> SEQ ID NO 202
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 202
tcgagcggnc gcccgggcag gtctgccaac accaagattg gcccccgccg catccacaca    60
gtccgtgtgc ggggaggtaa caagaaatac cgtgccctga ggttggacgt ggggaatttc   120
tcctggggct cagagtgttg tactcgtaaa acaaggatca tcgatgttgt ctacaatgca   180
tctaataacg agctggttcg taccaagacc ctggtgaaga attgcatcgt gctcatcgac   240
agcacaccgt accgacagtg gtacgagtcc cactatgcgc tgcccctggg ccgcaagaag   300
ggagccaagc tgactcctga ggaagaagag attttaaaca aaaaacgatc taanaaaaaa   360
aaaacaat                                                            368

<210> SEQ ID NO 203
<211> LENGTH: 340
<212> TYPE: DNA
<213> ORGANISM: Homo sapien

<400> SEQUENCE: 203
agcgtggtcg cggccgaggt gaaatggtat tcagcttcct ggcacttctg gtcagcaacc    60
cagtgttggg caacaaatga tctttgagga acatggtttt aggcggacca caccgcccac   120
aacggccacc cccataaggc ataggccaag accatacccg ccgaatgtag gacaagaagc   180
```

```
tctctctcag acaaccatct catgggcccc attccaggac acttctgagt acatcatttc      240
atgtcatcct gttggcactg atgaagaacc cttacagttc agggttcctg gaacttctac      300
cagtgccact ctgacaggac ctgcccgggc ggccgctcga                            340
```

<210> SEQ ID NO 204
<211> LENGTH: 341
<212> TYPE: DNA
<213> ORGANISM: Homo sapien

<400> SEQUENCE: 204

```
tcgagcggcc gcccgggcag gtcctgtcag agtggcactg gtagaagttc caggaaccct       60
gaactgtaag ggttcttcat cagtgccaac aggatgacat gaaatgatgt actcagaagt      120
gtcctggaat ggggcccatg agatggttgt ctgagagaga gcttcttgtc ctacattcgg      180
cgggtatggt cttggcctat gccttatggg ggtggccgtt gtgggcggtg tggtccgcct      240
aaaaccatgt tcctcaaaga tcatttgttg cccaacactg ggttgctgac cagaagtgcc      300
aggaagctga ataccatttc acctcggccg cgaccacgct a                          341
```

<210> SEQ ID NO 205
<211> LENGTH: 770
<212> TYPE: DNA
<213> ORGANISM: Homo sapien
<220> FEATURE:
<221> NAME/KEY: misc_feature
<222> LOCATION: (1)...(770)
<223> OTHER INFORMATION: n = A,T,C or G

<400> SEQUENCE: 205

```
tcgagcggcc gcccgggcag gtctcccttc ttgcggccca ggggcagcgc atagtgggac       60
tcgtaccact gtcggtacgg tgtgctgtcg atgagcacga tgcaattctt caccagggtc      120
ttggtacgaa ccagctcgtt attagatgca ttgtagacaa catcgatgat ccttgtttta      180
cgagtacaac actctgagcc ccaggagaaa ttccccacgt ccaacctcag ggcacggtat      240
ttcttgttac ctccccgcac acggactgtg tggatgcggc ggggccaag  ctgactcctg      300 aggaagaaga gattttaaac aaaaaacgat ctaaaaaaat tcagaagaaa tatgatgaaa      360
ggaaaaagaa tgccaaaatc agcagtctcc tggaggagca gttccagcag ggcaagcttc      420
ttgcgtgcat cgcttcaagg ccgggacagt gtgaccgagc agatggctat gtgctagagg      480
gcaaagaagt ggagttctat cttaagaaaa tcagggccca gaatggtgng tcttcaacta      540
atccaagggg gagtttcaga ccagtgcaat cagcaaaaac attgatactg ntggccaaat      600
ttattggtgc agggcttgca cantangann ggctgggtct tggggcttgg attggnacaa      660
gctttggcag cctttctttt ggttttgcca aaaaccttt  gntgaagang anacctnggg      720
cggacccctt aaccgattcc acnccnggng gcgttctang gnccncttg                  770
```

<210> SEQ ID NO 206
<211> LENGTH: 810
<212> TYPE: DNA
<213> ORGANISM: Homo sapien
<220> FEATURE:
<221> NAME/KEY: misc_feature
<222> LOCATION: (1)...(810)
<223> OTHER INFORMATION: n = A,T,C or G

<400> SEQUENCE: 206

```
agcgtggtcg cggccgaggt ctgctgcttc agcgaagggt ttctggcata accaatgata       60
```

-continued

| | |
|---|---|
| aggctgccaa agactgttcc aataccagca ccagaaccag ccactcctac tgttgcagca | 120 |
| cctgcaccaa taaatttggc agcagtatca atgtctctgc tgattgcact ggtctgaaac | 180 |
| tcccttttgga ttagctgaga cacaccattc tgggccctga ttttcctaag atagaactcc | 240 |
| aactctttgc cctctagcac atagccatct gctcggtcac actgtcccgg ccttgaagcg | 300 |
| atgcacgcaa gaagcttgcc ctgctggaac tgctcctcca ggagactgct gattttggca | 360 |
| ttcttttttcc tttcatcata tttcttctga atttttttag atcgtttttt gtttaaaatc | 420 |
| tcttcttcct caggagtcag cttggccccc gccgcatcca cacagtccgt gtgcggggag | 480 |
| gtaacaagaa ataccgtgcc ctgaggttgg acgtggggaa tttctcctgg ggctcagagt | 540 |
| ggtgtactcg taaaacaagg atcatcgatg gtgnctacaa tgcatctaat aacgagctgg | 600 |
| gtcggaccca aagaacctgg ngaanaaatg gatcgnctca tcgacaggac accgtacccg | 660 |
| acagggnac gantcccact atgcgcttgc ccctgggccg caanaaagga aaactgcccg | 720 |
| ggcggccntc gaaagcccaa ttntggaaaa aatccatcac actgggnggc cngtcgagca | 780 |
| tgcatntana ggggcccatt ccccctnann | 810 |

<210> SEQ ID NO 207
<211> LENGTH: 257
<212> TYPE: DNA
<213> ORGANISM: Homo sapien

<400> SEQUENCE: 207

| | |
|---|---|
| tcgagcggcc gcccgggcag gtccccaacc aaggctgcaa cctggatgcc atcaaagtct | 60 |
| tctgcaacat ggagactggt gagacctgcg tgtaccccac tcagcccagt gtggcccaga | 120 |
| agaactggta catcagcaag aaccccaagg acaagaggca tgtctggttc ggcgagagca | 180 |
| tgaccgatgg attccagttc gagtatggcg gccagggctc cgaccctgcc gatgtggacc | 240 |
| tcggccgcga ccacgct | 257 |

<210> SEQ ID NO 208
<211> LENGTH: 257
<212> TYPE: DNA
<213> ORGANISM: Homo sapien

<400> SEQUENCE: 208

| | |
|---|---|
| agcgtggtcg cggccgaggt ccacatcggc agggtcggag ccctggccgc catactcgaa | 60 |
| ctggaatcca tcggtcatgc tctcgccgaa ccagacatgc ctcttgtcct tggggttctt | 120 |
| gctgatgtac cagttcttct gggccacact gggctgagtg gggtacacgc aggtctcacc | 180 |
| agtctccatg ttgcagaaga ctttgatggc atccaggttg cagccttggt tggggacctg | 240 |
| cccgggcggc cgctcga | 257 |

<210> SEQ ID NO 209
<211> LENGTH: 747
<212> TYPE: DNA
<213> ORGANISM: Homo sapien
<220> FEATURE:
<221> NAME/KEY: misc_feature
<222> LOCATION: (1)...(747)
<223> OTHER INFORMATION: n = A,T,C or G

<400> SEQUENCE: 209

| | |
|---|---|
| tcgagcggcc gcccgggcag gtccaccaca cccaattcct tgctggtatc atggcagccg | 60 |
| ccacgtgcca ggattaccgg ctacatcatc aagtatgaga agcctgggtc tcctcccaga | 120 |
| gaagtggtcc ctcggccccg ccctggtgtc acagaggcta ctattactgg cctggaaccg | 180 |

```
ggaaccgaat atacaatttta tgtcattgcc ctgaagaata atcagaagag cgagcccctg    240
attggaagga aaaagacaga cgagcttccc caactggtaa cccttccaca ccccaatctt    300
catggaccag agatcttgga tgttccttcc acagttcaaa agaccccttt cgtcacccac    360
cctgggtatg acactggaaa tggtattcag cttcctggca cttctggtca gcaacccagt    420
gttgggcaac aaatgatctt tgaggaacat ggntttaggc ggaccacacc gcccacaacg    480
gccaccccca taaggcatag gccaagacca tacccgccga atgtaggaca agaagctntn    540
tntcanacac catntnatgg gccccattcc aggacacttc tgagtacatc atttatgnca    600
tctgtggcac ttgatgaaaa cccttacagt tcagggttct ggaacttta ccaggcctnt    660 tacaggactn ggccggacnc cttaagccna ttncaccctg gggcgttcta nggtcccact    720
cgnncactgg ngaaaatggc tactgtn                                        747
```

<210> SEQ ID NO 210
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 210

```
agcgtggtcg cggccgaggt ccactagagg tctgtgtgcc attgcccagg cagagtctct     60
gcgttacaaa ctcctaggag ggcttgctgt gcggagggcc tgctatggtg tgctgcggtt    120
catcatggaa agtgggggcca aaggctgcga ggttgtggtg tctgngaaac tccnaggaca    180
ngagggctaa attccatgaa gtttgtggat ggcctgatga tccacaatcg gagaccctgt    240
taactactac cgtctnaccn cctgctgtnc ncccccnttt ctgctnaana catngggntn    300
ntncttgncc ntccttgggt ngaanatnna atngcctncc cnttcntanc nctactngnt    360
ccananttgg cctttaaana atccnccttg ccttnnncac tgttcanntn tttnntcgta    420
aaccctatna nttnnattan atnntnnnnn nctcaccccc ctcntcattn anccnatang    480
ctnnnaantc cttnanncct cccncccnnt ncnctcntac tnantncttc tnncccatta    540
cnnagctctt tcntttaana taatgnngcc nngctctnca tntctacnat ntgnnnaatn    600
ccccncnccc cnancgnntt tttgacctnn naacctcctt tcctcttccc tncnnaaatt    660
ncnnanttcc ncnttccnnc ntttcggntn ntccatnct ttccannnct tcantctanc    720
ncnctncaac ttattttcct ntcatccctt nttctttaca nncccctnn tctactcnnc    780 nnttncatta natttgaaac tnccacnnct anttncctcn ctctacnntt ttattttncg    840
ntcnctctac ntaatantt aatnanttnt cn                                   872
```

<210> SEQ ID NO 211
<211> LENGTH: 517
<212> TYPE: DNA
<213> ORGANISM: Homo sapien
<220> FEATURE:
<221> NAME/KEY: misc_feature
<222> LOCATION: (1)...(517)
<223> OTHER INFORMATION: n = A,T,C or G

<400> SEQUENCE: 211

```
tcgagcggcc gcccgggcag gtctgccaag gagaccctgt tatgctgtgg ggactggctg     60
gggcatggca ggcggctctg gcttccacc cttctgttct gagatggggg tggtgggcag    120
```

```
tatctcatct ttgggttcca caatgctcac gtggtcaggc aggggcttct tagggccaat      180
cttaccagtt gggtcccagg gcagcatgat cttcaccttg atgcccagca caccctgtct      240
gagcaacacg tggcgcacaa gcagtgtcaa cgtagtaagt taacagggtc tccgctgtgg      300
atcatcaggc catccacaaa cttcatggat ttagccctct gtcctcggag tttcccagac      360
accacaacct cgcagccttt ggccccactc tccatgatga accgcagcac accatagcag      420
gccctccgca caagcaagcc ctcctaagaa tttgtaacgc ananactctg ctggcaatgg      480
cacacaaacc tctagtggac ctcggncgcg accacgc                              517
```

<210> SEQ ID NO 212
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 212

```
tcgagcggcc gcccgggcag gtctggtcca ggatagcctg cgagtcctcc tactgctact      60
ccagacttga catcatatga atcatactgg ggagaatagt tctgaggacc agtagggcat     120
gattcacaga ttccagggg gccaggagaa ccaggggacc ctggttgtcc tggaatacca      180
gggtcaccat ttctcccagg ataccagga gggcctggat ctcccttggg gccttgaggt      240
ccttgaccat taggagggcg agtaggagca gttggaggct gtgggcaaac tgcacaacat      300
tctccaaatg gaatttctgg gttggggcag tctaattctt gatccgtcac atattatgtc      360
atcgcagaga acgatcctg agtcacagac acatatttgg catggttctg gcttccagac       420
atctctatcc gncataggac tgaccaagat gggaacatcc tccttcaaca agcttnctgt      480
tgtgccaaaa ataatagtgg gatgaagcag accgagaagt anccagctcc cctttttgca      540
caaagcntca tcatgtctaa atatcagaca tgagacttct ttgggcaaaa aaggagaaaa     600
agaaaaagca gttcaaagta nccnccatca agttggttcc ttgcccnttc agcacccggg      660
ccccgttata aaacacctng ggccggaccc ccctt                                695
```

<210> SEQ ID NO 213
<211> LENGTH: 804
<212> TYPE: DNA
<213> ORGANISM: Homo sapien
<220> FEATURE:
<221> NAME/KEY: misc_feature
<222> LOCATION: (1)...(804)
<223> OTHER INFORMATION: n = A,T,C or G

<400> SEQUENCE: 213

```
agcgtggtcg cggccgaggt gttttatgac gggcccggtg ctgaagggca gggaacaact      60
tgatggtgct actttgaact gcttttcttt tctccttttt gcacaaagag tctcatgtct     120
gatatttaga catgatgagc tttgtgcaaa aggggagctg gctacttctc gctctgcttc      180
atcccactat tattttggca caacaggaag ctgttgaagg aggatgttcc catcttggtc      240
agtcctatgc ggatagagat gtctggaagc cagaaccatg ccaaatatgt gtctgtgact      300
caggatccgt tctctgcgat gacataatat gtgacgatca agaattagac tgccccaacc      360
cagaaattcc atttggagaa tgttgtgcag tttgcccaca gcctccaact gctcctactc      420
gccctcctaa tggtcaagga cctcaaggcc ccaagggaga tccaggccct cctggtattc      480
ctgggagaaa tggtgaccct ggtattccag acaaccagg gtcccctggt tctcctggcc       540
```

```
ccctggaat cnggngaatc atgccctact ggtcctcaaa ctattctccc anatgattca      600
tatgatgtca agtctgggat agcnagtang ganggactcg caggctattc tggaccanac     660
ctgccggggg ggcgttcgaa agcccgaatc tgcananntn cnttcacact ggcggccgtc     720
gagctgcttt aaaagggcca ttccnccttt agngnggggg antacaatta ctnggcggcg    780
ttttanancg cgngnctggg aaat                                            804
```

<210> SEQ ID NO 214
<211> LENGTH: 594
<212> TYPE: DNA
<213> ORGANISM: Homo sapien
<220> FEATURE:
<221> NAME/KEY: misc_feature
<222> LOCATION: (1)...(594)
<223> OTHER INFORMATION: n = A,T,C or G

<400> SEQUENCE: 214

```
agcgtggtcg cggccgaggt ccacatcggc agggtcggag ccctggccgc catactcgaa      60
ctggaatcca tcggtcatgc tctcgccgaa ccagacatgc ctcttgtcct tggggttctt     120
gctgatgtac cagttcttct gggccacact gggctgagtg gggtacacgc aggtctcacc     180
agtctccatg ttgcagaaga ctttgatggc atccaggttg cagccttggt tggggtcaat     240
ccagtactct ccactcttcc agtcagagtg gcacatcttg aggtcacggc aggtgcgggc     300
ggggttcttg cggctgccct ctgggctccg gatgttctcg atctgctggc tcaggctctt     360
gagggtggtg tccacctcga ggtcacggtc acgaaccaca ttggcatcat cagcccggta    420
gtagcggcca ccatcgtgag ccttctcttg angtggctgg ggcaggaact gaagtcgaaa    480
ccagcgctgg gaggaccagg gggaccaana ggtccaggaa gggcccgggg gggaccaaca    540
ggaccagcat caccaagtgc gacccgcgag aacctgcccg gccgnccgct cgaa          594
```

<210> SEQ ID NO 215
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 215

```
tcgagcgnnc gcccgggcag gtctcgcggt cgcactggtg atgctggtcc tgttggtccc      60
cccggccctc ctggacctcc tggtccccct ggtcctccca gcgctggttt cgacttcagc    120
ttcctgcccc agccacctca agagaaggct cacgatggtg gccgctacta ccgggctgat    180
gatgccaatg tggttcgtga ccgtgacctc gaggtggaca ccaccctcaa gagcctgagc    240
cagcagatcg agaacatccg gagcccagag ggcagccgca agaaccccgc ccgcacctgc    300
cgtgacctca agatgtgcca ctctgactgg aagagtggag agtactggat tgaccccaac    360
caaggctgca acctggatgc catcaaagtc ttctgcaaca tggagactgg tgagacctgc    420
gtgtacccca ctcagcccag tgtggcccag aagaactggt acatcagcaa gaaccccaag    480
gacaagaggc atgtctggtt cggcgagagc atgaccgatg gattccagtt cgagtatggc    540
ggccagggct cccacccgtc cgatgtggac ctccggccgc gaccacccct              590
```

<210> SEQ ID NO 216
<211> LENGTH: 801
<212> TYPE: DNA

```
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 216
tngagcggcc gcccgggcag gntgnnaacg ctggtcctgc tggtcctcct ggcaaggctg      60
gtgaagatgg tcaccctgga aaacccggac gacctggtga gagaggagtt gttggaccac     120
aggtgctcg tggtttccct ggaactcctg gacttcctgg cttcaaaggc attaggggac     180
acaatggtct ggatggattg aagggacagc ccggtgctcc tggtgtgaag ggtgaacctg     240
gtgcccctgg tgaaaatgga actccaggtc aaacaggagc ccgtgggctt cctggtgaga     300
gaggaccgtg ttggtgcccc tggcccanac ctcggccgcg accacgctaa gcccgaattt     360
ccagcacact ggnggccgtt actantggat ccgagctcgg taccaagctt ggcgtaatca     420
tggtcatagc tgtttcctgn gtgaaattgt tatccgctca caatttcaca cancatacga     480
agccggaaag cataaagtgt aaagccttgg ggtgctaatg agtgagctaa ctcncattaa     540
attgcgttgc gctcactgcc cgcttttcca nnngggaaac cntggcntng ccngcttgcn     600
ttaantgaaa tccgccnacc cccgggaaa agncggtttg cngtattggg gcncttttc     660
cctttcctcg gnttacttga nttantgggc tttggncgnt tcgggttgng gcgancnggt     720
tcaacntcac nccaaaggng gnaaacggt tttcccanaa tccgggggnt ancccaangn     780
aaaacatnng ncnaangggc t                                                801

<210> SEQ ID NO 217
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 217
agcgtggttn gcggccgagg tctgggccag gggcaccaac acgtcctctc tcaccaggaa      60
gcccacgggc tcctgtttga cctggagttc cattttcacc aggggcacca ggttcaccct     120
tcacaccagg agcaccgggc tgtcccttca atccatncag accattgtgn ccctaatgc     180
ctttgaagcc aggaagtcca ggagttccag ggaaaccacc gagcaccctg tggtccaaca     240
actcctctct caccaggtcg tccgggtttt ccagggtgac catcttcacc agccttgcca     300
ggaggaccag caggaccagc gttaccaacc tgcccgggcg gccgctcga                  349

<210> SEQ ID NO 218
<211> LENGTH: 372
<212> TYPE: DNA
<213> ORGANISM: Homo sapien

<400> SEQUENCE: 218
tcgagcggcc gcccgggcag gtccattttc tccctgacgg tcccacttct ctccaatctt      60
gtagttcaca ccattgtcat ggcaccatct agatgaatca catctgaaat gaccacttcc     120
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ttgacagagt tgcccacggt aacaacctct tcccgaacct tatgcctctg     300
ctggtctttc agtgcctcca ctatgatgtt gtaggtggca cctctggtga ggacctcggc     360
```

```
cgcgaccacg ct                                                            372
```

<210> SEQ ID NO 219
<211> LENGTH: 374
<212> TYPE: DNA
<213> ORGANISM: Homo sapien

<400> SEQUENCE: 219

```
agcgtggtcg cggccgaggt cctcaccaga ggtgccacct acaacatcat agtggaggca    60
ctgaaagacc agcagaggca taaggttcgg gaagaggttg ttaccgtggg caactctgtc   120
aacgaaggct tgaaccaacc tacggatgac tcgtgctttg acccctacac agtttcccat   180
tatgccgttg gagatgagtg ggaacgaatg tctgaatcag gctttaaact gttgtgccag   240
tgcttaggct ttggaagtgg tcatttcaag atgtgattca tctagatggt gccatgacaa   300
tggtgtgaac tacaagattg gagagaagtg ggaccgtcag ggagaaaatg gacctgcccg   360
ggccggccgc tcga                                                      374
```

<210> SEQ ID NO 220
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 220

```
tcgagcgnnc gcccgggcag gtccagtagt gccttcggga ctgggttcac ccccaggtct    60
gcggcagttg tcacagcgcc agccccgctg gcctccaaag catgtgcagg agcaaatggc   120
accgagatat tccttctgcc actgttctcc tacgtggtat gtcttcccat catcgtaaca   180
cgttgcctca tgagggtcac acttgaattc tccttttccg ttcccaagac atgtgcagct   240
catttggctg gctctatagt ttggggaaag tttgttgaaa ctgtgccact gacctttact   300
tcctccttct ctactggagc tttcgtacct tccacttctg ctgttggtaa aatggtggat   360
cttctatcaa tttcattgac agtacccact tctcccaaac atccaggaa atagtgattt    420
cagagcgatt aggagaacca aattatgggg cagaaataag gggcttttcc acaggttttc   480
ctttggagga agatttcagt ggtgacttta aaagaatact caacagtgtc ttcatcccca   540
tagcaaaaga agaaacngta aatgatggaa ngcttctgga gatgccnnca tttaagggac   600
ncccagaact tcaccatcta caggacctac ttcagtttac annaagncac atantctgac   660
tcanaaagga cccaagtagc nccatggnca gcacttttag cctttcccct ggggaaaann   720
ttacnttctt aaanccntgg ccnngacccc cttaagncca aattntggaa aanttccntn   780
cnnctggggg gcngttcnac atgcntttna agggcccaat tncccccnt              828
```

<210> SEQ ID NO 221
<211> LENGTH: 476
<212> TYPE: DNA
<213> ORGANISM: Homo sapien

<400> SEQUENCE: 221

```
tcgagcggcc gcccgggcag gtgtcggagt ccagcacggg aggcgtggtc ttgtagttgt    60
tctccggctg cccattgctc tcccactcca cggcgatgtc gctgggatag aagcctttga   120
ccaggcaggt caggctgacc tggttcttgg tcatctcctc ccgggatggg ggcagggtgt   180
```

-continued

| | |
|---|---|
| acacctgtgg ttctcggggc tgcccttttgg cttttggagat ggttttctcg atggggggctg | 240 |
| ggagggcttt gttggagacc ttgcacttgt actccttgcc attcagccag tcctggtgca | 300 |
| ggacggtgag gacgctgacc acacggtacg tgctgtttgta ctgctcctcc cgcggctttg | 360 |
| tcttggcatt atgcacctcc acgccgtcca cgtaccagtt gaacttgacc tcagggtctt | 420 |
| cgtggctcac gtccaccacc acgcatgtaa cctcagacct cggccgcgac cacgct | 476 |

<210> SEQ ID NO 222
<211> LENGTH: 477
<212> TYPE: DNA
<213> ORGANISM: Homo sapien

<400> SEQUENCE: 222

| | |
|---|---|
| agcgtggtcg cggccgaggt ctgaggttac atgcgtggtg gtggacgtga gccacgaaga | 60 |
| ccctgaggtc aagttcaact ggtacgtgga cggcgtggag gtgcataatg ccaagacaaa | 120 |
| gccgcgggag gagcagtaca acagcacgta ccgtgtggtc agcgtcctca ccgtcctgca | 180 |
| ccaggactgg ctgaatggca aggagtacaa gtgcaaggtc tccaacaaag ccctcccagc | 240 |
| ccccatcgag aaaaccatct ccaaagccaa agggcaagcc cgagaaccca ggtgtaca | 300 |
| ccctgccccc atcccgggag gagatgacca agaaccaggt cagcctgacc tgcctggtca | 360 |
| aaggcttcta tcccagcgac atcgccgtgg agtgggagag caatgggcag ccggagaaca | 420 |
| actacaagac cacgcctccc gtgctggact ccgacacctg cccgggcggc cgctcga | 477 |

<210> SEQ ID NO 223
<211> LENGTH: 361
<212> TYPE: DNA
<213> ORGANISM: Homo sapien

<400> SEQUENCE: 223

| | |
|---|---|
| tcgagcggcc gcccgggcag gttgaatggc tcctcgctga ccaccccggt gctggtggtg | 60 |
| ggtacagagc tccgatgggt gaaaccattg acatagagac tgtccctgtc cagggtgtag | 120 |
| gggcccagct cagtgatgcc gtgggtcagc tggctcagct tccagtacag ccgctctctg | 180 |
| tccagtccag ggcttttggg gtcaggacga tgggtgcaga cagcatccac tctggtggct | 240 |
| gccccatcct tctcaggcct gagcaaggtc agtctgcaac cagagtacag agagctgaca | 300 |
| ctggtgttct tgaacaaggg cataagcaga ccctgaagga cacctcggcc gcgaccacgc | 360 |
| t | 361 |

<210> SEQ ID NO 224
<211> LENGTH: 361
<212> TYPE: DNA
<213> ORGANISM: Homo sapien

<400> SEQUENCE: 224

| | |
|---|---|
| agcgtggtcg cggccgaggt gtccttcagg gtctgcttat gcccttgttc aagaacacca | 60 |
| gtgtcagctc tctgtactct ggttgcagac tgacccttgct caggcctgag aaggatgggg | 120 |
| cagccaccag agtggatgct gtctgcaccc atcgtcctga cccaaaaagc cctggactgg | 180 |
| acagagagcg gctgtactgg aagctgagcc agctgaccca cggcatcact gagctgggcc | 240 |
| cctacaccct ggacagggac agtctctatg tcaatggttt cacccatcgg agctctgtac | 300 |
| ccaccaccag caccggggtg gtcagcgagg agccattcaa cctgcccggg cggccgctcg | 360 |
| a | 361 |

<210> SEQ ID NO 225
<211> LENGTH: 766
<212> TYPE: DNA
<213> ORGANISM: Homo sapien
<220> FEATURE:
<221> NAME/KEY: misc_feature
<222> LOCATION: (1)...(766)
<223> OTHER INFORMATION: n = A,T,C or G

<400> SEQUENCE: 225

| | | | | | |
|---|---|---|---|---|---|
| agcgtggtcg | cggccgaggt | cctgtcagag | tggcactggt | agaagttcca | ggaaccctga | 60 |
| actgtaaggg | ttcttcatca | gtgccaacag | gatgacatga | aatgatgtac | tcagaagtgt | 120 |
| cctggaatgg | ggcccatgag | atggttgtct | gagagagagc | ttcttgtcct | acattcggcg | 180 |
| ggtatggtct | tggcctatgc | cttatggggg | tggccgttgt | gggcggtgtg | gtccgcctaa | 240 |
| aaccatgttc | ctcaaagatc | atttgttgcc | caacactggg | ttgctgacca | gaagtgccag | 300 |
| gaagctgaat | accatttcca | gtgtcatacc | agggtgggt | gacgaaaggg | gtctttttgaa | 360 |
| ctgtggaagg | aacatccaag | atctctggtc | catgaagatt | ggggtgtgga | agggttacca | 420 |
| gttggggaag | ctcgtctgtc | tttttccttc | caatcagggg | ctcgctcttc | tgattattct | 480 |
| tcagggcaat | gacataaatt | gtatattcgg | tcccggttcc | aggccagtaa | tagtagcctc | 540 |
| tgtgacacca | gggcggggcc | gagggaccct | tctnttggaa | gagaccagct | tctcatactt | 600 |
| gatgatgagn | ccggtaatcc | tggcacgtgg | nggttgcatg | atnccaccaa | ggaaatnggn | 660 |
| gggggnggac | ctgcccggcg | gccgttcnaa | agcccaattc | cacacacttg | gnggccgtac | 720 |
| tatggatccc | actcngtcca | acttggngga | atatggcata | acttttt | | 766 |

<210> SEQ ID NO 226
<211> LENGTH: 364
<212> TYPE: DNA
<213> ORGANISM: Homo sapien

<400> SEQUENCE: 226

| | | | | | |
|---|---|---|---|---|---|
| tcgagcggcc | gcccgggcag | gtccttgacc | ttttcagcaa | gtgggaaggt | gtaatccgtc | 60 |
| tccacagaca | aggccaggac | tcgtttgtac | ccgttgatga | tagaatgggg | tactgatgca | 120 |
| acagttgggt | agccaatctg | cagacagaca | ctggcaacat | tgcggacacc | ctccaggaag | 180 |
| cgagaatgca | gagtttcctc | tgtgatatca | agcacttcag | ggttgtagat | gctgccattg | 240 |
| tcgaacacct | gctggatgac | cagcccaaag | gagaagggg | agatgttgag | catgttcagc | 300 |
| agcgtggctt | cgctggctcc | cactttgtct | ccagtcttga | tcagacctcg | gccgcgacca | 360 |
| cgct | | | | | | 364 |

<210> SEQ ID NO 227
<211> LENGTH: 275
<212> TYPE: DNA
<213> ORGANISM: Homo sapien

<400> SEQUENCE: 227

| | | | | | |
|---|---|---|---|---|---|
| agcgtggtcg | cggccgaggt | ctgtcctaca | gtcctcagga | ctctactccc | tcagcagcgt | 60 |
| ggtgaccgtg | ccctccagca | acttcggcac | ccagacctac | acctgcaacg | tagatcacaa | 120 |
| gcccagcaac | accaaggtgg | acaagagagt | tgagcccaaa | tcttgtgaca | aaactcacac | 180 |
| atgcccaccg | tgcccagcac | ctgaactcct | gggggaccg | tcagtcttcc | tcttccccg | 240 |
| catccccctt | ccaaacctgc | ccgggcggcc | gctcg | | | 275 |

<210> SEQ ID NO 228

<211> LENGTH: 275
<212> TYPE: DNA
<213> ORGANISM: Homo sapien

<400> SEQUENCE: 228

| | | | | | |
|---|---|---|---|---|---|
| cgagcggccg | cccgggcagg | tttggaaggg | ggatgcgggg | gaagaggaag | actgacggtc | 60 |
| cccccaggag | ttcaggtgct | gggcacggtg | ggcatgtgtg | agttttgtca | caagatttgg | 120 |
| gctcaactct | cttgtccacc | ttggtgttgc | tgggcttgtg | atctacgttg | caggtgtagg | 180 |
| tctgggtgcc | gaagttgctg | gagggcacgg | tcaccacgct | gctgagggag | tagagtcctg | 240 |
| aggactgtag | gacagacctc | ggccgcgacc | acgct | | | 275 |

<210> SEQ ID NO 229
<211> LENGTH: 40
<212> TYPE: DNA
<213> ORGANISM: Homo sapien
<220> FEATURE:
<221> NAME/KEY: misc_feature
<222> LOCATION: (1)...(40)
<223> OTHER INFORMATION: n = A,T,C or G

<400> SEQUENCE: 229
nggnnggtcc ggncngncag gaccactcnt cttcgaaata    40

<210> SEQ ID NO 230
<211> LENGTH: 208
<212> TYPE: DNA
<213> ORGANISM: Homo sapien

<400> SEQUENCE: 230

| | | | | | |
|---|---|---|---|---|---|
| agcgtggtcg | cggccgaggt | cctcacttgc | ctcctgcaaa | gcaccgatag | ctgcgctctg | 60 |
| gaagcgcaga | tctgttttaa | agtcctgagc | aatttctcgc | accagacgct | ggaagggaag | 120 |
| tttgcgaatc | agaagttcag | tggacttctg | ataacgtcta | atttcacgga | gcgccacagt | 180 |
| accaggacct | gcccgggcgg | ccgctcga | | | | 208 |

<210> SEQ ID NO 231
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 231

| | | | | | |
|---|---|---|---|---|---|
| tcgagcggcc | gcccgggcag | gtcctggtac | tgnggcgctc | cgtgaaatta | gacgttatca | 60 |
| gaagtccact | gaacttctga | ttcgcaaact | tcccttccag | cgtctggtgc | gagaaattgc | 120 |
| tcaggacttt | aaaacagatc | tgcgcttcca | gagcgcagct | atcggtgctt | tgcaggaggc | 180 |
| aagtgaggac | ctcggccgcg | accacgct | | | | 208 |

<210> SEQ ID NO 232
<211> LENGTH: 332
<212> TYPE: DNA
<213> ORGANISM: Homo sapien

<400> SEQUENCE: 232

| | | | | | |
|---|---|---|---|---|---|
| tcgagcggcc | gcccgggcag | gtccacatcg | gcagggtcgg | agccctggcc | gccatactcg | 60 |
| aactggaatc | catcggtcat | gctctcgccg | aaccagacat | gcctcttgtc | cttggggttc | 120 |
| ttgctgatgt | accagttctt | ctgggccaca | ctgggctgag | tggggtacac | gcaggtctca | 180 |

```
ccagtctcca tgttgcagaa gactttgatg gcatccaggt tgcagccttg gttggggtca    240
atccagtact ctccactctt ccagtcagag tggcacatct tgaggtcacg gcaggtgcgg    300
gcggggttct tgacctcggc cgcgaccacg ct                                  332
```

<210> SEQ ID NO 233
<211> LENGTH: 415
<212> TYPE: DNA
<213> ORGANISM: Homo sapien
<220> FEATURE:
<221> NAME/KEY: misc_feature
<222> LOCATION: (1)...(415)
<223> OTHER INFORMATION: n = A,T,C or G

<400> SEQUENCE: 233

```
gtgggnttga acccntttna nctccgcttg gtaccgagct cggatccact agtaacggcc    60
gccagtgtgc tggaattcgg cttagcgtgg tcgcggccga ggtcaagaac cccgcccgca    120
cctgccgtga cctcaagatg tgccactctg actggaagag tggagagtac tggattgacc    180
ccaaccaagg ctgcaacctg gatgccatca aagtcttctg caacatggag actggtgaga    240
cctgcgtgta ccccactcag cccagtgtgg cccagaagaa ctggtacatc agcaagaacc    300
ccaaggacaa gaggcatgtc tggttcggcg agagcatgac cgatggattc cagttcgagt    360
atggcggcca gggctccgac cctgccgatg tggacctgcc cgggcggccg ctcga         415
```

<210> SEQ ID NO 234
<211> LENGTH: 776
<212> TYPE: DNA
<213> ORGANISM: Homo sapien
<220> FEATURE:
<221> NAME/KEY: misc_feature
<222> LOCATION: (1)...(776)
<223> OTHER INFORMATION: n = A,T,C or G

<400> SEQUENCE: 234

```
agcgtggtcg cggccgaggt ctgggatgct cctgctgtca cagtgagata ttacaggatc    60
acttacggag aaacaggagg aaatagccct gtccaggagt tcactgtgcc tgggagcaag    120
tctacagcta ccatcagcgg ccttaaacct ggagttgatt ataccatcac tgtgtatgct    180
gtcactggcc gtggagacag ccccgcaagc agcaagccaa tttccattaa ttaccgaaca    240
gaaattgaca aaccatccca gatgcaagtg accgatgttc aggacaacag cattagtgtc    300
aagtggctgc cttcaagttc ccctgttact ggttacagag taaccaccac tcccaaaaat    360
ggaccaggac caacaaaaac taaaactgca ggtccagatc aaacagaaat gactattgaa    420
ggcttgcagc ccacagtgga gtatgtggtt aagtgtctat gctcagaatc caagcggaga    480
gaagtcagcc tctggttcag actgnaagta accaacattg atcgcctaaa ggactggcat    540
tcactgatgn ggatgccgat tccatcaaaa ttgnttggga aaacccacag gggcaagttt    600
ncangtcnag gnggacctac tcgagccctg aggatggaat ccttgactnt tccttnncct    660 gatgggaaa aaaaaccttn aaaacttgaa ggacctgccc gggcggccgt ncaaaaccca    720
attccacccc cttgggggcg ttctatgggn cccactcgga ccaaacttgg ggtaan       776
```

<210> SEQ ID NO 235
<211> LENGTH: 805
<212> TYPE: DNA
<213> ORGANISM: Homo sapien
<220> FEATURE:
<221> NAME/KEY: misc_feature
<222> LOCATION: (1)...(805)

<223> OTHER INFORMATION: n = A,T,C or G

<400> SEQUENCE: 235

| | | | | | |
|---|---|---|---|---|---|
| tcgagcggcc | gcccgggcag | gtccttgcag | ctctgcagtg | tcttcttcac | catcaggtgc | 60 |
| agggaatagc | tcatggattc | catcctcagg | gctcgagtag | gtcaccctgt | acctggaaac | 120 |
| ttgcccctgt | gggctttccc | aagcaatttt | gatggaatcg | gcatccacat | cagtgaatgc | 180 |
| cagtccttta | gggcgatcaa | tgttggttac | tgcagtctga | accagaggct | gactctctcc | 240 |
| gcttggattc | tgagcataga | cactaaccac | atactccact | gtgggctgca | agccttcaat | 300 |
| agtcatttct | gtttgatctg | gacctgcagt | tttagttttt | gttggtcctg | gtccattttt | 360 |
| gggagtggtg | gttactctgt | aaccagtaac | aggggaactt | gaaggcagcc | acttgacact | 420 |
| aatgctgttg | tcctgaacat | cggtcacttg | catctgggat | ggtttgtcaa | tttctgttcg | 480 |
| gtaattaatg | gaaattggct | tgctgcttgc | ggggcttgtc | tccacggcca | gtgacagcat | 540 |
| acacagtgat | ggtataatca | actccaggtt | taagccgctg | atggtagctg | aaactttgct | 600 |
| ccaggcacaa | gtgaactcct | gacagggcta | tttcctnctg | ttctccgtaa | gtgatcctgt | 660 |
| aatatctcac | tgggacagca | ggangcattc | caaaacttcg | ggcngaccc | cctaagccga | 720 |
| attntgcaat | atncatcaca | ctggcgggcg | ctcgancatt | cattaaaagg | cccaatcncc | 780 |
| cctataggga | gtntantaca | attng | | | | 805 |

<210> SEQ ID NO 236
<211> LENGTH: 262
<212> TYPE: DNA
<213> ORGANISM: Homo sapien

<400> SEQUENCE: 236

| | | | | | |
|---|---|---|---|---|---|
| tcgagcggcc | gcccgggcag | gtcacttttg | gtttttggtc | atgttcggtt | ggtcaaagat | 60 |
| aaaaactaag | tttgagagat | gaatgcaaag | gaaaaaaata | ttttccaaag | tccatgtgaa | 120 |
| attgtctccc | attttttttgg | cttttgaggg | ggttcagttt | gggttgcttg | tctgtttccg | 180 |
| ggttgggggg | aaagttggtt | gggtgggagg | gagccaggtt | gggatggagg | gagtttacag | 240 |
| gaagcagaca | gggccaacgt | cg | | | | 262 |

<210> SEQ ID NO 237
<211> LENGTH: 372
<212> TYPE: DNA
<213> ORGANISM: Homo sapien

<400> SEQUENCE: 237

| | | | | | |
|---|---|---|---|---|---|
| agcgtggtcg | cggccgaggt | cctcaccaga | ggtgccacct | acaacatcat | agtggaggca | 60 |
| ctgaaagacc | agcagaggca | taaggttcgg | gaagaggttg | ttaccgtggg | caactctgtc | 120 |
| aacgaaggct | tgaaccaacc | tacgatgac | tcgtgctttg | accctacac | agtttcccat | 180 |
| tatgccgttg | gagatgagtg | ggaacgaatg | tctgaatcag | gctttaaact | gttgtgccag | 240 |
| tgcttaggct | ttggaagtgg | tcatttcaga | tgtgattcat | ctagatggtg | ccatgacaat | 300 |
| ggtgtgaact | acaagattgg | agagaagtgg | gaccgtcagg | gagaaaatgg | acctgcccgg | 360 |
| gcggccgctc | ga | | | | | 372 |

<210> SEQ ID NO 238
<211> LENGTH: 372
<212> TYPE: DNA
<213> ORGANISM: Homo sapien

<400> SEQUENCE: 238

| | |
|---|---|
| tcgagcggcc gcccgggcag gtccattttc tccctgacgg tcccacttct ctccaatctt | 60 |
| gtagttcaca ccattgtcat ggcaccatct agatgaatca catctgaaat gaccacttcc | 120 |
| aaagcctaag cactggcaca acagtttaaa gcctgattca gacattcgtt cccactcatc | 180 |
| tccaacggca taatgggaaa ctgtgtaggg gtcaaagcac gagtcatccg taggttggtt | 240 |
| caagccttcg ttgacagagt tgcccacggt aacaacctct tcccgaacct tatgcctctg | 300 |
| ctggtctttc agtgcctcca ctatgatgtt gtaggtggca cctctggtga ggacctcggc | 360 |
| cgcgaccacg ct | 372 |

<210> SEQ ID NO 239
<211> LENGTH: 720
<212> TYPE: DNA
<213> ORGANISM: Homo sapien
<220> FEATURE:
<221> NAME/KEY: misc_feature
<222> LOCATION: (1)...(720)
<223> OTHER INFORMATION: n = A,T,C or G

<400> SEQUENCE: 239

| | |
|---|---|
| tcgagcggcc gcccgggcag gtccaccata agtcctgata caaccacgga tgagctgtca | 60 |
| ggagcaaggt tgatttcttt cattggtccg gtcttctcct tgggggtcac ccgcactcga | 120 |
| tatccagtga gctgaacatt gggtggtgtc cactgggcgc tcaggcttgt gggtgtgacc | 180 |
| tgagtgaact tcaggtcagt tggtgcagga atagtggtta ctgcagtctg aaccagaggc | 240 |
| tgactctctc cgcttggatt ctgagcatag acactaacca catactccac tgtgggctgc | 300 |
| aagccttcaa tagtcatttc tgtttgatct ggacctgcag ttttagtttt tgttggtcct | 360 |
| ggtccatttt tgggagtggt ggttactctg taaccagtaa caggggaact tgaaggcagc | 420 |
| cacttgacac taatgctgtt gtcctgaaca tcggtcactt gcatctggga tggtttgnca | 480 |
| atttctgttc ggtaattaat ggaaattggc ttgctgcttg cggggctgtc tccacggcca | 540 |
| gtgacagcat acacagngat ggnatnatca actccaagtt taaggccctg atggtaactt | 600 |
| taaacttgct cccagccagn gaacttccgg acagggtatt tcttctggtt ttccgaaagn | 660 |
| gancctggaa tnntctcctt ggancagaag gancntccaa aacttgggcc ggaacccctt | 720 |

<210> SEQ ID NO 240
<211> LENGTH: 691
<212> TYPE: DNA
<213> ORGANISM: Homo sapien
<220> FEATURE:
<221> NAME/KEY: misc_feature
<222> LOCATION: (1)...(691)
<223> OTHER INFORMATION: n = A,T,C or G

<400> SEQUENCE: 240

| | |
|---|---|
| agcgtggtcg cggccgaggt cctgtcagag tggcactggt agaagttcca ggaaccctga | 60 |
| actgtaaggg ttcttcatca gtgccaacag gatgacatga aatgatgtac tcagaagtgt | 120 |
| cctggaatgg ggcccatgag atggttgtct gagagagagc ttcttgtcct acattcggcg | 180 |
| ggtatggtct tggcctatgc cttatggggg tggccgttgt gggcggtgtg gtccgcctaa | 240 |
| aaccatgttc ctcaaagatc atttgttgcc caacactggg ttgctgacca gaagtgccag | 300 |
| gaagctgaat accatttcca gtgtcatacc caggggtgggt gacgaaaggg gtcttttgaa | 360 |
| ctgtggaagg aacatccaag atctctggtc catgaagatt ggggtgtgga agggttacca | 420 |
| gttggggaag ctcgtctgtc ttttccttcc caatcagggg ctcgctcttc tgattattct | 480 |

| | |
|---|---|
| tcagggcaat gacataaatt gtatattcgg ttcccggttc caggccagta atagtagcct | 540 |
| cttgtgacac caggcggggc ccanggacca cttctctggg angagaccca gcttctcata | 600 |
| cttgatgatg taacccggta atcctgcacg tggcggctgn catgatacca ncaaggaatt | 660 |
| gggtgnggng gacctgcccg gcggccctcn a | 691 |

<210> SEQ ID NO 241
<211> LENGTH: 808
<212> TYPE: DNA
<213> ORGANISM: Homo sapien
<220> FEATURE:
<221> NAME/KEY: misc_feature
<222> LOCATION: (1)...(808)
<223> OTHER INFORMATION: n = A,T,C or G

<400> SEQUENCE: 241

| | |
|---|---|
| agcgtggtcg cggccgaggt ctgggatgct cctgctgtca cagtgagata ttacaggatc | 60 |
| acttacggag aaacaggagg aaatagccct gtccaggagt tcactgtgcc tgggagcaag | 120 |
| tctacagcta ccatcagcgg ccttaaacct ggagttgatt ataccatcac tgtgtatgct | 180 |
| gtcactggcc gtggagacag ccccgcaagc agcaagccaa tttccattaa ttaccgaaca | 240 |
| gaaattgaca aaccatccca gatgcaagtg accgatgttc aggacaacag cattagtgtc | 300 |
| aagtggctgc cttcaagttc ccctgttact ggttacagag taaccaccac tcccaaaaat | 360 |
| ggaccaggac caacaaaaac taaaactgca ggtccagatc aaacagaaat gactattgaa | 420 |
| ggcttgcagc ccacagtgga gtatgtggtt agtgtctatg ctcagaatcc aagcggagag | 480 |
| agtcagcctc tggttcagac tgcagtaacc actattcctg caccaactga cctgaagttc | 540 |
| actcaggtca cacccacaag cctgagccgc cagtggacac cacccaatgt tcactcactg | 600 |
| gatatcgagt gcgggtgacc cccaaggaga agacccggac ccatgaaaga aatcaacctt | 660 |
| gctcctgaca gctcatccgn gggtgtatca ggacttatgg gggactgccc cggcnggccg | 720 |
| ntcgaaancg aattntgaaa tttccttcnc actgggnggc gnttcgagct tncttntana | 780 |
| nggcccaatt cncctntagn gggtcgtn | 808 |

<210> SEQ ID NO 242
<211> LENGTH: 26
<212> TYPE: DNA
<213> ORGANISM: Homo sapien
<220> FEATURE:
<221> NAME/KEY: misc_feature
<222> LOCATION: (1)...(26)
<223> OTHER INFORMATION: n = A,T,C or G

<400> SEQUENCE: 242

| | |
|---|---|
| agcgtggtcg cggccgaggt cnagga | 26 |

<210> SEQ ID NO 243
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 243

| | |
|---|---|
| tcgagcggcc gcccgggcag gtccaccaca cccaattcct tgctggtatc atggcagccg | 60 |
| ccacgtgcca ggattaccgg ctacatcatc aagtatgaga agcctgggtc tcctcccaga | 120 |
| gaagtggtcc ctcggccccg ccctggtgtc acagaggcta ctattactgg cctggaaccg | 180 |

```
ggaaccgaat atacaattta tgtcattgcc ctgaagaata atcagaagag cgagcccctg    240
attggaagga aaaagacaga cgagcttccc caactggtaa cccttccaca ccccaatctt    300
catggaccag agatcttgga tgttccttcc acagttcaaa agaccccttt cgtcacccac    360
cctgggtatg acactggaaa tggtattcag cttcctggca cttctggtca gcaacccagt    420
gttgggcaac aaatgatctt tgaggaacat ggttttaggc ggaccacacc gcccacaacg    480
ggcaccccca taaggnatag gccaagacca taccccgccg aatgtaggac aagaagctct    540
ntctcaacaa ccatctcatg ggccccattc caggacactt ctgagtacat catttcatgt    600
catcctggtg ggcacttgat gaanaaccct tacagttcag ggttcctgga acttctacca    660
gngccacttc tgacaggganc ttgggcgnga ccaccct                            697

<210> SEQ ID NO 244
<211> LENGTH: 373
<212> TYPE: DNA
<213> ORGANISM: Homo sapien

<400> SEQUENCE: 244
agcgtggtcg cggccgaggt ccatttctc cctgacggtc ccacttctct ccaatcttgt      60
agttcacacc attgtcatgg caccatctag atgaatcaca tctgaaatga ccacttccaa    120
agcctaagca ctggcacaac agtttaaagc ctgattcaga cattcgttcc cactcatctc    180
caacggcata tgggaaact gtgtaggggt caaagcacga gtcatccgta ggttggttca    240
agccttcgtt gacagagttg cccacggtaa caacctcttc ccgaaccta tgcctctgct    300 ggtctttcag tgcctccact atgatgttgt aggtggcacc tctggtgagg acctgcccgg    360
gcggcccgct cga                                                      373

<210> SEQ ID NO 245
<211> LENGTH: 307
<212> TYPE: DNA
<213> ORGANISM: Homo sapien

<400> SEQUENCE: 245
agcgtggtcg cggccgaggt gtgccccaga ccaggaattc ggcttcgacg ttggccctgt     60
ctgcttcctg taaactccct ccatcccaac ctggctccct cccacccaac caactttccc    120 cccaaccccgg aaacagacaa gcaacccaaa ctgaacccc tcaaaagcca aaaaatggg     180 agacaatttc acatggactt tggaaaatat ttttttcctt tgcattcatc tctcaaactt    240 agttttatc tttgaccaac cgaacatgac caaaaaccaa aagtgacctg cccgggcggc    300
cgctcga                                                             307

<210> SEQ ID NO 246
<211> LENGTH: 372
<212> TYPE: DNA
<213> ORGANISM: Homo sapien

<400> SEQUENCE: 246
tcgagcggcc gcccgggcag gtcctcacca gaggtgccac ctacaacatc atagtggagg     60
cactgaaaga ccagcagagg cataaggttc gggaagaggt tgttaccgtg ggcaactctg    120
tcaacgaagg cttgaaccaa cctacggatg actcgtgctt tgaccctac acagtttccc    180 attatgccgt tggagatgag tgggaacgaa tgtctgaatc aggctttaaa ctgttgtgcc    240
agtgcttagg ctttggaagt ggtcatttca gatgtgattc atctagatgg tgccatgaca    300
```
atggtgtgaa ctacaagatt ggagagaagt gggaccgtca gggagaaaat ggacctcggc   360
cgcgaccacg ct   372

<210> SEQ ID NO 247
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 247
tcgagcggcc gcccgggcag gtaccggggt ggtcagcgag gagccattca cactgaactt   60
caccatcaac aacctgcggt atgaggagaa catgcagcac cctggctcca ggaagttcaa   120
caccacggag agggtccttc agggcctgct caggtccctg ttcaagagca ccagtgttgg   180
ccctctgtac tctggctgca gactgacttt gctcagacct gagaaacatg gggcagccac   240
tggagtggac gccatctgca ccctccgcct tgatcccact ggtnctggac tggacanana   300
gcggctatac ttgggagctg anccnaacct ttggcggnga cnccnctt   348

<210> SEQ ID NO 248
<211> LENGTH: 304
<212> TYPE: DNA
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 248
gaggactggc tcagctccca gtatagccgc tctctgtcca gtccaggacc agtgggatca   60
aggcggaggg tgcagatggc gtccactcca gtggctgccc catgtttctc aagtctgagc   120
aaagncagtc tgcagccaga gtacagaggg ccaacactgg tgctcttgaa cagggacctg   180
agcaggccct gaaggaccct ctccgtggtg ttgaacttcc tggagccagg gtgctgcatg   240
ttctcctcat accgcaggtt gttgatggtg aagttcagtg tgaatggctc ctcgctgacc   300
accc   304

<210> SEQ ID NO 249
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 249
agcgtggtcg cggccgaggt ccaccacacc caattccttg ctggtatcat ggcagccgcc   60
acgtgccagg attaccggct acatcatcaa gtatgagaag cctgggtctc ctcccagaga   120
agtggtccct cggccccgcc ctggtgtcac agaggctact attactggcc tggaaccggg   180
aaccgaatat acaatttatg tcattgccct gaagaataat cagaagagcg agcccctgat   240
tggaaggaaa aagacagacg agcttcccca actggtaacc cttccacacc ccaatcttca   300
tggaccanan ancttggatn gtcctttcac nggttnaaaa aacccttttc gccccccac   360 cttggggatt aaccttggga aangggggatt tnaccnttcc   400

<210> SEQ ID NO 250
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 250

| | | | | | |
|---|---|---|---|---|---|
| tcgagcggcc | gcccgggcag | gtcctgtcag | agtggcactg | gtagaagttc | caggaacccct | 60 |
| gaactgtaag | ggttcttcat | cagtgccaac | aggatgacat | gaaatgatgt | actcagaagt | 120 |
| gtcctggaat | ggggcccatg | agatggttgt | ctgagagaga | gcttcttgtc | ctacattcgg | 180 |
| cgggtatggt | cttggcctat | gccttatggg | ggtggccgtt | gtgggcggtg | tggtccgcct | 240 |
| aaaaccatgt | tcctcaaaga | tcatttgttg | cccaacactg | ggttgctgac | cagaagtgcc | 300 |
| aggaagctga | ataccatttc | cagtgtcata | cccagggngg | gtgaccaaag | ggggtcnttt | 360 |
| ngacctggng | aaaggaacca | tccaaaanct | ctgncccatg | | | 400 |

<210> SEQ ID NO 251
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 251

| | | | | | |
|---|---|---|---|---|---|
| agcgtggncg | cggccgaggt | ctgaggatgt | aaactcttcc | caggggaagg | ctgaagtgct | 60 |
| gaccatggtg | ctactgggtc | cttctgagtc | agatatgtga | ctgatgngaa | ctgaagtagg | 120 |
| tactgtagat | ggtgaagtct | gggtgtccct | aaatgctgca | tctccagagc | cttccatcat | 180 |
| taccgtttct | tcttttgcta | tgggatgaga | cactgttgag | tattctctaa | agtcaccact | 240 |
| gaaatcttcc | tccaaaggaa | aacctgtgga | aaagccccctt | atttctgccc | cataatttgg | 300 |
| ttctcctaat | cnctctgaaa | tcactatttc | cctggaangt | ttgggaaaaa | nngggcnacc | 360 |
| tgncantgga | aantggatan | aaagatccca | ccatttacc | caacnagcag | aaagtgggaa | 420 |
| nggtaccgaa | aagctccaag | taanaaaaag | gagggaagta | aaggtcaagt | gggcaccagt | 480 |
| ttcaaacaaa | actttcccca | aactatanaa | ccca | | | 514 |

<210> SEQ ID NO 252
<211> LENGTH: 501
<212> TYPE: DNA
<213> ORGANISM: Homo sapien
<220> FEATURE:
<221> NAME/KEY: misc_feature
<222> LOCATION: (1)...(501)
<223> OTHER INFORMATION: n = A,T,C or G

<400> SEQUENCE: 252

| | | | | | |
|---|---|---|---|---|---|
| aagcggccgc | ccgggcaggn | ncagnagtgc | cttcgggact | gggntcaccc | ccaggtctgc | 60 |
| ggcagttgtc | acagcgccag | ccccgctggc | tccaaaagca | tgtgcaggag | caaatggcac | 120 |
| cgagatattc | cttctgccac | tgttctccta | cgtggtatgt | cttcccatca | tcgtaacacg | 180 |
| ttgcctcatg | agggtcacac | ttgaattctc | cttttccgtt | cccaagacat | gtgcagctca | 240 |
| tttggctggc | tctatagttt | ggggaaagtt | tgttgaaact | gtgccactga | cctttacttc | 300 |
| ctccttctct | actggagctt | tccgtacctt | ccacttctgc | tgntggnaaa | aagggnggaa | 360 |

| cntcttatca atttcattgg acagtancec nctttctncc caaaacatnc aagggaaaat | 420 |
| attgattncn agagcggatt aaggaacaac ccnaattatg ggggccagaa ataaaggggg | 480 |
| cttttccaca ggtnttttcc t | 501 |

<210> SEQ ID NO 253
<211> LENGTH: 226
<212> TYPE: DNA
<213> ORGANISM: Homo sapien

<400> SEQUENCE: 253

| tcgagcggcc gcccgggcag gtctgcaggc tattgtaagt gttctgagca catatgagat | 60 |
| aacctgggcc aagctatgat gttcgatacg ttaggtgtat taaatgcact tttgactgcc | 120 |
| atctcagtgg atgacagcct tctcactgac agcagagatc ttcctcactg tgccagtggg | 180 |
| caggagaaag agcatgctgc gactggacct cggccgcgac cacgct | 226 |

<210> SEQ ID NO 254
<211> LENGTH: 226
<212> TYPE: DNA
<213> ORGANISM: Homo sapien

<400> SEQUENCE: 254

| agcgtggtcg cggccgaggt ccagtcgcag catgctcttt ctcctgccca ctggcacagt | 60 |
| gaggaagatc tctgctgtca gtgagaaggc tgtcatccac tgagatggca gtcaaaagtg | 120 |
| catttaatac acctaacgta tcgaacatca tagcttggcc caggttatct catatgtgct | 180 |
| cagaacactt acaatagcct gcagacctgc ccgggcggcc gctcga | 226 |

<210> SEQ ID NO 255
<211> LENGTH: 427
<212> TYPE: DNA
<213> ORGANISM: Homo sapien
<220> FEATURE:
<221> NAME/KEY: misc_feature
<222> LOCATION: (1)...(427)
<223> OTHER INFORMATION: n = A,T,C or G

<400> SEQUENCE: 255

| cgagcggccg cccgggcagg tccagactcc aatccagaga accaccaagc cagatgtcag | 60 |
| aagctacacc atcacaggtt tacaaccagg cactgactac aagatctacc tgtacacctt | 120 |
| gaatgacaat gctcggagct cccctgtggt catcgacgcc tccactgcca ttgatgcacc | 180 |
| atccaacctg cgtttcctgg ccaccacacc caattccttg ctggtatcat ggcagccgcc | 240 |
| acgtgccagg attaccggct acatcatcaa gtatgagaag cctgggtctc ctcccagaga | 300 |
| agtggtccct cggccccgcc ctggtgncac agaagctact attactggcc tggaaccggg | 360 |
| aaccgaatat acaatttatg tcattgccct gaagaataat canaagagcg agccctgat | 420 |
| tggaagg | 427 |

<210> SEQ ID NO 256
<211> LENGTH: 535
<212> TYPE: DNA
<213> ORGANISM: Homo sapien
<220> FEATURE:
<221> NAME/KEY: misc_feature
<222> LOCATION: (1)...(535)
<223> OTHER INFORMATION: n = A,T,C or G

<400> SEQUENCE: 256

-continued

| | | |
|---|---|---|
| agcgtggtcg cggccgaggt cctgtcagag tggcactggt agaagttcca ggaaccctga | 60 |
| actgtaaggg ttcttcatca gtgccaacag gatgacatga aatgatgtac tcagaagtgt | 120 |
| cctggaatgg ggcccatgag atggttgtct gagagagagc ttcttgtcct gtcttttcc | 180 |
| ttccaatcag gggctcgctc ttctgattat tcttcagggc aatgacataa attgtatatt | 240 |
| cggttcccgg ttccaggcca gtaatagtag cctctgtgac accagggcgg ggccgaggga | 300 |
| ccacttctct gggaggagac ccaggcttct catacttgat gatgtanccg gtaatcctgg | 360 |
| caccgtggcg gctgccatga taccagcaag gaattgggtg tggtggccaa gaaacgcagg | 420 |
| ttggatggtg catcaatggc agtggaggcg tcgatnacca caggggagct ccgancattg | 480 |
| tcattcaagg tggacaggta gaatcttgta atcaggtgcc tggtttgtaa acctg | 535 |

<210> SEQ ID NO 257
<211> LENGTH: 544
<212> TYPE: DNA
<213> ORGANISM: Homo sapien
<220> FEATURE:
<221> NAME/KEY: misc_feature
<222> LOCATION: (1)...(544)
<223> OTHER INFORMATION: n = A,T,C or G

<400> SEQUENCE: 257

| | | |
|---|---|---|
| tcgagcggcc gcccgggcag gtttcgtgac cgtgacctcg aggtggacac caccctcaag | 60 |
| agcctgagcc agcagatcga gaacatccgg agcccagagg gcagccgcaa gaaccccgcc | 120 |
| cgcacctgcc gtgacctcaa gatgtgccac tctgactgga gagtggaga gtactggatt | 180 |
| gaccccaacc aaggctgcaa cctggatgcc atcaaagtct tctgcaacat ggagactggt | 240 |
| gagacctgcg tgtaccccac tcagcccagt gtggcccaga gaactggta catcagcaag | 300 |
| aaccccaagg acaagaagca tgtctggttc ggcgaaagca tgaccgatgg attccagttc | 360 |
| gagtatggcg ccagggctc cgaccctgcc gatgtggacc tcggccgcga ccacgctaag | 420 |
| cccgaattcc agcacactgg cggccgttac tagtgggatc cgagcttcgg taccaagctt | 480 |
| ggcgtaatca tgggncatag ctgtttcctg ngtgaaaatg gtattccgct tcacaatttc | 540 |
| ccac | 544 |

<210> SEQ ID NO 258
<211> LENGTH: 418
<212> TYPE: DNA
<213> ORGANISM: Homo sapien

<400> SEQUENCE: 258

| | | |
|---|---|---|
| agcgtggtcg cggccgaggt ccacatcggc agggtcggag ccctggccgc catactcgaa | 60 |
| ctggaatcca tcggtcatgc tctcgccgaa ccagacatgc ctcttgtcct tgggttctt | 120 |
| gctgatgtac cagttcttct gggccacact gggctgagtg gggtacacgc aggtctcacc | 180 |
| agtctccatg ttgcagaaga ctttgatggc atccaggttg cagccttggt tggggtcaat | 240 |
| ccagtactct ccactcttcc agtcagagtg gcacatcttg aggtcacggc aggtgcgggc | 300 |
| ggggttcttg cggctgccct ctgggctccg gatgttctcg atctgctggc tcaagctctt | 360 |
| gaagggtggt gtccacctcg aggtcacggt cacgaaacct gcccgggcgg ccgctcga | 418 |

<210> SEQ ID NO 259
<211> LENGTH: 377
<212> TYPE: DNA
<213> ORGANISM: Homo sapien
<220> FEATURE:
<221> NAME/KEY: misc_feature

```
<222> LOCATION: (1)...(377)
<223> OTHER INFORMATION: n = A,T,C or G

<400> SEQUENCE: 259
agcgtggtcg cggccgaggt caagaacccc gcccgcacct gccgtgacct caagatgtgc      60
cactctgact ggaagagtgg agagtactgg attgacccca accaaggctg caacctggat     120
gccatcaaag tcttctgcaa catggagact ggtgagacct cgtgtaccc cactcagccc     180 agtgtggccc agaagaactg gtacatcagc aagaacccca aggacaagag gcatgtctgg     240
ttcggcgaga gcatgaccga tggattccag ttcgagtatg cggccaggg ctccgaccct     300 gccgatgtgg acctgcccgn gccggnccgc tcgaaaagcc cnaatttcca gncacacttg     360
gccggccgtt actactg                                                    377

<210> SEQ ID NO 260
<211> LENGTH: 332
<212> TYPE: DNA
<213> ORGANISM: Homo sapien

<400> SEQUENCE: 260
tcgagcggcc gcccgggcag gtccacatcg gcaggtcgg agccctggcc gccatactcg      60
aactggaatc catcggtcat gctctcgccg aaccagacat gcctcttgtc cttgggttc     120 ttgctgatgt accagttctt ctgggccaca ctgggctgag tggggtacac gcaggtctca     180
ccagtctcca tgttgcagaa gactttgatg gcatccaggt tgcagccttg gttggggtca     240
atccagtact ctccactctt ccagtcagag tggcacatct tgaggtcacg gcaggtgcgg     300
gcggggttct tgacctcggc cgcgaccacg ct                                   332

<210> SEQ ID NO 261
<211> LENGTH: 94
<212> TYPE: DNA
<213> ORGANISM: Homo sapien

<400> SEQUENCE: 261
cgagcggccg cccgggcagg tcccccccct tttttttttt tttttttttt tttttttttt      60
tttttttttt tttttttttt tttttttttt tttt                                  94

<210> SEQ ID NO 262
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 262
agcgtggtcg cggccgaggt ctggcattcc ttcgacttct ctccagccga gcttcccaga      60
acatcacata tcactgcaaa aatagcattg catacatgga tcaggccagt ggaaatgtaa     120
agaaggccct gaagctgatg gggtcaaatg aaggtgaatt caaggctgaa ggaaatagca     180
aattcaccta cacagttctg gaggatggtt gcacgaaaca cactggggaa tggagcaaaa     240
cagtctttga atatcgaaca cgcaaggctg tgagactacc tattgtagat attgcaccct     300
atgacattgg tggtcctgat caagaatttg gtgtggacgt tggccctgtt tgcttttat     360 aaaccaaact ctatctgaaa tcccaacaaa aaaatttaa ctccatatgt gntcctcttg     420
ttctaatctt ggcaaccagt gcaagtgacc gacaaaattc cagttattta tttccaaaat     480
```

```
gtttggaaac agtataattt gacaaagaaa aaaggatact tctctttttt tggctggtcc    540
accaaataca attcaaaagg cttttttggtt ttatttttt anccaattcc aatttcaaaa    600
tgtctcaatg gngcttataa taaaataaac tttcacccctt nttttntgat              650
```

<210> SEQ ID NO 263
<211> LENGTH: 573
<212> TYPE: DNA
<213> ORGANISM: Homo sapien
<220> FEATURE:
<221> NAME/KEY: misc_feature
<222> LOCATION: (1)...(573)
<223> OTHER INFORMATION: n = A,T,C or G

<400> SEQUENCE: 263

```
agcgtggtcg cggccgaggt ctgggatgct cctgctgtca cagtgagata ttacaggatc     60
acttacggag aaacaggagg aaatagccct gtccaggagt tcactgtgcc tgggagcaag    120
tctacagcta ccatcagcgg ccttaaacct ggagttgatt ataccatcac tgtgtatgct    180
gtcactggcc gtggagacag ccccgcaagc agcaagccaa tttccattaa ttaccgaaca    240
gaaattgaca accatcccca gatgcaagtg accgatgttc aggacaacag cattagtgtc    300
aagtggctgc cttcaagttc ccctgttact ggttacagaa gtaaccacca ctcccaaaaa    360
tggaccagga ccaacaaaaa ctaaaactgc aggtccagat caaacagaaa atggactatt    420
gaaggcttgc agcccacagt ggaagtatgt ggntaggngt ctatgctcag aatcccaagc    480
cggagaaagt cagccttctg gtttagactg cagtaaccaa cattgatcgc cctaaaggac    540
tggncattca cttggatggt ggatgtccaa ttc                                 573
```

<210> SEQ ID NO 264
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 264

```
tcgagcggcc gcccgggcag gtccttgcag ctctgcagng tcttcttcac catcaggtgc     60
agggaatagc tcatggattc catcctcagg gctcgagtag gtcaccctgt acctggaaac    120
ttgcccctgt gggctttccc aagcaatttt gatggaatcg acatccacat cagngaatgc    180
cagtccttta gggcgatcaa tgttggttac tgcagtctga accagaggct gactctctcc    240
gcttggattc tgagcataga cactaaccac atactccact gtgggctgca agccttcaat    300
agtcatttct gtttgatctg gacctgcagt tttaagtttt tggtggtcct gncccatttt    360
tgggaagtgg gggggttactc tgtaaccagt aacaggggaa cttgaaggca gccacttgac    420
actaatgctg ttgtcctgaa catcggtcac ttgcatctgg ggatggtttt gacaatttct    480
ggttcggcaa attaatggaa attggcttgc tgcttggcgg ggctgnctcc acgggccagt    540
gacagcatac                                                           550
```

<210> SEQ ID NO 265
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 265

```
tcgagcggcc gcccgggcag gtccttgcag ctctgcagtg tcttcttcac catcaggtgc      60
agggaatagc tcatggattc catcctcagg gctcgagtag gtcaccctgt acctggaaac     120
ttgcccctgt gggctttccc aagcaatttt gatggaatcg acatccacat cagtgaatgc    180
cagtccttta gggcgatcaa tgttggttac tgcagtctga accagaggct gactctctcc    240
gcttggattc tgagcataga cactaaccac atactccact gtgggctgca agccttcaat    300
agtcatttct gtttgatctg gacctgcagt tttaagtttt tgttggncct gnnccatttt    360
tggggaaggg gtggttactc ttgtaaccag taacagggga acttgaagca gccacttgac    420
actaatgctg gtgcctgaa catcggtcac ttgcatctgg gatggtttgg tcaatttctg     480
ttcggtaatt aatgggaaat tggcttactg gcttgcgggg gctgtctcca cggncagtga    540
caagcataca caggngatgg gtataatcaa ctccaggttt aaggccnctg atggta         596
```

<210> SEQ ID NO 266
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 266

```
agcgtggtcg cggccgaggt ctgggatgct cctgctgtca cagtgagata ttacaggatc      60
acttacggag aaacaggagg aaatagccct gtccaggagt tcactgtgcc tgggagcaag    120
tctacagcta ccatcagcgg ccttaaacct ggagttgatt ataccatcac tgtgtatgct    180
gtcactggcc gtggagacag ccccgcaagc agtaagccaa tttccattaa ttaccgaaca    240
gaaattgaca aaccatccca gatgcaagtg accgatgttc aggacaacag cattagtgtc    300
aagtggctgc cttcaagttc ccctgttact ggttacagag taaccaccac tcccaaaaat    360
gggaccagga ccaacaaaaa actaaaactg canggtccag atcaaacaga aatgactatt    420
gaaggcttgc agcccacagt ggagtatgtg ggttagtgtc tatgctcaga atnccaagcg    480
gagagagtca gcctctggtt cagact                                          506
```

<210> SEQ ID NO 267
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 267

```
tcgagcggcc gcccgggcag gtcagcgctc tcaggacgtc accaccatgg cctgggctct      60
gctcctcctc accctcctca ctcagggcac agggtcctgg gcccagtctg ccctgactca    120
gcctccctcc gcgtccgggt ctcctggaca gtcagtcacc atctcctgca ctggaaccag    180
cagtgacgtt ggtgcttatg aatttgtctc ctggtaccaa caacacccag gcaaggcccc    240
caaactcatg atttctgagg tcactaagcg gccctcaggg gtccctgatc gcttctctgg    300
ctccaagtct ggcaacacgg cctccctgac cgtctctggg ctccangctg aggatgangc    360
tgattattac tggaagctca tatgcaggca acaacaattg ggtgttcggc ggaagggacc    420
```

```
aagctgaccg tnctaaggtc aagcccaagg cttgccccc  tcggtcactc tgttcccacc    480
ctcctctgaa gaagctttca agccaacaan gncacactgg gtgtgtctca taagtggact    540
ttctaccc                                                             548
```

<210> SEQ ID NO 268
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 268

```
agcgtggtcg cggccgaggt ctgtagcttc tgtgggactt ccactgctca ggcgtcaggc     60
tcaggtagct gctggccgcg tacttgttgt tgctttgntt ggagggtgtg gtggtctcca    120
ctcccgcctt gacgggctg  ctatctgcct tccaggccac tgtcacggct cccgggtaga    180
agtcacttat gagacacacc agtgtggcct tgttggcttg aagctcctca gaggagggtg    240
ggaacagagt gaccgagggg gcagccttgg gctgacctag gacggtcagc ttggtccctc    300
cgccgaacac ccaattgttg ttgcctgcat atgagctgca gtaataatca gcctcatcct    360
cagcctggag cccagagacn gtcaagggag gcccgtgttt gccaagactt ggaagccaga    420
naagcgatca gggaccctg  agggccgctt tacngacctc aaaaaatcat gaatttgggg    480
ggcctttgcc tgggngttgg ttggtnacca gnaaaacaaa atttcataaa gcaccaacgt    540
cactgctggt ttccagtgca ngaanatggt gaactgaant gtcc                     584
```

<210> SEQ ID NO 269
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 269

```
agcgtggtcg cggccgaggt ccagcatcag gagccccgcc ttgccggctc tggtcatcgc     60 cttcttttt  gtggcctgaa acgatgtcat caattcgcag tagcagaact gccgtctcca    120
ctgctgtctt ataagtctgc agcttcacag ccaatggctc ccatatgccc agttccttca    180
tgtccaccaa agtacccgtc tcaccattta caccccaggt ctcacagttc tcctgggtgt    240
gcttggcccg aagggaggta agtanacgga tggtgctggt cccacagttc tggatcaggg    300
tacgaggaat gacctctagg gcctgggcna caagccctgt atggacctgc ccgggcgggc    360
ccgctcga                                                             368
```

<210> SEQ ID NO 270
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 270

```
tcgagcggcc gcccgggcag gtccatacag ggctgttgcc caggccctag aggncattcc     60
ttgtaccctg atccagaact gtgggaccag caccatccgt ctacttacct cccttcgggc    120
```

```
caagcacacc caggagaact gtgagacctg gggtgtaaat ggngagacgg gtactttggt      180
ggacatgaag gaactgggca tatgggagcc attggctgng aagctgcana cttataagac      240
agcagtggag acggcagttc tgctactgcg aattgatgac atcgtttcag gccacaaaaa      300
gaaaggcgat gaccanagcc ggcaaggcgg ggcttcctga tgctggacct cggccgccga      360
ccacgctt                                                               368
```

<210> SEQ ID NO 271
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 271

```
agcgtggtcg cggccgaggt ccactagagg tctgtgtgcc attgcccagg cagagtctct       60
gcgttacaaa ctcctaggag ggcttgctgt gcggagggcc tgctatggtg tgctgcggtt      120
catcatggag agtggggcca aaggctgcga ggttgtggtg tctgggaaac tccgaggaca      180
gagggctaaa tccatgaagt ttgtggatgg cctgatgatc cacagcggag accctgttaa      240
ctactacgtt gacactgctg tgcgccacgt gttgctcana cagggtgtgc tgggcatcaa      300
ggtgaagatc atgctgccct gggacccanc tggcaaaaat ggcccttaaa aacccttgc      360 cntgaccacg tgaaccattt gtgngaaccc caagatgaan atacttgccc accaccccc      420 attc                                                                   424
```

<210> SEQ ID NO 272
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 272

```
tcgagcggcc gcccgggcag gtctgccaag gagaccctgt tatgctgtgg ggactggctg       60
gggcatggca ggcggctctg gcttcccacc cttctgttct gagatggggg tggtgggcag      120
tatctcatct ttgggttcca caatgctcac gtggtcaggc agggcttct tagggccaat       180 cttaccagtt gggtcccagg gcagcatgat cttcaccttg atgcccagca cccctgtct       240 gagcaacacg tggcgcacag cagtgtcaac gtagtagtta acagggtctc cgctgtggat      300
catcaggcca tccacaaact tcatggattt agccctctgt cctcggagtt tcccaaaaca      360
ccacaacctc gccagccttt gggccccact tcttcatgaa tgaaaccgca gcacaccatt      420
ancaaggccc ttccgcacag gnaagccctt cctaaggagt tttgtaaacg caaaaaactc      480
ttgcctgggg caaatgggca cacagacctn tantnggacc ttggnccgcg aaccaccgct      540
t                                                                      541
```

<210> SEQ ID NO 273
<211> LENGTH: 579
<212> TYPE: DNA
<213> ORGANISM: Homo sapien
<220> FEATURE:
<221> NAME/KEY: misc_feature
<222> LOCATION: (1)...(579)

<223> OTHER INFORMATION: n = A,T,C or G

<400> SEQUENCE: 273

| | | | | | |
|---|---|---|---|---|---|
| agcgtggtcg | cggccgaggt | ctggccctcc | tggcaaggct | ggtgaagatg | gtcaccctgg | 60 |
| aaaacccgga | cgacctggtg | agagaggagt | tgttggacca | cagggtgctc | gtggtttccc | 120 |
| tggaactcct | ggacttcctg | gcttcaaagg | cattagggga | cacaatggtc | tggatggatt | 180 |
| gaagggacag | cccggtgctc | ctggtgtgaa | gggtgaacct | ggngcccctg | gtgaaaatgg | 240 |
| aactccaggt | caaacaggag | cccgngggct | tcctggngag | agaggacgtg | ttggtgcccc | 300 |
| tggcccanac | ctgcccgggc | ggccgctcna | aaagccgaaa | tccagnacac | tggcggccgn | 360 |
| tactantgga | atccgaactt | cggtaccaaa | gcttggccgt | aatcatggcc | atagcttgtt | 420 |
| ccctggggng | gaaattggta | ttccgctncc | aattccacac | aacataccga | acccggaaag | 480 |
| cattaaagtg | taaaagccct | ggggggggcct | aaatgangtg | agcntaactc | ncatttaatt | 540 |
| ggcgttgcgc | ttcactgccc | cgcttttcca | gtccgggna | | | 579 |

<210> SEQ ID NO 274
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 274

| | | | | | |
|---|---|---|---|---|---|
| tcgagcggcc | gcccgggcag | gtctgggcca | ggggcaccaa | cacgtcctct | ctcaccagga | 60 |
| agcccacggg | ctcctgtttg | acctggagtt | ccattttcac | caggggcacc | aggttcaccc | 120 |
| ttcacaccag | gagcaccggg | ctgtcccttc | aatccatcca | gaccattgtg | nccctaatg | 180 |
| cctttgaagc | caggaagtcc | aggagttcca | gggaaaccac | gagcaccctg | tggtccaaca | 240 |
| actcctctct | caccaggtcg | tccgggtttt | ccagggtgac | catcttcacc | agccttgcca | 300 |
| ggagggccag | acctcggccg | cgaccacgct | | | | 330 |

<210> SEQ ID NO 275
<211> LENGTH: 97
<212> TYPE: DNA
<213> ORGANISM: Homo sapien
<220> FEATURE:
<221> NAME/KEY: misc_feature
<222> LOCATION: (1)...(97)
<223> OTHER INFORMATION: n = A,T,C or G

<400> SEQUENCE: 275

| | | | | | |
|---|---|---|---|---|---|
| ancgtggtcg | cggccgaggt | cctcaccaga | ggtgncacct | acaacatcat | agtggaggca | 60 |
| ctgaaagacc | ancagaggca | taaggttcgg | gaagagg | | | 97 |

<210> SEQ ID NO 276
<211> LENGTH: 610
<212> TYPE: DNA
<213> ORGANISM: Homo sapien
<220> FEATURE:
<221> NAME/KEY: misc_feature
<222> LOCATION: (1)...(610)
<223> OTHER INFORMATION: n = A,T,C or G

<400> SEQUENCE: 276

| | | | | | |
|---|---|---|---|---|---|
| tcgagcggcc | gcccgggcag | gtccattttc | tccctgacgg | tcccacttct | ctccaatctt | 60 |
| gtagttcaca | ccattgtcat | ggcaccatct | agatgaatca | catctgaaat | gaccacttcc | 120 |

```
aaagcctaag cactggcaca acagtttaaa gcctgattca gacattcgtt cccactcatc     180
tccaacggca taatgggaaa ctgtgtaggg gtcaaagcac gagtcatccg taggttggtt     240
caagccttcg ttgacagagt tgtccacggt aacaacctct tcccgaacct tatgcctctg     300
ctggtctttc agtgcctcca ctatgatgtt gtaggtggca cctctggtga ggacctcngn     360
ccngaacaac gcttaagccc gnattctgca gaataatccc atcacacttg gcggccgctt     420
cgancatgca tcntaaaagg ggccccaatt tcccccttat aagngaaacc gtatttncca     480
atttcactgg ncccgccgnt tttacaaacg ncggtgaact ggggaaaaac cctggcggtt     540
acccaacttt aatcgccntt ggcagcacaa tcccccnttt tcgnccancn tgggcgtaaa     600
taaccgaaaa                                                           610

<210> SEQ ID NO 277
<211> LENGTH: 38
<212> TYPE: DNA
<213> ORGANISM: Homo sapien
<220> FEATURE:
<221> NAME/KEY: misc_feature
<222> LOCATION: (1)...(38)
<223> OTHER INFORMATION: n = A,T,C or G

<400> SEQUENCE: 277
ancgnggtcg cggccgangt ntttttttctt ntttttttt                           38

<210> SEQ ID NO 278
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 278
agcgtggtcg cggccgaggt ctgaggttac atgcgtggtg gtggacgtga gccacgaaga      60
ccctgaggtc aagttcaact ggtacgtgga cggcgtggag gtgcataatg ccaagacaaa     120
gccgcgggag gagcagtaca acagcacgta ccgggnggtc agcgtcctca ccgtcctgca     180
ccagaattgg ttgaatggca aggagtacaa gngcaaggtt tccaacaaag ccntcccagc     240
ccccntcgaa aaaccatttc caaagccaaa agggcagccc cgagaaccac aggtgtacac     300
cctgccccca tcccgggagg aaaagancaa naaccnggtt cagccttaac ttgcttggtc     360
naangctttt tatcccaacg nacttccccc ntggaantgg gaaaaaccaa tgggccaanc     420
cgaaaaacaa ttacaannaac ccc                                           443

<210> SEQ ID NO 279
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 279
tcgagcggcc gcccgggcag gtgtcggagt ccagcacggg aggcgtggtc ttgtagttgt      60
tctccggctg cccattgctc tcccactcca cggcgatgtc gctgggatag aagcctttga     120
ccaggcaggt caggctgacc tggttcttgg tcatctcctc ccgggatggg ggcagggtga     180
```

| | | |
|---|---|---|
| acacctgggg ttctcggggc ttgccctttg gttttgaana tggttttctc gatgggggct | 240 | |
| ggaagggctt tgttgnaaac cttgcacttg actccttgcc attcacccag ncctggngca | 300 | |
| ggacggngag gacnctnacc acacggaacc gggctggtgg actgctcc | 348 | |

<210> SEQ ID NO 280
<211> LENGTH: 149
<212> TYPE: DNA
<213> ORGANISM: Homo sapien
<220> FEATURE:
<221> NAME/KEY: misc_feature
<222> LOCATION: (1)...(149)
<223> OTHER INFORMATION: n = A,T,C or G

<400> SEQUENCE: 280

| | |
|---|---|
| agcgtggtcg cggacgangt cctgtcagag tggnactggt agaagttcca ngaaccctga | 60 |
| actgtaaggg ttcttcatca gtgccaacag gatgacatga aatgatgtac tcagaagngn | 120 |
| cctggaatgg ggcccatgan atggttgcc | 149 |

<210> SEQ ID NO 281
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 281

| | |
|---|---|
| tcgagcggcc gcccgggcag gtccaccaca cccaattcct tgctggtatc atggcagccg | 60 |
| ccacgtgcca ggattaccgg ctacatcatc aagtatgaga agcctgggtc tcctcccaga | 120 |
| gaagtggtcc ctcggccccg ccctggtgtc acagaggcta ctattactgg cctggaaccg | 180 |
| ggaaccgaat atacaattta tgtcattgcc ctgaagaata atcagaagag cgagcccctg | 240 |
| attggaagga aaaagacaga cgagcttccc caactggtaa cccttccaca ccccaatctt | 300 |
| catggaccag agatcttgga tgttccttcc acagttcaaa agacccettt cggcaccccc | 360 |
| cctgggtatg aacctgggaa aanggnantt aanctttcct ggca | 404 |

<210> SEQ ID NO 282
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 282

| | |
|---|---|
| agcgtggtcg cggccgaggt ctgggatgct cctgctgtca cagtgagata ttacaggatc | 60 |
| acttacggag aaacaggagg aaatagccct gtccaggagt tcactgtgcc tgggagcaag | 120 |
| tctacagcta ccatcagcgg ccttaaacct ggagttgatt ataccatcac tgtgtatgct | 180 |
| gtcactggcc gtggagacag ccccgcaagc agcaagccaa tttccattaa ttaccgaaca | 240 |
| gaaattgaca aaccatccca gatgcaagtg accgatgttc aggacaacag cattagtgtc | 300 |
| aagtggctgc cttcaaggtn ccctggtact gggttacaga ntaaccacca ctcccaaaaa | 360 |
| tggaccagga accacaaaaa cttaaactgc agggtccaga tcaaaacaga aatgactatt | 420 |
| gaangcttgc agcccacagt gggagtatgn gggtagtgnc tatgcttcag aatccaagcg | 480 |
| gaaaaangtc aagccttntg ggttcaa | 507 |

<210> SEQ ID NO 283
<211> LENGTH: 325
<212> TYPE: DNA
<213> ORGANISM: Homo sapien
<220> FEATURE:
<221> NAME/KEY: misc_feature
<222> LOCATION: (1)...(325)
<223> OTHER INFORMATION: n = A,T,C or G

<400> SEQUENCE: 283

```
tcgagcggcc gcccgggcag gtccttgcag ctctgcagtg tcttcttcac catcaggtgc    60
agggaatagc tcatggattc catcctcagg gctcgagtag gtcaccctgt acctggaaac   120
ttgcccctgt gggctttccc aagcaatttt gatggaatcg acatccacat cagtgaatgc   180
cagtccttta gggcgatcaa tgttggttac tgcagnctga accagaggct gactctctcc   240
gcttggattc tgagcataga cactaaccac atactccact gtgggctgca anccttcaat   300
aanncatttc tgtttgatct ggacc                                         325
```

<210> SEQ ID NO 284
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 284

```
tcgagcggcc gcccgggcag gtctggtggg gtcctggcac acgcacatgg gggngttgnt    60
ctnatccagc tgcccagccc ccattggcga gtttgagaag gtgtgcagca atgacaacaa   120
naccttcgac tcttcctgcc acttctttgc cacaaagtgc accctggagg gcaccaagaa   180
gggccacaag ctccacctgg actacatcgg gccttgcaaa tacatccccc cttgcctgga   240
ctctgagctg accgaattcc cccttgcgca tgcgggactg gctcaagaac cgtcctggca   300
cccttgtatg anaggatgag agacacnacc c                                  331
```

<210> SEQ ID NO 285
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 285

```
agcgtggtcg cggccgaggt ctgtcctaca gtcctcagga ctctactccc tcagcagcgt    60
ggtgaccgtg ccctccagca acttcggcac ccagacctac acctgcaacg tagatcacaa   120
gcccagcaac accaaggtgg acaagagagt tgagcccaaa tcttgtgaca aaactcacac   180
atgcccaccg tgcccagcac ctgaactcct gggggaccg tcagtcttcc tcttccccg   240
catccccctt ccaaacctgc ccgggcggcc gctcgaaagc cgaattccag cacactggcg   300
gccggtacta gtggancena acttggnanc caacctggng gaantaatgg gcataanctg   360
tttctgggg gaaattggta tccngtttac aattcccnca caacatacga gccggaagca   420
taaaagngta aaagcctggg ggnggcctan tgaagtgaag ctaaactcac attaattngc   480
gttgccgctc actggcccgc ttttccagc                                     509
```

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286

| | | | | | |
|---|---|---|---|---|---|
| tcgagcggcc | gcccgggcag | gtttggaagg | gggatgcggg | ggaagaggaa | gactgacggt | 60 |
| ccccccagga | gttcaggtgc | tgggcacggt | gggcatgtgt | gagttttgtc | acaagatttg | 120 |
| ggctcaactc | tcttgtccac | cttggtgttg | ctgggcttgt | gatctacgtt | gcaggtgtag | 180 |
| gtctgggngc | cgaagttgct | ggagggcacg | gtcaccacgc | tgctgaggga | gtagagtcct | 240 |
| gaggactgta | ngacagacct | cggccgngac | cacgctaagc | cgaattctgc | agatatccat | 300 |
| cacactggcg | gccgctccga | gcatgcattt | tagagg | | | 336 |

<210> SEQ ID NO 287
<211> LENGTH: 30
<212> TYPE: DNA
<213> ORGANISM: Homo sapien
<220> FEATURE:
<221> NAME/KEY: misc_feature
<222> LOCATION: (1)...(30)
<223> OTHER INFORMATION: n = A,T,C or G

<400> SEQUENCE: 287
agcgtggncg cggacganga caacaacccc    30

<210> SEQ ID NO 288
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 288

| | | | | | |
|---|---|---|---|---|---|
| tcgagcggcc | gcccgggcag | gnccacatcg | gcagggtcgg | agccctggcc | gccatactcg | 60 |
| aactggaatc | catcggtcat | gctcttgccg | aaccagacat | gcctcttgtc | cttggggttc | 120 |
| ttgctgatgn | accagttctt | ctgggccaca | ctgggctgag | tggggtacac | gcaggtctca | 180 |
| ccagtctcca | tgttgcagaa | gactttgatg | gcatccaggt | tgcagccttg | gttggggtca | 240 |
| atccagtact | ctccactctt | ccagtcagag | tggcacatct | tgaggtcacg | gcaggtgcgg | 300 |
| gcggggttct | tgacct | | | | | 316 |

<210> SEQ ID NO 289
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 289

| | | | | | |
|---|---|---|---|---|---|
| agcgtggtcg | cggccgaggt | ccagcctgga | gataanggtg | aaggtggtgc | cccggactt | 60 |
| ccaggtatag | ctggacctcg | tggtagccct | ggtgagagag | gtgaaactgg | ccctccagga | 120 |
| cctgctggtt | tccctggtgc | tcctggacag | aatggtgaac | ctggnggtaa | aggagaaaga | 180 |

```
ggggctccgg ntganaaagg tgaaggaggc cctcctgnat tggcaggggc cccangactt    240
agaggtggag ctggccccc  tggccccgaa ggaggaaagg gtgctgctgg tcctcctggg    300
ccacctgg                                                              308

<210> SEQ ID NO 290
<211> LENGTH: 324
<212> TYPE: DNA
<213> ORGANISM: Homo sapien
<220> FEATURE:
<221> NAME/KEY: misc_feature
<222> LOCATION: (1)...(324)
<223> OTHER INFORMATION: n = A,T,C or G

<400> SEQUENCE: 290
tcgagcggcc gcccgggcag gtctgggcca ggaggaccaa taggaccagt aggacccctt    60
gggccatctt tccctgggac accatcagca cctggaccgc ctggttcacc cttgtcaccc   120
tttggaccag gacttccaag acctcctctt tctccaggca ttccttgcag accaggagta   180
ccancagcac caggtggccc aggaggacca gcagcaccct ttcctccttc gggaccaggg   240
ggaccagctc cacctctaag tcctggggcc cctgccaatc caggagggcc tccttcacct   300
ttctcacccg gagcccctct ttct                                           324

<210> SEQ ID NO 291
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 291
tcgagcggcc gcccgggcag gtccaccggg atattcgggg gtctggcagg aatgggaggc    60
atccagaacg agaaggagac catgcaaagc ctgaacgacc gcctggcctc ttacctggac   120
agagtgagga gcctggagac cgacaaccgg aggctggaga gcaaaatccg ggagcacttg   180
gagaagaagg gaccccaggt cagagactgg agccattact tcaagatcat cgaggacctg   240
agggctcana tcttcgcaaa tactgcngac aatgcccg                            278

<210> SEQ ID NO 292
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 292
atgcgnggtc gcggccgang accanctctg gctcatactt gactctaaag ncntcaccag    60
nanttacggn cattgccaat ctgcagaacg atgcgggcat tgtccgcant atttgcgaag   120
atctgagccc tcaggncctc gatgatcttg aagtaanggc tccagtctct gacctggggt   180
cccttcttct ccaagtgctc ccggattttg ctctccagcc tccggttctc ggtctccaag   240
ncttctcact ctgtccagga aaagaggcca ggcggncgat cagggctttt gcatggact    299

<210> SEQ ID NO 293
<211> LENGTH: 101
<212> TYPE: DNA
```

<213> ORGANISM: Homo sapien

<400> SEQUENCE: 293

| agcgtggtcg cggccgaggt tgtacaagct tttttttttt tttttttttt tttttttttt | 60 |
| tttttttttt tttttttttt tttttttttt tttttttttt t | 101 |

<210> SEQ ID NO 294
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 294

| tcgagcggcc gcccgggcag gtctgccaac accaagattg ccccccgccg catccacaca | 60 |
| gttngtgtgc ggggaggtaa caagaaatac cgtgccctga ggntggacgn ggggaatttc | 120 |
| tcctggggct cagagtgttg tactcgtaaa acaaggatca tcgatgttgt ctacaatgca | 180 |
| tctaataacg agctggttcg taccaagacc ctggtgaaga attgcatcgt gctcatngac | 240 |
| agcacaccgt accgacagtg ggtaccgaag tcccactatg cncct | 285 |

<210> SEQ ID NO 295
<211> LENGTH: 216
<212> TYPE: DNA
<213> ORGANISM: Homo sapien

<400> SEQUENCE: 295

| tcgagcggcc gcccgggcag gtccaccaca cccaattcct tgctggtatc atggcagccg | 60 |
| ccacgtgcca ggattaccgg ctacatcatc aagtatgaga agcctgggtc tcctcccaga | 120 |
| gaagtggtcc ctcggccccg ccctggtgtc acagaggcta ctattactgg cctggaaccg | 180 |
| ggaaccgaat atacaattta tgtcattgcc ctgaag | 216 |

<210> SEQ ID NO 296
<211> LENGTH: 414
<212> TYPE: DNA
<213> ORGANISM: Homo sapien
<220> FEATURE:
<221> NAME/KEY: misc_feature
<222> LOCATION: (1)...(414)
<223> OTHER INFORMATION: n = A,T,C or G

<400> SEQUENCE: 296

| agcgtgntcn cggccgagga tggggaagct cgnctgtctt tttccttcca atcagggggct | 60 |
| nnntcttctg attattcttc aggcaanga cataaattgt atattcggnt cccggttcca | 120 |
| gnccagtaat agtagcctct gtgacaccag ggcggggccg agggaccact tctctgggag | 180 |
| gagacccagg cttctcatac ttgatgatga agccggtaat cctggcacgt gggcggctgc | 240 |
| catgatacca ccaangaatt gggtgtggtg gacctgcccg ggcgggccgc tcgaaaancc | 300 |
| gaattcntgc aagaatatcc atcacacttg ggcgggccgn tcgaaccatg catcntaaaa | 360 |
| gggcccaat tcccccccta ttaggngaag ccncatttaa caaattccac ttgg | 414 |

<210> SEQ ID NO 297
<211> LENGTH: 376
<212> TYPE: DNA
<213> ORGANISM: Homo sapien
<220> FEATURE:
<221> NAME/KEY: misc_feature

```
<222> LOCATION: (1)...(376)
<223> OTHER INFORMATION: n = A,T,C or G

<400> SEQUENCE: 297
tcgagcggcc gcccgggcag gtctcgcggt cgcactggtg atgctggtcc tgttggtccc      60
cccggccctc ctggacctcc tggtccccct ggtcctccca gcgctggttt cgacttcagc     120
ttcctgcccc agccacctca agagaaggct cacgatggtg ccgctacta ccgggctgat      180 gatgccaatg tggttcgtga ccgtgacctc gaggtggaca ccaccctcaa gagccttgag     240
ccagcagaat cgaaaacatt cggaacccaa gaagggcaag cccgcaaaga aaccccgccc     300
gcacctggcc gngaacctcc aagaangtgc ccacntcttg actgggaaaa aaagggaaaa     360
ntacttggaa ttggac                                                    376

<210> SEQ ID NO 298
<211> LENGTH: 357
<212> TYPE: DNA
<213> ORGANISM: Homo sapien
<220> FEATURE:
<221> NAME/KEY: misc_feature
<222> LOCATION: (1)...(357)
<223> OTHER INFORMATION: n = A,T,C or G

<400> SEQUENCE: 298
agcgtggtcg cggccgaggt ccacatcggc agggtcggag ccctggccgc catactcgaa      60
ctggaatcca tcgtcatgc tctcgccgaa ccagacatgc ctcttgtcct tggggttctt      120
gctgatgtac cagttcttct gggccacact gggctgagtg gggtacacgc aggtctcacc     180
agtctccatg ttgcagaaga ctttgatggc atccaggttg cagccttggt tggggtcaat     240
ccagtactct ccactcttcc agtcagaagt ggcacatctt gaggtcacgg cagggtgcgg     300
gcggggttct tgcgggctgc ccttctgggc tcccggaatg ttctnngaac ttgctgg       357

<210> SEQ ID NO 299
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 299
agcgtggtcg cggccgaggt ccactagagg tctgtgtgcc attgcccagg cagagtctct      60
gcgttacaaa ctcctaggag ggcttgctgt gcggagggcc tgctatgtg tgctgcggtt     120 catcatggag agtggggcca aaggctgcga ggttgtggtg tctgggaaac tccgaggaca     180
gagggctaaa tccatgaagt ttgtggatgg cctgatgatc cacagcggag accctgttaa     240
ctactacgtt gacacttgct tgtgcgccac gtgttgctca nacangggtg ggctgggcat     300 caaggng                                                              307

<210> SEQ ID NO 300
<211> LENGTH: 351
<212> TYPE: DNA
<213> ORGANISM: Homo sapien

<400> SEQUENCE: 300
tcgagcggcc gcccgggcag gtctgccaag gagaccctgt tatgctgtgg ggactggctg      60
gggcatggca ggcggctctg gcttcccacc cttctgttct gagatggggg tggtgggcag     120
```

| | |
|---|---|
| tatctcatct ttgggttcca caatgctcac gtggtcaggc aggggcttct tagggccaat | 180 |
| cttaccagtt gggtcccagg gcagcatgat cttcaccttg atgcccagca caccctgtct | 240 |
| gagcaacacg tggcgcacag caagtgtcaa cgtaagtaag ttaacagggt ctccgctgtg | 300 |
| gatcatcagg ccatccacaa acttcatgga tttaaccctc tgtcctcgga g | 351 |

<210> SEQ ID NO 301
<211> LENGTH: 330
<212> TYPE: DNA
<213> ORGANISM: Homo sapien

<400> SEQUENCE: 301

| | |
|---|---|
| tcgagcggcc gcccgggcag gtgtttcaga ggttccaagg tccactgtgg aggtcccagg | 60 |
| agtgctggtg gtgggcacag aggtccgatg ggtgaaacca ttgacataga gactgttcct | 120 |
| gtccagggtg taggggccca gctctttgat gccattggcc agttggctca gctcccagta | 180 |
| cagccgctct ctgttgagtc cagggctttt ggggtcaaga tgatggatgc agatggcatc | 240 |
| cactccagtg gctgctccat ccttctcgga cctgagagag gtcagtctgc agccagagta | 300 |
| cagagggcca acactggtgt tctttgaata | 330 |

<210> SEQ ID NO 302
<211> LENGTH: 317
<212> TYPE: DNA
<213> ORGANISM: Homo sapien
<220> FEATURE:
<221> NAME/KEY: misc_feature
<222> LOCATION: (1)...(317)
<223> OTHER INFORMATION: n = A,T,C or G

<400> SEQUENCE: 302

| | |
|---|---|
| agcgtggtcg cggccgaggt ctgtactggg agctaagcaa actgaccaat gacattgaag | 60 |
| agctgggccc ctacccctg acaggaaca gtctctatgt caatggtttc acccatcaga | 120 |
| gctctgtgnc caccaccagc actcctggga cctccacagt ggatttcaga acctcaggga | 180 |
| ctccatcctc cctctccagc cccacaatta tggctgctgg ccctctcctg gtaccattca | 240 |
| ccctcaactt caccatcacc aacctgcagt atggggagga catgggtcac cctgnctcca | 300 |
| ggaagttcaa caccaca | 317 |

<210> SEQ ID NO 303
<211> LENGTH: 283
<212> TYPE: DNA
<213> ORGANISM: Homo sapien
<220> FEATURE:
<221> NAME/KEY: misc_feature
<222> LOCATION: (1)...(283)
<223> OTHER INFORMATION: n = A,T,C or G

<400> SEQUENCE: 303

| | |
|---|---|
| tcgagcggcc gcccggacag gtctgggcgg atagcaccgg gcatattttg gaatggatga | 60 |
| ggtctggcac cctgagcagt ccagcgagga cttggtctta gttgagcaat ttggctagga | 120 |
| ggatagtatg cagcacggnt ctgagnctgt gggatagctg ccatgaagta acctgaagga | 180 |
| ggtgctggct ggtangggtt gattacaggg ttgggaacag ctcgtacact tgccattctc | 240 |
| tgcatatact ggttagtgag gtgagcctgg ccctcttctt ttg | 283 |

<210> SEQ ID NO 304
<211> LENGTH: 72
<212> TYPE: DNA
<213> ORGANISM: Homo sapien

```
<220> FEATURE:
<221> NAME/KEY: misc_feature
<222> LOCATION: (1)...(72)
<223> OTHER INFORMATION: n = A,T,C or G

<400> SEQUENCE: 304
agcgtggtcg cggccgaggt gagccacagg tgaccggggc tgaagctggg gctgctggnc    60
ctgctggtcc tg                                                        72

<210> SEQ ID NO 305
<211> LENGTH: 245
<212> TYPE: DNA
<213> ORGANISM: Homo sapien
<220> FEATURE:
<221> NAME/KEY: misc_feature
<222> LOCATION: (1)...(245)
<223> OTHER INFORMATION: n = A,T,C or G

<400> SEQUENCE: 305
cagcngctcc nacggggcct gnggaccaa caacaccgtt ttcaccctta ggcccttttgg    60 ctcctctttc tcctttagca ccaggttgac cagcagcncc ancaggacca gcaaatccat   120
tggggccagc aggaccgacc tcaccacgtt caccaggct tccccgagga ccagcaggac    180
cagcaggacc agcagcccca gcttcgcccc ggtcacctgt ggctcacctc ggccgcgacc   240
acgct                                                              245

<210> SEQ ID NO 306
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 306
tcgagcggtc gcccgggcag gtccaccggg atagccgggg gtctggcagg aatgggaggc    60
atccagaacg agaaggagac catgcaaagc ctgaacgacc gcctggcctc ttacctggac   120
agagtgagga gcctggagac cganaaccgg aggctggana gcaaaatccg ggagcacttg   180
gagaagaagg gacccccaggt caagagactg gagccattac ttcaagatca tcgagggacc   240
tggagg                                                             246

<210> SEQ ID NO 307
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 307
agcgnggtcg cggccgaggt ccagctctgt ctcatacttg actctaaagt catcagcagc    60
aagacgggca ttgtcaatct gcagaacgat gcgggcattg tccgcagtat ttgcgaagat   120
ctgagccctc aggtcctcga tgatcttgaa gtaatggctc cagtctctga cctgggtcc    180 cttcttctcc aagtgctccc ggattttgct ctccagcctc cggttctcgg tctccaggct   240
cctcactctg tccaggtaag aaggcccagg cggtcgttca ggctttgcat ggtctccttc   300
tcgttctgga tgcctcccat tcctgccaga ccc                               333
```

<210> SEQ ID NO 308
<211> LENGTH: 310
<212> TYPE: DNA
<213> ORGANISM: Homo sapien

<400> SEQUENCE: 308

| | | | | | |
|---|---|---|---|---|---|
| tcgagcggcc | gcccgggcag | gtcaggaagc | acattggtct | tagagccact | gcctcctgga | 60 |
| ttccacctgt | gctgcggaca | tctccaggga | gtgcagaagg | gaagcaggtc | aaactgctca | 120 |
| gatcagtcag | actggctgtt | ctcagttctc | acctgagcaa | ggtcagtctg | cagccagagt | 180 |
| acagagggcc | aacactggtg | ttcttgaaca | agggcttgag | cagaccctgc | agaaccctct | 240 |
| tccgtggtgt | tgaacttcct | ggaaaccagg | gtgttgcatg | tttttcctca | taatgcaagg | 300 |
| ttggtgatgg | | | | | | 310 |

<210> SEQ ID NO 309
<211> LENGTH: 429
<212> TYPE: DNA
<213> ORGANISM: Homo sapien

<400> SEQUENCE: 309

| | | | | | |
|---|---|---|---|---|---|
| agcgtggtcg | cggccgaggt | ccacatcggc | agggtcggag | ccctggccgc | catactcgaa | 60 |
| ctggaatcca | tcggtcatgc | tctcgccgaa | ccagacatgc | ctcttgtcct | tggggttctt | 120 |
| gctgatgtac | cagttcttct | gggccacact | gggctgagtg | gggtacaccg | caggtctcac | 180 |
| cagtctccat | gttgcagaag | actttgatgg | catccaggtt | gcagccttgg | ttggggtcaa | 240 |
| tccagtactc | tccactcttc | cagtcagaag | tgggcacatc | ttgaggtcac | ggcaggtgc | 300 |
| cgggccgggg | gttcttgcgg | cttgccctct | gggctccgga | tgttctcgat | ctgcttggct | 360 |
| caggctcttg | agggtgggtg | tccacctcga | ggtcacggtc | accgaaacct | gcccgggcgg | 420 |
| cccgctcga | | | | | | 429 |

<210> SEQ ID NO 310
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 310

| | | | | | |
|---|---|---|---|---|---|
| tcgagcggtc | gcccgggcag | gtttcgtgac | cgtgacctcg | aggtggacac | caccctcaag | 60 |
| agcctgagcc | agcagatcga | gaacatccgg | agcccagagg | gcagccgcaa | gaaccccgcc | 120 |
| cgcacctgcc | gtgacctcaa | gatgtgccac | tctgactgga | agagtggaga | gtactggatt | 180 |
| gaccccaacc | aaggctgcaa | cctggatgcc | atcaaagtct | tctgcaacat | ggagactggt | 240 |
| gagacctgcg | tgtaccccac | tcagcccagt | gtgggcccag | aagaaactgg | tacatcagca | 300 |
| aggaacccca | aggacaagag | gcattgtctt | ggttcggcga | gnagcatgac | ccgatggatt | 360 |
| ccagtttcga | gtattggcgg | ccagggcttc | ccgacccttg | ccgatgtgga | cctcggccgc | 420 |
| gaccaccgct | | | | | | 430 |

<210> SEQ ID NO 311
<211> LENGTH: 2996
<212> TYPE: DNA
<213> ORGANISM: Homo sapien

<400> SEQUENCE: 311

```
cagccaccgg agtggatgcc atctgcaccc accgccctga ccccacaggc cctgggctgg      60
acagagagca gctgtatttg gagctgagcc agctgaccca cagcatcact gagctgggcc     120
cctacaccct ggacagggac agtctctatg tcaatggttt cacacagcgg agctctgtgc     180
ccaccactag cattcctggg accccacag tggacctggg aacatctggg actccagttt     240
ctaaacctgg tccctcggct gccagccctc tcctggtgct attcactctc aacttcacca     300
tcaccaacct gcggtatgag gagaacatgc agcaccctgg ctccaggaag ttcaacacca     360
cggagagggt ccttcaggc ctggtccctg ttcaagagca ccagtgttgg ccctctgtac      420
tctggctgca gactgacttt gctcaggcct gaaaaggatg ggacagccac tggagtggat     480
gccatctgca cccaccaccc tgaccccaaa agccctaggc tggacagaga gcagctgtat     540
tgggagctga ccagctgac ccacaatatc actgagctgg ccctatgc cctggacaac       600 gacagcctct ttgtcaatgg tttcactcat cggagctctg tgtccaccac cagcactcct     660
gggaccccca cagtgtatct gggagcatct aagactccag cctcgatatt tggcccttca     720
gctgccagcc atctcctgat actattcacc ctcaacttca ccatcactaa cctgcggtat     780
gaggagaaca tgtggcctgg ctccaggaag ttcaacacta cagagagggt ccttcagggc     840
ctgctaaggc ccttgttcaa gaaccagt gttggccctc tgtactctgg ctgcaggctg       900
accttgctca ggcagagaa agatggggaa gccaccggag tggatgccat ctgcacccac      960
cgccctgacc ccacaggccc tgggctggac agagagcagc tgtatttgga gctgagccag    1020
ctgacccaca gcatcactga gctgggcccc tacacactgg acagggacag tctctatgtc    1080
aatggtttca cccatcggag ctctgtaccc accaccagca ccgggtggt cagcgaggag     1140 ccattcacac tgaacttcac catcaacaac ctgcgctaca tggcggacat gggccaaccc    1200
ggctccctca gttcaacat cacagacaac gtcatgaagc acctgctcag tcctttgttc     1260
cagaggagca gcctgggtgc acggtacaca ggctgcaggg tcatcgcact aaggtctgtg    1320
aagaacggtg ctgagacacg ggtggacctc ctctgcacct acctgcagcc cctcagcggc    1380
ccaggtctgc ctatcaagca ggtgttccat gagctgagcc agcagaccca tggcatcacc    1440
cggctgggcc cctactctct ggacaaagac agcctctacc ttaacggtta caatgaacct    1500
ggtccagatg agcctcctac aactcccaag ccagccacca cattcctgcc tcctctgtca    1560
gaagccacaa cagccatggg gtaccacctg aagaccctca cactcaactt caccatctcc    1620
aatctccagt attcaccaga tatgggcaag ggctcagcta cattcaactc caccgagggg    1680
gtccttcagc acctgctcag acccttgttc cagaagagca gcatgggccc cttctacttg    1740
ggttgccaac tgatctccct caggcctgag aaggatgggg cagccactgg tgtggacacc    1800
acctgcacct accaccctga ccctgtgggc ccgggctgg acatacagca gctttactgg    1860
gagctgagtc agctgaccca tggtgtcacc caactgggct ctatgtcct ggacagggat    1920 agcctcttca tcaatggcta tgcaccccag aatttatcaa tccggggcga gtaccagata    1980
aatttccaca ttgtcaactg gaacctcagt aatccagacc ccacatcctc agagtacatc    2040
accctgctga gggacatcca ggacaaggtc accacactct acaaaggcag tcaactacat    2100
gacacattcc gcttctgcct ggtcaccaac ttgacgatgg actccgtgtt ggtcactgtc    2160
aaggcattgt tctcctccaa tttggacccc agcctggtgg agcaagtctt tctagataag    2220
accctgaatg cctcattcca ttggctgggc tccacctacc agttggtgga catccatgtg    2280
acagaaatgg agtcatcagt ttatcaacca acaagcagct ccagcaccca gcacttctac    2340
```

-continued

```
ctgaatttca ccatcaccaa cctaccatat tcccaggaca aagcccagcc aggcaccacc    2400
aattaccaga ggaacaaaag gaatattgag gatgcgctca accaactctt ccgaaacagc    2460
agcatcaaga gttattttc tgactgtcaa gtttcaacat tcaggtctgt ccccaacagg     2520
caccacaccg gggtggactc cctgtgtaac ttctcgccac tggctcggag agtagacaga    2580
gttgccatct atgaggaatt tctgcggatg acccggaatg gtacccagct gcagaacttc    2640
accctggaca ggagcagtgt ccttgtggat gggtatttc caacagaaa tgagcccta     2700 actgggaatt ctgaccttcc cttctgggct gtcatcctca tcggcttggc aggactcctg    2760
ggactcatca catgcctgat ctgcggtgtc ctggtgacca cccgccggcg aagaaggaa     2820 ggagaataca acgtccagca acagtgccca ggctactacc agtcacacct agacctggag    2880
gatctgcaat gactggaact tgccggtgcc tggggtgcct ttcccccagc cagggtccaa    2940
agaagcttgg ctggggcaga aataaaccat attggtcgga cacaaaaaaa aaaaaa       2996
```

<210> SEQ ID NO 312
<211> LENGTH: 914
<212> TYPE: PRT
<213> ORGANISM: Homo sapien

<400> SEQUENCE: 312

```
Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
```

-continued

```
                 260                 265                 270
Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685
```

```
Leu Asp Lys Thr Leu Asn Ala Ser Phe His Trp Leu Gly Ser Thr Tyr
        690                 695                 700

Gln Leu Val Asp Ile His Val Thr Glu Met Glu Ser Ser Val Tyr Gln
705                 710                 715                 720

Pro Thr Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
        755                 760                 765

Arg Asn Ser Ser Ile Lys Ser Tyr Phe Ser Asp Cys Gln Val Ser Thr
770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
                805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
        835                 840                 845

Glu Pro Leu Thr Gly Asn Ser Asp Leu Pro Phe Trp Ala Val Ile Leu
850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
                885                 890                 895

Gln Gln Gln Cys Pro Gly Tyr Tyr Gln Ser His Leu Asp Leu Glu Asp
            900                 905                 910

Leu Gln

<210> SEQ ID NO 313
<211> LENGTH: 656
<212> TYPE: DNA
<213> ORGANISM: Homo sapiens

<400> SEQUENCE: 313
acagccagtc ggagctgcaa gtgttctggg tggatcgcgy atatgcactc aaaatgctct    60
ttgtaaagga aagccacaac atgtccaagg gacctgaggc gacttggagg ctgagcaaag   120
tgcagtttgt ctacgactcc tcggagaaaa cccacttcaa agacgcagtc agtgctggga   180
agcacacagc caactcgcac cacctctctg ccttggtcac ccccgctggg aagtcctatg   240
agtgtcaagc tcaacaaacc atttcactgg cctctagtga tccgcagaag acggtcacca   300
tgatcctgtc tgcggtccac atccaacctt ttgacattat ctcagatttt gtcttcagtg   360
aagagcataa atgcccagtg gatgagcggg agcaactgga agaaaccttg ccctgatttt   420
tgggctcat cttgggcctc gtcatcatgg taacactcgc gatttaccac gtccaccaca   480
aaatgactgc caaccaggtg cagatccctc gggacagatc ccagtataag cacatgggct   540
agaggccgtt aggcaggcac ccctattcc tgctccccca actggatcag gtagaacaac   600
aaaagcactt ttccatcttg tacacgagat acaccaacat agctacaatc aaacag        656

<210> SEQ ID NO 314
<211> LENGTH: 519
<212> TYPE: DNA
```

<213> ORGANISM: Homo sapiens

<400> SEQUENCE: 314

| | | | | | |
|---|---|---|---|---|---|
| tgtgcgtgga | ccagtcagct | tccgggtgtg | actggagcag | ggcttgtcgt | cttcttcaga | 60 |
| gtcactttgc | aggggttggt | gaagctgctc | ccatccatgt | acagctccca | gtctactgat | 120 |
| gtttaaggat | ggtctcggtg | gttaggccca | ctagaataaa | ctgagtccaa | tacctctaca | 180 |
| cagttatgtt | taactgggct | ctctgacacc | gggaggaagg | tggcggggtt | taggtgttgc | 240 |
| aaacttcaat | ggtatgcgg | ggatgttcac | agagcaagct | ttggtatcta | gctagtctag | 300 |
| cattcattag | ctaatggtgt | cctttggtat | ttattaaaat | caccacagca | tagggggact | 360 |
| ttatgtttag | gttttgtcta | agagttagct | tatctgcttc | ttgtgctaac | agggctattg | 420 |
| ctaccaggga | ctttggacat | ggggccagc | gtttggaaac | ctcatctagt | ttttttgaga | 480 |
| gataggccac | tggccttgga | cctcggccgc | gaccacgct | | | 519 |

<210> SEQ ID NO 315
<211> LENGTH: 441
<212> TYPE: DNA
<213> ORGANISM: Homo sapiens

<400> SEQUENCE: 315

| | | | | | |
|---|---|---|---|---|---|
| cacagagcgt | ttattgacac | caccactcct | gaaaattggg | atttcttatt | aggttcccct | 60 |
| aaaagttccc | atgttgatta | catgtaaata | gtcacatata | tacaatgaag | gcagtttctt | 120 |
| cagaggcaac | cagggtttat | agtgctaggt | aaatgtcatc | tcttttgtgc | tactgactca | 180 |
| ttgtcaaacg | tctctgcact | gttttcagcc | tctccacgtt | gcctctgtcc | tgcttcttag | 240 |
| ttccttcttt | gtgacaaacc | aaaagaataa | gaggatttag | aacaggactg | cttttcccct | 300 |
| atgatttaaa | aattccaatg | actttcgccc | ttgggagaaa | tttccaagga | aatctctctc | 360 |
| gctcgctctc | tccgttttcc | tttgtgagct | tctgggggag | ggttagtggt | gacttttga | 420 |
| tacgaaaaaa | tgcattttgt | g | | | | 441 |

<210> SEQ ID NO 316
<211> LENGTH: 247
<212> TYPE: DNA
<213> ORGANISM: Homo sapiens

<400> SEQUENCE: 316

| | | | | | |
|---|---|---|---|---|---|
| tggcgcggct | gctggatttc | accttcttgc | acctgccggt | gagcgcctgg | ggtctaaagg | 60 |
| ggcgggatac | tccattatgg | cccctcgccc | tgtagggctg | gaatagttag | aaaaggcaac | 120 |
| ccagtctagc | ttggtaagaa | gagagacatg | ccccccaacct | cggcgccctt | tttcctcacg | 180 |
| atctgctgtc | cttacttcag | cgactgcagg | agcttcacct | gcaagaaaac | agcattgagc | 240 |
| tgctgac | | | | | | 247 |

<210> SEQ ID NO 317
<211> LENGTH: 409
<212> TYPE: DNA
<213> ORGANISM: Homo sapiens

<400> SEQUENCE: 317

| | | | | | |
|---|---|---|---|---|---|
| tgacagggct | cctggagttg | ttaagtcacc | aagtagctgc | agggatgga | cactgcccca | 60 |
| cacgatgtgg | gatgaacagc | agccttggtt | tgtagcccag | ggtgtccatg | gatttgaccc | 120 |
| gaatgctccc | tggaggccct | gtggcgagga | caggcactga | atggtccaga | ccctctggct | 180 |
| ggaggagtgg | tggagccagg | actgggcctt | cagccatgag | ggctagaata | acctgacctc | 240 |

```
ttgcattcta acactgggtc attaatgaca cctttccagt ggatgttgca aaaaccaaca    300
ctgtcaggaa cctggccctg ggagggctca ggtgagctca caaggagagg tcaagccaag    360
ccaaagggta ggkaacacac aacaccaggg gaaaccagcc cccaaacca               409
```

<210> SEQ ID NO 318
<211> LENGTH: 320
<212> TYPE: DNA
<213> ORGANISM: Homo sapiens
<220> FEATURE:
<221> NAME/KEY: misc_feature
<222> LOCATION: (1)...(320)
<223> OTHER INFORMATION: n = A,T,C or G

<400> SEQUENCE: 318

```
caaggnagat cttaagnggg gtcntatgta agtgtgctcc tggctccagg gttcctggag     60
cctcacgagg tcaggggaac ccttgtagaa ctccaccagc agcatcatct cgtgaaggat    120
gtcattggtc aggaagctgt cctggacgta ggccatctcc acatccatgg ggatgccata    180
gtcactgggc ctttgctcgg gaggaggcat cacccagaaa ggcgagatct tggactcggg    240 gcctggttg ccagaatagt aaggggagca nagcagggcg aggcagggct ggaagccatt    300
gctggagccc tgcagccgca                                                320
```

<210> SEQ ID NO 319
<211> LENGTH: 212
<212> TYPE: DNA
<213> ORGANISM: Homo sapiens
<220> FEATURE:
<221> NAME/KEY: misc_feature
<222> LOCATION: (1)...(212)
<223> OTHER INFORMATION: n = A,T,C or G

<400> SEQUENCE: 319

```
tgaagcaata gcgcccccat tttacaggcg gagcatggaa gccagagagg tgggtggggg     60 aggggtcct tccctggctc aggcagatgg gaagatgagg aagccgctga agacgctgtc    120
ggcctcagag ccctggtaaa tgtgacccct tttggggtct ttttcaaccc anacctggtc    180
accctgctgc agacctcggc cgcgaccacg ct                                  212
```

<210> SEQ ID NO 320
<211> LENGTH: 769
<212> TYPE: DNA
<213> ORGANISM: Homo sapiens

<400> SEQUENCE: 320

```
tggaggtgta gcagtgagag gagatytcag gcaagagtgt cacagcagag ccctaaascc     60
tccaactcac cagtgagaga tgagactgcc cagtactcag ccttcatctc ctgggccacc    120
tggagggcgt ctttctccat cagcgcatac tgagcagggg tactcagatc cttcttggaa    180
cctacaagga agagaagcac actggaaggg tcattctcct tcagggcatc ggccagccac    240
tgcctgccat gggagtgga aagtaaggga tgagtgagtc tgcagggccc ctcccactga    300
cattcatagg cccaattacc ccctctctgg tcctacatgc attcttcttc ttcctgacca    360 ccctctgtt ctgaaccctc tcttcccgga gcctcccatt atattgcagg atgctcactt    420
acttggtatg ttccagagat gccacatcat tcaggttgaa gacaatgatg atggcttgga    480
agagtggcag aaacagcccc aggttgacag ggaagacact actgctcatt tccccaatcc    540
ttccagctcc atatgagaaa gccatgtgca ctctgagacc cacctacccc acttcaccca    600
```

| | |
|---|---|
| gccccttacc ttgagctcct ctatagtagg ttgatgcaat gcatttgaac ctctcctgcc | 660 |
| cagcggtatc ccaactggaa ggaaggaaga gtgaagcaca ggtatgtatc ttgggggtg | 720 |
| tgggtgctgg ggagaaggga tagctggaag gggtgtggaa gcactcaca | 769 |

<210> SEQ ID NO 321
<211> LENGTH: 690
<212> TYPE: DNA
<213> ORGANISM: Homo sapiens
<220> FEATURE:
<221> NAME/KEY: misc_feature
<222> LOCATION: (1)...(690)
<223> OTHER INFORMATION: n = A,T,C or G

<400> SEQUENCE: 321

| | |
|---|---|
| tgggctgtgg gcggcacctg tgctctgcag gccagacagc gatagaagcc tttgtctgtg | 60 |
| cctactcccc cggaggcaac tgggaggtca acgggaagac aatcatcccc tataagaagg | 120 |
| gtgcctggtg ttcgctctgc acagccagtg tctcaggctg cttcaaagcc tgggaccatg | 180 |
| caggggggct ctgtgaggtc cccaggaatc cttgtcgcat gagctgccag aaccatggac | 240 |
| gtctcaacat cagcacctgc cactgccact gtcccctgg ctacacgggc agatactgcc | 300 |
| aagtgaggtg cagcctgcag tgtgtgcacg gccggttccg ggaggaggag tgctcgtgcg | 360 |
| tctgtgacat cggctacggg ggagcccagt gtgccaccaa ggtgcatttt cccttccaca | 420 |
| cctgtgacct gaggatcgac ggagactgct tcatggtgtc ttcagaggca gacacctatt | 480 |
| acagaagcca ggatgaaatg tcagaggaat ggcgggggtgc tggcccagat caagagccag | 540 |
| aaagtgcagg acatcctcgc cttctatctg ggccgcctgg agaccaccaa cgaggtgact | 600 |
| gacagtgact ttgagaccag gaacttctgg atngggctca cctacaagac cgccaaggac | 660 |
| tccttncgct gggccacagg ggagcaccag | 690 |

<210> SEQ ID NO 322
<211> LENGTH: 104
<212> TYPE: DNA
<213> ORGANISM: Homo sapiens

<400> SEQUENCE: 322

| | |
|---|---|
| gtcgcaagcc ggagcaccac catgtagcct ttcccgaagt accggacctt ctcctcctcc | 60 |
| acgctcacat cacggacatc atggagcagg accaccacct ggtc | 104 |

<210> SEQ ID NO 323
<211> LENGTH: 118
<212> TYPE: DNA
<213> ORGANISM: Homo sapiens

<400> SEQUENCE: 323

| | |
|---|---|
| gggccctggg cgcttccaaa tgacccagga ggtggtctgc gacgaatgcc ctaatgtcaa | 60 |
| actagtgaat gaagaacgaa cactggaagt agaaatagag cctggggtga gagacgga | 118 |

<210> SEQ ID NO 324
<211> LENGTH: 354
<212> TYPE: DNA
<213> ORGANISM: Homo sapiens

<400> SEQUENCE: 324

| | |
|---|---|
| tgctctccgg gagcttgaag aagaaactgg ctacaaaggg gacattgccg aatgttctcc | 60 |
| agcggtctgt atggacccag gcttgtcaaa ctgtactata cacatcgtga cagtcaccat | 120 |
| taacggagat gatgccgaaa acgcaaggcc gaagccaaag ccaggggatg gagagtttgt | 180 |

```
ggaagtcatt tctttaccca agaatgacct gctgcagaga cttgatgctc tggtagctga    240
agaacatctc acagtggacg ccagggtcta ttcctacgct ctagcgctga aacatgcaaa    300
tgcaaagcca tttgaagtgc ccttcttgaa attttaagcc caaatatgac actg          354
```

<210> SEQ ID NO 325
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n = A,T,C or G

<400> SEQUENCE: 325

```
ncatgcttga atgggctcct ggtgagagat tgcccctgg tggtgaaaca atcgtgtgtg     60
cccactgata ccaagaccaa tgaaagagac acagttaagc agcaatccat ctcatttcca    120
ggcacttcaa taggtcgctg attggtcctt gcaccagcag tggtagtcgt acctatttca    180
gagaggtctg aaattcaggt tcttagtttg ccagggacag gccctacctt atattttttt    240
ccatcttcat catccacttc tgcttacagt ttgctgctta caataactta atgatggatt    300
gagttatctg ggtggtctct agccatctgg gcagtgtggt tctgtctaac caaagggcat    360
tggcctcaaa ccctgcattt ggtttagggg ctaacagagc tcctcagata atcttcacac    420
acatgtaact gctggagatc ttattctatt atgaataaga aacgagaagt ttttccaaag    480
tgttagtcag gatctgaagg ctgtcattca gataacccag ctttcctttt ggcttttag     540 cccattcaga ctttgccaga gtcaagccaa ggattgcttt tttgctacag ttttctgcca    600
aatggcctag ttcctgagta cctggaaacc agagagaaag ag                       642
```

<210> SEQ ID NO 326
<211> LENGTH: 455
<212> TYPE: DNA
<213> ORGANISM: Homo sapiens

<400> SEQUENCE: 326

```
tccgtgagga tgagcttcga gtccttcacc aggcactgca ggggcacagt cacgtcaatc    60
accttcacct tctcgctctt cctgctcttg tcattgacaa acttcccgta ccaggcattg    120
acgatgatga ggcccattct ggactcttct gcctcaatta tccttcggac agattcctgc    180
atcagccgga cagcggactc cgcctcttgc ttcttctgca gcacatcggt ggcggcgctt    240
tccctctgct tctccaattc cttctctttc tgagccctga ggtatggttt gatgatcaga    300
cggtgcatgg caaagtagac cactagaggc cccacggtgg catagaacat ggcgctgggc    360
agaagctggt ccgtcaagtg aatagggaag aagtatgtct gactggccct gttgagcttg    420
actttgagag aaacgccctg tggaactcca acgct                               455
```

<210> SEQ ID NO 327
<211> LENGTH: 321
<212> TYPE: DNA
<213> ORGANISM: Homo sapiens

<400> SEQUENCE: 327

```
ttcactgtga actcgcagtc ctcgatgaac tcgcacagat gtgacagccc tgtctccttg    60
ctctctgagt tctcttcaat gatgctgatg atgcagtcca cgatagcgcg cttatactca    120
aagccaccct cttcccgcag catggtgaac aggaagttca taggacggc gtgtttgcga     180
```

```
ggatatttct gacacagggc actgatggcc tggacaacca ccaccttgaa ttcatccgag      240
atttctgaca tgaaggagga gatctgcttc atgaggcggt cgatgctgct ctcgctgccc      300
gtcttaagga gggtggtgat g                                                321
```

<210> SEQ ID NO 328
<211> LENGTH: 476
<212> TYPE: DNA
<213> ORGANISM: Homo sapiens
<220> FEATURE:
<221> NAME/KEY: misc_feature
<222> LOCATION: (1)...(476)
<223> OTHER INFORMATION: n = A,T,C or G

<400> SEQUENCE: 328

```
tgcaggaggg gccatggggg ctgtgaatgg gatgcagccc catggtgtcc ctgataaatc       60
cagtgtgcag tctgatgaag tctgggtggg tgtggtctac gggctggcag ctaccatgat      120
ccaagaggta atgcactcct tttcccatct ctccaccatc tgtatcctgg ccmagaaaaa      180
cttcccttca aaccaaccaa aatttccttt caaaggcata acccaaatgc catccttggt      240
ccggtctaat aaagcctccc ccattttttcc cctggtatgc attcccaggc tccctggcct     300
tncagggctt nctgtctgtg ggtcatagtt tatctcctcc cacttgctgg gagctccttg      360
aaggcaaaga ctctactgcc tccatctatc cagtggaagt ggctcttcag agggtgccaa      420
gttagtatgt atgactgtca tctctcccaa cagggcctga cttggsaggg cttcca          476
```

<210> SEQ ID NO 329
<211> LENGTH: 340
<212> TYPE: DNA
<213> ORGANISM: Homo sapiens

<400> SEQUENCE: 329

```
cgagggagat tgccagcacc ctgatggaga gtgagatgat ggagatcttg tcagtgctag       60
ctaagggtga ccacagccct gtcacaaggg ctgctgcagc ctgcctggac aaagcagtgg      120
aatatgggct tatccaaccc aaccaagatg gagagtgagg gggttgtccc tgggcccaag      180
gctcatgcac acgctaccta ttgtggcacg gagagtaagg acggaagcag ctttggctgg      240
tggtggctgg catgcccaat actcttgccc atcctcgctt gctgcccctag gatgtcctct     300 gttctgagtc agcggccacg ttcagtcaca cagccctgct                            340
```

<210> SEQ ID NO 330
<211> LENGTH: 277
<212> TYPE: DNA
<213> ORGANISM: Homo sapiens

<400> SEQUENCE: 330

```
tgtcaccatc acattggtgc caaatacccca gaagacatcg tagatgaaga gtccgcccag      60
caggatgcag ccagtgctga cattgttgag gtgcaggagc tctactccat taagggagaa      120
ggccaggcca aaaaggttgt tggcaatcca gtgcttcctc agcaggtacc agacgccaac      180
gatgctgctc aggcccaggc acaccaggtc cttggtgtca aattcataat tgatgatctc      240
ctccttgttt tcccagaacc ctgtgtgaag agcagac                               277
```

<210> SEQ ID NO 331
<211> LENGTH: 136
<212> TYPE: DNA
<213> ORGANISM: Homo sapiens

<400> SEQUENCE: 331

```
ttgcttccca cctcctttct ctgtcctctc ctgaggttct gccttacaat ggggacactg       60
atacaaacca cacacacaat gaggatgaaa acagataaca ggtaaaatga cctcacctgc      120
ccgggcggcc gctcga                                                      136
```

<210> SEQ ID NO 332
<211> LENGTH: 184
<212> TYPE: DNA
<213> ORGANISM: Homo sapiens

<400> SEQUENCE: 332

```
ttgtgagata aacgcagata ctgcaatgca ttaaaacgct tgaaatactc atcagggatg       60
ttgctgatct tattgttgtc taagtagaga gttagaagag agacagggag accagaaggc      120
agtctggcta tctgattgaa gctcaagtca aggtattcga gtgatttaag acctttaaaa      180
gcag                                                                   184
```

<210> SEQ ID NO 333
<211> LENGTH: 384
<212> TYPE: DNA
<213> ORGANISM: Homo sapiens

<400> SEQUENCE: 333

```
cggaaaactt cgaggaattg ctcaaagtgc tgggggtgaa tgtgatgctg aggaagattg       60
ctgtggctgc agcgtccaag ccagcagtgg agatcaaaca ggagggagac actttctaca      120
tcaaaacctc caccaccgtg cgcaccacag agattaactt caaggttggg gaggagtttg      180
aggagcagac tgtggatggg aggccctgta agagcctggt gaaatgggag agtgagaata      240
aaatggtctg tgagcagaag ctcctgaagg gagagggccc caagacctcg tggaccagag      300
aactgaccaa cgatggggaa ctgatcctga ccatgacggc ggatgacgtt gtgtgcacca      360
gggtctacgt ccgagagtga gcgg                                             384
```

<210> SEQ ID NO 334
<211> LENGTH: 169
<212> TYPE: DNA
<213> ORGANISM: Homo sapiens
<220> FEATURE:
<221> NAME/KEY: misc_feature
<222> LOCATION: (1)...(169)
<223> OTHER INFORMATION: n = A,T,C or G

<400> SEQUENCE: 334

```
cnacaaacag agcagacacc ctggatccgg tcctgctact ggccaggacg gctggaccgt       60
aaaattgaat ttccacttcc tgaccgccgc cagaagagat tgattttctc cactatcact      120
agcaagatga acctctctga ggaggttgac ttggaagact atgtngccc                  169
```

<210> SEQ ID NO 335
<211> LENGTH: 185
<212> TYPE: DNA
<213> ORGANISM: Homo sapiens

<400> SEQUENCE: 335

```
ccaggtttgc agcccaggct gcacatcagg ggactgcctc gcaatacttc atgctgttgc       60
tgctgactga tggtgctgtg acggatgtgg aagccacacg tgaggctgtg gtgcgtgcct      120
cgaacctgcc catgtcagtg atcattgtgg gtgtgggtgg tgctgacttt gaggccatgg      180
agcag                                                                  185
```

<210> SEQ ID NO 336
<211> LENGTH: 358
<212> TYPE: DNA
<213> ORGANISM: Homo sapiens
<220> FEATURE:
<221> NAME/KEY: misc_feature
<222> LOCATION: (1)...(358)
<223> OTHER INFORMATION: n = A,T,C or G

<400> SEQUENCE: 336

| | | |
|---|---|---|
| ctgcccctgc cttacggcgg ccaganacac acccaggatg gcattggccc caaacttgga | 60 |
| tttgttctca gtcccatcca actccagcat caggttgtcc agtttctctt gctccaccac | 120 |
| agagagacct gagctgatga gggctggcgc gatggtggag ttgatgtggt ccactgcctt | 180 |
| caggacacct ttgcctaagt aacgctgttt gtctccatcc ctcagctcca gggcctcata | 240 |
| gatgcccgta gaggctccac tgggcactgc agcccggaaa agacctttgg cagtatagag | 300 |
| atccacctcc actgtggggt tcccgcggga gtccaggatc tcccgggccc agatcttc | 358 |

<210> SEQ ID NO 337
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n = A,T,C or G

<400> SEQUENCE: 337

| | | |
|---|---|---|
| cacaaagcca ccagccnggg aaatcagaat ttacttgatg caactgactt gtaatagcca | 60 |
| gaaatcctgc ccagcatggg attcagaacc tggtctgcaa ccaaatccac cgtcaaagtt | 120 |
| catacaggat aaaacaaatt caattgcctt ttccacatta atagcatcaa gcttccccaa | 180 |
| caaagccaaa gttgccaccg cacaaaaaga gaatcttgtg tcaatttctc cctactttat | 240 |
| aaaagtagat ttttcacatc ccatgaagca g | 271 |

<210> SEQ ID NO 338
<211> LENGTH: 326
<212> TYPE: DNA
<213> ORGANISM: Homo sapiens
<220> FEATURE:
<221> NAME/KEY: misc_feature
<222> LOCATION: (1)...(326)
<223> OTHER INFORMATION: n = A,T,C or G

<400> SEQUENCE: 338

| | | |
|---|---|---|
| ctgtgctccc gactngnnca tctcaggtac caccgactgc actgggcggg gccctctggg | 60 |
| gggaaaggct ccacggggca gggatacatc tcgaggccag tcatcctctg gaggcagccc | 120 |
| aatcaggtca aagattttgc ccaactggtc ggcttcagag tttccacaga agagaggctt | 180 |
| tcgacgaaac atctctgcaa agatacagcc aacactccac atgtccacag gtgttgcata | 240 |
| tgtggactgc agaagaactt cgggagctcg gtaccagagt gtaacaacca cgggtgtaag | 300 |
| tgccatctgg tagctgtaga ttctgg | 326 |

<210> SEQ ID NO 339
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n = A,T,C or G

<400> SEQUENCE: 339

```
ttcacctgag gactcatttc gtgcccttg ttgacttcaa gcaaagncct tcanggtctn      60
caaggacgnc acatttccac ttgcgaatgn nctcanggct catcttgaag aanaagnanc    120
ccaagtgctg gatcccagac tcgggggtaa ccttgtgggt aagagctcat ccagtttatg    180
ctttaggacg tccanctact cggggagct ggaagcctgc gtggatgcgg ccctgctgga     240
cctcggccgc gaccacgcta                                                 260
```

<210> SEQ ID NO 340
<211> LENGTH: 220
<212> TYPE: DNA
<213> ORGANISM: Homo sapiens
<220> FEATURE:
<221> NAME/KEY: misc_feature
<222> LOCATION: (1)...(220)
<223> OTHER INFORMATION: n = A,T,C or G

<400> SEQUENCE: 340

```
ctggaagccc ggctnggnct ggcagcggaa ggagccaggc aggttcacgc agcggtgctg     60
gcagtagcgg tagcggcact cgtctatgtc cacacactcg ggcccgatct tgcggtaacc   120
atcagggcag gtgcactgat aggagccagg caagttatgg cagtcctggc tggggcgaca   180
gtcgtgcagg gcctgggcac actcgtccac atccacacag                          220
```

<210> SEQ ID NO 341
<211> LENGTH: 384
<212> TYPE: DNA
<213> ORGANISM: Homo sapiens

<400> SEQUENCE: 341

```
ctgctaccag gggagcgaga gctgactatc ccagcctcgg ctaatgtatt ctacgccatg     60
gatggagctt cacacgattt cctcctgcgg cagcggcgaa ggtcctctac tgctacaccg   120
ggcgtcacca gtggcccgtc tgcctcagga actcctccga gtgagggagg aggggctcc    180
tttcccagga tcaaggccac aggaggaag attgcacggg cactgttctg aggaggaagc   240
cccgttggct tacagaagtc atggtgttca taccagatgt gggtagccat cctgaatggt   300
ggcaattata tcacattgag acagaaattc agaaagggag ccagccaccc tggggcagtg   360
aagtgccact ggtttaccag acag                                           384
```

<210> SEQ ID NO 342
<211> LENGTH: 245
<212> TYPE: DNA
<213> ORGANISM: Homo sapiens

<400> SEQUENCE: 342

```
ctggctaagc tcatcattgt tactggtggg caccatgtcc ttgaagcttc aggcaagcaa     60
tgtaaccaac aagaatgacc ccaagtccat caactctcga gtcttcattg gaaacctcaa   120
cacagctctg gtgaagaaat cagatgtgga gaccatcttc tctaagtatg gccgtgtggc   180
cggctgttct gtgcacaagg gctatgcctt tgttcagtac tccaatgagc gccatgcccg   240
ggcag                                                                245
```

<210> SEQ ID NO 343
<211> LENGTH: 611
<212> TYPE: DNA
<213> ORGANISM: Homo sapiens

<400> SEQUENCE: 343

```
ccaaaaaaat caagatttaa ttttttatt tgcactgaaa aactaatcat aactgttaat      60
tctcagccat ctttgaagct tgaaagaaga gtctttggta ttttgtaaac gttagcagac    120
tttcctgcca gtgtcagaaa atcctattta tgaatcctgt cggtattcct tggtatctga   180
aaaaaatacc aaatagtacc atacatgagt tatttctaag tttgaaaaat aaaaagaaat    240
tgcatcacac taattacaaa atacaagttc tggaaaaaat attttcttc attttaaaac    300
tttttttaac taataatggc tttgaaagaa gaggcttaat ttgggggtgg taactaaaat    360
caaaagaaat gattgacttg agggtctctg tttggtaaga atacatcatt agcttaaata    420
agcagcagaa ggttagtttt aattatgtag cttctgttaa tattaagtgt tttttgtctg    480
ttttacctca atttgaacag ataagtttgc ctgcatgctg gacatgcctc agaaccatga    540
atagcccgta ctagatcttg ggaacatgga tcttagagtc ctttggaata agttcttata    600
taaataccc  c                                                         611
```

<210> SEQ ID NO 344
<211> LENGTH: 311
<212> TYPE: DNA
<213> ORGANISM: Homo sapiens
<220> FEATURE:
<221> NAME/KEY: misc_feature
<222> LOCATION: (1)...(311)
<223> OTHER INFORMATION: n = A,T,C or G

<400> SEQUENCE: 344

```
nctcgaaaaa gcccaagaca gcagaagcag acacctccag tgaactagca aagaaaagca     60
aagaagtatt cagaaaagag atgtcccagt tcatcgtcca gtgcctgaac ccttaccgga   120
aacctgactg caaagtggga agaattacca caactgaaga cttttaaacat ctggctcgca   180
agctgactca cggtgttatg aataaggagc tgaagtactg taagaatcct gaggacctgg   240
agtgcaatga gaatgtgaaa cacaaaacca aggantacat taanaagtac atgcannaan    300
tttggggctt g                                                         311
```

<210> SEQ ID NO 345
<211> LENGTH: 201
<212> TYPE: DNA
<213> ORGANISM: Homo sapiens

<400> SEQUENCE: 345

```
cacacggtca tcccgactgc caacctggag gcccaggccc tgtggaagga gccgggcagc     60
aatgtcacca tgagtgtgga tgctgagtgt gtgcccatgg tcaggacct tctcaggtac    120
ttctactccc gaaggattga catcaccctg tcgtcagtca agtgcttcca caagctggcc    180
tctgcctatg gggccaggca g                                             201
```

<210> SEQ ID NO 346
<211> LENGTH: 370
<212> TYPE: DNA
<213> ORGANISM: Homo sapiens

<400> SEQUENCE: 346

```
ctgctccagg gcgtggtgtg ccttcgtggc ctctgcctcc tccgaggagc caggctgtgt     60
tctcttcaga atgttctgga gcagcagttt gaggcgggtg atgcgttgga agggcagaat   120
cagaaaggac ttgagggaaa ggcgctggca gacgggtcg ctctccagct tctccaagac    180
ctcccggaaa ttgctgttgc tattcatcag gctctggaag gtgcgttcct gataggtctg    240
```

```
gttggtgaca taaggcaggt agacccggcg gaagtctggg gcgtggttca ggactacgtc    300
acatacttgg aaggagaaga tattgttctc aaagttctct tccaggtctg aaaggaacgt    360
ggcgctgacg                                                           370
```

<210> SEQ ID NO 347
<211> LENGTH: 416
<212> TYPE: DNA
<213> ORGANISM: Homo sapiens
<220> FEATURE:
<221> NAME/KEY: misc_feature
<222> LOCATION: (1)...(416)
<223> OTHER INFORMATION: n = A,T,C or G

<400> SEQUENCE: 347

```
ctgttgtgct gtgtatggac gtgggcttta ccatgagtaa ctccattcct ggtatagaat    60
ccccatttga acaagcaaag aaggtgataa ccatgtttgt acagcgacag gtgtttgctg    120
agaacaagga tgagattgct ttagtcctgt ttggtacaga tggcactgac aatccccttt    180
ctggtgggga tcagtatcag aacatcacag tgcacagaca tctgatgcta ccagattttg    240
atttgctgga ggacattgaa agcaaaatcc aaccaggttc tcaacaggct gacttcctgg    300
atgcactaat cgtgagcatg gatgtgattc aacatgaaac aataggaaag aagtttggag    360
aagaggcata ttgaaatatt cactgacctc aagcagcccg attcagcaaa agtcan       416
```

<210> SEQ ID NO 348
<211> LENGTH: 351
<212> TYPE: DNA
<213> ORGANISM: Homo sapiens

<400> SEQUENCE: 348

```
gtacaggaga ggatggcagg tgcagagcgg gcactgagct ctgcaggtga aagggctcgg    60
cagttggatg ctctcctgga ggctctgaaa ttgaaacggg caggaaatag tctggcagcc    120
tctacagcag aagaaacggc aggcagtgcc cagggacgag caggagacag atgccttcct    180
cttgtctcaa ctgcaaagag gcgttccttc ctctttcact aatcctcctc agcacagacc    240
ctttacgggt gtcaggctgg gggacagtaa ggtctttccc ttcccacaag gccatatctc    300
aggctgtctc agtgggggga aaccttggac aatacccggg ctttcttggg c            351
```

<210> SEQ ID NO 349
<211> LENGTH: 207
<212> TYPE: DNA
<213> ORGANISM: Homo sapiens
<220> FEATURE:
<221> NAME/KEY: misc_feature
<222> LOCATION: (1)...(207)
<223> OTHER INFORMATION: n = A,T,C or G

<400> SEQUENCE: 349

```
nccgggacat ctccaccctc aacagtggca agaagagcct ggagactgaa cacaaggcct    60
tgaccagtga gattgcactg ctgcagtcca ggctgaagac agagggctct gatctgtgcg    120
acagagtgag cgaaatgcag aagctggatg cacaggtcaa ggagctggtg ctgaagtcgg    180
cggtggaggc tgagcgcctg gtggctg                                        207
```

<210> SEQ ID NO 350
<211> LENGTH: 323
<212> TYPE: DNA
<213> ORGANISM: Homo sapiens

<400> SEQUENCE: 350

| | | |
|---|---|---|
| ccatacaggg ctgttgccca ggccctagag gtcattcctc gtaccctgat ccagaactgt | 60 |
| ggggccagca ccatccgtct acttacctcc cttcgggcca agcacaccca ggagaactgt | 120 |
| gagacctggg gtgtaaatgg tgagacgggt actttggtgg acatgaagga actgggcata | 180 |
| tgggagccat tggctgtgaa gctgcagact tataagacag cagtgcagac ggcagttctg | 240 |
| ctactgcgaa ttgatgacat cgtttcaggc cacgaaaaga aggcgatga ccagagccgg | 300 |
| caaggcgggg ctcctgatgc tgg | 323 |

<210> SEQ ID NO 351
<211> LENGTH: 353
<212> TYPE: DNA
<213> ORGANISM: Homo sapiens
<220> FEATURE:
<221> NAME/KEY: misc_feature
<222> LOCATION: (1)...(353)
<223> OTHER INFORMATION: n = A,T,C or G

<400> SEQUENCE: 351

| | | |
|---|---|---|
| cgccgcatcc cntggtccct tccantccct tttcctttnt cngggaacgt gtatgcggtt | 60 |
| tgttttgtt tgtagggtt tttttcctc tccacctctc cctgtctctt ttgctccatg | 120 |
| ttgtccgttt ctgtggggtt aggtttatgt ttttaatcat ctgaggtcac gtctatttcc | 180 |
| tccggactcg cctgcttggt ggcgattctc caccggttaa tatggtgcgt cccttttttc | 240 |
| ttttgttgcg aatctgagcc ttcttcctcc agcttctgcc ttttgaactt tgttcttcgg | 300 |
| ttctgaaacc atacttttac ctgagtttcc gtgaggctga ggctgtgtgc caa | 353 |

<210> SEQ ID NO 352
<211> LENGTH: 467
<212> TYPE: DNA
<213> ORGANISM: Homo sapiens

<400> SEQUENCE: 352

| | | |
|---|---|---|
| ctgcccacac tgatcacttg cgagatgtcc ttagggtaca agaacaggaa ttgaagtctg | 60 |
| aatttgagca gaacctgtct gagaaactct ctgaacaaga attacaattt cgtcgtctca | 120 |
| gtcaagagca agttgacaac tttactctgg atataaatac tgcctatgcc agactcagag | 180 |
| gaatcgaaca ggctgttcag agccatgcag ttgctgaaga ggaagccaga aaagcccacc | 240 |
| aactctggct ttcagtggag gcattaaagt acagcatgaa gacctcatct gcagaaacac | 300 |
| ctactatccc gctgggtagt gcagttgagg ccatcaaagc caactgttct gataatgaat | 360 |
| tcacccaagc tttaaccgca gctatccctc cagagtccct gacccgtggg gtgtacagtg | 420 |
| aagagaccct tagagcccgt ttctatgctg ttcaaaaact ggcccga | 467 |

<210> SEQ ID NO 353
<211> LENGTH: 350
<212> TYPE: DNA
<213> ORGANISM: Homo sapiens

<400> SEQUENCE: 353

| | | |
|---|---|---|
| ctgctgcagc cacagtagtt cctcccatgg tgggtggccc tcctggtcct gctggcccag | 60 |
| gaaatctgtc cccaccagga acagccctg gaaaacggcc ccgtcctcta ccaccttgtg | 120 |
| gaaatgctgc acgggaactg cctcctggag gaccagcttt accttcccca gacatttgtc | 180 |
| ctgattgtgt agttttcctg gactgcattt caaattgact caggaactgt ttattgcatg | 240 |
| gagttacaac aggattctga ccatgaagtt ctcttttagg taacagatcc attaactttt | 300 |

```
ttgaagatgc ttcagatcca acaccaacaa gggcaaaccc ctttgactgg            350
```

<210> SEQ ID NO 354
<211> LENGTH: 351
<212> TYPE: DNA
<213> ORGANISM: Homo sapiens

<400> SEQUENCE: 354

```
atttagatga gatctgaggc atggagacat ggagacagta tacagactcc tagatttaag    60
ttttaggttt tttgcttttc taatcaccaa ttcttatata caatgtatat tttagactcg   120
agcagatgat catcttcatc ttaagtcatt cctttttgact gagtatggca ggattagagg   180
gaatggcagt atagatcaat gtcttttttct gtaaagtata ggaaaaacca gagaggaaaa   240
aaagagctga caattggaag gtagtagaaa attgacgata atttcttctt aacaaataat    300
agttgtatat acaaggaggc tagtcaacca gattttattt gttgagggcg a             351
```

<210> SEQ ID NO 355
<211> LENGTH: 308
<212> TYPE: DNA
<213> ORGANISM: Homo sapiens

<400> SEQUENCE: 355

```
ttttggcgca gtttttacag attttattaa agtcgaagct attggtcttg gaagatgaaa     60
atgcaaatgt tgatgaggtg gaattgaagc cagataccttaataaaatta tatcttggtt    120
ataaaaataa gaaattaagg gttaacatca atgtgccaat gaaaaccgaa cagaagcagg    180
aacaagaaac cacacacaaa aacatcgagg aagaccgcaa actactgatt caggcggcca    240
tcgtgagaat catgaagatg aggaaggttc tgaaacacca gcagttactt ggcgaggtcc   300
tcactcag                                                             308
```

<210> SEQ ID NO 356
<211> LENGTH: 207
<212> TYPE: DNA
<213> ORGANISM: Homo sapiens

<400> SEQUENCE: 356

```
ctgtcccaag tgctcccaga aggcaggatt ctgaagacca ctccagcgat atgttcaact     60
atgaagaata ctgcaccgcc aacgcagtca ctgggccttg ccgtgcatcc ttcccacgct    120
ggtactttga cgtggagagg aactcctgca ataacttcat ctatggaggc tgccggggca    180
ataagaacag ctaccgctct gaggagg                                         207
```

<210> SEQ ID NO 357
<211> LENGTH: 188
<212> TYPE: DNA
<213> ORGANISM: Homo sapiens
<220> FEATURE:
<221> NAME/KEY: misc_feature
<222> LOCATION: (1)...(188)
<223> OTHER INFORMATION: n = A,T,C or G

<400> SEQUENCE: 357

```
tcgaccacgc cctcgtagcg catgngctnc aggacgatgc tcagagtgat gaacacccccg    60
gtgcggccca cgccagcact gcagtgcacc gtgataggcc catcctgtcc aaactgctcc    120
ttggtcttat gcacctgccc gatgaagtca atgaatccct cgcctgtctt gggcacgccc    180
tgctctgg                                                             188
```

<210> SEQ ID NO 358
<211> LENGTH: 291
<212> TYPE: DNA
<213> ORGANISM: Homo sapiens

<400> SEQUENCE: 358

```
ctgggagcat cggcaagcta ctgccttaaa atccgatctc cccgagtgca caatttctgt      60
cccttttaag ggttcacaac actaaagatt tcacatgaaa gggttgtgat tgatttgagc     120
aggcaggcgg tacgtgacag gggctgcatg caccggtggt cagagagaaa cagaacaggg     180
cagggaattt cacaatgttc ttctatacaa tggctggaat ctatgaataa catcagtttc     240
taagttatgg gttgattttt aactactggg tttaggccag gcaggcccag g              291
```

<210> SEQ ID NO 359
<211> LENGTH: 117
<212> TYPE: DNA
<213> ORGANISM: Homo sapiens
<220> FEATURE:
<221> NAME/KEY: misc_feature
<222> LOCATION: (1)...(117)
<223> OTHER INFORMATION: n = A,T,C or G

<400> SEQUENCE: 359

```
gccaccacac tccagcctgg gcaatacagc aagactgtct caaaaaaaaa aaaaaaaaa       60
cccaaaaaaa ctcaaaaang taatgaatga tacccaangn gccttttcta gaaaaag        117
```

<210> SEQ ID NO 360
<211> LENGTH: 394
<212> TYPE: DNA
<213> ORGANISM: Homo sapiens

<400> SEQUENCE: 360

```
ctgttcctct ggggtggtcc agttctagag tgggagaaag ggagtcaggc gcattgggaa      60
tcgtggttcc agtctggttg cagaatctgc acatttgcca agaaattttc cctgtttgga     120
aagtttgccc cagcttttccc gggcacacca ccttttgtcc caagtgtctg ccggtcgacc    180
aatctgcctg ccacacattg accaagccag acccggttca cccagctcga ggatcccagg     240
ttgaagagtg gcccccttgag gccctggaaa gaccaatcac tggacttctt cccttgagag    300
tcagaggtca cccgtgattc tgcctgcacc ttatcattga tctgcagtga tttctgcaaa     360
tcaagagaaa ctctgcaggg cactcccctg tttc                                 394
```

<210> SEQ ID NO 361
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 361

```
ctgggcggat agcaccgggc atattttntt natggatgag gtctggcacc ctgagcagtc      60
cagcgaggac ttggtcttag ttgagcaatt tggctaggag gatagtatgc agcacggttc     120
tgagtctgtg ggatagctgc catgaagtaa cctgaaggag gtgctggctg gtagggggttg    180
attacagggt tgggaacagc tcgtacactt gccattctct gcatatactg gttagtgagg     240
tgagcctggc gctcttcttt gcgctgagct aaagctacat acaatggctt tgtggacctc     300
ggccgcgacc acgctaagcc gaattccagc acactggcgg ccgttactag tggatccgag     360
```

```
ctcggtacca agcttggcgt aatcatggtc atag                                    394
```

<210> SEQ ID NO 362
<211> LENGTH: 268
<212> TYPE: DNA
<213> ORGANISM: Homo sapiens

<400> SEQUENCE: 362

```
ctgcgcgtgg accagtcagc ttccgggtgt gactggagca gggcttgtcg tcttcttcag         60
agtcactttg caggggttgg tgaagctgct cccatccatg tacagctccc agtctactga       120
tgtttaagga tggtctcggt ggttaggccc actagaataa actgagtcca atacctctac       180
acagttatgt ttaactgggc tctctgacac cgggaggaag gtggcgggt ttaggtgttg        240
caaacttcaa tggttatgcg gggatgtt                                          268
```

<210> SEQ ID NO 363
<211> LENGTH: 323
<212> TYPE: DNA
<213> ORGANISM: Homo sapiens

<400> SEQUENCE: 363

```
ccttgacctt ttcagcaagt gggaaggtgt aatccgtctc cacagacaag gccaggactc        60
gtttgtaccc gttgatgata aatgggta ctgatgcaac agttgggtag ccaatctgca        120
gacagacact ggcaacattg cggacaccct ccaggaagcg agaatgcaga gtttcctctg      180
tgatatcaag cacttcaggg ttgtagatgc tgccattgtc gaacacctgc tggatgacca       240
gcccaaagga gaagggggag atgttgagca tgttcagcag cgtggcttcg ctggctccca      300
ctttgtctcc agtcttgatc aga                                              323
```

<210> SEQ ID NO 364
<211> LENGTH: 393
<212> TYPE: DNA
<213> ORGANISM: Homo sapiens
<220> FEATURE:
<221> NAME/KEY: misc_feature
<222> LOCATION: (1)...(393)
<223> OTHER INFORMATION: n = A,T,C or G

<400> SEQUENCE: 364

```
ccaagctctc catcgtcccc gtgcgcagng gctactgggg gaacaagatc ggcaagcccc        60
acactgtccc ttgcaaggtg acaggccgct gcggctctgt gctggtacgc ctcatcactg      120
cacccagggg cactggcatc gtctccgcac ctgtgcctaa gaagctgctc atgatggctg      180
gcatcgatga ctgctacacc tcagcccggg gctgcactgc caccctgggc aacttcgcca      240
aggccacctt tgatgccatt tctaagacct acagctacct gacccccgac ctctggaagg     300
agactgtatt caccaagtct ccctatcagg agttcactga ccacctcgtc aagacccaca    360
ccagagtctc cgtgcagcgg actcaggctc cag                                   393
```

<210> SEQ ID NO 365
<211> LENGTH: 371
<212> TYPE: DNA
<213> ORGANISM: Homo sapiens

<400> SEQUENCE: 365

```
cctcctcaga gcggtagctg ttcttattgc cccggcagcc tccatagatg aagttattgc        60
aggagttcct ctccacgtca aagtaccagc gtgggaagga tgcacggcaa ggcccagtga      120
```

-continued

| | | |
|---|---|---|
| ctgcgttggc ggtgcagtat tcttcatagt tgaacatatc gctggagtgg tcttcagaat | 180 | |
| cctgccttct gggagcactt gggacagagg aatccgctgc attcctgctg gtggacctcg | 240 | |
| gccgcgacca cgctaagccg aattccagca cactggcggc cgttactagt ggatccgagc | 300 | |
| tcggtaccaa gcttggcgta atcatggtca tagctgtttc ctgtgtgaaa ttgttatccg | 360 | |
| ctcacaattc c | 371 | |

<210> SEQ ID NO 366
<211> LENGTH: 393
<212> TYPE: DNA
<213> ORGANISM: Homo sapiens

<400> SEQUENCE: 366

| | | |
|---|---|---|
| atttcttgcc agatgggagc tctttggtga agactccttt cgggaaaagt ttttggctt | 60 | |
| cttcttcagg gatggttgga aggaccatca cactatcccc atccttccaa tcaactgggg | 120 | |
| tggcaaccct tttttctgct gtcagctgga gagagatgac taccctgaga atctcatcaa | 180 | |
| agttcctgcc agtggtagct gggtagagga tagacagctt cagcttctta tcaggaccaa | 240 | |
| aaacaaacac cacacgagct gccacaggca tgcccttttc atccttctct gctggatcca | 300 | |
| gcatgcccaa caggatggca agctcccgat tcctatcatc gatgatggga aaaggtaact | 360 | |
| tttctgtggg ctcttcacaa ttgtaagcat tga | 393 | |

<210> SEQ ID NO 367
<211> LENGTH: 327
<212> TYPE: DNA
<213> ORGANISM: Homo sapiens
<220> FEATURE:
<221> NAME/KEY: misc_feature
<222> LOCATION: (1)...(327)
<223> OTHER INFORMATION: n = A,T,C or G

<400> SEQUENCE: 367

| | | |
|---|---|---|
| ccagctctgt ctcatacttg actctaaagt cttnagcagc aagacgggca ttgnnaatct | 60 | |
| gcagaacgat gcgggcattg tccacagtat ttgcgaagat ctgagccctc aggtcctcga | 120 | |
| tgatcttgaa gtaatggctc cagtctctga cctggggtcc cttcttctcc aagtgctccc | 180 | |
| ggattttgct ctccagcctc cggttctcgg tctccaggct cctcactctg tccaggtaag | 240 | |
| aggccaggcg gtcgttcagg ctttgcatgg tctccttctc gttctggatg cctcccattc | 300 | |
| ctgccagacc cccggctatc ccggtgg | 327 | |

<210> SEQ ID NO 368
<211> LENGTH: 306
<212> TYPE: DNA
<213> ORGANISM: Homo sapiens
<220> FEATURE:
<221> NAME/KEY: misc_feature
<222> LOCATION: (1)...(306)
<223> OTHER INFORMATION: n = A,T,C or G

<400> SEQUENCE: 368

| | | |
|---|---|---|
| ctggagaagg acttcagcag tttnaagaag tactgccaag tcatccgtgt cattgcccac | 60 | |
| acccagatgc gcctgcttcc tctgcgccag aagaaggccc acctgatgga gatccaggtg | 120 | |
| aacggaggca ctgtggccga gaagctggac tgggcccgcg agaggcttga gcagcaggta | 180 | |
| cctgtgaacc aagtgtttgg gcaggatgag atgatcgacg tcatcggggt gaccaagggc | 240 | |
| aaaggctaca aggggtcac cagtcgttgg cacaccaaga agctgccccg caagacccac | 300 | |
| cgagga | 306 | |

<210> SEQ ID NO 369
<211> LENGTH: 394
<212> TYPE: DNA
<213> ORGANISM: Homo sapiens

<400> SEQUENCE: 369

| | | | | | |
|---|---|---|---|---|---|
| tcgacccaca | ccggaacacg | gagagctggg | ccagcattgg | cacttgatag | gatttcccgt | 60 |
| cggctgccac | gaaagtgcgt | ttctttgtgt | tctcgggttg | gaaccgtgat | ttccacagac | 120 |
| ccttgaaata | cactgcgttg | acgaggacca | gtctggtgag | cacaccatca | ataagatctg | 180 |
| gggacagcag | attgtcaatc | atatccctgg | tttcattttt | aacccatgca | ttgatggaat | 240 |
| cacaggcaga | ggctggatcc | tcaaagttca | cattccggac | ctcacactgg | aacacatctt | 300 |
| tgttccttgt | aacaaaaggc | acttcaattt | cagaggcatt | cttaacaaac | acggcgttag | 360 |
| ccactgtcac | aatgtcttta | ttcttcttgg | agac | | | 394 |

<210> SEQ ID NO 370
<211> LENGTH: 653
<212> TYPE: DNA
<213> ORGANISM: Homo sapiens

<400> SEQUENCE: 370

| | | | | | |
|---|---|---|---|---|---|
| ccaccacacc | caattccttg | ctggtatcat | ggcagccgcc | acgtgccagg | attaccggct | 60 |
| acatcatcaa | gtatgagaag | cctgggtctc | ctcccagaga | agtggtccct | cggccccgcc | 120 |
| ctggtgtcac | agaggctact | attactggcc | tggaaccggg | aaccgaatat | acaatttatg | 180 |
| tcattgccct | gaagaataat | cagaagagcg | agcccctgat | tggaaggaaa | aagacagacg | 240 |
| agcttcccca | actggtaacc | cttccacacc | ccaatcttca | tggaccagag | atcttggatg | 300 |
| ttccttccac | agttcaaaag | accccttttcg | tcacccaccc | tgggtatgac | actggaaatg | 360 |
| gtattcagct | tcctggcact | tctggtcagc | aacccagtgt | tgggcaacaa | atgatctttg | 420 |
| aggaacatgg | ttttaggcgg | accacaccgc | ccacaacggc | cacccccata | aggcataggc | 480 |
| caagaccata | cccgccgaat | gtaggacaag | aagctctctc | tcagacaacc | atctcatggg | 540 |
| ccccattcca | ggacacttct | gagtacatca | tttcatgtca | tcctgttggc | actgatgaag | 600 |
| aacccttaca | gttcagggtt | cctggaactt | ctaccagtgc | cactctgaca | gga | 653 |

<210> SEQ ID NO 371
<211> LENGTH: 268
<212> TYPE: DNA
<213> ORGANISM: Homo sapiens

<400> SEQUENCE: 371

| | | | | | |
|---|---|---|---|---|---|
| ctgcccagcc | cccattggcg | agtttgagaa | ggtgtgcagc | aatgacaaca | agaccttcga | 60 |
| ctcttcctgc | cacttctttg | ccacaaagtg | caccctggag | ggcaccaaga | agggccacaa | 120 |
| gctccacctg | gactacatcg | ggccttgcaa | atacatcccc | ccttgcctgg | actctgagct | 180 |
| gaccgaattc | cccctgcgca | tgcgggactg | gctcaagaac | gtcctggtca | ccctgtatga | 240 |
| gagggatgag | gacaacaacc | ttctgact | | | | 268 |

<210> SEQ ID NO 372
<211> LENGTH: 392
<212> TYPE: DNA
<213> ORGANISM: Homo sapiens

<400> SEQUENCE: 372

```
gctggtgccc ctggtgaacg tggacctcct ggattggcag gggccccagg acttagaggt    60
ggaactggtc ccctggtcc cgaaggagga aagggtgctg ctggtcctcc tgggccacct    120
ggtgctgctg gtactcctgg tctgcaagga atgcctggag aaagaggagg tcttggaagt    180
cctggtccaa agggtgacaa gggtgaacca ggcggtccag gtgctgatgg tgtcccaggg    240
aaagatggcc caagggtcc tactggtcct attggtcctc ctggcccagc tggccagcct    300
ggagataagg gtgaaggtgg tgcccccgga cttccaggta tagctggacc tcgtggtagc    360
cctggtgaga gaggtgaaac ctcggccgcg ac                                  392
```

<210> SEQ ID NO 373
<211> LENGTH: 388
<212> TYPE: DNA
<213> ORGANISM: Homo sapiens
<220> FEATURE:
<221> NAME/KEY: misc_feature
<222> LOCATION: (1)...(388)
<223> OTHER INFORMATION: n = A,T,C or G

<400> SEQUENCE: 373

```
ccaagcgctc agatcggcaa ggggcaccan ttttgatctg cccagtgcac agccccacaa    60
ccaggtcagc gatgaaggta tcttcagtct ccccgaacg atgagacacc atgacgcccc    120
aaccattggc ctgggccagc ttgcacgcct gaagagactc ggtcacggag ccaatctggt    180
tgactttgag caggaggcag ttgcaggact tctcgttcac ggccttggcg atcctctttg    240
ggttggtcac tgtgagatca tcccccacta cctggattcc tgcactggct gtgaacttct    300
gccaagctcc ccagtcatcc tggtcaaagg gatcttcgat agacaccact gggtagtcct    360
tgatgaagga cttgtacagg tcagccag                                       388
```

<210> SEQ ID NO 374
<211> LENGTH: 393
<212> TYPE: DNA
<213> ORGANISM: Homo sapiens

<400> SEQUENCE: 374

```
ctgacgaccg cgtgaacccc tgcattgggg gtgtcatcct cttccatgag acactctacc    60
agaaggcgga tgatgggcgt cccttccccc aagttatcaa atccaagggc ggtgttgtgg    120
gcatcaaggt agacaagggc gtggtccccc tggcagggac aaatggcgag actaccaccc    180
aagggttgga tgggctgtct gagcgctgtg cccagtacaa gaaggacgga ctgacttcg    240 ccaagtggcg ttgtgtgctg aagattgggg aacacacccc ctcagccctc gccatcatgg    300
aaaatgccaa tgttctggcc cgttatgcca gtatctgcca gcagaatggc attgtgccca    360
tcgtggagcc tgagatcctc cctgatgggg acc                                 393
```

<210> SEQ ID NO 375
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 375

```
ccacaaatgg cgtggtccat gtcatcaccn ttnttctgca gcctccagcc aacagacctc    60
aggaaagagg ggatgaactt gcagactctg cgcttgagat cttcaaacaa gcatcagcgt    120
tttccagggc ttcccagagg tctgtgcgac tagcccctgt ctatcaaaag ttattagaga    180
```

```
ggatgaagca ttagcttgaa gcactacagg aggaatgcac cacggcagct ctccgccaat    240
ttctctcaga tttccacaga gactgtttga atgttttcaa aaccaagtat cacactttaa    300
tgtacatggg ccgcaccata atgagatgtg agccttgtgc atgtggggga ggagggagag    360
agatgtactt tttaaatcat gttcccccta aaca                                394
```

<210> SEQ ID NO 376
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 376

```
ctgcccagcc cccattggcg agtttgattn ggtgtgcagc aatgacaaca agaccttcga    60
ctcttcctgc cacttctttg ccacaaagtg caccctggag ggcaccaaga agggccacaa    120
gctccacctg gactacatcg ggccttgcaa atacatcccc ccttgcctgg actctgagct    180
gaccgaattc cccctgcgca tgcgggactg gctcaagaac gtcctggtca ccctgtatga    240
gagggatgag gacaacaacc ttctgactga gaagcagaag ctgcgggtga agaagatcca    300
tgagaatgag aagcgcctgg aggcaggaga ccaccccgtg gagctgctgg cccgggactt    360
cgagaagaac tataacatgt acatcttccc tg                                  392
```

<210> SEQ ID NO 377
<211> LENGTH: 292
<212> TYPE: DNA
<213> ORGANISM: Homo sapiens

<400> SEQUENCE: 377

```
caatgtttga tgcttaaccc ccccaatttc tgtgagatgg atggccagtg caagcgtgac    60
ttgaagtgtt gcatgggcat gtgtgggaaa tcctgcgttt ccctgtgaa agcttgattc     120 ctgccatatg gaggaggctc tggagtcctg ctctgtgtgg tccaggtcct ttccaccctg    180
agacttggct ccaccactga tatcctcctt tggggaaagg cttggcacac agcaggcttt    240
caagaagtgc cagttgatca atgaataaat aaacgagcct atttctcttt gc            292
```

<210> SEQ ID NO 378
<211> LENGTH: 395
<212> TYPE: DNA
<213> ORGANISM: Homo sapiens

<400> SEQUENCE: 378

```
ctgctgcttc agcgaagggt ttctggcata tccaatgata aggctgccaa agactgttcc    60
aataccagca ccagaaccag ccactcctac tgttgcagca cctgcaccaa taaatttggc    120
agcagtatca atgtctctgc tgattgcact ggtctgaaac tcccctttgga ttagctgaga    180 cacaccattc tgggccctga ttttcctaag atagaactcc aactctttgc cctctagcac    240
atagccatct gctcggccac actgtcccgg ccttgaagcg atgcacgcaa gaagcttgcc    300
ctgctggaac tgctcctcca ggagactgct gattttggca ttcttttttcc tttcatcata    360 tttcttctga attttttaga tcgttttttg tttaa                               395
```

<210> SEQ ID NO 379
<211> LENGTH: 223
<212> TYPE: DNA

<213> ORGANISM: Homo sapiens

<400> SEQUENCE: 379

```
ccagatgaaa tgctgccgca atggctgtgg gaaggtgtcc tgtgtcactc ccaatttctg      60
agctccagcc accaccaggc tgagcagtga ggagagaaag tttctgcctg gccctgcatc     120
tggttccagc ccacctgccc tcccttttt cgggactctg tattccctct tgggctgacc     180
acagcttctc cctttcccaa ccaataaagt aaccactttc agc                      223
```

<210> SEQ ID NO 380
<211> LENGTH: 317
<212> TYPE: DNA
<213> ORGANISM: Homo sapiens
<220> FEATURE:
<221> NAME/KEY: misc_feature
<222> LOCATION: (1)...(317)
<223> OTHER INFORMATION: n = A,T,C or G

<400> SEQUENCE: 380

```
tcgaccacag tattccaacc ctcctgtgcn tngagaagtg atggagggtg ctgacaacca     60
gggtgcagga gaacaaggta gaccagtgag gcagaatatg tatcggggat atagaccacg    120
attccgcagg ggccctcctc gccaaagaca gcctagagag gacggcaatg aagaagataa    180
agaaaatcaa ggagatgaga cccaaggtca gcagccacct caacgtcggt accgccgcaa    240
cttcaattac cgacgcagac gcccagaaaa ccctaaacca agatggcaa agagacaaa    300
agcagccgat ccaccag                                                  317
```

<210> SEQ ID NO 381
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 381

```
cctgaaggaa gagctggcct acctgaatnn naaccatgag gaggaaatca gtacgctgag     60
gggccaagtg ggaggccagg tcagtgtgga ggtggattcc gctccgggca ccgatctcgc    120
caagatcctg agtgacatgc gaagccaata tgaggtcatg gccgagcaga accggaagga    180
tgctgaagcc tggttcacca gccggactga agaattgaac cggaggtcg ctggccacac    240
ggagcagctc cagatgagca ggtccgaggt tactgacctg cggcgcaccc ttcagggtct    300
tgagattgag ctgcagtcac agacctcggc cgcgaccacg ctaagccgaa ttccagcaca    360
ctggcggccg ttactagtgg atccgagctc gg                                 392
```

<210> SEQ ID NO 382
<211> LENGTH: 234
<212> TYPE: DNA
<213> ORGANISM: Homo sapiens

<400> SEQUENCE: 382

```
cctcgatgtc taaatgagcg tggtaaagga tggtgcctgc tggggtctcg tagataccctc    60
gggacttcat tccaatgaag cggttctcca cgatgtcaat acggcccacg ccatgcttgc    120
ccgcgacttc gttcaggtac atgaagagct ccaaggaggt ctggtgggtg gtgccatcct    180
tgacgttggt caccttcaca gggacccctt ttttgaactc catctccaga atgt          234
```

```
<210> SEQ ID NO 383
<211> LENGTH: 396
<212> TYPE: DNA
<213> ORGANISM: Homo sapiens
<220> FEATURE:
<221> NAME/KEY: misc_feature
<222> LOCATION: (1)...(396)
<223> OTHER INFORMATION: n = A,T,C or G

<400> SEQUENCE: 383
ccttgacctt  ttcagcaagt  gggaaggtgt  tttccgtctc  cacagacaag  gccaggactc      60
gtttgnaccc  gttgatgata  gaatggggta  ctgatgcaac  agttgggtag  ccaatctgca     120
gacagacact  ggcaacattg  cggacaccca  ggatttcaat  ggtgcccctg  gagattttag     180
tggtgatacc  taaagcctgg  aaaaggagg   tcttctcggg  cccgagacca  gtgttctggg     240
ctggcacagt  gacttcacat  ggggcaatgg  caccagcacg  ggcagcagac  ctgcccgggc     300
ggccgctcga  aagccgaatt  ccagcacact  ggcggccgtt  actagtggat  ccgagctcgg     360
taccaagctt  ggcgtaatca  tggtcatagc  tgtttc                                 396

<210> SEQ ID NO 384
<211> LENGTH: 396
<212> TYPE: DNA
<213> ORGANISM: Homo sapiens

<400> SEQUENCE: 384
gctgaatagg  cacagagggc  acctgtacac  cttcagacca  gtctgcaacc  tcaggctgag      60
tagcagtgaa  ctcaggagcg  ggagcagtcc  attcaccctg  aaattcctcc  ttggtcactg     120
ccttctcagc  agcagcctgc  tcttcttttt  caatctcttc  aggatctctg  tagaagtaca     180
gatcaggcat  gacctcccat  gggtgttcac  gggaaatggt  gccacgcatg  cgcagaactt     240
cccgagccag  catccaccac  atcaaaccca  ctgagtgagc  tcccttgttg  ttgcatggga     300
tggcaatgtc  cacatagcgc  agaggagaat  ctgtgttaca  cagcgcaatg  gtaggtaggt     360
taacataaga  tgcctccgtg  agaggctggt  ggtcag                                 396

<210> SEQ ID NO 385
<211> LENGTH: 2943
<212> TYPE: DNA
<213> ORGANISM: Homo sapiens

<400> SEQUENCE: 385
cagccaccgg  agtggatgcc  atctgcaccc  accgccctga  ccccacaggc  cctgggctgg      60
acagagagca  gctgtatttg  gagctgagcc  agctgaccca  cagcatcact  gagctgggcc     120
cctacaccct  ggacagggac  agtctctatg  tcaatggttt  cacacagcgg  agctctgtgc     180
ccaccactag  cattcctggg  accccacag   tggacctggg  aacatctggg  actccagttt     240
ctaaacctgg  tccctcggct  gccagccctc  tcctggtgct  attcactctc  aacttccacca    300
tcaccaacct  gcggtatgag  gagaacatgc  agcaccctgg  ctccaggaag  ttcaacacca     360
cggagagggt  ccttcaggcc  ctggtccctg  ttcaagagca  ccagtgttgg  ccctctgtac     420
tctggctgca  gactgacttt  gctcaggcct  gaaaaggatg  ggacagccac  tggagtggat     480
gccatctgca  cccaccaccc  tgaccccaaa  agccctaggc  tggacagaga  gcagctgtat     540
tgggagctga  gccagctgac  ccacaatatc  actgagctgg  gccctatgc   cctggacaac     600
gacagcctct  tgtcaatgg   tttcactcat  cggagctctg  tgtccaccac  cagcactcct     660
gggacccca   cagtgtatct  gggagcatct  aagactccag  cctcgatatt  tggcccttca     720
```

-continued

```
gctgccagcc atctcctgat actattcacc ctcaacttca ccatcactaa cctgcggtat    780
gaggagaaca tgtggcctgg ctccaggaag ttcaacacta cagagagggt ccttcagggc    840
ctgctaaggc ccttgttcaa gaacaccagt gttggccctc tgtactctgg ctgcaggctg    900
accttgctca ggccagagaa agatggggaa gccaccggag tggatgccat ctgcacccac    960
cgccctgacc ccacaggccc tgggctggac agagagcagc tgtatttgga gctgagccag   1020
ctgacccaca gcatcactga gctgggcccc tacacactgg acagggacag tctctatgtc   1080
aatggtttca cccatcggag ctctgtaccc accaccagca ccggggtggt cagcgaggag   1140
ccattcacac tgaacttcac catcaacaac ctgcgctaca tggcggacat gggccaaccc   1200
ggctcccctca gttcaacat cacagacaac gtcatgaagc acctgctcag tcctttgttc   1260
cagaggagca gcctgggtgc acggtacaca ggctgcaggg tcatcgcact aaggtctgtg   1320
aagaacggtg ctgagacacg ggtggacctc ctctgcacct acctgcagcc cctcagcggc   1380
ccaggtctgc ctatcaagca ggtgttccat gagctgagcc agcagaccca tggcatcacc   1440
cggctgggcc cctactctct ggacaaagac agcctctacc ttaacggtta caatgaacct   1500
ggtccagatg agcctcctac aactcccaag ccagccacca cattcctgcc tcctctgtca   1560
gaagccacaa cagccatggg gtaccacctg aagaccctca cactcaactt caccatctcc   1620
aatctccagt attcaccaga tatgggcaag ggctcagcta cattcaactc caccgagggg   1680
gtccttcagc acctgctcag acccttgttc cagaagagca gcatgggccc cttctacttg   1740
ggttgccaac tgatctccct caggcctgag aaggatgggg cagccactgg tgtggacacc   1800
acctgcacct accaccctga ccctgtgggc cccgggctgg acatacagca gctttactgg   1860
gagctgagtc agctgaccca tgggtgtcacc caactgggct tctatgtcct ggacagggat   1920
agcctcttca tcaatggcta tgcaccccag aatttatcaa tccggggcga gtaccagata   1980
aatttccaca ttgtcaactg gaacctcagt aatccagacc ccacatcctc agagtacatc   2040
accctgctga gggacatcca ggacaaggtc accacactct acaaaggcag tcaactacat   2100
gacacattcc gcttctgcct ggtcaccaac ttgacgatgg actccgtgtt ggtcactgtc   2160
aaggcattgt tctcctccaa tttggacccc agcctggtgg agcaagtctt tctagataag   2220
accctgaatg cctcattcca ttggctgggc tccacctacc agttggtgga catccatgtg   2280
acagaaatgg agtcatcagt ttatcaacca acaagcagct ccagcaccca gcacttctac   2340
ctgaatttca ccatcaccaa cctaccatat tcccaggaca aagcccagcc aggcaccacc   2400
aattaccaga ggaacaaaag gaatattgag gatgcggcac cacccgggg tggactccct   2460
gtgtaacttc tcgccactgg ctcggagagt agacagagtt gccatctatg aggaatttct   2520
gcggatgacc cggaatggta cccagctgca gaacttcacc ctggacagga gcagtgtcct   2580
tgtggatggg tattttccca acagaaatga gcccttaact gggaattctg accttcccct   2640
ctgggctgtc atcctcatcg gcttggcagg actcctggga ctcatcacat gcctgatctg   2700
cggtgtcctg gtgaccaccc gccggcgaa gaaggaagga gaatacaacg tccagcaaca   2760
gtgcccaggc tactaccagt cacacctaga cctggaggat ctgcaatgac tggaacttgc   2820
cggtgcctgg ggtgcctttc ccccagccag ggtccaaaga agcttggctg gggcagaaat   2880
aaaccatatt ggtcggaaaa aaaaaaaaaa aaaaaaaaa aaaaaaaaa aaaaaaaaa   2940
aaa                                                                2943
```

<210> SEQ ID NO 386
<211> LENGTH: 2608

-continued

<212> TYPE: DNA
<213> ORGANISM: Homo sapiens

<400> SEQUENCE: 386

```
gttcaagagc accagtgttg gccctctgta ctctggctgc agactgactt tgctcaggcc      60
tgaaaaggat gggacagcca ctggagtgga tgccatctgc acccaccacc ctgaccccaa     120
aagccctagg ctggacagag agcagctgta ttgggagctg agccagctga cccacaatat     180
cactgagctg gcccctatg ccctggacaa cgacagcctc tttgtcaatg gtttcactca     240
tcggagctct gtgtccacca ccagcactcc tgggaccccc acagtgtatc tgggagcatc     300
taagactcca gcctcgatat ttggcccttc agctgccagc catctcctga tactattcac     360
cctcaacttc accatcacta acctgcggta tgaggagaac atgtggcctg gctccaggaa     420
gttcaacact acagagaggg tccttcaggg cctgctaagg cccttgttca gaacaccag     480
tgttggcccct ctgtactctg gctgcaggct gaccttgctc aggccagaga agatggggga    540
agccaccgga gtggatgcca tctgcaccca ccgccctgac ccacaggcc ctgggctgga     600
cagagagcag ctgtatttgg agctgagcca gctgacccac agcatcactg agctgggccc    660
ctacacactg gacagggaca gtctctatgt caatggtttc acccatcgga gctctgtacc    720
caccaccagc accggggtgg tcagcgagga gccattcaca ctgaacttca ccatcaacaa    780
cctgcgctac atggcggaca tgggccaacc cggctccctc aagttcaaca tcacagacaa    840
cgtcatgaag cacctgctca gtcctttgtt ccagaggagc agcctgggtg cacggtacac    900
aggctgcagg gtcatcgcac taaggtctgt gaagaacggt gctgagacac gggtggacct    960
cctctgcacc tacctgcagc ccctcagcgg cccaggtctg cctatcaagc aggtgttcca   1020
tgagctgagc cagcagaccc atggcatcac ccggctgggc ccctactctc tggacaaaga   1080
cagcctctac cttaacggtt acaatgaacc tggtccagat gagcctccta caactcccaa   1140
gccagccacc acattcctgc tcctctgtc agaagccaca acagccatgg ggtaccacct   1200
gaagaccctc acactcaact tcaccatctc caatctccag tattcaccag atatgggcaa   1260
gggctcagct acattcaact ccaccgaggg ggtccttcag cacctgctca gacccttgtt   1320
ccagaagagc agcatgggcc ccttctactt gggttgccaa ctgatctccc tcaggcctga   1380
gaaggatggg gcagccactg gtgtggacac cacctgcacc taccaccctg accctgtggg   1440
ccccgggctg gacatacagc agctttactg ggagctgagt cagctgaccc atggtgtcac   1500
ccaactgggc ttctatgtcc tggacaggga tagcctcttc atcaatggct atgcacccca   1560
gaatttatca atccggggcg agtaccagat aaatttccac attgtcaact ggaacctcag   1620
taatccagac cccacatcct cagagtacat caccctgctg agggacatcc aggacaaggt   1680
caccacactc tacaaaggca gtcaactaca tgacacattc gcttctgcc tggtcaccaa   1740
cttgacgatg gactccgtgt tggtcactgt caaggcattg ttctcctcca atttggaccc   1800
cagcctggtg gagcaagtct ttctagataa gaccctgaat gcctcattcc attggctggg   1860
ctccacctac cagttggtgg acatccatgt gacagaaatg gagtcatcag tttatcaacc   1920
aacaagcagc tccagcaccc agcacttcta cctgaatttc accatcacca acctaccata   1980
ttcccaggac aaagcccagc caggcaccac caattaccag aggaacaaaa ggaatattga   2040
ggatgcgctc aaccaactct tccgaaacag cagcatcaag agttatttt ctgactgtca   2100
agtttcaaca ttcaggtctg tccccaacag gcaccacacc ggggtggact ccctgtgtaa   2160
cttctcgcca ctggctcgga gagtagacag agttgccatc tatgaggaat ttctgcggat   2220
```

```
gacccggaat ggtacccagc tgcagaactt caccctggac aggagcagtg tccttgtgga    2280
tgggtatttt cccaacagaa atgagccctt aactgggaat tctgaccttc ccttctgggc    2340
tgtcatcctc atcggcttgg caggactcct gggactcatc acatgcctga tctgcggtgt    2400
cctggtgacc acccgccggc ggaagaagga aggagaatac aacgtccagc aacagtgccc    2460
aggctactac cagtcacacc tagacctgga ggatctgcaa tgactggaac ttgccggtgc    2520
ctggggtgcc tttcccccag ccagggtcca agaagcttg gctggggcag aaataaacca    2580
tattggtcgg acacaaaaaa aaaaaaaa                                        2608

<210> SEQ ID NO 387
<211> LENGTH: 1761
<212> TYPE: DNA
<213> ORGANISM: Homo sapiens

<400> SEQUENCE: 387
ctgaacttca ccatcaacaa cctgcgctac atggcggaca tgggccaacc cggctccctc      60
aagttcaaca tcacagacaa cgtcatgaag cacctgctca gtcctttgtt ccagaggagc     120
agcctgggtg cacggtacac aggctgcagg gtcatcgcac taaggtctgt gaagaacggt     180
gctgagacac gggtggacct cctctgcagg taggtgcaga ggaggtccac ggcatcaccc     240
ggctgggccc ctactctctg acaaagaca gcctctacct taacgctccc aagccagcca      300
ccacattcct gcctcctctg tcagaagcca acagccat ggggtaccac ctgaagaccc        360
tcacactcaa cttcaccatc tccaatctcc agtattcacc agatatgggc aagggctcag     420
ctacattcaa ctccaccgag ggggtccttc agcacctgct cagacccttg ttccagaaga     480
gcagcatggg cccctctac ttgggttgcc aactgatctc cctcaggcct gagaaggatg       540
gggcagccac tggtgtggac accacctgca cctaccaccc tgaccctgtg gccccgggc      600 tggacataca gcagctttac tgggagctga gtcagctgac ccatggtgtc acccaactgg     660
gcttctatgt cctggacagg gatagcctct catcaatgg ctatgcaccc cagaatttat       720
caatccgggg cgagtaccag ataaatttcc acattgtcaa ctggaacctc agtaatccag     780
accccacatc ctcagagtac atcaccctgc tgagggacat ccaggacaag gtcaccacac     840
tctacaaagg cagtcaacta catgacacat tccgcttctg cctggtcacc aacttgacga     900
tggactccgt gttggtcact gtcaaggcat tgttctcctc caatttggac cccagcctgg     960
tggagcaagt ctttctagat aagaccctga atgcctcatt ccattggctg gctccacct    1020 accagttggt ggacatccat gtgacagaaa tggagtcatc agtttatcaa ccaacaagca    1080
gctccagcac ccagcacttc tacctgaatt tcaccatcac caacctacca tattcccagg    1140
acaaagccca gccaggcacc accaattacc agaggaacaa aaggaatatt gaggatgcgc    1200
tcaaccaact cttccgaaac agcagcatca agagttattt ttctgactgt caagtttcaa    1260
cattcaggtc tgtccccaac aggcaccaca ccggggtgga ctccctgtgt aacttctcgc    1320
cactggctcg gagagtagac agagttgcca tctatgagga atttctgcgg atgacccgga    1380
atggtaccca gctgcagaac ttcaccctgg acaggagcag tgtccttgtg atgggtatt    1440 ttcccaacag aaatgagccc ttaactggga attctgacct tcccttctgg gctgtcatcc    1500
tcatcggctt ggcaggactc ctgggactca tcacatgcct gatctgcggt gtcctggtga    1560
ccacccgccg gcggaagaag gaaggagaat acaacgtcca gcaacagtgc ccaggctact    1620
accagtcaca cctagacctg gaggatctgc aatgactgga acttgccggt gcctggggtg    1680 ccttccccc agccagggtc caagaagct tggctggggc agaaataaac catattggtc     1740
```
ggacacaaaa aaaaaaaaaa a                                       1761

<210> SEQ ID NO 388
<211> LENGTH: 772
<212> TYPE: PRT
<213> ORGANISM: Homo sapiens

<400> SEQUENCE: 388

Met Ser Met Val Ser His Ser Gly Ala Leu Cys Pro Pro Leu Ala Phe
                  5                  10                  15

Leu Gly Pro Pro Gln Trp Thr Trp Glu His Leu Gly Leu Gln Phe Leu
             20                  25                  30

Asn Leu Val Pro Arg Leu Pro Ala Leu Ser Trp Cys Tyr Ser Leu Ser
         35                  40                  45

Thr Ser Pro Ser Pro Thr Cys Gly Met Arg Arg Thr Cys Ser Thr Leu
     50                  55                  60

Ala Pro Gly Ser Ser Thr Pro Arg Arg Gly Ser Phe Arg Ala Trp Ser
 65                  70                  75                  80

Leu Phe Lys Ser Thr Ser Val Gly Pro Leu Tyr Ser Gly Cys Arg Leu
                 85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
    355                 360                 365

-continued

```
Pro Leu Phe Gln Arg Ser Ser Leu Gly Ala Arg Tyr Thr Gly Cys Arg
    370                 375                 380
Val Ile Ala Leu Arg Ser Val Lys Asn Gly Ala Glu Thr Arg Val Asp
385                 390                 395                 400
Leu Leu Cys Thr Tyr Leu Gln Pro Leu Ser Gly Pro Gly Leu Pro Ile
                405                 410                 415
Lys Gln Val Phe His Glu Leu Ser Gln Gln Thr His Gly Ile Thr Arg
                420                 425                 430
Leu Gly Pro Tyr Ser Leu Asp Lys Asp Ser Leu Tyr Leu Asn Gly Tyr
            435                 440                 445
Asn Glu Pro Gly Pro Asp Glu Pro Pro Thr Thr Pro Lys Pro Ala Thr
    450                 455                 460
Thr Phe Leu Pro Pro Leu Ser Glu Ala Thr Thr Ala Met Gly Tyr His
465                 470                 475                 480
Leu Lys Thr Leu Thr Leu Asn Phe Thr Ile Ser Asn Leu Gln Tyr Ser
                485                 490                 495
Pro Asp Met Gly Lys Gly Ser Ala Thr Phe Asn Ser Thr Glu Gly Val
            500                 505                 510
Leu Gln His Leu Leu Arg Pro Leu Phe Gln Lys Ser Ser Met Gly Pro
    515                 520                 525
Phe Tyr Leu Gly Cys Gln Leu Ile Ser Leu Arg Pro Glu Lys Asp Gly
    530                 535                 540
Ala Ala Thr Gly Val Asp Thr Thr Cys Thr Tyr His Pro Asp Pro Val
545                 550                 555                 560
Gly Pro Gly Leu Asp Ile Gln Gln Leu Tyr Trp Glu Leu Ser Gln Leu
                565                 570                 575
Thr His Gly Val Thr Gln Leu Gly Phe Tyr Val Leu Asp Arg Asp Ser
            580                 585                 590
Leu Phe Ile Asn Gly Tyr Ala Pro Gln Asn Leu Ser Ile Arg Gly Glu
        595                 600                 605
Tyr Gln Ile Asn Phe His Ile Val Asn Trp Asn Leu Ser Asn Pro Asp
    610                 615                 620
Pro Thr Ser Ser Glu Tyr Ile Thr Leu Leu Arg Asp Ile Gln Asp Lys
625                 630                 635                 640
Val Thr Thr Leu Tyr Lys Gly Ser Gln Leu His Asp Thr Phe Arg Phe
                645                 650                 655
Cys Leu Val Thr Asn Leu Thr Met Asp Ser Val Leu Val Thr Val Lys
            660                 665                 670
Ala Leu Phe Ser Ser Asn Leu Asp Pro Ser Leu Val Glu Gln Val Phe
        675                 680                 685
Leu Asp Lys Thr Leu Asn Ala Ser Phe His Trp Leu Gly Ser Thr Tyr
    690                 695                 700
Gln Leu Val Asp Ile His Val Thr Glu Met Glu Ser Ser Val Tyr Gln
705                 710                 715                 720
Pro Thr Ser Ser Ser Thr Gln His Phe Tyr Leu Asn Phe Thr Ile
                725                 730                 735
Thr Asn Leu Pro Tyr Ser Gln Asp Lys Ala Gln Pro Gly Thr Thr Asn
            740                 745                 750
Tyr Gln Arg Asn Lys Arg Asn Ile Glu Asp Ala Ala Pro His Arg Gly
        755                 760                 765
Gly Leu Pro Val
    770
```

```
<210> SEQ ID NO 389
<211> LENGTH: 833
<212> TYPE: PRT
<213> ORGANISM: Homo sapiens

<400> SEQUENCE: 389
```

| | | | | | | | | | | | | | | |
|---|---|---|---|---|---|---|---|---|---|---|---|---|---|---|
| Phe | Lys | Ser | Thr | Ser | Val | Gly | Pro | Leu | Tyr | Ser | Gly | Cys | Arg | Leu | Thr |
| | | | | 5 | | | | | 10 | | | | | 15 |
| Leu | Leu | Arg | Pro | Glu | Lys | Asp | Gly | Thr | Ala | Thr | Gly | Val | Asp | Ala | Ile |
| | | | | 20 | | | | | 25 | | | | | 30 |
| Cys | Thr | His | Pro | Asp | Pro | Lys | Ser | Pro | Arg | Leu | Asp | Arg | Glu | Gln |
| | | | 35 | | | | | 40 | | | | | 45 |
| Leu | Tyr | Trp | Glu | Leu | Ser | Gln | Leu | Thr | His | Asn | Ile | Thr | Glu | Leu | Gly |
| | 50 | | | | | 55 | | | | | 60 |
| Pro | Tyr | Ala | Leu | Asp | Asn | Asp | Ser | Leu | Phe | Val | Asn | Gly | Phe | Thr | His |
| 65 | | | | | 70 | | | | | 75 | | | | | 80 |
| Arg | Ser | Ser | Val | Ser | Thr | Thr | Ser | Thr | Pro | Gly | Thr | Pro | Thr | Val | Tyr |
| | | | | | 85 | | | | | 90 | | | | | 95 |
| Leu | Gly | Ala | Ser | Lys | Thr | Pro | Ala | Ser | Ile | Phe | Gly | Pro | Ser | Ala | Ala |
| | | | | 100 | | | | | 105 | | | | | 110 |
| Ser | His | Leu | Leu | Ile | Leu | Phe | Thr | Leu | Asn | Phe | Thr | Ile | Thr | Asn | Leu |
| | | | 115 | | | | | 120 | | | | | 125 |
| Arg | Tyr | Glu | Glu | Asn | Met | Trp | Pro | Gly | Ser | Arg | Lys | Phe | Asn | Thr | Thr |
| | 130 | | | | | 135 | | | | | 140 |
| Glu | Arg | Val | Leu | Gln | Gly | Leu | Leu | Arg | Pro | Leu | Phe | Lys | Asn | Thr | Ser |
| 145 | | | | | 150 | | | | | 155 | | | | | 160 |
| Val | Gly | Pro | Leu | Tyr | Ser | Gly | Cys | Arg | Leu | Thr | Leu | Leu | Arg | Pro | Glu |
| | | | | 165 | | | | | 170 | | | | | 175 |
| Lys | Asp | Gly | Glu | Ala | Thr | Gly | Val | Asp | Ala | Ile | Cys | Thr | His | Arg | Pro |
| | | | 180 | | | | | 185 | | | | | 190 |
| Asp | Pro | Thr | Gly | Pro | Gly | Leu | Asp | Arg | Glu | Gln | Leu | Tyr | Leu | Glu | Leu |
| | | 195 | | | | | 200 | | | | | 205 |
| Ser | Gln | Leu | Thr | His | Ser | Ile | Thr | Glu | Leu | Gly | Pro | Tyr | Thr | Leu | Asp |
| | 210 | | | | | 215 | | | | | 220 |
| Arg | Asp | Ser | Leu | Tyr | Val | Asn | Gly | Phe | Thr | His | Arg | Ser | Ser | Val | Pro |
| 225 | | | | | 230 | | | | | 235 | | | | | 240 |
| Thr | Thr | Ser | Thr | Gly | Val | Val | Ser | Glu | Glu | Pro | Phe | Thr | Leu | Asn | Phe |
| | | | 245 | | | | | 250 | | | | | 255 |
| Thr | Ile | Asn | Asn | Leu | Arg | Tyr | Met | Ala | Asp | Met | Gly | Gln | Pro | Gly | Ser |
| | | | 260 | | | | | 265 | | | | | 270 |
| Leu | Lys | Phe | Asn | Ile | Thr | Asp | Asn | Val | Met | Lys | His | Leu | Leu | Ser | Pro |
| | | 275 | | | | | 280 | | | | | 285 |
| Leu | Phe | Gln | Arg | Ser | Ser | Leu | Gly | Ala | Arg | Tyr | Thr | Gly | Cys | Arg | Val |
| | 290 | | | | | 295 | | | | | 300 |
| Ile | Ala | Leu | Arg | Ser | Val | Lys | Asn | Gly | Ala | Glu | Thr | Arg | Val | Asp | Leu |
| 305 | | | | | 310 | | | | | 315 | | | | | 320 |
| Leu | Cys | Thr | Tyr | Leu | Gln | Pro | Leu | Ser | Gly | Pro | Gly | Leu | Pro | Ile | Lys |
| | | | 325 | | | | | 330 | | | | | 335 |
| Gln | Val | Phe | His | Glu | Leu | Ser | Gln | Gln | Thr | His | Gly | Ile | Thr | Arg | Leu |
| | | | 340 | | | | | 345 | | | | | 350 |
| Gly | Pro | Tyr | Ser | Leu | Asp | Lys | Asp | Ser | Leu | Tyr | Leu | Asn | Gly | Tyr | Asn |
| | | 355 | | | | | 360 | | | | | 365 |
| Glu | Pro | Gly | Pro | Asp | Glu | Pro | Pro | Thr | Thr | Pro | Lys | Pro | Ala | Thr | Thr |
| | 370 | | | | | 375 | | | | | 380 |

-continued

```
Phe Leu Pro Pro Leu Ser Glu Ala Thr Thr Ala Met Gly Tyr His Leu
385                 390                 395                 400

Lys Thr Leu Thr Leu Asn Phe Thr Ile Ser Asn Leu Gln Tyr Ser Pro
                405                 410                 415

Asp Met Gly Lys Gly Ser Ala Thr Phe Asn Ser Thr Glu Gly Val Leu
            420                 425                 430

Gln His Leu Leu Arg Pro Leu Phe Gln Lys Ser Ser Met Gly Pro Phe
        435                 440                 445

Tyr Leu Gly Cys Gln Leu Ile Ser Leu Arg Pro Glu Lys Asp Gly Ala
    450                 455                 460

Ala Thr Gly Val Asp Thr Thr Cys Thr Tyr His Pro Asp Pro Val Gly
465                 470                 475                 480

Pro Gly Leu Asp Ile Gln Gln Leu Tyr Trp Glu Leu Ser Gln Leu Thr
                485                 490                 495

His Gly Val Thr Gln Leu Gly Phe Tyr Val Leu Asp Arg Asp Ser Leu
            500                 505                 510

Phe Ile Asn Gly Tyr Ala Pro Gln Asn Leu Ser Ile Arg Gly Glu Tyr
        515                 520                 525

Gln Ile Asn Phe His Ile Val Asn Trp Asn Leu Ser Asn Pro Asp Pro
    530                 535                 540

Thr Ser Ser Glu Tyr Ile Thr Leu Leu Arg Asp Ile Gln Asp Lys Val
545                 550                 555                 560

Thr Thr Leu Tyr Lys Gly Ser Gln Leu His Asp Thr Phe Arg Phe Cys
                565                 570                 575

Leu Val Thr Asn Leu Thr Met Asp Ser Val Leu Val Thr Val Lys Ala
            580                 585                 590

Leu Phe Ser Ser Asn Leu Asp Pro Ser Leu Val Glu Gln Val Phe Leu
        595                 600                 605

Asp Lys Thr Leu Asn Ala Ser Phe His Trp Leu Gly Ser Thr Tyr Gln
    610                 615                 620

Leu Val Asp Ile His Val Thr Glu Met Glu Ser Ser Val Tyr Gln Pro
625                 630                 635                 640

Thr Ser Ser Ser Thr Gln His Phe Tyr Leu Asn Phe Thr Ile Thr
                645                 650                 655

Asn Leu Pro Tyr Ser Gln Asp Lys Ala Gln Pro Gly Thr Thr Asn Tyr
            660                 665                 670

Gln Arg Asn Lys Arg Asn Ile Glu Asp Ala Leu Asn Gln Leu Phe Arg
        675                 680                 685

Asn Ser Ser Ile Lys Ser Tyr Phe Ser Asp Cys Gln Val Ser Thr Phe
    690                 695                 700

Arg Ser Val Pro Asn Arg His His Thr Gly Val Asp Ser Leu Cys Asn
705                 710                 715                 720

Phe Ser Pro Leu Ala Arg Arg Val Asp Arg Val Ala Ile Tyr Glu Glu
                725                 730                 735

Phe Leu Arg Met Thr Arg Asn Gly Thr Gln Leu Gln Asn Phe Thr Leu
            740                 745                 750

Asp Arg Ser Ser Val Leu Val Asp Gly Tyr Phe Pro Asn Arg Asn Glu
        755                 760                 765

Pro Leu Thr Gly Asn Ser Asp Leu Pro Phe Trp Ala Val Ile Leu Ile
    770                 775                 780

Gly Leu Ala Gly Leu Leu Gly Leu Ile Thr Cys Leu Ile Cys Gly Val
785                 790                 795                 800
```

-continued

```
Leu Val Thr Thr Arg Arg Lys Lys Glu Gly Glu Tyr Asn Val Gln
            805                 810                 815

Gln Gln Cys Pro Gly Tyr Tyr Gln Ser His Leu Asp Leu Glu Asp Leu
            820                 825                 830

Gln

<210> SEQ ID NO 390
<211> LENGTH: 438
<212> TYPE: PRT
<213> ORGANISM: Homo sapiens

<400> SEQUENCE: 390

Met Gly Tyr His Leu Lys Thr Leu Thr Leu Asn Phe Thr Ile Ser Asn
                5                   10                  15

Leu Gln Tyr Ser Pro Asp Met Gly Lys Gly Ser Ala Thr Phe Asn Ser
            20                  25                  30

Thr Glu Gly Val Leu Gln His Leu Leu Arg Pro Leu Phe Gln Lys Ser
        35                  40                  45

Ser Met Gly Pro Phe Tyr Leu Gly Cys Gln Leu Ile Ser Leu Arg Pro
    50                  55                  60

Glu Lys Asp Gly Ala Ala Thr Gly Val Asp Thr Thr Cys Thr Tyr His
65                  70                  75                  80

Pro Asp Pro Val Gly Pro Gly Leu Asp Ile Gln Gln Leu Tyr Trp Glu
                85                  90                  95

Leu Ser Gln Leu Thr His Gly Val Thr Gln Leu Gly Phe Tyr Val Leu
            100                 105                 110

Asp Arg Asp Ser Leu Phe Ile Asn Gly Tyr Ala Pro Gln Asn Leu Ser
        115                 120                 125

Ile Arg Gly Glu Tyr Gln Ile Asn Phe His Ile Val Asn Trp Asn Leu
    130                 135                 140

Ser Asn Pro Asp Pro Thr Ser Ser Glu Tyr Ile Thr Leu Leu Arg Asp
145                 150                 155                 160

Ile Gln Asp Lys Val Thr Thr Leu Tyr Lys Gly Ser Gln Leu His Asp
                165                 170                 175

Thr Phe Arg Phe Cys Leu Val Thr Asn Leu Thr Met Asp Ser Val Leu
            180                 185                 190

Val Thr Val Lys Ala Leu Phe Ser Ser Asn Leu Asp Pro Ser Leu Val
        195                 200                 205

Glu Gln Val Phe Leu Asp Lys Thr Leu Asn Ala Ser Phe His Trp Leu
    210                 215                 220

Gly Ser Thr Tyr Gln Leu Val Asp Ile His Val Thr Glu Met Glu Ser
225                 230                 235                 240

Ser Val Tyr Gln Pro Thr Ser Ser Ser Thr Gln His Phe Tyr Leu
                245                 250                 255

Asn Phe Thr Ile Thr Asn Leu Pro Tyr Ser Gln Asp Lys Ala Gln Pro
            260                 265                 270

Gly Thr Thr Asn Tyr Gln Arg Asn Lys Arg Asn Ile Glu Asp Ala Leu
        275                 280                 285

Asn Gln Leu Phe Arg Asn Ser Ser Ile Lys Ser Tyr Phe Ser Asp Cys
    290                 295                 300

Gln Val Ser Thr Phe Arg Ser Val Pro Asn Arg His His Thr Gly Val
305                 310                 315                 320

Asp Ser Leu Cys Asn Phe Ser Pro Leu Ala Arg Arg Val Asp Arg Val
                325                 330                 335
```

```
Ala Ile Tyr Glu Glu Phe Leu Arg Met Thr Arg Asn Gly Thr Gln Leu
            340                 345                 350

Gln Asn Phe Thr Leu Asp Arg Ser Ser Val Leu Val Asp Gly Tyr Phe
        355                 360                 365

Pro Asn Arg Asn Glu Pro Leu Thr Gly Asn Ser Asp Leu Pro Phe Trp
    370                 375                 380

Ala Val Ile Leu Ile Gly Leu Ala Gly Leu Leu Gly Leu Ile Thr Cys
385                 390                 395                 400

Leu Ile Cys Gly Val Leu Val Thr Thr Arg Arg Arg Lys Lys Glu Gly
            405                 410                 415

Glu Tyr Asn Val Gln Gln Gln Cys Pro Gly Tyr Tyr Gln Ser His Leu
            420                 425                 430

Asp Leu Glu Asp Leu Gln
            435

<210> SEQ ID NO 391
<211> LENGTH: 2627
<212> TYPE: DNA
<213> ORGANISM: Homo sapiens

<400> SEQUENCE: 391
```

| | | | | | |
|---|---|---|---|---|---|
| ccacgcgtcc | gcccacgcgt | ccggaaggca | gcggcagctc | cactcagcca | gtacccagat | 60 |
| acgctgggaa | ccttccccag | ccatggcttc | cctggggcag | atcctcttct | ggagcataat | 120 |
| tagcatcatc | attattctgg | ctggagcaat | gcactcatca | ttggctttg | gtatttcagg | 180 |
| gagacactcc | atcacagtca | ctactgtcgc | ctcagctggg | aacattgggg | aggatggaat | 240 |
| cctgagctgc | acttttgaac | tgacatcaa | actttctgat | atcgtgatac | aatggctgaa | 300 |
| ggaaggtgtt | ttaggcttgg | tccatgagtt | caaagaaggc | aaagatgagc | tgtcggagca | 360 |
| ggatgaaatg | ttcagaggcc | ggacagcagt | gtttgctgat | caagtgatag | ttggcaatgc | 420 |
| ctctttgcgg | ctgaaaaacg | tgcaactcac | agatgctggc | acctacaaat | gttatatcat | 480 |
| cacttctaaa | ggcaagggga | atgctaacct | tgagtataaa | actggagcct | tcagcatgcc | 540 |
| ggaagtgaat | gtggactata | tgccagctc | agagaccttg | cggtgtgagg | ctccccgatg | 600 |
| gttccccccag | cccacagtgg | tctgggcatc | ccaagttgac | cagggagcca | acttctcgga | 660 |
| agtctccaat | accagctttg | agctgaactc | tgagaatgtg | accatgaagg | ttgtgtctgt | 720 |
| gctctacaat | gttacgatca | caacacata | ctcctgtatg | attgaaaatg | acattgccaa | 780 |
| agcaacaggg | gatatcaaag | tgacagaatc | ggagatcaaa | aggcggagtc | acctacagct | 840 |
| gctaaactca | aaggcttctc | tgtgtgtctc | ttctttcttt | gccatcagct | gggcacttct | 900 |
| gcctctcagc | ccttacctga | tgctaaaata | atgtgccttg | gccacaaaaa | agcatgcaaa | 960 |
| gtcattgtta | caacagggat | ctacagaact | atttccacca | cagatatgac | ctagttttat | 1020 |
| atttctggga | ggaaatgaat | tcatatctag | aagtctggag | tgagcaaaca | agagcaagaa | 1080 |
| acaaaaagaa | gccaaaagca | gaaggctcca | atatgaacaa | gataaatcta | tcttcaaaga | 1140 |
| catattagaa | gttgggaaaa | taattcatgt | gaactagaca | agtgtgttaa | gagtgataag | 1200 |
| taaaatgcac | gtggagacaa | gtgcatcccc | agatctcagg | gacctccccc | tgcctgtcac | 1260 |
| ctggggagtg | agaggacagg | atagtgcatg | ttctttgtct | ctgaattttt | agttatatgt | 1320 |
| gctgtaatgt | tgctctgagg | aagcccctgg | aaagtctatc | ccaacatatc | cacatcttat | 1380 |
| attccacaaa | ttaagctgta | gtatgtaccc | taagacgctg | ctaattgact | gccacttcgc | 1440 |
| aactcagggg | cggctgcatt | ttagtaatgg | gtcaaatgat | tcactttta | tgatgcttcc | 1500 |

-continued

```
aaaggtgcct tggcttctct tcccaactga caaatgccaa agttgagaaa aatgatcata    1560
attttagcat aaacagagca gtcggcgaca ccgatttat aaataaactg agcaccttct    1620
ttttaaacaa acaaatgcgg gtttatttct cagatgatgt tcatccgtga atggtccagg    1680
gaaggacctt tcaccttgac tatatggcat tatgtcatca caagctctga ggcttctcct    1740
ttccatcctg cgtggacagc taagacctca gttttcaata gcatctagag cagtgggact    1800
cagctggggt gatttcgccc cccatctccg ggggaatgtc tgaagacaat tttggttacc    1860
tcaatgaggg agtggaggag gatacagtgc tactaccaac tagtggataa aggccaggga    1920
tgctgctcaa cctcctacca tgtacaggac gtctccccat acaactacc caatccgaag    1980 tgtcaactgt gtcaggacta agaaaccctg gttttgagta gaaagggcc tggaaagagg    2040 ggagccaaca aatctgtctg cttcctcaca ttagtcattg gcaaataagc attctgtctc    2100
tttggctgct gcctcagcac agagagccag aactctatcg ggcaccagga taacatctct    2160
cagtgaacag agttgacaag gcctatggga aatgcctgat gggattatct tcagcttgtt    2220
gagcttctaa gtttctttcc cttcattcta ccctgcaagc caagttctgt aagaaaatg     2280 cctgagttct agctcaggtt ttcttactct gaatttagat ctccagaccc ttcctggcca    2340
caattcaaat taaggcaaca aacatatacc ttccatgaag cacacacaga cttttgaaag    2400
caaggacaat gactgcttga attgaggcct tgaggaatga agctttgaag gaaaagaata    2460
ctttgtttcc agcccccttc ccacactctt catgtgttaa ccactgcctt cctggacctt    2520
ggagccacgg tgactgtatt acatgttgtt atagaaaact gattttagag ttctgatcgt    2580
tcaagagaat gattaaatat acatttccta caccaaaaaa aaaaaaa                  2627
```

<210> SEQ ID NO 392
<211> LENGTH: 309
<212> TYPE: PRT
<213> ORGANISM: Homo sapiens

<400> SEQUENCE: 392

```
His Ala Ser Ala His Ala Ser Gly Arg Gln Arg Gln Leu His Ser Ala
             5                   10                  15

Ser Thr Gln Ile Arg Trp Glu Pro Ser Pro Ala Met Ala Ser Leu Gly
         20                  25                  30

Gln Ile Leu Phe Trp Ser Ile Ile Ser Ile Ile Ile Leu Ala Gly
         35                  40                  45

Ala Ile Ala Leu Ile Ile Gly Phe Gly Ile Ser Arg His Ser Ile
     50                  55                  60

Thr Val Thr Thr Val Ala Ser Ala Gly Asn Ile Gly Glu Asp Gly Ile
 65                  70                  75                  80

Leu Ser Cys Thr Phe Glu Pro Asp Ile Lys Leu Ser Asp Ile Val Ile
                 85                  90                  95

Gln Trp Leu Lys Glu Gly Val Leu Gly Leu Val His Glu Phe Lys Glu
            100                 105                 110

Gly Lys Asp Glu Leu Ser Glu Gln Asp Glu Met Phe Arg Gly Arg Thr
        115                 120                 125

Ala Val Phe Ala Asp Gln Val Ile Val Gly Asn Ala Ser Leu Arg Leu
    130                 135                 140

Lys Asn Val Gln Leu Thr Asp Ala Gly Thr Tyr Lys Cys Tyr Ile Ile
145                 150                 155                 160

Thr Ser Lys Gly Lys Gly Asn Ala Asn Leu Glu Tyr Lys Thr Gly Ala
                165                 170                 175
```

-continued

```
Phe Ser Met Pro Glu Val Asn Val Asp Tyr Asn Ala Ser Ser Glu Thr
            180                 185                 190

Leu Arg Cys Glu Ala Pro Arg Trp Phe Pro Gln Pro Thr Val Val Trp
        195                 200                 205

Ala Ser Gln Val Asp Gln Gly Ala Asn Phe Ser Glu Val Ser Asn Thr
    210                 215                 220

Ser Phe Glu Leu Asn Ser Glu Asn Val Thr Met Lys Val Val Ser Val
225                 230                 235                 240

Leu Tyr Asn Val Thr Ile Asn Asn Thr Tyr Ser Cys Met Ile Glu Asn
                245                 250                 255

Asp Ile Ala Lys Ala Thr Gly Asp Ile Lys Val Thr Glu Ser Glu Ile
            260                 265                 270

Lys Arg Arg Ser His Leu Gln Leu Leu Asn Ser Lys Ala Ser Leu Cys
        275                 280                 285

Val Ser Ser Phe Phe Ala Ile Ser Trp Ala Leu Leu Pro Leu Ser Pro
    290                 295                 300

Tyr Leu Met Leu Lys
305

<210> SEQ ID NO 393
<211> LENGTH: 282
<212> TYPE: PRT
<213> ORGANISM: Homo sapiens

<400> SEQUENCE: 393

Met Ala Ser Leu Gly Gln Ile Leu Phe Trp Ser Ile Ile Ser Ile Ile
                5                   10                  15

Ile Ile Leu Ala Gly Ala Ile Ala Leu Ile Ile Gly Phe Gly Ile Ser
            20                  25                  30

Gly Arg His Ser Ile Thr Val Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240
```

```
Thr Glu Ser Glu Ile Lys Arg Arg Ser His Leu Gln Leu Leu Asn Ser
            245                 250                 255

Lys Ala Ser Leu Cys Val Ser Ser Phe Phe Ala Ile Ser Trp Ala Leu
        260                 265                 270

Leu Pro Leu Ser Pro Tyr Leu Met Leu Lys
        275                 280
```

<210> SEQ ID NO 394
<211> LENGTH: 20
<212> TYPE: PRT
<213> ORGANISM: Homo sapiens

<400> SEQUENCE: 394

```
Met Ala Ser Leu Gly Gln Ile Leu Phe Trp Ser Ile Ile Ser Ile Ile
 1               5                  10                  15

Ile Ile Leu Ala
        20
```

<210> SEQ ID NO 395
<211> LENGTH: 20
<212> TYPE: PRT
<213> ORGANISM: Homo sapiens

<400> SEQUENCE: 395

```
Ile Ile Ile Leu Ala Gly Ala Ile Ala Leu Ile Ile Gly Phe Gly Ile
 1               5                  10                  15

Ser Gly Arg His
        20
```

<210> SEQ ID NO 396
<211> LENGTH: 20
<212> TYPE: PRT
<213> ORGANISM: Homo sapiens

<400> SEQUENCE: 396

```
Ile Ser Gly Arg His Ser Ile Thr Val Thr Thr Val Ala Ser Ala Gly
 1               5                  10                  15

Asn Ile Gly Glu
        20
```

<210> SEQ ID NO 397
<211> LENGTH: 20
<212> TYPE: PRT
<213> ORGANISM: Homo sapiens

<400> SEQUENCE: 397

```
Gly Asn Ile Gly Glu Asp Gly Ile Leu Ser Cys Thr Phe Glu Pro Asp
 1               5                  10                  15

Ile Lys Leu Ser
        20
```

<210> SEQ ID NO 398
<211> LENGTH: 20
<212> TYPE: PRT
<213> ORGANISM: Homo sapiens

<400> SEQUENCE: 398

```
Asp Ile Lys Leu Ser Asp Ile Val Ile Gln Trp Leu Lys Glu Gly Val
 1               5                  10                  15

Leu Gly Leu Val
        20
```

<210> SEQ ID NO 399
<211> LENGTH: 20
<212> TYPE: PRT
<213> ORGANISM: Homo sapiens

<400> SEQUENCE: 399

Val Leu Gly Leu Val His Glu Phe Lys Glu Gly Lys Asp Glu Leu Ser
 1               5                  10                  15

Glu Gln Asp Glu
            20

<210> SEQ ID NO 400
<211> LENGTH: 20
<212> TYPE: PRT
<213> ORGANISM: Homo sapiens

<400> SEQUENCE: 400

Ser Glu Gln Asp Glu Met Phe Arg Gly Arg Thr Ala Val Phe Ala Asp
 1               5                  10                  15

Gln Val Ile Val
            20

<210> SEQ ID NO 401
<211> LENGTH: 20
<212> TYPE: PRT
<213> ORGANISM: Homo sapiens

<400> SEQUENCE: 401

Asp Gln Val Ile Val Gly Asn Ala Ser Leu Arg Leu Lys Asn Val Gln
 1               5                  10                  15

Leu Thr Asp Ala
            20

<210> SEQ ID NO 402
<211> LENGTH: 21
<212> TYPE: PRT
<213> ORGANISM: Homo sapiens

<400> SEQUENCE: 402

Val Gln Leu Thr Asp Ala Gly Thr Tyr Lys Cys Tyr Ile Ile Thr Ser
 1               5                  10                  15

Lys Gly Lys Gly Asn
            20

<210> SEQ ID NO 403
<211> LENGTH: 20
<212> TYPE: PRT
<213> ORGANISM: Homo sapiens

<400> SEQUENCE: 403

Lys Gly Lys Gly Asn Ala Asn Leu Glu Tyr Lys Thr Gly Ala Phe Ser
 1               5                  10                  15

Met Pro Glu Val
            20

<210> SEQ ID NO 404
<211> LENGTH: 20
<212> TYPE: PRT
<213> ORGANISM: Homo sapiens

<400> SEQUENCE: 404

```
Ser Met Pro Glu Val Asn Val Asp Tyr Asn Ala Ser Ser Glu Thr Leu
1               5                   10                  15

Arg Cys Glu Ala
            20

<210> SEQ ID NO 405
<211> LENGTH: 20
<212> TYPE: PRT
<213> ORGANISM: Homo sapiens

<400> SEQUENCE: 405

Leu Arg Cys Glu Ala Pro Arg Trp Phe Pro Gln Pro Thr Val Val Trp
1               5                   10                  15

Ala Ser Gln Val
            20

<210> SEQ ID NO 406
<211> LENGTH: 20
<212> TYPE: PRT
<213> ORGANISM: Homo sapiens

<400> SEQUENCE: 406

Trp Ala Ser Gln Val Asp Gln Gly Ala Asn Phe Ser Glu Val Ser Asn
1               5                   10                  15

Thr Ser Phe Glu
            20

<210> SEQ ID NO 407
<211> LENGTH: 20
<212> TYPE: PRT
<213> ORGANISM: Homo sapiens

<400> SEQUENCE: 407

Asn Thr Ser Phe Glu Leu Asn Ser Glu Asn Val Thr Met Lys Val Val
1               5                   10                  15

Ser Val Leu Tyr
            20

<210> SEQ ID NO 408
<211> LENGTH: 20
<212> TYPE: PRT
<213> ORGANISM: Homo sapiens

<400> SEQUENCE: 408

Val Ser Val Leu Tyr Asn Val Thr Ile Asn Asn Thr Tyr Ser Cys Met
1               5                   10                  15

Ile Glu Asn Asp
            20

<210> SEQ ID NO 409
<211> LENGTH: 20
<212> TYPE: PRT
<213> ORGANISM: Homo sapiens

<400> SEQUENCE: 409

Met Ile Glu Asn Asp Ile Ala Lys Ala Thr Gly Asp Ile Lys Val Thr
1               5                   10                  15

Glu Ser Glu Ile
            20

<210> SEQ ID NO 410
<211> LENGTH: 20
```

-continued

```
<212> TYPE: PRT
<213> ORGANISM: Homo sapiens

<400> SEQUENCE: 410

Thr Glu Ser Glu Ile Lys Arg Arg Ser His Leu Gln Leu Leu Asn Ser
  1               5                  10                  15

Lys Ala Ser Leu
         20

<210> SEQ ID NO 411
<211> LENGTH: 20
<212> TYPE: PRT
<213> ORGANISM: Homo sapiens

<400> SEQUENCE: 411

Ser Lys Ala Ser Leu Cys Val Ser Ser Phe Phe Ala Ile Ser Trp Ala
  1               5                  10                  15

Leu Leu Pro Leu
         20

<210> SEQ ID NO 412
<211> LENGTH: 20
<212> TYPE: PRT
<213> ORGANISM: Homo sapiens

<400> SEQUENCE: 412

Ser Ser Phe Phe Ala Ile Ser Trp Ala Leu Leu Pro Leu Ser Pro Tyr
  1               5                  10                  15

Leu Met Leu Lys
         20

<210> SEQ ID NO 413
<211> LENGTH: 35
<212> TYPE: PRT
<213> ORGANISM: Homo sapiens

<400> SEQUENCE: 413

Ile Ser Gly Arg His Ser Ile Thr Val Thr Thr Val Ala Ser Ala Gly
  1               5                  10                  15

Asn Ile Gly Glu Asp Gly Ile Leu Ser Cys Thr Phe Glu Pro Asp Ile
             20                  25                  30

Lys Leu Ser
         35

<210> SEQ ID NO 414
<211> LENGTH: 35
<212> TYPE: PRT
<213> ORGANISM: Homo sapiens

<400> SEQUENCE: 414

Val Leu Gly Leu Val His Glu Phe Lys Glu Gly Lys Asp Glu Leu Ser
  1               5                  10                  15

Glu Gln Asp Glu Met Phe Arg Gly Arg Thr Ala Val Phe Ala Asp Gln
             20                  25                  30

Val Ile Val
         35

<210> SEQ ID NO 415
<211> LENGTH: 65
<212> TYPE: PRT
<213> ORGANISM: Homo sapiens
```

<400> SEQUENCE: 415

Lys Gly Lys Gly Asn Ala Asn Leu Glu Tyr Lys Thr Gly Ala Phe Ser
1               5                   10                  15
Met Pro Glu Val Asn Val Asp Tyr Asn Ala Ser Ser Glu Thr Leu Arg
            20                  25                  30
Cys Glu Ala Pro Arg Trp Phe Pro Gln Pro Thr Val Val Trp Ala Ser
        35                  40                  45
Gln Val Asp Gln Gly Ala Asn Phe Ser Glu Val Ser Asn Thr Ser Phe
    50                  55                  60
Glu
65

<210> SEQ ID NO 416
<211> LENGTH: 10
<212> TYPE: PRT
<213> ORGANISM: Homo sapiens

<400> SEQUENCE: 416

Lys Leu Ser Asp Ile Val Ile Gln Trp Leu
1               5                   10

<210> SEQ ID NO 417
<211> LENGTH: 10
<212> TYPE: PRT
<213> ORGANISM: Homo sapiens

<400> SEQUENCE: 417

Ser Leu Gly Gln Ile Leu Phe Trp Ser Ile
1               5                   10

<210> SEQ ID NO 418
<211> LENGTH: 10
<212> TYPE: PRT
<213> ORGANISM: Homo sapiens

<400> SEQUENCE: 418

Leu Leu Asn Ser Lys Ala Ser Leu Cys Val
1               5                   10

<210> SEQ ID NO 419
<211> LENGTH: 10
<212> TYPE: PRT
<213> ORGANISM: Homo sapiens

<400> SEQUENCE: 419

Ser Leu Cys Val Ser Ser Phe Phe Ala Ile
1               5                   10

<210> SEQ ID NO 420
<211> LENGTH: 10
<212> TYPE: PRT
<213> ORGANISM: Homo sapiens

<400> SEQUENCE: 420

Val Leu Tyr Asn Val Thr Ile Asn Asn Thr
1               5                   10

<210> SEQ ID NO 421
<211> LENGTH: 10
<212> TYPE: PRT
<213> ORGANISM: Homo sapiens

<400> SEQUENCE: 421

Ile Leu Phe Trp Ser Ile Ile Ser Ile Ile
1               5                   10

<210> SEQ ID NO 422
<211> LENGTH: 10
<212> TYPE: PRT
<213> ORGANISM: Homo sapiens

<400> SEQUENCE: 422

Leu Leu Pro Leu Ser Pro Tyr Leu Met Leu
1               5                   10

<210> SEQ ID NO 423
<211> LENGTH: 10
<212> TYPE: PRT
<213> ORGANISM: Homo sapiens

<400> SEQUENCE: 423

Cys Met Ile Glu Asn Asp Ile Ala Lys Ala
1               5                   10

<210> SEQ ID NO 424
<211> LENGTH: 10
<212> TYPE: PRT
<213> ORGANISM: Homo sapiens

<400> SEQUENCE: 424

Lys Thr Gly Ala Phe Ser Met Pro Glu Val
1               5                   10

<210> SEQ ID NO 425
<211> LENGTH: 10
<212> TYPE: PRT
<213> ORGANISM: Homo sapiens

<400> SEQUENCE: 425

Trp Ala Leu Leu Pro Leu Ser Pro Tyr Leu
1               5                   10

<210> SEQ ID NO 426
<211> LENGTH: 10
<212> TYPE: PRT
<213> ORGANISM: Homo sapiens

<400> SEQUENCE: 426

Ile Ile Leu Ala Gly Ala Ile Ala Leu Ile
1               5                   10

<210> SEQ ID NO 427
<211> LENGTH: 10
<212> TYPE: PRT
<213> ORGANISM: Homo sapiens

<400> SEQUENCE: 427

Gln Leu Thr Asp Ala Gly Thr Tyr Lys Cys
1               5                   10

<210> SEQ ID NO 428
<211> LENGTH: 10
<212> TYPE: PRT
<213> ORGANISM: Homo sapiens

<400> SEQUENCE: 428

Ala Leu Leu Pro Leu Ser Pro Tyr Leu Met

```
1               5              10
```

<210> SEQ ID NO 429
<211> LENGTH: 10
<212> TYPE: PRT
<213> ORGANISM: Homo sapiens

<400> SEQUENCE: 429

```
Gln Leu Leu Asn Ser Lys Ala Ser Leu Cys
 1               5              10
```

<210> SEQ ID NO 430
<211> LENGTH: 10
<212> TYPE: PRT
<213> ORGANISM: Homo sapiens

<400> SEQUENCE: 430

```
Ile Leu Ser Cys Thr Phe Glu Pro Asp Ile
 1               5              10
```

<210> SEQ ID NO 431
<211> LENGTH: 10
<212> TYPE: PRT
<213> ORGANISM: Homo sapiens

<400> SEQUENCE: 431

```
Trp Leu Lys Glu Gly Val Leu Gly Leu Val
 1               5              10
```

<210> SEQ ID NO 432
<211> LENGTH: 10
<212> TYPE: PRT
<213> ORGANISM: Homo sapiens

<400> SEQUENCE: 432

```
Leu Gln Leu Leu Asn Ser Lys Ala Ser Leu
 1               5              10
```

<210> SEQ ID NO 433
<211> LENGTH: 10
<212> TYPE: PRT
<213> ORGANISM: Homo sapiens

<400> SEQUENCE: 433

```
Gln Ile Leu Phe Trp Ser Ile Ile Ser Ile
 1               5              10
```

<210> SEQ ID NO 434
<211> LENGTH: 10
<212> TYPE: PRT
<213> ORGANISM: Homo sapiens

<400> SEQUENCE: 434

```
Gly Ile Ser Gly Arg His Ser Ile Thr Val
 1               5              10
```

<210> SEQ ID NO 435
<211> LENGTH: 10
<212> TYPE: PRT
<213> ORGANISM: Homo sapiens

<400> SEQUENCE: 435

```
Phe Glu Pro Asp Ile Lys Leu Ser Asp Ile
 1               5              10
```

```
<210> SEQ ID NO 436
<211> LENGTH: 9
<212> TYPE: PRT
<213> ORGANISM: Homo sapiens

<400> SEQUENCE: 436

Ala Leu Leu Pro Leu Ser Pro Tyr Leu
 1               5

<210> SEQ ID NO 437
<211> LENGTH: 9
<212> TYPE: PRT
<213> ORGANISM: Homo sapiens

<400> SEQUENCE: 437

Ser Leu Cys Val Ser Ser Phe Phe Ala
 1               5

<210> SEQ ID NO 438
<211> LENGTH: 9
<212> TYPE: PRT
<213> ORGANISM: Homo sapiens

<400> SEQUENCE: 438

Ile Leu Phe Trp Ser Ile Ile Ser Ile
 1               5

<210> SEQ ID NO 439
<211> LENGTH: 9
<212> TYPE: PRT
<213> ORGANISM: Homo sapiens

<400> SEQUENCE: 439

Gln Leu Leu Asn Ser Lys Ala Ser Leu
 1               5

<210> SEQ ID NO 440
<211> LENGTH: 9
<212> TYPE: PRT
<213> ORGANISM: Homo sapiens

<400> SEQUENCE: 440

Lys Val Val Ser Val Leu Tyr Asn Val
 1               5

<210> SEQ ID NO 441
<211> LENGTH: 9
<212> TYPE: PRT
<213> ORGANISM: Homo sapiens

<400> SEQUENCE: 441

Ile Leu Ala Gly Ala Ile Ala Leu Ile
 1               5

<210> SEQ ID NO 442
<211> LENGTH: 9
<212> TYPE: PRT
<213> ORGANISM: Homo sapiens

<400> SEQUENCE: 442

Trp Leu Lys Glu Gly Val Leu Gly Leu
 1               5

<210> SEQ ID NO 443
```

```
<211> LENGTH: 9
<212> TYPE: PRT
<213> ORGANISM: Homo sapiens

<400> SEQUENCE: 443

Ile Ile Leu Ala Gly Ala Ile Ala Leu
1               5

<210> SEQ ID NO 444
<211> LENGTH: 9
<212> TYPE: PRT
<213> ORGANISM: Homo sapiens

<400> SEQUENCE: 444

Asn Val Thr Met Lys Val Val Ser Val
1               5

<210> SEQ ID NO 445
<211> LENGTH: 9
<212> TYPE: PRT
<213> ORGANISM: Homo sapiens

<400> SEQUENCE: 445

Glu Met Phe Arg Gly Arg Thr Ala Val
1               5

<210> SEQ ID NO 446
<211> LENGTH: 9
<212> TYPE: PRT
<213> ORGANISM: Homo sapiens

<400> SEQUENCE: 446

Ala Val Phe Ala Asp Gln Val Ile Val
1               5

<210> SEQ ID NO 447
<211> LENGTH: 9
<212> TYPE: PRT
<213> ORGANISM: Homo sapiens

<400> SEQUENCE: 447

Leu Leu Pro Leu Ser Pro Tyr Leu Met
1               5

<210> SEQ ID NO 448
<211> LENGTH: 9
<212> TYPE: PRT
<213> ORGANISM: Homo sapiens

<400> SEQUENCE: 448

Leu Leu Asn Ser Lys Ala Ser Leu Cys
1               5

<210> SEQ ID NO 449
<211> LENGTH: 9
<212> TYPE: PRT
<213> ORGANISM: Homo sapiens

<400> SEQUENCE: 449

Val Ile Gln Trp Leu Lys Glu Gly Val
1               5

<210> SEQ ID NO 450
<211> LENGTH: 9
<212> TYPE: PRT
```

```
<213> ORGANISM: Homo sapiens

<400> SEQUENCE: 450

Ala Ile Ser Trp Ala Leu Leu Pro Leu
 1               5

<210> SEQ ID NO 451
<211> LENGTH: 9
<212> TYPE: PRT
<213> ORGANISM: Homo sapiens

<400> SEQUENCE: 451

Ser Leu Gly Gln Ile Leu Phe Trp Ser
 1               5

<210> SEQ ID NO 452
<211> LENGTH: 9
<212> TYPE: PRT
<213> ORGANISM: Homo sapiens

<400> SEQUENCE: 452

Ile Ala Leu Ile Ile Gly Phe Gly Ile
 1               5

<210> SEQ ID NO 453
<211> LENGTH: 9
<212> TYPE: PRT
<213> ORGANISM: Homo sapiens

<400> SEQUENCE: 453

Cys Thr Phe Glu Pro Asp Ile Lys Leu
 1               5

<210> SEQ ID NO 454
<211> LENGTH: 9
<212> TYPE: PRT
<213> ORGANISM: Homo sapiens

<400> SEQUENCE: 454

Ile Val Gly Asn Ala Ser Leu Arg Leu
 1               5

<210> SEQ ID NO 455
<211> LENGTH: 9
<212> TYPE: PRT
<213> ORGANISM: Homo sapiens

<400> SEQUENCE: 455

Gly Gln Ile Leu Phe Trp Ser Ile Ile
 1               5
```

COMPOSITIONS AND METHODS FOR THE THERAPY AND DIAGNOSIS OF OVARIAN CANCER

CROSS REFERENCE TO RELATED APPLICATIONS

This application is a continuation-in-part of U.S. application Ser. No. 09/636,801, filed Aug. 10, 2000, now abandoned, which is a continuation-in-part of U.S. application Ser. No. 09/617,747, filed Jul. 17, 2000, now abandoned which is a continuation-in-part of U.S. application Ser. No. 09/404,879, filed Sep. 24, 1999, U.S. Pat. No. 6,468,546, which is a continuation-in-part of U.S. application Ser. No. 09/338,933, filed Jun. 23, 1999, U.S. Pat. No. 6,488,931, which is a continuation-in-part of U.S. application Ser. No. 09/216,003, filed Dec. 17, 1998, and Ser. No. 09/215,681, filed Dec. 17, 1998, U.S. Pat. No. 6,528,253.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer. In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of SEQ ID NOs:1–81, 313–331, 359, 366, 379, 385–387, 391 and complements of such polynucleotides.

The present invention further provides polynucleotides that encode a polypeptide as described above or a portion thereof, expression vectors comprising such polynucleotides and host cells transformed or transfected with such expression vectors.

Within other aspects, the present invention provides pharmaceutical compositions and vaccines. Pharmaceutical compositions may comprise a physiologically acceptable carrier or excipient in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, 313–331, 359, 366, 379, 385–387 or 391; (ii) a polynucleotide encoding such a polypeptide; (iii) an antibody that specifically binds to such a polypeptide; (iv) an antigen-presenting cell that expresses such a polypeptide and/or (v) a T cell that specifically reacts with such a polypeptide. Vaccines may comprise a non-specific immune response enhancer in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, 313–331, 359, 366, 379, 385–387 or 391; (ii) a polynucleotide encoding such a polypeptide; (iii) an anti-idiotypic antibody that is specifically bound by an antibody that specifically binds to such a polypeptide; (iv) an antigen-presenting cell that expresses such a polypeptide and/or (v) a T cell that specifically reacts with such a polypeptide.

The present invention further provides, in other aspects, fusion proteins that comprise at least one polypeptide as described above, as well as polynucleotides encoding such fusion proteins.

Within related aspects, pharmaceutical compositions comprising a fusion protein or polynucleotide encoding a fusion protein in combination with a physiologically acceptable carrier are provided.

Vaccines are further provided, within other aspects, comprising a fusion protein or polynucleotide encoding a fusion protein in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for stimulating and/or expanding T cells, comprising contacting T cells with (a) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–387 or 391; (b) a polynucleotide encoding such a polypeptide and/or (c) an antigen presenting cell that expresses such a polypeptide under conditions and for a time sufficient to permit the stimulation and/or expansion of T cells. Such polypeptide, polynucleotide and/or antigen presenting cell(s) may be present within a pharmaceutical composition or vaccine, for use in stimulating and/or expanding T cells in a mammal.

Within other aspects, the present invention provides methods for inhibiting the development of ovarian cancer in a patient, comprising administering to a patient T cells prepared as described above.

Within further aspects, the present invention provides methods for inhibiting the development of ovarian cancer in a patient, comprising the steps of: (a) incubating $CD4^+$ and/or $CD8^+$ T cells isolated from a patient with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–387 or 391; (ii) a polynucleotide encoding such a polypeptide; or (iii) an antigen-presenting cell that expresses such a polypeptide; such that T cells proliferate; and (b) administering to the patient an effective amount of the proliferated T cells, and thereby inhibiting the development of ovarian cancer in the patient. The proliferated cells may be cloned prior to administration to the patient.

The present invention also provides, within other aspects, methods for identifying secreted tumor antigens. Such methods comprise the steps of: (a) implanting tumor cells in an immunodeficient mammal; (b) obtaining serum from the immunodeficient mammal after a time sufficient to permit secretion of tumor antigens into the serum; (c) immunizing an immunocompetent mammal with the serum; (d) obtaining antiserum from the immunocompetent mammal; and (e) screening a tumor expression library with the antiserum, and therefrom identifying a secreted tumor antigen. A preferred method for identifying a secreted ovarian carcinoma antigen comprises the steps of: (a) implanting ovarian carcinoma cells in a SCID mouse; (b) obtaining serum from the SCID mouse after a time sufficient to permit secretion of ovarian carcinoma antigens into the serum; (c) immunizing an immunocompetent mouse with the serum; (d) obtaining antiserum from the immunocompetent mouse; and (e) screening an ovarian carcinoma expression library with the antiserum, and therefrom identifying a secreted ovarian carcinoma antigen.

The present invention also discloses antibody epitopes recognized by the O8E polyclonal anti-sera which epitopes are presented herein as SEQ ID NOs: 394–415.

Further disclosed by the present invention are 10-mer and 9-mer peptides predicted to bind HLA-0201 which peptides are disclosed herein as SEQ ID NOs: 416–435 and SEQ ID NOs: 436–455, respectively.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A–1S (SEQ ID NOs:1–71) depict partial sequences of polynucleotides encoding representative secreted ovarian carcinoma antigens.

FIGS. 2A–2C depict full insert sequences for three of the clones of FIG. 1. FIG. 2A shows the sequence designated O7E (11731; SEQ ID NO:72), FIG. 2B shows the sequence designated O9E (11785; SEQ ID NO:73) and FIG. 2C shows the sequence designated O8E (13695; SEQ ID NO:74).

FIG. 3 presents results of microarray expression analysis of the ovarian carcinoma sequence designated O8E.

FIG. 4 presents a partial sequence of a polynucleotide (designated 3g; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO:76).

FIG. 6 presents the ovarian carcinoma polynucleotide designated 6b (SEQ ID NO:77).

FIGS. 7A and 7B present the ovarian carcinoma polynucleotides designated 8e (SEQ ID NO:78) and 8h (SEQ ID NO:79).

FIG. 8 presents the ovarian carcinoma polynucleotide designated 12c (SEQ ID NO:80).

FIG. 9 presents the ovarian carcinoma polynucleotide designated 12h (SEQ ID NO:81).

FIG. 10 depicts results of microarray expression analysis of the ovarian carcinoma sequence designated 3f.

FIG. 11 depicts results of microarray expression analysis of the ovarian carcinoma sequence designated 6b.

FIG. 12 depicts results of microarray expression analysis of the ovarian carcinoma sequence designated 8e.

FIG. 13 depicts results of microarray expression analysis of the ovarian carcinoma sequence designated 12c.

FIG. 14 depicts results of microarray expression analysis of the ovarian carcinoma sequence designated 12h.

FIGS. 15A–15E-2 depict partial sequences of additional polynucleotides encoding representative secreted ovarian carcinoma antigens (SEQ ID NOs:82–310).

FIG. 23 shows the ELISA analysis of anti-O8E rabbit sera.

FIG. 24 shows the ELISA analysis of affinity purified rabbit anti-O8E polyclonal antibody.

DETAILED DESCRIPTION OF THE INVENTION

Figure 16:
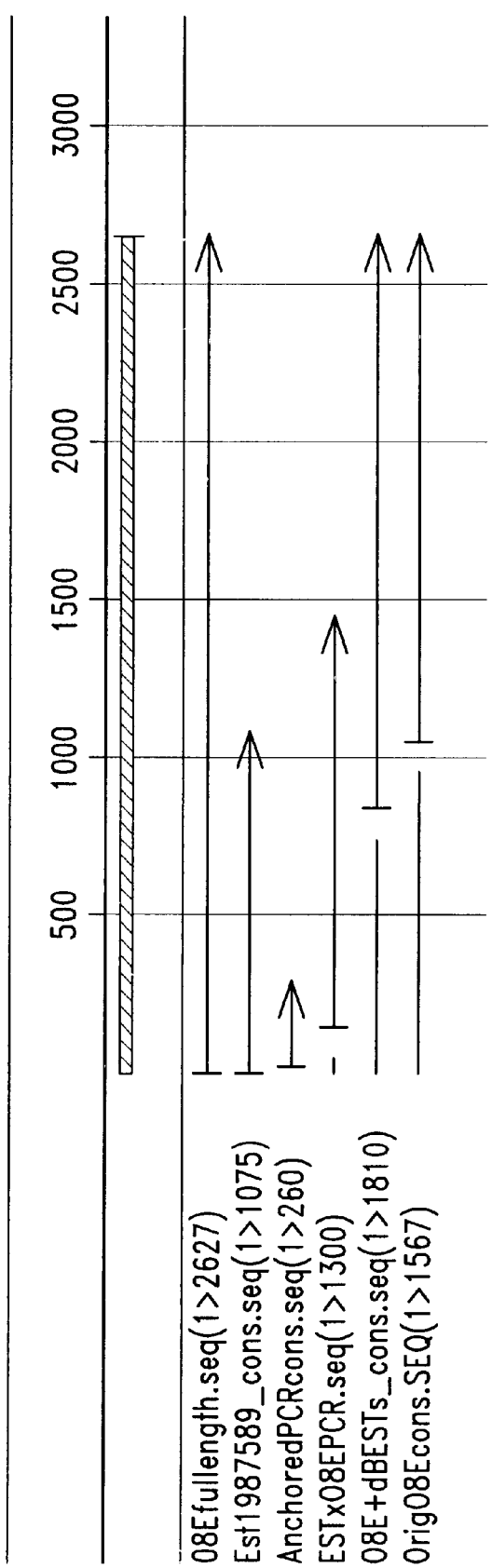
FIG. 16 is a diagram illustrating the location of various partial O8E sequences within the full length sequence.

As noted above, the present invention is generally directed to compositions and methods for the therapy of cancer, such as ovarian cancer. The compositions described herein may include immunogenic polypeptides, polynucleotides encoding such polypeptides, binding agents such as antibodies that bind to a polypeptide, antigen presenting cells (APCs) and/or immune system cells (e.g., T cells).

Polypeptides of the present invention generally comprise at least an immunogenic portion of an ovarian carcinoma protein or a variant thereof. Certain ovarian carcinoma proteins have been identified using an immunoassay technique, and are referred to herein as ovarian carcinoma antigens. An "ovarian carcinoma antigen" is a protein that is expressed by ovarian tumor cells (preferably human cells) at a level that is at least two fold higher than the level in normal ovarian cells. Certain ovarian carcinoma antigens react detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, certain ovarian carcinoma antigens provided herein are secreted antigens. Certain nucleic acid sequences of the subject invention generally comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain partial ovarian carcinoma polynucleotide sequences are presented herein. Proteins encoded by genes comprising such polynucleotide sequences (or complements thereof) are also considered ovarian carcinoma proteins.

Antibodies are generally immune system proteins, or antigen-binding fragments thereof, that are capable of binding to at least a portion of an ovarian carcinoma polypeptide as described herein. T cells that may be employed within the compositions provided herein are generally T cells (e.g., $CD4^+$ and/or $CD8^+$) that are specific for such a polypeptide. Certain methods described herein further employ antigen-presenting cells (such as dendritic cells or macrophages) that express an ovarian carcinoma polypeptide as provided herein.

Ovarian Carcinoma Polynucleotides

Any polynucleotide that encodes an ovarian carcinoma protein or a portion or other variant thereof as described herein is encompassed by the present invention. Preferred polynucleotides comprise at least 15 consecutive nucleotides, preferably at least 30 consecutive nucleotides, and more preferably at least 45 consecutive nucleotides, that encode a portion of an ovarian carcinoma protein. More preferably, a polynucleotide encodes an immunogenic portion of an ovarian carcinoma protein, such as an ovarian carcinoma antigen. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions such that the immunogenicity of the encoded polypeptide is not diminished, relative to a native ovarian carcinoma protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof.

The percent identity for two polynucleotide or polypeptide sequences may be readily determined by comparing sequences using computer algorithms well known to those of ordinary skill in the art, such as Megalign, using default parameters. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. Optimal alignment of sequences for comparison may be conducted, for example, using the Megalign program in the Lasergene suite of bioinformatics software (DNASTAR, Inc., Madison, Wis.), using default parameters. Preferably, the percentage of sequence identity is determined by comparing two optimally aligned sequences over a window of comparison of at least 20 positions, wherein the portion of the polynucleotide or polypeptide sequence in the window may comprise additions or deletions (i.e., gaps) of 20% or less, usually 5 to 15%, or 10 to 12%, relative to the reference sequence (which does not contain additions or deletions). The percent identity may be calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native ovarian carcinoma protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera from SCID mice implanted with late passage ovarian tumors. Ovarian carcinoma polynucleotides may also be identified using any of a variety of techniques designed to evaluate differential gene expression. Alternatively, polynucleotides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma antigens are provided in FIGS. 1A–1S (SEQ ID NOS:1 to 71) and FIGS. 15A to 15E-2 (SEQ ID NOs:82 to 310). The sequences provided in FIGS. 1A–1S appear to be novel. For sequences in FIGS. 15A–15E-2, database searches revealed matches having substantial identity. These polynucleotides were isolated by serological screening of an ovarian tumor cDNA expression library, using a technique designed to identify secreted tumor antigens. Briefly, a late passage ovarian tumor expression library was prepared from a SCID-derived human ovarian tumor (OV9334) in the vector λ-screen (Novagen). The sera used for screening were obtained by injecting immunocompetent mice with sera from SCID mice implanted with one late passage ovarian tumors. This technique permits the identification of cDNA molecules that encode immunogenic portions of secreted tumor antigens.

The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

Other nucleic acid sequences of cDNA molecules encoding portions of ovarian carcinoma proteins are provided in FIGS. 4–9 (SEQ ID NOs:75–81), as well as SEQ ID NOs:313–384. These sequences were identified by screening a microarray of cDNAs for tumor-associated expression (i.e., expression that is at least five fold greater in an ovarian tumor than in normal ovarian tissue, as determined using a representative assay provided herein). Such screens were performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). SEQ ID NOs:311 and 391 provide full length sequences incorporating certain of these nucleic acid sequences.

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996; Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/ Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10-10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of an ovarian carcinoma protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Ovarian Carcinoma Polypeptides

Within the context of the present invention, polypeptides may comprise at least an immunogenic portion of an ovarian carcinoma protein or a variant thereof, as described herein. As noted above, certain ovarian carcinoma proteins are ovarian carcinoma antigens that are expressed by ovarian tumor cells and react detectably within an immunoassay (such as an ELISA) with antisera generated against serum from an immunodeficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera, antibodies and T cells may be prepared as described herein, and using well known techniques. An immunogenic portion of a native ovarian carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies. A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with ovarian carcinoma protein-specific antisera may be enhanced or unchanged, relative to the native ovarian carcinoma protein, or may be diminished by less than 50%, and preferably less than 20%, relative to the native ovarian carcinoma protein. Such variants may generally be identified by modifying one of the above polypeptide sequences and evaluating the reactivity of the modified polypeptide with ovarian carcinoma protein-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity to the native polypeptide. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian carcinoma protein or a variant of such a protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen present cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to an ovarian carcinoma protein. As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Binding agents may be further capable of differentiating between patients with and without a cancer, such as ovarian cancer, using the representative assays provided herein. In other words, antibodies or other binding agents that bind to a ovarian carcinoma antigen will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, leukophoresis, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies. A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof Preferred radionuclides include $^{90}$Y, $^{123}$I, $^{125}$I, $^{131}$I, $^{186}$Re, $^{188}$Re, 211At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of an ovarian carcinoma protein. Such antibodies may be raised against an antibody, or antigen-binding fragment thereof, that specifically binds to an immunogenic portion of an ovarian carcinoma protein, using well known techniques. Anti-idiotypic antibodies that mimic an immunogenic portion of an ovarian carcinoma protein are those antibodies that bind to an antibody, or antigen-binding fragment thereof, that specifically binds to an immunogenic portion of an ovarian carcinoma protein, as described herein.

T Cells

Immunotherapeutic compositions may also, or alternatively, comprise T cells specific for an ovarian carcinoma protein. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. No. 5,240,856; U.S. Pat. No. 5,215,926; WO 89/06280; WO 91/16116 and WO 92/07243). Alternatively, T cells may be derived from related or unrelated humans, non-human animals, cell lines or cultures.

T cells may be stimulated with an ovarian carcinoma polypeptide, polynucleotide encoding an ovarian carcinoma polypeptide and/or an antigen presenting cell (APC) that expresses such a polypeptide. Such stimulation is performed under conditions and for a time sufficient to permit the generation of T cells that are specific for the polypeptide. Preferably, an ovarian carcinoma polypeptide or polynucleotide is present within a delivery vehicle, such as a microsphere, to facilitate the generation of specific T cells.

T cells are considered to be specific for an ovarian carcinoma polypeptide if the T cells kill target cells coated with an ovarian carcinoma polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an ovarian carcinoma polypeptide (200 ng/ml–100 µg/ml, preferably 100 ng/ml–25 µg/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). T cells that have been activated in response to an ovarian carcinoma polypeptide, polynucleotide or ovarian carcinoma polypeptide-expressing APC may be $CD4^+$ and/or $CD8^+$. Ovarian carcinoma polypeptide-specific T cells may be expanded using standard techniques. Within preferred embodiments, the T cells are derived from a patient or a related or unrelated donor and are administered to the patient following stimulation and expansion.

For therapeutic purposes, $CD4^+$ or $CD8^+$ T cells that proliferate in response to an ovarian carcinoma polypeptide, polynucleotide or APC can be expanded in number either in vitro or in vivo. Proliferation of such T cells in vitro may be accomplished in a variety of ways. For example, the T cells can be re-exposed to an ovarian carcinoma polypeptide, with or without the addition of T cell growth factors, such as interleukin-2, and/or stimulator cells that synthesize an ovarian carcinoma polypeptide. Alternatively, one or more T cells that proliferate in the presence of an ovarian carcinoma polypeptide can be expanded in number by cloning. Methods for cloning cells are well known in the art, and include limiting dilution. Following expansion, the cells may be administered back to the patient as described, for example, by Chang et al., *Crit. Rev. Oncol. Hematol.* 22:213, 1996.

Pharmaceutical Compositions and Vaccines

Within certain aspects, polypeptides, polynucleotides, binding agents and/or immune system cells as described herein may be incorporated into pharmaceutical compositions or vaccines. Pharmaceutical compositions comprise one or more such compounds or cells and a physiologically acceptable carrier. Vaccines may comprise one or more such compounds or cells and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-$\gamma$, IL-2 and IL-12) tend to favor the induction of cell mediated immune responses to an administered antigen. In contrast, high levels of Th2-type cytokines (e.g., IL-4, IL-5, IL-6, IL-10 and TNF-$\beta$) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436,727; 4,877,611; 4,866,034 and 4,912,094). Also preferred is AS-2 (SmithKline Beecham). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a ovarian carcinoma antigen (or portion or other variant thereof) such that the antigen, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456–460, 1997. Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as ovarian cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. Within certain preferred embodiments, a patient is afflicted with ovarian cancer. Such cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immuno response-modifying agents (such as tumor vaccines, bacterial adjuvants and/or cytokines).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T lymphocytes (such as CD8$^+$ cytotoxic T lymphocytes and CD4$^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157: 177, 1997).

Alternatively, a vector expressing a polypeptide recited herein may be introduced into stem cells taken from a patient and clonally propagated in vitro for autologous transplant back into the same patient.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration), orally or in the bed of a resected tumor. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to an ovarian carcinoma antigen generally correlate with an improved clinical outcome. Such immune responses may generally be evaluated using standard proliferation, cytotoxicity or cytokine assays, which may be performed using samples obtained from a patient before and after treatment.

Screens for Identifying Secreted Ovarian Carcinoma Antigens

The present invention provides methods for identifying secreted tumor antigens. Within such methods, tumors are implanted into immunodeficient animals such as SCID mice and maintained for a time sufficient to permit secretion of tumor antigens into serum. In general, tumors may be implanted subcutaneously or within the gonadal fat pad of an immunodeficient animal and maintained for 1–9 months, preferably 1–4 months. Implantation may generally be performed as described in WO 97/18300. The serum containing secreted antigens is then used to prepare antisera in immunocompetent mice, using standard techniques and as described herein. Briefly, 50–100 μL of sera (pooled from three sets of immunodeficient mice, each set bearing a different SCID-derived human ovarian tumor) may be mixed 1:1 (vol:vol) with an appropriate adjuvant, such as RIBI-MPL or MPL+TDM (Sigma Chemical Co., St. Louis, Mo.) and injected intraperitoneally into syngeneic immunocompetent animals at monthly intervals for a total of 5 months. Antisera from animals immunized in such a manner may be obtained by drawing blood after the third, fourth and fifth immunizations. The resulting antiserum is generally precleared of *E. coli* and phage antigens and used (generally following dilution, such as 1:200) in a serological expression screen.

The library is typically an expression library containing cDNAs from one or more tumors of the type that was implanted into SCID mice. This expression library may be prepared in any suitable vector, such as λ-screen (Novagen). cDNAs that encode a polypeptide that reacts with the antiserum may be identified using standard techniques, and sequenced. Such cDNA molecules may be further characterized to evaluate expression in tumor and normal tissue, and to evaluate antigen secretion in patients.

The methods provided herein have advantages over other methods for tumor antigen discovery. In particular, all antigens identified by such methods should be secreted or released through necrosis of the tumor cells. Such antigens may be present on the surface of tumor cells for an amount of time sufficient to permit targeting and killing by the immune system, following vaccination.

Methods for Detecting Cancer

In general, a cancer may be detected in a patient based on the presence of one or more ovarian carcinoma proteins and/or polynucleotides encoding such proteins in a biological sample (such as blood, sera, urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of protein that binds to the agent in the biological sample. Polynucleotide primers and probes may be used to detect the level of mRNA encoding a tumor protein, which is also indicative of the presence or absence of a cancer. In general, an ovarian carcinoma-associated sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian carcinoma proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use ovarian carcinoma polypeptides to detect antibodies that bind to such polypeptides in a biological sample. The detection of such ovarian carcinoma protein specific antibodies may correlate with the presence of a cancer.

A cancer may also, or alternatively, be detected based on the presence of T cells that specifically react with an ovarian carcinoma protein in a biological sample. Within certain methods, a biological sample comprising $CD4^+$ and/or $CD8^+$ T cells isolated from a patient is incubated with an ovarian carcinoma protein, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with an ovarian carcinoma protein (e.g., 5–25 µg/ml). It may be desirable to incubate another aliquot of a T cell sample in the absence of ovarian carcinoma protein to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding an ovarian carcinoma protein in a biological sample. For example, at least two oligonucleotide primers may be employed in a polymerase chain reaction (PCR) based assay to amplify a portion of an ovarian carcinoma protein cDNA derived from a biological sample, wherein at least one of the oligonucleotide primers is specific for (i.e., hybridizes to) a polynucleotide encoding the ovarian carcinoma protein. The amplified cDNA is then separated and detected using techniques well known in the art, such as gel electrophoresis. Similarly, oligonucleotide probes that specifically hybridize to a polynucleotide encoding an ovarian carcinoma protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an ovarian carcinoma protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence provided herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, ovarian carcinoma proteins and polynucleotides encoding such proteins may be used as markers for monitoring the progression of cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple ovarian carcinoma protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian carcinoma protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding an ovarian carcinoma protein in a biological sample. Such kits generally comprise at least one oligonucleotide probe or primer, as described above, that hybridizes to a polynucleotide encoding an ovarian carcinoma protein. Such an oligonucleotide may be used, for example, within a PCR or hybridization assay. Additional components that may be present within such kits include a second oligonucleotide and/or a diagnostic reagent or container to facilitate the detection of a polynucleotide encoding an ovarian carcinoma protein.

The following Examples are offered by way of illustration and not by way of limitation.

EXAMPLES

Example 1

Identification of Representative Ovarian Carcinoma Protein cDNAs

This Example illustrates the identification of cDNA molecules encoding ovarian carcinoma proteins.

Anti-SCID mouse sera (generated against sera from SCID mice carrying late passage ovarian carcinoma) was precleared of *E. coli* and phage antigens and used at a 1:200 dilution in a serological expression screen. The library screened was made from a SCID-derived human ovarian tumor (OV9334) using a directional RH oligo(dT) priming cDNA library construction kit and the λScreen vector (Novagen). A bacteriophage lambda screen was employed. Approximately 400,000 pfu of the amplified OV9334 library were screened.

196 positive clones were isolated. Certain sequences that appear to be novel are provided in FIGS. 1A–1S and SEQ ID NOs:1 to 71. Three complete insert sequences are shown in FIGS. 2A–2C (SEQ ID NOs:72 to 74). Other clones having known sequences are presented in FIGS. 15A–15E-2 (SEQ ID NOs:82 to 310). Database searches identified the following sequences that were substantially identical to the sequences presented in FIGS. 15A–15E-2.

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs Using Microarray Technology

This Example illustrates the identification of ovarian carcinoma polynucleotides by PCR subtraction and microarray analysis. Microarrays of cDNAs were analyzed for ovarian tumor-specific expression using a Synteni (Palo Alto, Calif.) microarray, according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

A PCR subtraction was performed using a tester comprising cDNA of four ovarian tumors (three of which were metastatic tumors) and a driver of cDNA form five normal tissues (adrenal gland, lung, pancreas, spleen and brain). cDNA fragments recovered from this subtraction were subjected to DNA microarray analysis where the fragments were PCR amplified, adhered to chips and hybridized with fluorescently labeled probes derived from mRNAs of human ovarian tumors and a variety of normal human tissues. In this analysis, the slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens. The fluorescent results were analyzed and clones that displayed increased expression in ovarian tumors were further characterized by DNA sequencing and database searches to determine the novelty of the sequences.

Using such assays, an ovarian tumor antigen was identified that is a splice fusion between the human T-cell leukemia virus type I oncoprotein TAX (see Jin et al., *Cell* 93:81–91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this method are referred to herein as 3f, 6b, 8e, 8h, 12c and 12h. Sequences of these clones are shown in FIGS. 5 to 9 and SEQ ID NOs:76 to 81. Microarray analyses were performed as described above, and are presented in FIGS. 10 to 14. A full length sequence encompassing clones 3f, 6b, 8e and 12h was obtained by screening an ovarian tumor (SCID-derived) cDNA library. This 2996 base pair sequence (designated O772P) is presented in SEQ ID NO:311, and the encoded 914 amino acid protein sequence is shown in SEQ ID NO:312. PSORT analysis indicates a Type 1a transmembrane protein localized to the plasma membrane.

In addition to certain of the sequences described above, this screen identified the following sequences:

| Sequence | Comments |
|---|---|
| OV4vG11 (SEQ ID NO:313) | human clone 1119D9 on chromosome 20p12 |
| OV4vB11 (SEQ ID NO:314) | human UWGC:y14c094 from chromosome 6p21 |
| OV4vD9 (SEQ ID NO:315) | human clone 1049G16 chromosome 20q12–13.2 |
| OV4vD5 (SEQ ID NO:316) | human KIAA0014 gene |
| OV4vC2 (SEQ ID NO:317) | human KIAA0084 gene |
| OV4vF3 (SEQ ID NO:318) | human chromosome 19 cosmid R31167 |
| OV4VC1 (SEQ ID NO:319) | novel |
| OV4vH3 (SEQ ID NO:320) | novel |
| OV4vD2 (SEQ ID NO:321) | novel |
| O815P (SEQ ID NO:322) | novel |
| OV4vC12 (SEQ ID NO:323) | novel |
| OV4vA4 (SEQ ID NO:324) | novel |
| OV4vA3 (SEQ ID NO:325) | novel |
| OV4v2A5 (SEQ ID NO:326) | novel |
| O819P (SEQ ID NO:327) | novel |
| O818P (SEQ ID NO:328) | novel |
| O817P (SEQ ID NO:329) | novel |
| O816P (SEQ ID NO:330) | novel |
| Ov4vC5 (SEQ ID NO:331) | novel |
| 21721 (SEQ ID NO:332) | human lumican |
| 21719 (SEQ ID NO:333) | human retinoic acid-binding protein II |
| 21717 (SEQ ID NO:334) | human26S proteasome ATPase subunit |
| 21654 (SEQ ID NO:335) | human copine I |
| 21627 (SEQ ID NO:336) | human neuron specific gamma-2 enolase |
| 21623 (SEQ ID NO:337) | human geranylgeranyl transferase II |
| 21621 (SEQ ID NO:338) | human cyclin-dependent protein kinase |
| 21616 (SEQ ID NO:339) | human prepro-megakaryocyte potentiating factor |
| 21612 (SEQ ID NO:340) | human UPH1 |
| 21558 (SEQ ID NO:341) | human RalGDS-like 2 (RGL2) |
| 21555 (SEQ ID NO:342) | human autoantigen P542 |
| 21548 (SEQ ID NO:343) | human actin-related protein (ARP2) |
| 21462 (SEQ ID NO:344) | human huntingtin interacting protein |
| 21441 (SEQ ID NO:345) | human 90K product (tumor associated antigen) |
| 21439 (SEQ ID NO:346) | human guanine nucleotide regulator protein (tim1) |
| 21438 (SEQ ID NO:347) | human Ku autoimmune (p70/p80) antigen |
| 21237 (SEQ ID NO:348) | human S-laminin |
| 21436 (SEQ ID NO:349) | human ribophorin I |
| 21435 (SEQ ID NO:350) | human cytoplasmic chaperonin hTRiC5 |
| 21425 (SEQ ID NO:351) | humanEMX2 |
| 21423 (SEQ ID NO:352) | human p87/p89 gene |
| 21419 (SEQ ID NO:353) | human HPBRII-7 |
| 21252 (SEQ ID NO:354) | human T1-227H |
| 21251 (SEQ ID NO:355) | human cullin I |
| 21247 (SEQ ID NO:356) | kunitz type protease inhibitor (KOP) |
| 21244-1 (SEQ ID NO:357) | human protein tyrosine phosphatase receptor F (PTPRF) |
| 21718 (SEQ ID NO:358) | human LTR repeat |
| OV2-90 (SEQ ID NO:359) | novel |
| Human zinc finger (SEQ ID NO:360) | |
| Human polyA binding protein (SEQ ID NO:361) | |
| Human pleitrophin (SEQ ID NO:362) | |
| Human PAC clone 278C19 (SEQ ID NO:363) | |
| Human LLRep3 (SEQ ID NO:364) | |
| Human Kunitz type protease inhib (SEQ ID NO:365) | |
| Human KIAA0106 gene (SEQ ID NO:366) | |
| Human keratin (SEQ ID NO:367) | |
| Human HIV-1TAR (SEQ ID NO:368) | |
| Human glia derived nexin (SEQ ID NO:369) | |
| Human fibronectin (SEQ ID NO:370) | |
| Human ECMproBM40 (SEQ ID NO:371) | |
| Human collagen (SEQ ID NO:372) | |
| Human alpha enolase (SEQ ID NO:373) | |
| Human aldolase (SEQ ID NO:374) | |
| Human transf growth factor BIG H3 (SEQ ID NO:375) | |
| Human SPARC osteonectin (SEQ ID NO:376) | |
| Human SLP1 leucocyte protease (SEQ ID NO:377) | |
| Human mitochondrial ATP synth (SEQ ID NO:378) | |
| Human DNA seq clone 461P17 (SEQ ID NO:379) | |
| Human dbpB pro Y box (SEQ ID NO:380) | |
| Human 40 kDa keratin (SEQ ID NO:381) | |
| Human arginosuccinate synth (SEQ ID NO:382) | |
| Human acidic ribosomal phosphoprotein (SEQ ID NO:383) | |
| Human colon carcinoma laminin binding pro (SEQ ID NO:384) | |

This screen further identified multiple forms of the clone O772P, referred to herein as 21013, 21003 and 21008. PSORT analysis indicates that 21003 (SEQ ID NO:386; translated as SEQ ID NO:389) and 21008 (SEQ ID NO:387; translated as SEQ ID NO:390) represent Type 1a transmembrane protein forms of O772P. 21013 (SEQ ID NO:385; translated as SEQ ID NO:388) appears to be a truncated form of the protein and is predicted by PSORT analysis to be a secreted protein.

Additional sequence analysis resulted in a full length clone for O8E (2627 bp, which agrees with the message size observed by Northern analysis; SEQ ID NO:391). This nucleotide sequence was obtained as follows: the original O8E sequence (OrigO8Econs) was found to overlap by 33 nucleotides with a sequence from an EST clone (IMAGE#1987589). This clone provided 1042 additional nucleotides upstream of the original O8E sequence. The link between the EST and O8E was confirmed by sequencing multiple PCR fragments generated from an ovary primary tumor library using primers to the unique EST and the O8E sequence (EST×O8EPCR). Full length status was further indicated when anchored PCR from the ovary tumor library gave several clones (AnchoredPCR cons) that all terminated upstream of the putative start methionine, but failed to yield any additional sequence information. FIG. 16 presents a diagram that illustrates the location of each partial sequence within the full length O8E sequence.

Two protein sequences may be translated from the full length O8E. For "a" (SEQ ID NO:393) begins with a putative start methionine. A second form "b" (SEQ ID NO:392) includes 27 additional upstream residues to the 5' end of the nucleotide sequence.

Example 3

This example discloses the identification and characterization of antibody epitopes recognized by the O8E polyclonal anti-sera.

Rabbit anti-sera was raised against *E. coli* derived O8E recombinant protein and tested for antibody epitope recognition against 20 or 21 mer peptides that correspond to the O8E amino acid sequence. Peptides spanning amino acid regions 31 to 65, 76 to 110, 136 to 200 and 226 to 245 of the full length O8E protein were recognized by an acid eluted peak and/or a salt eluted peak from affinity purified anti-O8E sera. Thus, the corresponding amino acid sequences of the above peptides constitute the antibody epitopes recognized by affinity purified anti-O8E antibodies.

ELISA analysis of anti-O8E rabbit sera is shown in FIG. 23, and ELISA analysis of affinity purified rabbit anti-O8E polyclonal antibody is shown in FIG. 24.

Figure 17:
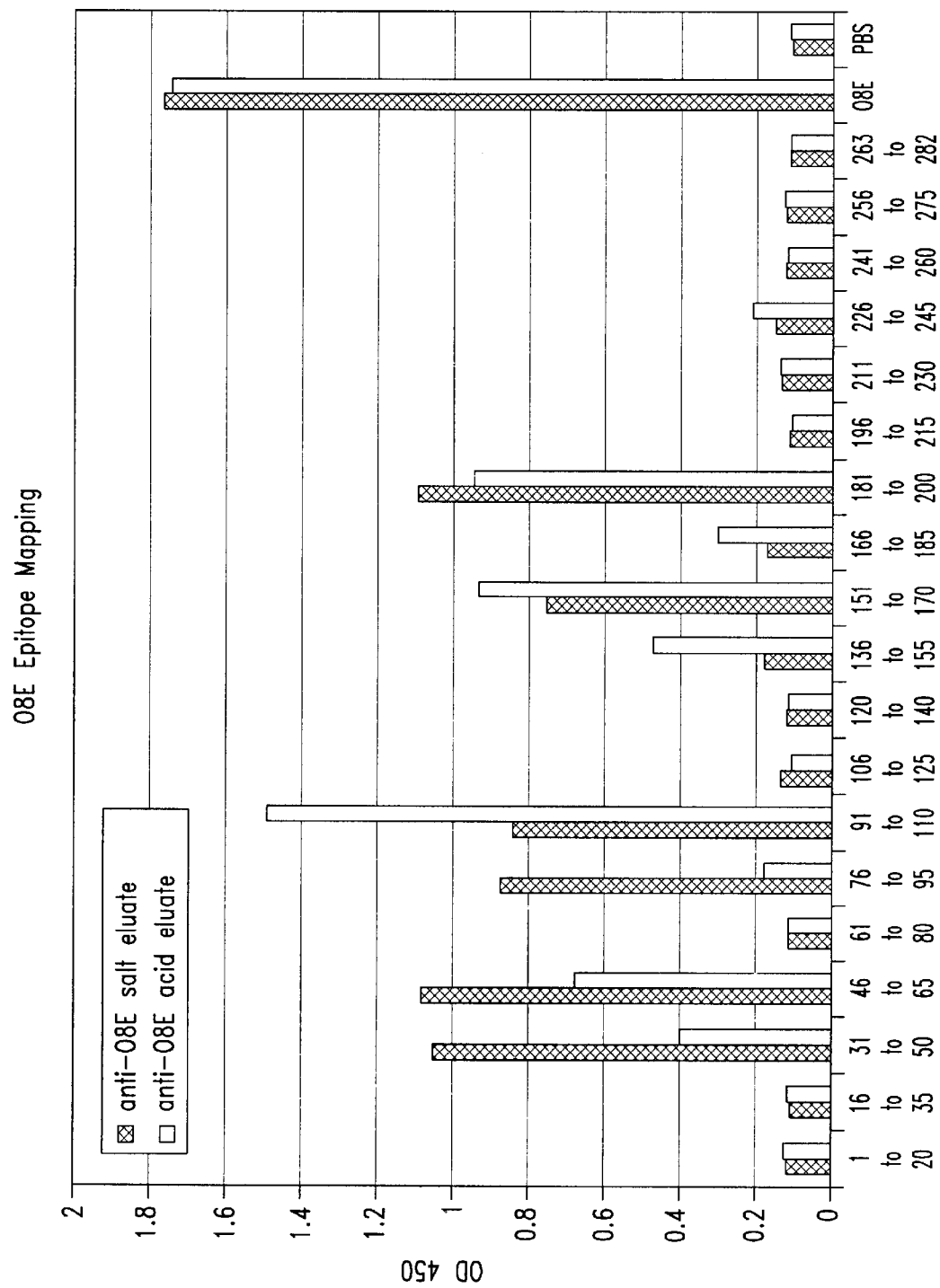
FIG. 17 is a graph illustrating the results of epitope mapping studies on O8E protein.

For epitope mapping, 20 or 21 mer peptides corresponding to the O8E protein were synthesized. For antibody affinity purification, rabbit anti-O8E sera was run over an O8E-sepharose column, then antibody was eluted with a salt buffer containing 0.5 M NaCl and 20 mM $PO_4$, followed by an acid elution step using 0.2 M Glycine, pH 2.3. Purified antibody was neutralized by the addition of 1M Tris, pH 8 and buffer exchanged into phosphate buffered saline (PBS). For enzyme linked immunosorbant assay (ELISA) analysis, O8E peptides and O8E recombinant protein were coated onto 96 well flat bottom plates at 2 µg/ml for 2 hours at room temperature (RT). Plates were then washed 5 times with PBS+0.1% Tween 20 and blocked with PBS+1% bovine serum albumin (BSA) for 1 hour. Affinity purified anti-O8E antibody, either an acid or salt eluted fraction, was then added to the wells at 1 µg/ml and incubated at RT for 1 hr. Plates were again washed, followed by the addition of donkey anti-rabbit-Ig-horseradish peroxidase (HRP) antibody for 1 hour at RT. Plates were washed, then developed by the addition of the chromagenic substrate 3,3',5,5'-tetramethylbenzidine (TMB) (described by Bos et al., *J. of immunoassay* 2:187–204 (1981); available from Sigma (St. Louis, Mo.)). The reaction was incubated 15 minutes at RT and then stopped by the addition of 1 N $H_2SO_4$. Plates were read at an optical denisty of 450 (OD450) in an automated plate reader. The sequences of peptides corresponding to the OE8 antibody epitopes are disclosed herein as SEQ ID NOs: 394–415. Antibody epitopes recognized by the O8E polyclonal anti-sera are disclosed herein in FIG. 17.

Example 4

This example discloses IHC analysis of O8E expression in ovarian cancer tissue samples.

For immunohistochemistry studies, paraffin-embedded formalin fixed ovarian cancer tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (anti-O8E rabbit affinity purified polyclonal antibody) was added to each section for 25 min followed by a 25 min incubation with an anti-rabbit biotinylated antibody. Endogenous peroxidase activity was blocked by three 1.5 min incubations with hydrogen peroxidase. The avidin biotin complex/horse radish peroxidase system was used along with DAB chromogen to visualize antigen expression. Slides were counterstained with hematoxylin. One (papillary serous carcinoma) of six ovarian cancer tissue sections displayed O8E immunoreactivity. O8E expression was localized to the plasma membrane.

Six ovarian cancer tissues were analyzed with the anti-O8E rabbit polyclonal antibody. One (papillary serous carcinoma) of six ovarian cancer tissue samples stained positive for O8E expression. O8E expression was localized to the surface membrane.

Example 5

This example discloses O8E peptides that are predicted to bind HLA-A2 and to be immunogenic for CD8 T cell responses in humans.

Potential HLA-A2 binding peptides of O8E were predicted by using the full-length open-reading frame (ORF) from O8E and running it through "Episeek," a program used to predict MHC binding peptides. The program used is based on the algorithm published by Parker, K.C. et al., *J. Immunol.* 152(1): 163–175 (1994) (incorporated by reference herein in its entirety). 10-mer and 9-mer peptides predicted to bind HLA-0201 are disclosed herein as SEQ ID NOs: 416–435 and SEQ ID NOs: 436–455, respectively.

Example 6

This example discloses O8E cell surface expression measured by fluoresence activated cell sorting.

Figure 18:
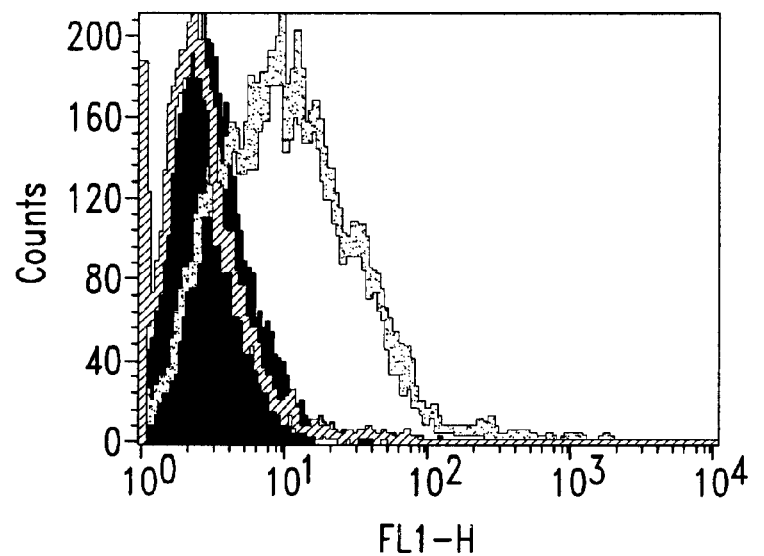
FIG. 18 is graph of a fluorescence activated cell sorting (FACS) analysis of O8E cell surface expression.
Figure 19:
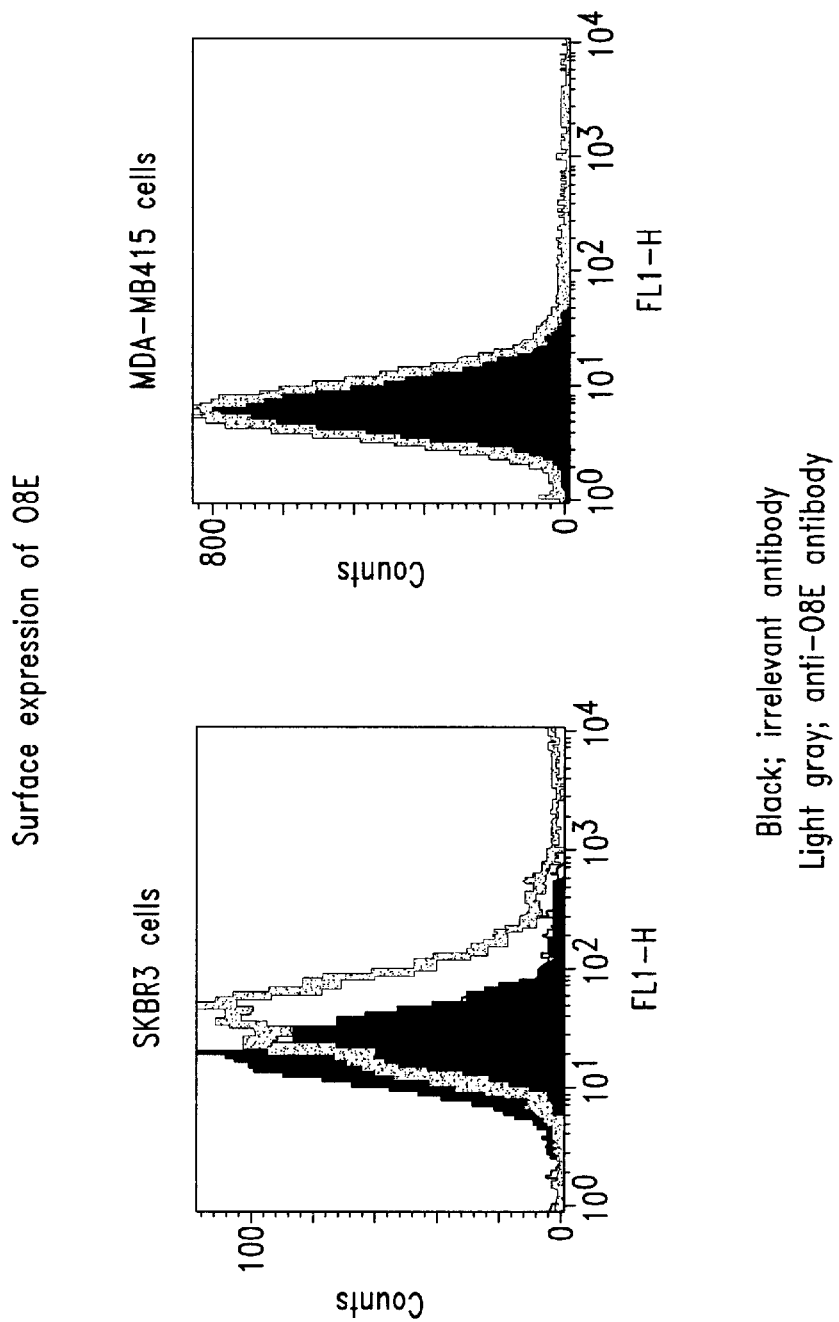
FIG. 19 is graph of a FACS analysis of O8E cell surface expression.

For FACS analysis, cells were washed with ice cold staining buffer (PBS/1% BSA/azide). Next, the cells were incubated for 30 minutes on ice with 10 micrograms/ml of affinity purified rabbit anti-B305D polyclonal antibody. The cells were washed 3 times with staining buffer and then incubated with a 1:100 dilution of a goat anti-rabbit Ig (H+L)-FITC reagent (Southern Biotechnology) for 30 minutes on ice. Following 3 washes, the cells were resuspended in staining buffer containing prodium iodide, a vital stain that allows for identification of permeable cells, and analyzed by FACS. O8E surface expression was confirmed on SKBR3 breast cancer cells and HEK293 cells that stably overexpress the cDNA for O8E. Neither MB415 cells nor HEK293 cells stably transfected with a control irrelevant plasmid DNA showed surface expression of O8E (FIGS. 18 and 19).

Example 7

This example further evaluates the expression and surface localization of O8E.

For expression and purification of antigen used for immunization, O8E expressed in an *E. coli* recombinant expression system was grown overnight in LB Broth with the appropriate antibiotics at 37° C. in a shaking incubator. The next morning, 10 ml of the overnight culture was added to 500 ml of 2×YT plus appropriate antibiotics in a 2L-baffled Erlenmeyer flask. When the Optical Density (at 560 nanometers) of the culture reached 0.4–0.6 the cells were induced with IPTG (1 mM). 4 hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the E. coli cells, this mixture was then run through the French Press at a pressure of 16,000 psi. The cells were then centrifuged again and the supernatant and pellet were checked by SDS-PAGE for the partitioning of the recombinant protein. For protein that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then evaluated for acceptable purity as determined by SDS-PAGE or HPLC, concentration as determined by Lowry assay or Amino Acid Analysis, identity as determined by amino terminal protein sequence, and endotoxin level as determined by the Limulus (LAL) assay. The proteins were then vialed after filtration through a 0.22 micron filter and the antigens were frozen until needed for immunization.

For generation of polyclonal anti-sera, 400 micrograms of each prostate antigen was combined with 100 micrograms of muramyldipeptide (MDP). Equal volume of Incomplete Freund's Adjuvant (IFA) was added and then mixed. Every four weeks animals were boosted with 100 micrograms of antigen mixed with an equal volume of IFA. Seven days following each boost the animal was bled. Sera was generated by incubating the blood at 4° C. for 12–24 hours followed by centrifugation.

For characterization of polyclonal antisera, 96 well plates were coated with antigen by incubating with 50 microliters (typically 1 micrgram)at 4 C for 20 hrs. 250 microliters of BSA blocking buffer was added to the wells and incubated at RT for 2 hrs. Plates were washed 6 times with PBS/0.01% tween. Anti-O8E rabbit sera or affinity purified anti-O8e antibody was diluted in PBS. Fifty microliters of diluted antibody was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB microwell Peroxidase Substrate was added to each well. Following a 15 minute incubation in the dark at room temperature the colorimetric reaction was stopped with 100 microliters of IN H2SO4 and read immediately at 450 nm. All polyclonal antibodies showed immunoreactivity to the O8E antigen.

For recombinant expression in mammalian HEK293 cells, full length O8E cDNA was subcloned into the mammalian expression vectors pcDNA3.1+ and pCEP4 (Invitrogen) which were modified to contain His and FLAG epitope tags, respectively. These constructs were transfected into HEK293 cells (ATCC) using Fugene 6 reagent (Roche). Briefly, HEK293 cells were plated at a density of 100,000 cells/ml in DMEM (Gibco) containing 10% FBS (Hyclone) and grown overnight. The following day, 2 ul of Fugene6 was added to 100 ul of DMEM containing no FBS and incubated for 15 minutes at room temperature. The Fugene6/DMEM mixture was then added to 1 ug of O8E/pCEP4 or O8E/pcDNA3.1 plasmid DNA and incubated for 15 minutes at room temperature. The Fugene/DNA mix was then added to the HEK293 cells and incubated for 48–72 hrs at 37° C. with 7% CO2. Cells were rinsed with PBS then collected and pelleted by is centrifugation. For Western blot analysis, whole cell lysates were generated by incubating the cells in Triton-X100 containing lysis buffer for 30 minutes on ice. Lysates were then cleared by centrifugation at 10,000 rpm for 5 minutes at 4 C. Samples were diluted with SDS-PAGE loading buffer containing beta-mercaptoethanol, then boiled for 10 minutes prior to loading the SDS-PAGE gel. Protein was transferred to nitrocellulose and probed using anti-O8E rabbit polyclonal sera #2333L at a dilution of 1:750. The blot was revealed with a goat anti-rabbit Ig coupled to HRP followed by incubation in ECL substrate.

For FACS analysis, cells were washed further with ice cold staining buffer (PBS+1%BSA+Azide). Next, the cells were incubated for 30 minutes on ice with 10 ug/ml of Protein A purified anti-O8E polyclonal sera. The cells were washed 3 times with staining buffer and then incubated with a 1:100 dilution of a goat anti-rabbit Ig(H+L)-FITC reagent (Southern Biotechnology) for 30 minutes on ice. Following 3 washes, the cells were resuspended in staining buffer containing Propidium Iodide (PI), a vital stain that allows for the identification of permeable cells, and analyzed by FACS.

Figure 20:
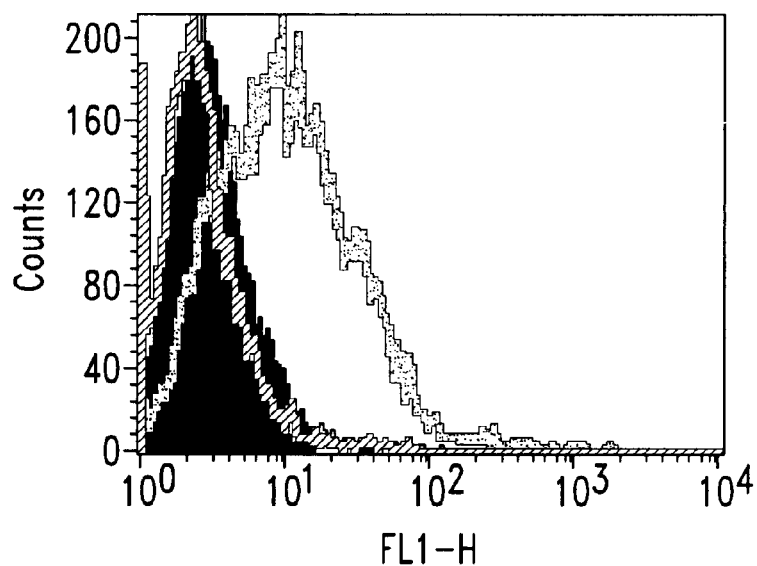
FIG. 20 shows FACS analysis results for O8E transfected HEK293 cells demonstrating cell surface expression of O8E.
Figure 21:
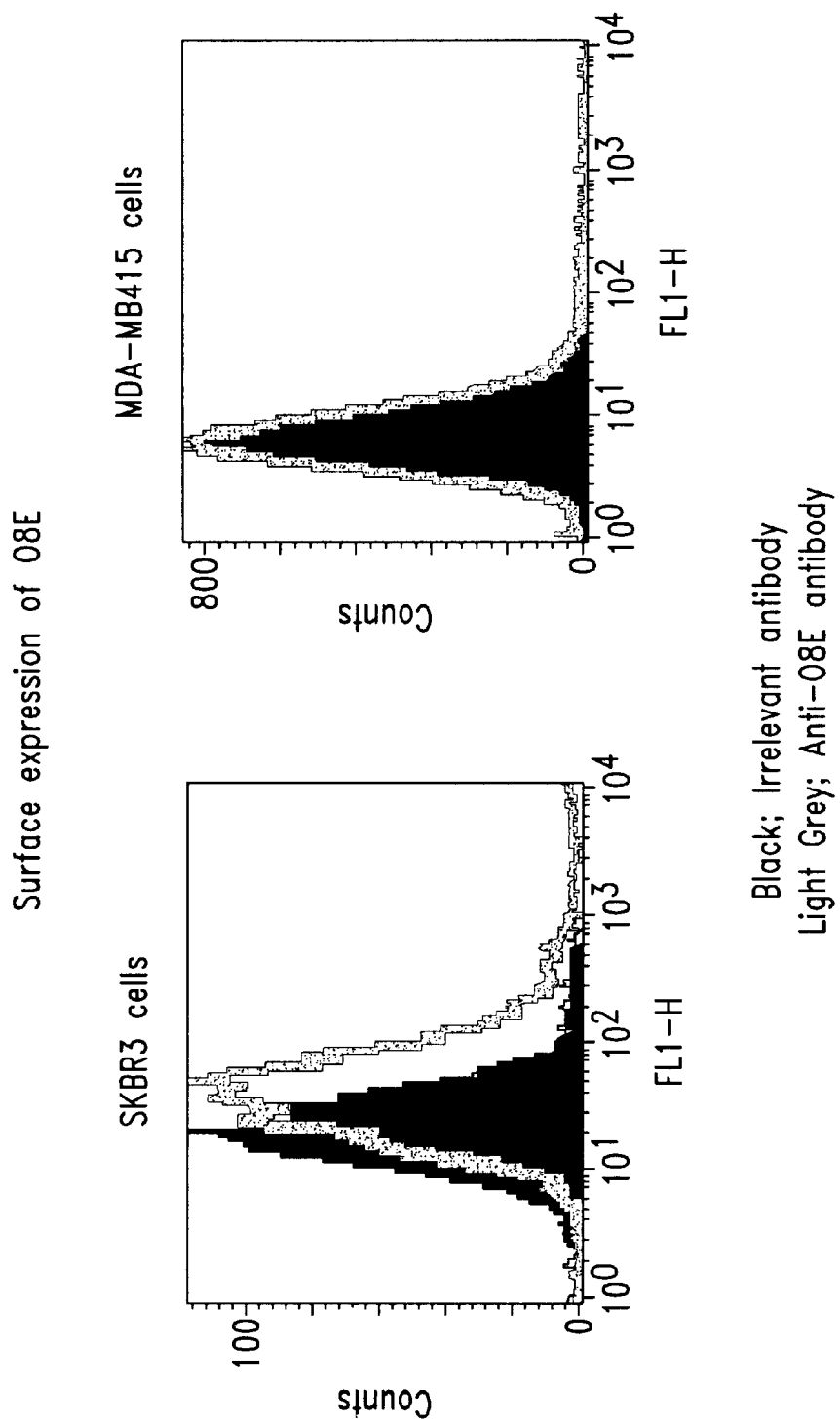
FIG. 21 shows FACS analysis results for SKBR3 breast tumor cells demonstrating cell surface expression of O8E.
Figure 22:
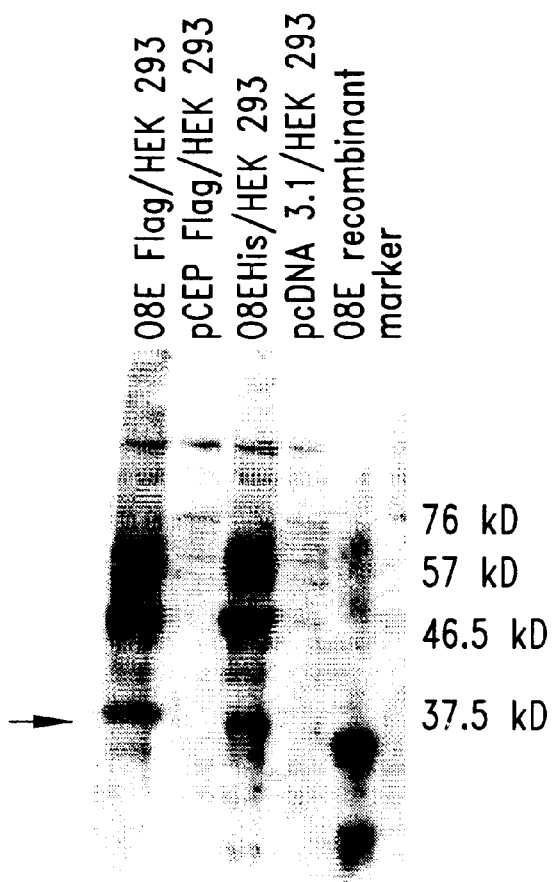
FIG. 22 shows O8E expression in HEK 293 cells. The cells were probed with anti-O8E rabbit polyclonal antisera #2333L.

From these experiments, the results of which are illustrated in FIGS. 20–21, O8E expression was detected on the surface of tranfected HEK293 cells and SKBR3 cells by FACS analysis using rabbit anti-O8E sera. Expression was also detected in transfected HEK293 cell lysates by Western blot analysis (FIG. 22).

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NOs:1–71 are ovarian carcinoma antigen polynucleotides shown in FIGS. 1A–1S.

SEQ ID NOs:72–74 are ovarian carcinoma antigen polynucleotides shown in FIGS. 2A–2C.

SEQ ID NO:75 is the ovarian carcinoma polynucleotide 3g (FIG. 4).

SEQ ID NO:76 is the ovarian carcinoma polynucleotide 3f (FIG. 5).

SEQ ID NO:77 is the ovarian carcinoma polynucleotide 6b (FIG. 6).

SEQ ID NO:78 is the ovarian carcinoma polynucleotide 8e (FIG. 7A).

SEQ ID NO:79 is the ovarian carcinoma polynucleotide 8h (FIG. 7B).

SEQ ID NO:80 is the ovarian carcinoma polynucleotide 12e (FIG. 8).

SEQ ID NO:81 is the ovarian carcinoma polynucleotide 12h (FIG. 9).

SEQ ID NOs:82–310 are ovarian carcinoma antigen polynucleotides shown in FIGS. 15A–15E-2.

SEQ ID NO:311 is a full length sequence of ovarian carcinoma polynucleotide O772P.

SEQ ID NO:312 is the O772P amino acid sequence.

SEQ ID NOs:313–384 are ovarian carcinoma antigen polynucleotides.

SEQ ID NOs:385–390 present sequences of O772P forms.

SEQ ID NO:391 is a full length sequence of ovarian carcinoma polynucleotide O8E.

SEQ ID NOs:392–393 are protein sequences encoded by O8E.

What is claimed is:

1. An isolated polynucleotide comprising the sequence of SEQ ID NO:311.

2. An isolated polynucleotide useful in the detection of ovarian cancer comprising a sequence having at least 90% identity to the entirety of SEQ ID NO:311.

3. An expression vector comprising a polynucleotide of any one of claims 1 and 2 operably linked to an expression control sequence.

4. A host cell transformed or transfected with an expression vector according to claim 3.

5. A complement of a polynucleotide sequence according to any one of the claims 1 and 2.

6. An expression vector comprising a polynucleotide of claim 5.

7. A host cell transformed or transfected with an expression vector according to claim 6.

* * * * *